(12) United States Patent
Dey et al.

(10) Patent No.: US 12,157,746 B2
(45) Date of Patent: Dec. 3, 2024

(54) TETRAHYDRO-1H-PYRAZINO[2,1-A]ISOINDOLYLQUINOLINE COMPOUNDS FOR THE TREATMENT OF AUTOIMMUNE DISEASE

(71) Applicant: F. HOFFMANN-LA ROCHE AG, Basel (CH)

(72) Inventors: Fabian Dey, Basel (CH); Hong Shen, Shanghai (CN); Hongtao Xu, Shanghai (CN); Hongying Yun, Shanghai (CN); Ge Zou, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 858 days.

(21) Appl. No.: 16/972,556

(22) PCT Filed: Jun. 3, 2019

(86) PCT No.: PCT/EP2019/064323
§ 371 (c)(1),
(2) Date: Dec. 4, 2020

(87) PCT Pub. No.: WO2019/233941
PCT Pub. Date: Dec. 12, 2019

(65) Prior Publication Data
US 2021/0371432 A1    Dec. 2, 2021

(30) Foreign Application Priority Data

| Jun. 5, 2018 | (WO) | PCT/CN2018/090004 |
| Sep. 12, 2018 | (EP) | 18193916 |
| May 8, 2019 | (WO) | PCT/CN2019/086019 |

(51) Int. Cl.
C07D 519/00    (2006.01)
C07D 487/04    (2006.01)

(52) U.S. Cl.
CPC ......... *C07D 519/00* (2013.01); *C07D 487/04* (2013.01)

(58) Field of Classification Search
CPC ................................................. C07D 519/00
See application file for complete search history.

(56) References Cited

U.S. PATENT DOCUMENTS

| 4,273,773 A | 6/1981 | Demerson et al. |
| 10,377,738 B2 | 8/2019 | McGowan et al. |
| 11,166,942 B2 | 11/2021 | Delgado Oyarzo et al. |
| 11,548,892 B1 | 1/2023 | Campbell et al. |
| 2014/0051689 A1 | 2/2014 | Bond et al. |
| 2015/0105370 A1 | 4/2015 | Carlson et al. |
| 2017/0174653 A1 | 6/2017 | Sherer et al. |
| 2018/0037570 A1* | 2/2018 | Sherer ................. A61P 25/28 |
| 2019/0185469 A1 | 6/2019 | Dyckman et al. |
| 2022/0144834 A1 | 5/2022 | Catalano et al. |
| 2023/0002375 A1 | 1/2023 | Dey et al. |
| 2023/0015242 A1 | 1/2023 | Dey et al. |
| 2023/0041743 A1 | 2/2023 | Shen et al. |

FOREIGN PATENT DOCUMENTS

| WO | 2011/106276 A1 | 9/2011 |
| WO | 2015/057655 A1 | 4/2015 |
| WO | 2015/057659 A1 | 4/2015 |
| WO | 2019/028302 A1 | 2/2017 |
| WO | 2017/106607 A1 | 6/2017 |
| WO | 2018/005586 A1 | 1/2018 |
| WO | 2018/026620 A1 | 2/2018 |
| WO | 2018/031434 A1 | 2/2018 |
| WO | 2018/047081 A1 | 3/2018 |
| WO | 2018/049089 A1 | 3/2018 |
| WO | 2019/018354 A1 | 1/2019 |
| WO | 2019/028301 A1 | 2/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |

(Continued)

OTHER PUBLICATIONS

Chaichian "Targeted Therapies in Systemic Lupus Erythematosus: A State-of-the-Art Review" J Clin Cell Immunol 2013.*
Mahieu "A critical review of clinical trials in systemic lupus erythematosus" Lupus (2016) 25, 1122-1140.*
Teruel "The genetic basis of systemic lupus erythematosus: What are the risk factors and what have we learned" Journal of Autoimmunity 74 (2016) 161e175.*
Wu "Toll-like receptors: potential targets for lupus treatment" Acta Pharmacologica Sinica (2015) 36: 1395-1407.*

(Continued)

Primary Examiner — David K O'Dell
(74) Attorney, Agent, or Firm — Bradley E. Davis

(57) ABSTRACT

The present invention relates to compounds of formula (I), wherein $R^1$ to $R^6$, m and n are I a described herein, and their pharmaceutically acceptable salt, enantiomer or diastereomer thereof, and compositions including the compounds and methods of using the compounds.

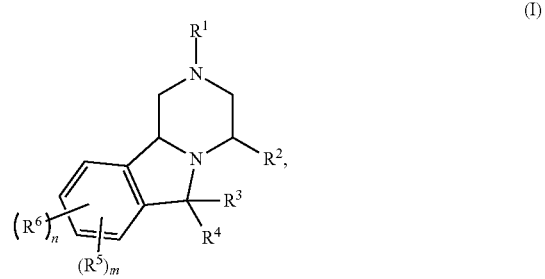

19 Claims, No Drawings

(56) References Cited

FOREIGN PATENT DOCUMENTS

| WO | 2019/126083 A1 | 6/2019 |
|---|---|---|
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |

OTHER PUBLICATIONS

Devaparu "Toll-like receptors in lupus nephritis" Journal of Biomedical Science (2018) 25:35.*
Bastin, R., et al., "Salt Selection and Optimisation Procedures for Pharmaceutical New Chemical Entities" Org Proc Res Dev 2000 4(5):427-435 (Jul. 19, 2000).
Belikov et al. Pharmaceutical Chemistry (Textbook pages in Russian with English translation attached), Moscow:MEDpress-inform,:pp. 27-29 ( 2007).
Kharkevich, D.A. et al. Pharmacology (Russian with English translation attached), 10th edition, Moscow:GEOTAR-Media,:pp. 73-74 ( 2010).
Knunyants, "Chemical Encyclopaedical Dictionary (English translation)" Soviet encyclopaedia:411 (1983).
"Types and mechanisms of reactions in organic chemistry (English translation)" Wayback Machine Internet Archive, URL: https://foxford.ru/wiki/himiya/tipy-i-mehanizmy-reaktsiy-vorganicheskoy- himii:1-6 (Feb. 1, 2016).
Zhulenko, et al., "Pharmacology (with English translation)" Student's Books and Educational Media for Higher Education Facilities:34-35 ( 2008).
Alper et al., "Discovery of potent, orally bioavailable in vivo efficacious antagonists of the TLR7/8 pathway" Bioorg. Med. Chem. Lett. 30(127366):1-5 ( 2020).
International Preliminary Report on Patentability for PCT/EP2019/064323 issued on Dec. 8, 2020.
International Search Report for PCT/EP2019/064323 mailed on Aug. 19, 2019.
Knoepfel et al., "Target-Based Identification and Optimization of 5-Indazol-5-yl Pyridones as Toll-like Receptor 7 and 8 Antagonists Using a Biochemical TLR8 Antagonist Competition Assay" J. Med. Chem. 63:8276-8295 ( 2020).
Mussari et al., "Discovery of Potent and Orally Bioavailable Small Molecule Antagonists of Toll-like Receptors 7/8/9 (TLR7/8/9)" ACS Med. Chem. Lett. 11:1751-1758 ( 2020).

* cited by examiner

TETRAHYDRO-1H-PYRAZINO[2,1-A]ISOINDOLYLQUINOLINE COMPOUNDS FOR THE TREATMENT OF AUTOIMMUNE DISEASE

CROSS-REFERENCE TO RELATED APPLICATIONS

This application is the National Stage Entry under 35 U.S.C. § 371 of International Application No. PCT/EP2019/064323, filed Jun. 3, 2019, which claims benefit of priority under 35 U.S.C. § 119 (a) to EP application Ser. No. 18/193,916.6 filed on Sep. 12, 2018 and to CN Application No. PCT/CN2019/086019 filed on May 8, 2019, and to CN Application No. PCT/CN2018/090004 filed on Jun. 5, 2018, each of which is incorporated herein by reference in its entirety.

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al Lancet 2011, 377, 721). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as auto-inflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7,8,9 is considered as a key node in a broad of autoimmune and auto-inflammatory diseases (Krieg, A. M. et al. Immunol. Rev. 2007, 220, 251. Jimdnez-Dalmaroni, M. J. et al Autoimmun Rev. 2016, 15, 1. Chen, J. Q., et al. Clinical Reviews in Allergy & Immunology 2016, 50, 1). Anti-RNA and anti-DNA antibodies are well established diagnostic markers of SLE, and these antibodies can deliver both self-RNA and self-DNA to endosomes. While self-RNA complexes can be recognized by TLR7 and TLR8, self-DNA complexes can trigger TLR9 activation. Indeed, defective clearance of self-RNA and self-DNA from blood and/or tissues is evident in SLE (Systemic Lupus Erythematosus) patients. TLR7 and TLR9 have been reported to be upregulated in SLE tissues, and correlate with chronicity and activity of lupus nephritis, respectively. In B cells of SLE patients, TLR7 expression correlates with anti-RNP antibody production, while TLR9 expression with IL-6 and anti-dsDNA antibody levels. Consistently, in lupus mouse models, TLR7 is required for anti-RNA antibodies, and TLR9 is required for anti-nucleosome antibody. On the other hand, overexpression of TLR7 or human TLR8 in mice promotes autoimmunity and auto-inflammation. Moreover, activation of TLR8 specifically contributes to inflammatory cytokine secretion of mDC/macrophages, neutrophil NETosis, induction of Th17 cells, and suppression of Treg cells. In addition to the described role of TLR9 in promoting autoantibody production of B cells, activation of TLR9 by self-DNA in pDC also leads to induction of type I IFNs and other inflammatory cytokines. Given these roles of TLR9 in both pDC and B cells, both as key contributors to the pathogenesis of autoimmune diseases, and the extensive presence of self-DNA complexes that could readily activate TLR9 in many patients with autoimmune diseases, it may have extra benefit to further block self-DNA mediated TLR9 pathways on top of inhibition of TLR7 and TLR8 pathways. Taken together, TLR7, 8, and 9 pathways represent new therapeutic targets for the treatment of autoimmune and auto-inflammatory diseases, for which no effective steroid-free and non-cytotoxic oral drugs exist, and inhibition of all these pathways from the very upstream may deliver satisfying therapeutic effects. As such, we invented oral compounds that target and suppress TLR7, TLR8 and TLR9 for the treatment of autoimmune and auto-inflammatory diseases.

SUMMARY OF THE INVENTION

The present invention relates to novel compounds of formula (I),

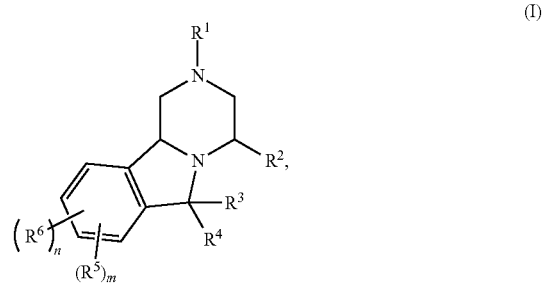

wherein
$R^1$ is

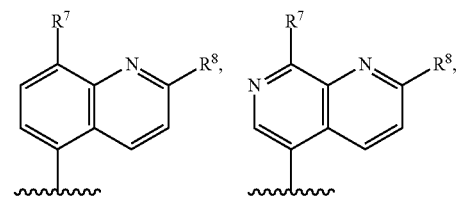

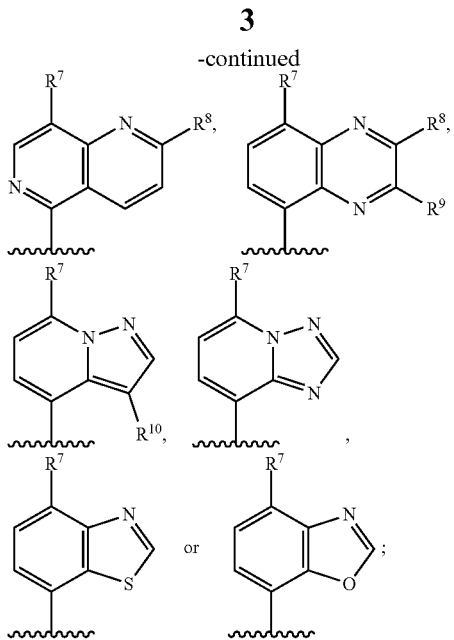

wherein R$^7$ is C$_{1-6}$alkyl, C$_{1-6}$alkoxy, haloC$_{1-6}$alkyl, halogen, nitro or cyano; R$^8$ is H or deuterium; R$^9$ is H, deuterium or C$_{1-6}$alkyl; R$^{10}$ is H or halogen;

R$^2$ is H or C$_{1-6}$alkyl;
R$^3$ is H;
R$^4$ is H;
R$^5$ is H, piperazinyl, halogen, C$_{1-6}$alkyl, halopyrrolidinylamino or hydroxypyrrolidinylC$_{1-6}$alkylamino;
R$^6$ is H;
(C$_{1-6}$alkyl)$_2$aminoC$_{1-6}$alkoxy;
(C$_{1-6}$alkyl)$_2$aminoC$_{1-6}$alkylamino; 1,2,3,4,6,6a-hexahydropyrrolo[3,4-c]pyrrolyl substituted by C$_{1-6}$alkoxy;
1,4-diazepanyl substituted by one or two substituents independently selected from hydroxy and C$_{1-6}$alkyl;
1,4-oxazepanyl substituted by amino;
1,4-oxazepanylamino;
1,6-diazaspiro[3.3]heptanyl;
2,5-diazabicyclo[2.2.1]heptanylcarbonyl;
2,6-diazaspiro[3.3]heptanyl unsubstituted or substituted by C$_{1-6}$alkyl;
2-oxa-7-azaspiro[3.4]octanyl substituted by amino;
3,4,4a,5,7,7a-hexahydro-2H-pyrrolo[3,4-b][1,4]oxazinyl;
3,4a,5,6,7,7a-hexahydro-2H-pyrrolo[3,4-b][1,4]oxazinyl;
3,8-diazabicyclo[3.2.1]octanylcarbonyl;
3-oxa-7,9-diazabicyclo[3.3.1]nonanyl;
3-oxo-1,5,6,7,8,8a-hexahydroimidazo[1,5-a]pyrazinyl;
5-oxa-2,8-diazaspiro[3.5]nonanyl;
9-oxa-3,7-diazabicyclo[3.3.1]nonanyl;
amino(C$_{1-6}$alkyl)piperidinylcarbonyl;
azetidinyl unsubstituted or substituted by one or two substituents independently selected from amino and C$_{1-6}$alkyl;
azetidinylamino;
azetidinyloxy;
C$_{1-6}$alkoxypiperidinylamino;
C$_{1-6}$alkoxypyrrolidinyl(C$_{1-6}$alkyl)amino;
C$_{1-6}$alkoxypyrrolidinylamino;
haloazetidinyl(C$_{1-6}$alkyl)amino;
halopyrrolidinylamino;
halopyrrolidinylC$_{1-6}$alkoxy;
halopyrrolidinylC$_{1-6}$alkylamino;
halopyrrolidinyloxy; hydroxypyrrolidinylC$_{1-6}$alkylamino;
morpholinylC$_{1-6}$alkylamino;
piperazinyl unsubstituted or substituted by C$_{1-6}$alkoxyC$_{1-6}$alkyl, hydroxyC$_{1-6}$alkyl or C$_{1-6}$alkyl;
piperazinylcarbonyl;
piperidinyl unsubstituted or substituted by one or two substituents independently selected from amino, C$_{1-6}$alkoxy and C$_{1-6}$alkyl;
piperidinylamino; or
pyrrolidinyl substituted by one, two or three substituents independently selected from amino, C$_{1-6}$alkoxy, C$_{1-6}$alkyl, C$_{1-6}$alkylamino, halogen, hydroxy and hydroxyC$_{1-6}$alkyl;

m is 0, 1, 2, or 3;
n is 1, 2, 3 or 4;
m+n≤4;
with the proviso that R$^3$ and R$^6$ are not H simultaneously;
or a pharmaceutically acceptable salt thereof.

Another object of the present invention is related to novel compounds of formula (I) or (Ia) or (Ib), their manufacture, medicaments based on a compound in accordance with the invention and their production as well as the use of compounds of formula (I) or (Ia) or (Ib) as TLR7 and/or TLR8 and/or TLR9 antagonist, and for the treatment or prophylaxis of systemic lupus erythematosus or lupus nephritis. The compounds of formula (I) or (Ia) or (Ib) show superior TLR7 and/or TLR8 and/or TLR9 antagonism activity. In addition, the compounds of formula (I) or (Ia) or (Ib) also show good hPBMC, cytotoxicity, solubility, human microsome stability and SDPK profiles, as well as low CYP inhibition.

DETAILED DESCRIPTION OF THE INVENTION

Definitions

The term "C$_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "C$_{1-6}$alkyl" groups are methyl, ethyl and n-propyl.

The term "halogen" and "halo" are used interchangeably herein and denote fluoro, chloro, bromo, or iodo.

The term "haloC$_{1-6}$alkyl" denotes an alkyl group wherein at least one of the hydrogen atoms of the alkyl group has been replaced by same or different halogen atoms, particularly fluoro atoms.

Examples of haloC$_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl, trifluoromethyl and trifluoroethyl.

The term "oxy" denotes —O—.
The term "C$_{1-6}$alkoxy" denotes C$_{1-6}$alkyl-O—.
The term "halopyrrolidinyl" denotes a pyrrolidinyl substituted once, twice or three times by halogen. Examples of halopyrrolidinyl include, but not limited to, difluoropyrrolidinyl and fluoropyrrolidinyl.

The term "haloazetidinyl" denotes a azetidinyl substituted once, twice or three times by halogen. Examples of halopyrrolidinyl include, but not limited to, difluoroazetidinyl and fluoroazetidinyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "cis-isomers" and "trans-isomers" denote the relative stereochemistry of the molecule or moiety. For example: the starting material of Example 16 (trans-3-(boc-amino)-4-methoxypyrrolidine,

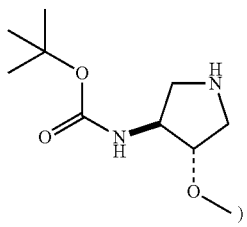

as the "trans-isomers" refers to a mixture of

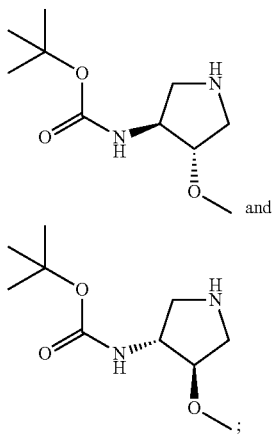

similarly, the starting material of Example 17 (cis-3-(boc-amino)-4-methoxypyrrolidine,

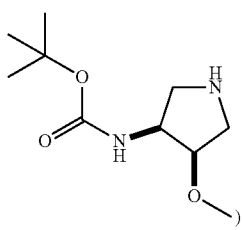

as the "cis-isomers" refers to a mixture of

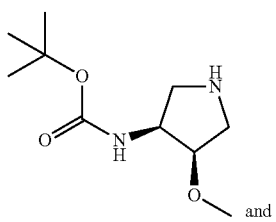

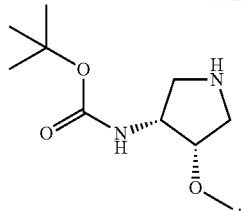

The way of showing relative stereochemistry also applies to the final compounds of this invention.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to (i) a compound of formula (I),

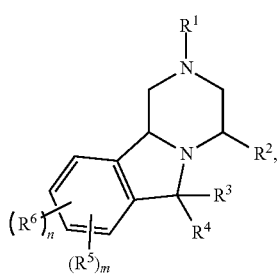

wherein
$R^1$ is

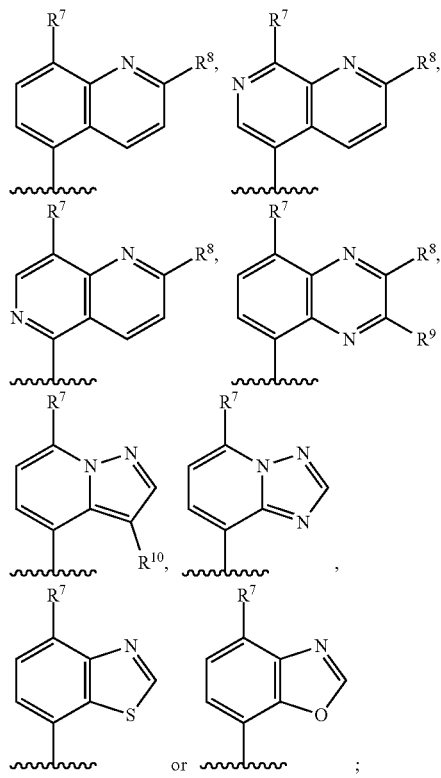

wherein $R^7$ is $C_{1-6}$alkyl, $C_{1-6}$alkoxy, halo$C_{1-6}$alkyl, halogen, nitro or cyano; $R^8$ is H or deuterium; $R^9$ is H, deuterium or $C_{1-6}$alkyl; $R^{10}$ is H or halogen;
$R^2$ is H or $C_{1-6}$alkyl;
$R^3$ is H;
$R^4$ is H;

$R^5$ is H, piperazinyl, halogen, $C_{1-6}$alkyl, halopyrrolidinylamino or hydroxypyrrolidinyl$C_{1-6}$alkylamino;
$R^6$ is H;
  $(C_{1-6}alkyl)_2$amino$C_{1-6}$alkoxy;
  $(C_{1-6}alkyl)_2$amino$C_{1-6}$alkylamino;
  1,2,3,4,6,6a-hexahydropyrrolo[3,4-c]pyrrolyl substituted by $C_{1-6}$alkoxy;
  1,4-diazepanyl substituted by one or two substituents independently selected from hydroxy and $C_{1-6}$alkyl;
  1,4-oxazepanyl substituted by amino;
  1,4-oxazepanylamino;
  1,6-diazaspiro[3.3]heptanyl;
  2,5-diazabicyclo[2.2.1]heptanylcarbonyl;
  2,6-diazaspiro[3.3]heptanyl unsubstituted or substituted by $C_{1-6}$alkyl;
  2-oxa-7-azaspiro[3.4]octanyl substituted by amino;
  3,4,4a,5,7,7a-hexahydro-2H-pyrrolo[3,4-b][1,4]oxazinyl;
  3,4a,5,6,7,7a-hexahydro-2H-pyrrolo[3,4-b][1,4]oxazinyl;
  3,8-diazabicyclo[3.2.1]octanylcarbonyl;
  3-oxa-7,9-diazabicyclo[3.3.1]nonanyl;
  3-oxo-1,5,6,7,8,8a-hexahydroimidazo[1,5-a]pyrazinyl;
  5-oxa-2,8-diazaspiro[3.5]nonanyl;
  9-oxa-3,7-diazabicyclo[3.3.1]nonanyl;
  amino($C_{1-6}$alkyl)piperidinylcarbonyl;
  azetidinyl unsubstituted or substituted by one or two substituents independently selected from amino and $C_{1-6}$alkyl;
  azetidinylamino;
  azetidinyloxy;
  $C_{1-6}$alkoxypiperidinylamino;
  $C_{1-6}$alkoxypyrrolidinyl($C_{1-6}$alkyl)amino;
  $C_{1-6}$alkoxypyrrolidinylamino;
  haloazetidinyl($C_{1-6}$alkyl)amino;
  halopyrrolidinylamino;
  halopyrrolidinyl$C_{1-6}$alkoxy;
  halopyrrolidinyl$C_{1-6}$alkylamino;
  halopyrrolidinyloxy;
  hydroxypyrrolidinyl$C_{1-6}$alkylamino;
  morpholinyl$C_{1-6}$alkylamino;
  piperazinyl unsubstituted or substituted by $C_{1-6}$alkoxy$C_{1-6}$alkyl, hydroxy$C_{1-6}$alkyl or $C_{1-6}$alkyl;
  piperazinylcarbonyl;
  piperidinyl unsubstituted or substituted by one or two substituents independently selected from amino, $C_{1-6}$alkoxy and $C_{1-6}$alkyl;
  piperidinylamino; or
  pyrrolidinyl substituted by one, two or three substituents independently selected from amino, $C_{1-6}$alkoxy, $C_{1-6}$alkyl, $C_{1-6}$alkylamino, halogen, hydroxy and hydroxy$C_{1-6}$alkyl;
m is 0, 1, 2, or 3;
n is 1, 2, 3 or 4;
m+n≤4;
with the proviso that $R^3$ and $R^6$ are not H simultaneously;
or a pharmaceutically acceptable salt thereof.

Another embodiment of present invention is (ii) a compound of formula (Ia),

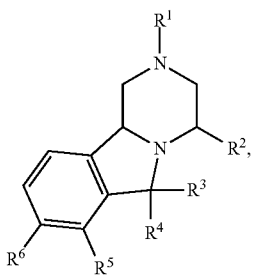

wherein
R¹ is

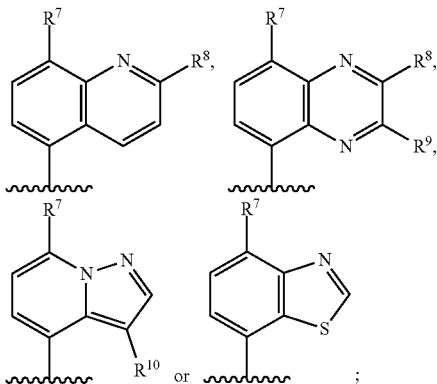

wherein R⁷ is $C_{1-6}$alkyl, halo$C_{1-6}$alkyl, halogen or cyano; R⁸ is H or deuterium; R⁹ is H or deuterium; R¹⁰ is H or halogen;
R² is H or $C_{1-6}$alkyl;
R³ is H;
R⁴ is H;
R⁵ is H, piperazinyl, halopyrrolidinylamino or hydroxypyrrolidinyl$C_{1-6}$alkylamino;
R⁶ is H;
($C_{1-6}$alkyl)₂amino$C_{1-6}$alkoxy;
($C_{1-6}$alkyl)₂amino$C_{1-6}$alkylamino;
1,2,3,4,6,6a-hexahydropyrrolo[3,4-c]pyrrolyl substituted by $C_{1-6}$alkoxy;
1,4-diazepanyl substituted by one or two substituents independently selected from hydroxy and $C_{1-6}$alkyl;
1,4-oxazepanyl substituted by amino;
1,4-oxazepanylamino;
1,6-diazaspiro[3.3]heptanyl;
2,5-diazabicyclo[2.2.1]heptanylcarbonyl;
2,6-diazaspiro[3.3]heptanyl unsubstituted or substituted by $C_{1-6}$alkyl;
2-oxa-7-azaspiro[3.4]octanyl substituted by amino;
3,4,4a,5,7,7a-hexahydro-2H-pyrrolo[3,4-b][1,4]oxazinyl;
3,4a,5,6,7,7a-hexahydro-2H-pyrrolo[3,4-b][1,4]oxazinyl;
3,8-diazabicyclo[3.2.1]octanylcarbonyl;
3-oxa-7,9-diazabicyclo[3.3.1]nonanyl;
3-oxo-1,5,6,7,8,8a-hexahydroimidazo[1,5-a]pyrazinyl;
5-oxa-2,8-diazaspiro[3.5]nonanyl;
9-oxa-3,7-diazabicyclo[3.3.1]nonanyl;
amino($C_{1-6}$alkyl)piperidinylcarbonyl;
azetidinyl unsubstituted or substituted by one or two substituents independently selected from amino and $C_{1-6}$alkyl;
azetidinylamino;
azetidinyloxy;
$C_{1-6}$alkoxypiperidinylamino;
$C_{1-6}$alkoxypyrrolidinyl($C_{1-6}$alkyl)amino;
$C_{1-6}$alkoxypyrrolidinylamino;
haloazetidinyl($C_{1-6}$alkyl)amino;
halopyrrolidinylamino;
halopyrrolidinyl$C_{1-6}$alkoxy;
halopyrrolidinyl$C_{1-6}$alkylamino;
halopyrrolidinyloxy;
hydroxypyrrolidinyl$C_{1-6}$alkylamino;
morpholinyl$C_{1-6}$alkylamino;
piperazinyl unsubstituted or substituted by $C_{1-6}$alkoxy$C_{1-6}$alkyl, hydroxy$C_{1-6}$alkyl or $C_{1-6}$alkyl;
piperazinylcarbonyl;
piperidinyl unsubstituted or substituted by one or two substituents independently selected from amino, $C_{1-6}$alkoxy and $C_{1-6}$alkyl;
piperidinylamino; or
pyrrolidinyl substituted by one, two or three substituents independently selected from amino, $C_{1-6}$alkoxy, $C_{1-6}$alkyl, $C_{1-6}$alkylamino, halogen, hydroxy and hydroxy$C_{1-6}$alkyl;
or a pharmaceutically acceptable salt thereof.

Another embodiment of present invention is (iii) a compound of formula (Ib),

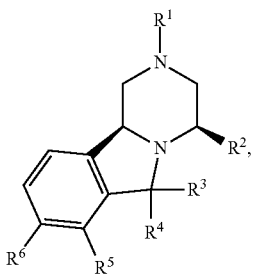

wherein
R¹ is

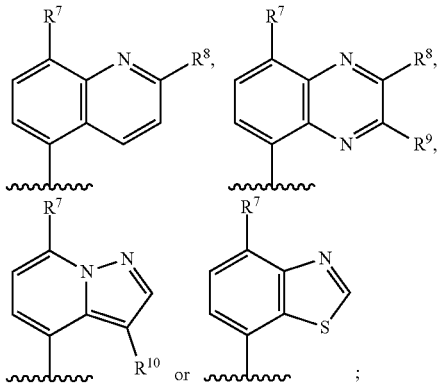

wherein R⁷ is $C_{1-6}$alkyl, halo$C_{1-6}$alkyl, halogen or cyano; R⁸ is H or deuterium; R⁹ is H or deuterium; R¹⁰ is H or halogen;
R² is H or $C_{1-6}$alkyl;
R³ is H;
R⁴ is H;

R⁵ is H, piperazinyl, halopyrrolidinylamino or hydroxypyrrolidinylC₁₋₆alkylamino;
R⁶ is H;
(C₁₋₆alkyl)₂aminoC₁₋₆alkoxy;
(C₁₋₆alkyl)₂aminoC₁₋₆alkylamino;
1,2,3,4,6,6a-hexahydropyrrolo[3,4-c]pyrrolyl substituted by C₁₋₆alkoxy;
1,4-diazepanyl substituted by one or two substituents independently selected from hydroxy and C₁₋₆alkyl;
1,4-oxazepanyl substituted by amino;
1,4-oxazepanylamino;
1,6-diazaspiro[3.3]heptanyl;
2,5-diazabicyclo[2.2.1]heptanylcarbonyl;
2,6-diazaspiro[3.3]heptanyl unsubstituted or substituted by C₁₋₆alkyl;
2-oxa-7-azaspiro[3.4]octanyl substituted by amino;
3,4,4a,5,7,7a-hexahydro-2H-pyrrolo[3,4-b][1,4]oxazinyl;
3,4a,5,6,7,7a-hexahydro-2H-pyrrolo[3,4-b][1,4]oxazinyl;
3,8-diazabicyclo[3.2.1]octanylcarbonyl;
3-oxa-7,9-diazabicyclo[3.3.1]nonanyl;
3-oxo-1,5,6,7,8,8a-hexahydroimidazo[1,5-a]pyrazinyl;
5-oxa-2,8-diazaspiro[3.5]nonanyl;
9-oxa-3,7-diazabicyclo[3.3.1]nonanyl;
amino(C₁₋₆alkyl)piperidinylcarbonyl;
azetidinyl unsubstituted or substituted by one or two substituents independently selected from amino and C₁₋₆alkyl;
azetidinylamino;
azetidinyloxy;
C₁₋₆alkoxypiperidinylamino;
C₁₋₆alkoxypyrrolidinyl(C₁₋₆alkyl)amino;
C₁₋₆alkoxypyrrolidinylamino;
haloazetidinyl(C₁₋₆alkyl)amino;
halopyrrolidinylamino;
halopyrrolidinylC₁₋₆alkoxy;
halopyrrolidinylC₁₋₆alkylamino;
halopyrrolidinyloxy;
hydroxypyrrolidinylC₁₋₆alkylamino;
morpholinylC₁₋₆alkylamino;
piperazinyl unsubstituted or substituted by C₁₋₆alkoxyC₁₋₆alkyl, hydroxyC₁₋₆alkyl or C₁₋₆alkyl;
piperazinylcarbonyl;
piperidinyl unsubstituted or substituted by one or two substituents independently selected from amino, C₁₋₆alkoxy and C₁₋₆alkyl;
piperidinylamino; or
pyrrolidinyl substituted by one, two or three substituents independently selected from amino, C₁₋₆alkoxy, C₁₋₆alkyl, C₁₋₆alkylamino, halogen, hydroxy and hydroxyC₁₋₆alkyl;
or a pharmaceutically acceptable salt thereof.

A further embodiment of present invention is (iv) a compound of formula (I) or (Ia) or (Ib) according to any one of (i) to (iii), or a pharmaceutically acceptable salt thereof, wherein R⁶ is H; (C₁₋₆alkoxyC₁₋₆alkyl)piperazinyl; (C₁₋₆alkyl)₂aminoC₁₋₆alkoxy; (C₁₋₆alkyl)₂aminoC₁₋₆alkylamino; (hydroxyC₁₋₆alkyl)piperazinyl; 1,4-oxazepanylamino; 1,6-diazaspiro[3.3]heptanyl; 2,5-diazabicyclo[2.2.1]heptanylcarbonyl; 2,6-diazaspiro[3.3]heptanyl; 3,4,4a,5,7,7a-hexahydro-2H-pyrrolo[3,4-b][1,4]oxazinyl; 3,4a,5,6,7,7a-hexahydro-2H-pyrrolo[3,4-b][1,4]oxazinyl; 3,8-diazabicyclo[3.2.1]octanylcarbonyl; 3-oxa-7,9-diazabicyclo[3.3.1]nonanyl; 3-oxo-1,5,6,7,8,8a-hexahydroimidazo[1,5-a]pyrazinyl; 5-oxa-2,8-diazaspiro[3.5]nonanyl; 9-oxa-3,7-diazabicyclo[3.3.1]nonanyl; amino(C₁₋₆alkoxy)piperidinyl; amino(C₁₋₆alkoxy)pyrrolidinyl; amino(C₁₋₆alkyl)azetidinyl; amino(C₁₋₆alkyl)piperidinyl; amino(C₁₋₆alkyl)piperidinylcarbonyl; amino(C₁₋₆alkyl)pyrrolidinyl; amino(hydroxy)(C₁₋₆alkyl)pyrrolidinyl; amino(hydroxy)pyrrolidinyl; amino(hydroxyC₁₋₆alkyl)pyrrolidinyl; amino-1,4-oxazepanyl; amino-2-oxa-7-azaspiro[3.4]octanyl; aminoazetidinyl; aminohalopyrrolidinyl; aminopyrrolidinyl; azetidinyl; azetidinylamino; azetidinyloxy; C₁₋₆alkoxy(C₁₋₆alkylamino)pyrrolidinyl; C₁₋₆alkoxy-1,2,3,4,6,6a-hexahydropyrrolo[3,4-c]pyrrolyl; C₁₋₆alkoxypiperidinylamino; C₁₋₆alkoxypyrrolidinyl(C₁₋₆alkyl)amino; C₁₋₆alkoxypyrrolidinylamino; C₁₋₆alkyl-2,6-diazaspiro[3.3]heptanyl; C₁₋₆alkylpiperazinyl; haloazetidinyl(C₁₋₆alkyl)amino; halopyrrolidinylamino; halopyrrolidinylC₁₋₆alkoxy; halopyrrolidinylC₁₋₆alkylamino; halopyrrolidinyloxy; hydroxy(C₁₋₆alkyl)-1,4-diazepanyl; hydroxy(C₁₋₆alkylamino)pyrrolidinyl; hydroxy-1,4-diazepanyl; hydroxypyrrolidinylC₁₋₆alkylamino; morpholinylC₁₋₆alkylamino; piperazinyl; piperazinylcarbonyl; piperidinyl or piperidinylamino.

A further embodiment of present invention is (v) a compound of formula (I) or (Ia) or (Ib) according to any one of (i) to (iv), or a pharmaceutically acceptable salt thereof, wherein R⁶ is H; (hydroxymethyl)piperazin-1-yl; 1,4-oxazepan-6-ylamino; 1,6-diazaspiro[3.3]heptan-6-yl; 2-(dimethylamino)ethoxy; 2-(dimethylamino)ethylamino; 2,5-diazabicyclo[2.2.1]heptanyl-2-carbonyl; 2,6-diazaspiro[3.3]heptan-2-yl; 2-morpholinylethylamino; 3-(methoxymethyl)piperazin-1-yl; 3,4,4a,5,7,7a-hexahydro-2H-pyrrolo[3,4-b][1,4]oxazin-6-yl; 3,4a,5,6,7,7a-hexahydro-2H-pyrrolo[3,4-b][1,4]oxazin-4-yl; 3,8-diazabicyclo[3.2.1]octanyl-3-carbonyl; 3a-methoxy-1,2,3,4,6,6a-hexahydropyrrolo[3,4-c]pyrrol-5-yl; 3-amino-3-(hydroxymethyl)pyrrolidin-1-yl; 3-amino-3-methyl-azetidin-1-yl; 3-amino-3-methyl-pyrrolidin-1-yl; 3-amino-4-fluoro-pyrrolidin-1-yl; 3-amino-4-hydroxy-pyrrolidin-1-yl; 3-amino-4-methoxy-1-piperidinyl; 3-amino-4-methoxy-pyrrolidin-1-yl; 3-aminoazetidin-1-yl; 3-aminopyrrolidin-1-yl; 3-fluoroazetidin-3-ylmethylamino; 3-hydroxy-4-(methylamino)pyrrolidin-1-yl; 3-hydroxypyrrolidin-1-ylethylamino; 3-methoxy-4-(methylamino)pyrrolidin-1-yl; 3-methoxy-4-piperidinylamino; 3-methylpiperazin-1-yl; 3-oxa-7,9-diazabicyclo[3.3.1]nonan-7-yl; 3-oxo-1,5,6,7,8,8a-hexahydroimidazo[1,5-a]pyrazin-2-yl;
3-piperidinylamino; 4-amino-3-hydroxy-3-methyl-pyrrolidin-1-yl; 4-amino-3-methoxy-1-piperidinyl; 4-amino-4-methyl-1-piperidinyl; 4-amino-4-methyl-piperidinyl-1-carbonyl; 4-fluoropyrrolidin-2-ylmethoxy; 4-fluoropyrrolidin-2-ylmethylamino; 4-fluoropyrrolidin-3-ylamino; 4-fluoropyrrolidin-3-yloxy; 4-methoxypyrrolidin-3-yl(methyl)amino; 4-methoxypyrrolidin-3-ylamino; 5-amino-2-oxa-7-azaspiro[3.4]octan-7-yl; 5-oxa-2,8-diazaspiro[3.5]nonan-2-yl; 5-oxa-2,8-diazaspiro[3.5]nonan-8-yl; 6-amino-1,4-oxazepan-4-yl; 6-hydroxy-1,4-diazepan-1-yl; 6-hydroxy-6-methyl-1,4-diazepan-1-yl; 6-methyl-2,6-diazaspiro[3.3]heptan-2-yl; 9-oxa-3,7-diazabicyclo[3.3.1]nonan-3-yl; azetidin-3-yl; azetidin-3-ylamino; azetidin-3-yloxy; hydroxy-1,4-diazepan-1-yl; morpholin-2-ylmethylamino; morpholin-3-ylmethylamino; piperazin-1-yl; piperazinyl-1-carbonyl or piperidin-4-yl.

A further embodiment of present invention is (vi) a compound of formula (I) or (Ia) or (Ib) according to any one of (i) to (v), or a pharmaceutically acceptable salt thereof, wherein R¹ is

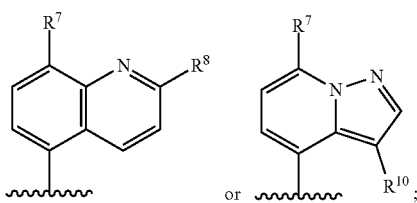

wherein $R^7$ is cyano; $R^8$ is H or deuterium; $R^{10}$ is H or halogen.

A further embodiment of present invention is (vii) a compound of formula (I) or (Ia) or (Ib) according to any one of (i) to (vi), or a pharmaceutically acceptable salt thereof, wherein $R^1$ is

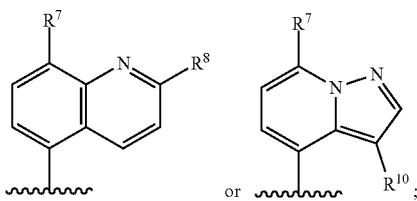

wherein $R^7$ is cyano; $R^8$ is H or deuterium; $R^{10}$ is H or fluoro.

A further embodiment of present invention is (viii) a compound of formula (I) or (Ia) or (Ib) according to any one of (i) to (vii), or a pharmaceutically acceptable salt thereof, wherein $R^2$ is $C_{1-6}$alkyl and $R^5$ is H.

A further embodiment of present invention is (ix) a compound of formula (I) or (Ia) or (Ib) according to (ii) or (iii), or a pharmaceutically acceptable salt thereof, wherein $R^6$ is $(C_{1-6}alkyl)_2aminoC_{1-6}alkylamino$;
1,4-diazepanyl substituted by hydroxy;
1,4-oxazepanyl substituted by amino;
3,4,4a,5,7,7a-hexahydro-2H-pyrrolo[3,4-b][1,4]oxazinyl;
5-oxa-2,8-diazaspiro[3.5]nonanyl;
9-oxa-3,7-diazabicyclo[3.3.1]nonanyl;
azetidinyl substituted twice by amino and $C_{1-6}$alkyl;
$C_{1-6}$alkoxypyrrolidinylamino;
halopyrrolidinylamino; or
pyrrolidinyl substituted by two or three substituents independently selected from amino, $C_{1-6}$alkoxy, $C_{1-6}$alkyl and hydroxy.

A further embodiment of present invention is (x) a compound of formula (I) or (Ia) or (Ib) according to any one of (i) to (ix), or a pharmaceutically acceptable salt thereof, wherein $R^6$ is $(C_{1-6}alkyl)_2aminoC_{1-6}alkylamino$; 3,4,4a,5,7,7a-hexahydro-2H-pyrrolo[3,4-b][1,4]oxazinyl; 5-oxa-2,8-diazaspiro[3.5]nonanyl; 9-oxa-3,7-diazabicyclo[3.3.1]nonanyl; amino($C_{1-6}$alkoxy)pyrrolidinyl; amino($C_{1-6}$alkyl)azetidinyl; amino($C_{1-6}$alkyl)pyrrolidinyl; amino(hydroxy)($C_{1-6}$alkyl)pyrrolidinyl; amino(hydroxy)pyrrolidinyl; amino-1,4-oxazepanyl; $C_{1-6}$alkoxypyrrolidinylamino; halopyrrolidinylamino or hydroxy-1,4-diazepanyl.

A further embodiment of present invention is (xi) a compound of formula (I) or (Ia) or (Ib) according to any one of (i) to (x), or a pharmaceutically acceptable salt thereof, wherein $R^6$ is 2-(dimethylamino)ethylamino; 3,4,4a,5,7,7a-hexahydro-2H-pyrrolo[3,4-b][1,4]oxazin-6-yl; 3-amino-3-methyl-azetidin-1-yl; 3-amino-3-methyl-pyrrolidin-1-yl; 3-amino-4-hydroxy-pyrrolidin-1-yl; 3-amino-4-methoxy-pyrrolidin-1-yl; 4-amino-3-hydroxy-3-methyl-pyrrolidin-1-yl; 4-fluoropyrrolidin-3-ylamino; 4-methoxypyrrolidin-3-ylamino; 5-oxa-2,8-diazaspiro[3.5]nonan-2-yl; 5-oxa-2,8-diazaspiro[3.5]nonan-8-yl; 6-amino-1,4-oxazepan-4-yl; 9-oxa-3,7-diazabicyclo[3.3.1]nonan-3-yl or hydroxy-1,4-diazepan-1-yl.

A further embodiment of present invention is (xii) a compound of formula (I) or (Ia) or (Ib) according to any one of (i) to (xi), or a pharmaceutically acceptable salt thereof, wherein $R^1$ is

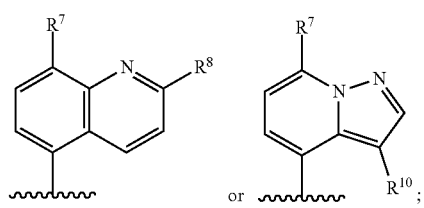

wherein $R^7$ is cyano; $R^8$ is H or deuterium; $R^{10}$ is H or halogen;
$R^2$ is $C_{1-6}$alkyl;
$R^3$ is H;
$R^4$ is H;
$R^5$ is H;
$R^6$ is $(C_{1-6}alkyl)_2aminoC_{1-6}alkylamino$;
1,4-diazepanyl substituted by hydroxy;
1,4-oxazepanyl substituted by amino;
3,4,4a,5,7,7a-hexahydro-2H-pyrrolo[3,4-b][1,4]oxazinyl;
5-oxa-2,8-diazaspiro[3.5]nonanyl;
9-oxa-3,7-diazabicyclo[3.3.1]nonanyl;
azetidinyl substituted twice by amino and $C_{1-6}$alkyl;
$C_{1-6}$alkoxypyrrolidinylamino;
halopyrrolidinylamino; or
pyrrolidinyl substituted by two or three substituents independently selected from amino, $C_{1-6}$alkoxy, $C_{1-6}$alkyl and hydroxy;
or a pharmaceutically acceptable salt thereof.

A further embodiment of present invention is (xiii) a compound of formula (I) or (Ia) or (Ib) according to any one of (i) to (xii), or a pharmaceutically acceptable salt thereof, wherein $R^1$ is

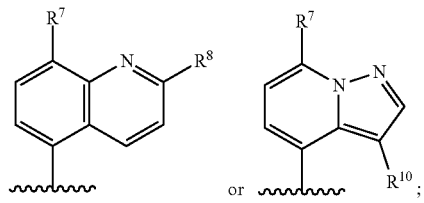

wherein $R^7$ is cyano; $R^8$ is H or deuterium; $R^{10}$ is H or halogen;
$R^2$ is $C_{1-6}$alkyl;
$R^3$ is H;
$R^4$ is H;
$R^5$ is H;
$R^6$ is $(C_{1-6}alkyl)_2aminoC_{1-6}alkylamino$; 3,4,4a,5,7,7a-hexahydro-2H-pyrrolo[3,4-b][1,4]oxazinyl; 5-oxa-2,8-diazaspiro[3.5]nonanyl; 9-oxa-3,7-diazabicyclo[3.3.1]nonanyl; amino($C_{1-6}$alkoxy)pyrrolidinyl; amino($C_{1-6}$alkyl)azetidinyl; amino($C_{1-6}$alkyl)pyrrolidinyl; amino(hydroxy)($C_{1-6}$alkyl)pyrrolidinyl; amino(hydroxy)

pyrrolidinyl; amino-1,4-oxazepanyl; C$_{1-6}$alkoxypyrrolidinylamino; halopyrrolidinylamino or hydroxy-1,4-diazepanyl; or a pharmaceutically acceptable salt thereof.

A further embodiment of present invention is (xiv) a compound of formula (I) or (Ia) or (Ib) according to any one of (i) to (xiii), or a pharmaceutically acceptable salt thereof, wherein
R$^1$ is

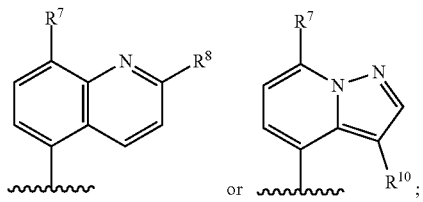

wherein R$^7$ is cyano; R$^8$ is H or deuterium; R$^{10}$ is H or fluoro;
R$^2$ is methyl;
R$^3$ is H;
R$^4$ is H;
R$^5$ is H;
R$^6$ is 2-(dimethylamino)ethylamino; 3,4,4a,5,7,7a-hexahydro-2H-pyrrolo[3,4-b][1,4]oxazin-6-yl; 3-amino-3-methyl-azetidin-1-yl; 3-amino-3-methyl-pyrrolidin-1-yl; 3-amino-4-hydroxy-pyrrolidin-1-yl; 3-amino-4-methoxy-pyrrolidin-1-yl; 4-amino-3-hydroxy-3-methyl-pyrrolidin-1-yl; 4-fluoropyrrolidin-3-ylamino; 4-methoxypyrrolidin-3-ylamino; 5-oxa-2,8-diazaspiro[3.5]nonan-2-yl; 5-oxa-2,8-diazaspiro[3.5]nonan-8-yl; 6-amino-1,4-oxazepan-4-yl; 9-oxa-3,7-diazabicyclo[3.3.1]nonan-3-yl or hydroxy-1,4-diazepan-1-yl;
or a pharmaceutically acceptable salt thereof.

The present invention relates to (i') a compound of formula (I),

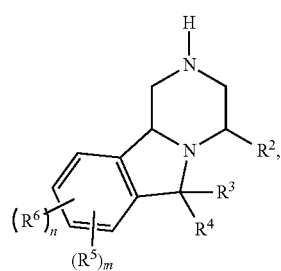

wherein
R$^1$ is

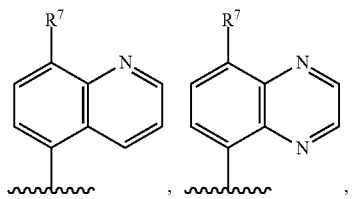

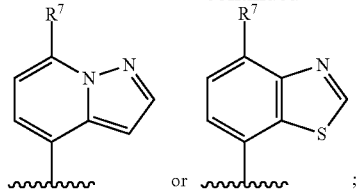

wherein R$^7$ is cyano;
R$^2$ is C$_{1-6}$alkyl;
R$^3$ is H;
R$^4$ is H;
R$^5$ is H or piperazinyl;
R$^6$ is H; (C$_{1-6}$alkylamino)C$_{1-6}$alkoxy; ((C$_{1-6}$alkyl)$_2$amino)C4alkylamino; (C$_{1-6}$alkoxypyrrolidinyl)amino; (halopyrrolidinyl)amino; (hydroxyC$_{1-6}$alkyl)piperazinyl; 1,4-diazepanyl substituted by hydroxy; 2-oxa-7-azaspiro[3.4]octanyl substituted by amino; 3-oxa-7,9-diazabicyclo[3.3.1]nonanyl; 5-oxa-2,8-diazaspiro[3.5]nonanyl; 9-oxa-3,7-diazabicyclo[3.3.1]nonanyl; aminoazetidinyl; aminopyrrolidinyl; azetidinyl; azetidinylamino; azetidinyloxy; piperazinyl; piperidinyl or pyrrolidinyl which is once or twice substituted by substituents independently selected from amino, hydroxy, hydroxyC$_{1-6}$alkyl, C$_{1-6}$alkoxy and C$_{1-6}$alkylamino;
m is 0, 1, 2, or 3;
n is 1, 2, 3 or 4;
m+n≤4;
with the proviso that R$^3$ and R$^6$ are not H simultaneously;
or a pharmaceutically acceptable salt, enantiomer or diastereomer thereof.

Another embodiment of present invention is (ii') a compound of formula (Ia),
wherein

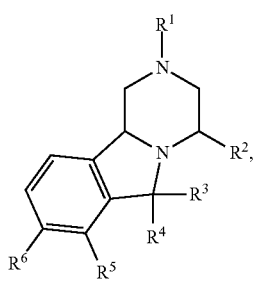

R$^1$ is

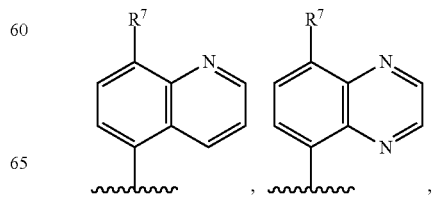

-continued

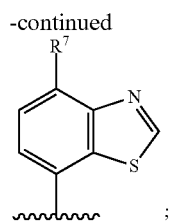

wherein R[7] is cyano;
R[2] is $C_{1-6}$alkyl;
R[3] is H;
R[4] is H;
R[5] is H or piperazinyl;
R[6] is H; $(C_{1-6}$alkylamino$)C_{1-6}$alkoxy; $((C_{1-6}$alkyl$)_2$amino)$C_{1-6}$alkylamino; $(C_{1-6}$alkoxypyrrolidinyl)amino; (halopyrrolidinyl)amino; (hydroxy$C_{1-6}$alkyl)piperazinyl; 1,4-diazepanyl substituted by hydroxy; 2-oxa-7-azaspiro[3.4]octanyl substituted by amino; 3-oxa-7,9-diazabicyclo[3.3.1]nonanyl; 5-oxa-2,8-diazaspiro[3.5]nonanyl; 9-oxa-3,7-diazabicyclo[3.3.1]nonanyl; aminoazetidinyl; aminopyrrolidinyl; azetidinyl; azetidinylamino; azetidinyloxy; piperazinyl; piperidinyl or pyrrolidinyl which is once or twice substituted by substituents independently selected from amino, hydroxy, hydroxy$C_{1-6}$alkyl, $C_{1-6}$alkoxy and $C_{1-6}$alkylamino;
with the proviso that R[3] and R[6] are not H simultaneously;
or a pharmaceutically acceptable salt, enantiomer or diastereomer thereof.

Another embodiment of present invention is (iii') a compound of formula (Ib),

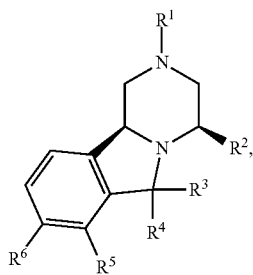

wherein
R[1] is

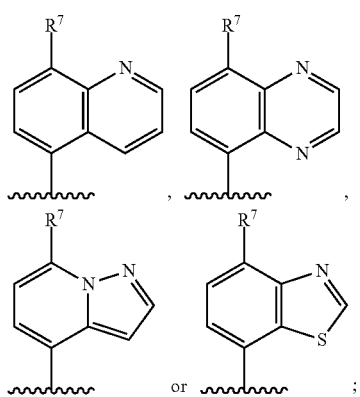

wherein R[7] is cyano;
R[2] is $C_{1-6}$alkyl;
R[3] is H;
R[4] is H;
R[5] is H or piperazinyl;
R[6] is H; $(C_{1-6}$alkylamino$)C_{1-6}$alkoxy; $((C_{1-6}$alkyl$)_2$amino)$C_{1-6}$alkylamino; $(C_{1-6}$alkoxypyrrolidinyl)amino; (halopyrrolidinyl)amino; (hydroxy$C_{1-6}$alkyl)piperazinyl; 1,4-diazepanyl substituted by hydroxy; 2-oxa-7-azaspiro[3.4]octanyl substituted by amino; 3-oxa-7,9-diazabicyclo[3.3.1]nonanyl; 5-oxa-2,8-diazaspiro[3.5]nonanyl; 9-oxa-3,7-diazabicyclo[3.3.1]nonanyl; aminoazetidinyl; aminopyrrolidinyl; azetidinyl; azetidinylamino; azetidinyloxy; piperazinyl; piperidinyl or pyrrolidinyl which is once or twice substituted by substituents independently selected from amino, hydroxy, hydroxy$C_{1-6}$alkyl, $C_{1-6}$alkoxy and $C_{1-6}$alkylamino;
with the proviso that R[3] and R[6] are not H simultaneously;
or a pharmaceutically acceptable salt, enantiomer or diastereomer thereof.

A further embodiment of present invention is (iv') a compound of formula (I) or (Ia) or (Ib) according to any one of (i') to (iii'), wherein R[6] is H; $(C_{1-6}$alkylamino$)C_{1-6}$alkoxy; $((C_{1-6}$alkyl$)_2$amino)$C_{1-6}$alkylamino; $(C_{1-6}$alkoxypyrrolidinyl)amino; (halopyrrolidinyl)amino; (hydroxy$C_{1-6}$alkyl)piperazinyl; 1,4-diazepanyl substituted by hydroxy; 2-oxa-7-azaspiro[3.4]octanyl substituted by amino; 3-oxa-7,9-diazabicyclo[3.3.1]nonanyl; 5-oxa-2,8-diazaspiro[3.5]nonanyl; 9-oxa-3,7-diazabicyclo[3.3.1]nonanyl; amino($C_{1-6}$alkoxy)pyrrolidinyl; amino(hydroxy)pyrrolidinyl; amino(hydroxy$C_{1-6}$alkyl)pyrrolidinyl; aminoazetidinyl; aminopyrrolidinyl; azetidinyl; azetidinylamino; azetidinyloxy; $C_{1-6}$alkoxy($C_{1-6}$alkylamino)pyrrolidinyl; piperazinyl or piperidinyl.

A further embodiment of present invention is (v') a compound of formula (I) or (Ia) or (Ib) according to any one of (i') to (iv'), wherein R[6] is $((C_{1-6}$alkyl$)_2$amino)$C_{1-6}$alkylamino; $(C_{1-6}$alkoxypyrrolidinyl)amino; (halopyrrolidinyl)amino; 1,4-diazepanyl substituted by hydroxy; 5-oxa-2,8-diazaspiro[3.5]nonanyl; 9-oxa-3,7-diazabicyclo[3.3.1]nonanyl or amino($C_{1-6}$alkoxy)pyrrolidinyl.

A further embodiment of present invention is (vi') a compound of formula (I) or (Ia) or (Ib) according to any one of (i') to (iv'), wherein R[6] is 9-oxa-3,7-diazabicyclo[3.3.1]nonanyl; (methoxypyrrolidinyl)amino; hydroxy-1,4-diazepanyl; 5-oxa-2,8-diazaspiro[3.5]nonanyl; (dimethylamino)ethylamino; (fluoropyrrolidinyl)amino or amino(methoxy)pyrrolidinyl.

A further embodiment of present invention is (vii') a compound of formula (I) or (Ia) or (Ib) according to any one of (i') to (vi'), wherein R[1] is

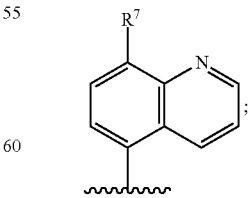

wherein R[7] is cyano.

A further embodiment of present invention is (viii') a compound of formula (I) or (Ia) or (Ib) according to any one of (i') to (vii'), wherein R[5] is H.

A further embodiment of present invention is (ix') a compound of formula (I) or (Ia) or (Ib) according to (ii') or (iii'), wherein
R¹ is

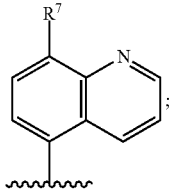

wherein R⁷ is cyano;
R² is C₁₋₆alkyl;
R³ is H;
R⁴ is H;
R⁵ is H;
R⁶ is ((C₁₋₆alkyl)₂amino)C₁₋₆alkylamino; (C₁₋₆alkoxypyrrolidinyl)amino; (halopyrrolidinyl)amino; 1,4-diazepanyl substituted by hydroxy; 5-oxa-2,8-diazaspiro[3.5]nonanyl; 9-oxa-3,7-diazabicyclo[3.3.1]nonanyl or amino(C₁₋₆alkoxy)pyrrolidinyl;
or a pharmaceutically acceptable salt, enantiomer or diastereomer thereof.

A further embodiment of present invention is (x') a compound of formula (I) or (Ia) or (Ib) according to any one of (i') to (ix'), wherein
R¹ is

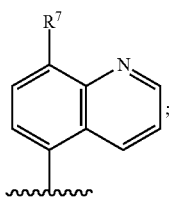

wherein R⁷ is cyano;
R² is methyl;
R³ is H;
R⁴ is H;
R⁵ is H;
R⁶ is 9-oxa-3,7-diazabicyclo[3.3.1]nonanyl; (methoxypyrrolidinyl)amino; hydroxy-1,4-diazepanyl; 5-oxa-2,8-diazaspiro[3.5]nonanyl; (dimethylamino)ethylamino; (fluoropyrrolidinyl)amino or amino(methoxy)pyrrolidinyl;
or a pharmaceutically acceptable salt, enantiomer or diastereomer thereof.

Another embodiment of present invention is that (xv) compounds of formula (I) or (Ia) or (Ib) are selected from the following:

5-[(4R,10bS)-4-methyl-8-piperazin-1-yl-3,4,6,10b-tetrahydro-1H-pyrazino[2,1-a]isoindol-2-yl]quinoline-8-carbonitrile;
5-[(4S,10bR)-4-methyl-8-piperazin-1-yl-3,4,6,10b-tetrahydro-1H-pyrazino[2,1-a]isoindol-2-yl]quinoline-8-carbonitrile;
5-(8-piperazin-1-yl-3,4,6,10b-tetrahydro-1H-pyrazino[2,1-a]isoindol-2-yl)quinoline-8-carbonitrile;
7-(8-piperazin-1-yl-3,4,6,10b-tetrahydro-1H-pyrazino[2,1-a]isoindol-2-yl)-1,3-benzothiazole-4-carbonitrile;
4-[(4R,10bS)-4-methyl-8-piperazin-1-yl-3,4,6,10b-tetrahydro-1H-pyrazino[2,1-a]isoindol-2-yl]pyrazolo[1,5-a]pyridine-7-carbonitrile;
7-[(4R,10bS)-4-methyl-8-piperazin-1-yl-3,4,6,10b-tetrahydro-1H-pyrazino[2,1-a]isoindol-2-yl]-1,3-benzothiazole-4-carbonitrile;
8-[(4R,10bS)-4-methyl-8-piperazin-1-yl-3,4,6,10b-tetrahydro-1H-pyrazino[2,1-a]isoindol-2-yl]quinoxaline-5-carbonitrile;
5-[(4R,10bS)-4-methyl-7-piperazin-1-yl-3,4,6,10b-tetrahydro-1H-pyrazino[2,1-a]isoindol-2-yl]quinoline-8-carbonitrile;
5-[(4R,10bS)-4-methyl-8-(4-piperidyl)-3,4,6,10b-tetrahydro-1H-pyrazino[2,1-a]isoindol-2-yl]quinoline-8-carbonitrile;
5-[(4R 10bS)-8-[(2R)-2-(hydroxymethyl)piperazin-1-yl]-4-methyl-3,4,6,10b-tetrahydro-1H-pyrazino[2,1-a]isoindol-2-yl]quinoline-8-carbonitrile;
5-[(4R,10bS)-8-[(2S)-2-(hydroxymethyl)piperazin-1-yl]-4-methyl-3,4,6,10b-tetrahydro-1H-pyrazino[2,1-a]isoindol-2-yl]quinoline-8-carbonitrile;
5-[(4R,10bS)-8-[(3S)-3-(hydroxymethyl)piperazin-1-yl]-4-methyl-3,4,6,10b-tetrahydro-1H-pyrazino[2,1-a]isoindol-2-yl]quinoline-8-carbonitrile;
5-[(4R,10bS)-4-methyl-8-(3-oxa-7,9-diazabicyclo[3.3.1]nonan-7-yl)-3,4,6,10b-tetrahydro-1H-pyrazino[2,1-a]isoindol-2-yl]quinoline-8-carbonitrile;
5-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]quinoline-8-carbonitrile;
5-[(4R,10bS)-8-(6-hydroxy-1,4-diazepan-1-yl)-4-methyl-3,4,6,10b-tetrahydro-1H-pyrazino[2,1-a]isoindol-2-yl]quinoline-8-carbonitrile;
5-[(4R,10bS)-8-[trans-3-amino-4-methoxy-pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-[(3S,4S)-3-amino-4-methoxy-pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-[cis-3-amino-4-methoxy-pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-(5-amino-2-oxa-7-azaspiro[3.4]octan-7-yl)-4-methyl-3,4,6,10b-tetrahydro-1H-pyrazino[2,1-a]isoindol-2-yl]quinoline-8-carbonitrile;
5-[(4R,10bS)-8-[3-amino-3-(hydroxymethyl)pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-[(3R)-3-aminopyrrolidin-1-yl]-4-methyl-3,4,6,10b-tetrahydro-1H-pyrazino[2,1-a]isoindol-2-yl]quinoline-8-carbonitrile;
5-[(4R,10bS)-8-[trans-3-amino-4-hydroxy-pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-(3-aminoazetidin-1-yl)-4-methyl-3,4,6,10b-tetrahydro-1H-pyrazino[2,1-a]isoindol-2-yl]quinoline-8-carbonitrile;
5-[(4R,10bS)-8-[(3S,4S)-3-methoxy-4-(methylamino)pyrrolidin-1-yl]-4-methyl-3,4,6,10b-tetrahydro-1H-pyrazino[2,1-a]isoindol-2-yl]quinoline-8-carbonitrile;
5-[(4R,10bS)-4-methyl-8-(5-oxa-2,8-diazaspiro[3.5]nonan-8-yl)-3,4,6,10b-tetrahydro-1H-pyrazino[2,1-a]isoindol-2-yl]quinoline-8-carbonitrile;

5-[(4R,10bS)-8-[2-(dimethylamino)ethoxy]-4-methyl-3,4,6,10b-tetrahydro-1H-pyrazino[2,1-a]isoindol-2-yl]quinoline-8-carbonitrile;

5-[(4R,10bS)-8-[2-(dimethylamino)ethylamino]-4-methyl-3,4,6,10b-tetrahydro-1H-pyrazino[2,1-a]isoindol-2-yl]quinoline-8-carbonitrile;

5-[(4R,10bS)-8-(azetidin-3-yloxy)-4-methyl-3,4,6,10b-tetrahydro-1H-pyrazino[2,1-a]isoindol-2-yl]quinoline-8-carbonitrile;

5-[(4R,10bS)-8-(azetidin-3-ylamino)-4-methyl-3,4,6,10b-tetrahydro-1H-pyrazino[2,1-a]isoindol-2-yl]quinoline-8-carbonitrile;

5-[(4R,10bS)-8-(azetidin-3-yl)-4-methyl-3,4,6,10b-tetrahydro-1H-pyrazino[2,1-a]isoindol-2-yl]quinoline-8-carbonitrile;

5-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3S,4S)-4-fluoropyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3R,4S)-4-fluoropyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3R,4R)-4-fluoropyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3R,4R)-4-methoxypyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]quinoline-8-carbonitrile;

5-[(4R,10bS)-8-(2,6-diazaspiro[3.3]heptan-2-yl)-4-methyl-3,4,6,10b-tetrahydro-1H-pyrazino[2,1-a]isoindol-2-yl]quinoline-8-carbonitrile;

5-[(4R,10bS)-8-(1,6-diazaspiro[3.3]heptan-6-yl)-4-methyl-3,4,6,10b-tetrahydro-1H-pyrazino[2,1-a]isoindol-2-yl]quinoline-8-carbonitrile;

5-[(4R,10bS)-4-methyl-8-(6-methyl-2,6-diazaspiro[3.3]heptan-2-yl)-3,4,6,10b-tetrahydro-1H-pyrazino[2,1-a]isoindol-2-yl]quinoline-8-carbonitrile;

5-[(4R,10bS)-8-(3-amino-3-methyl-azetidin-1-yl)-4-methyl-3,4,6,10b-tetrahydro-1H-pyrazino[2,1-a]isoindol-2-yl]quinoline-8-carbonitrile;

5-[(4R,10bS)-8-[(3S,4S)-3-amino-4-hydroxy-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3R,4R)-3-amino-4-hydroxy-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-(3a-methoxy-1,2,3,4,6,6a-hexahydropyrrolo[3,4-c]pyrrol-5-yl)-4-methyl-3,4,6,10b-tetrahydro-1H-pyrazino[2,1-a]isoindol-2-yl]quinoline-8-carbonitrile;

5-[(4R,10bS)-8-[(3S,4S)-3-hydroxy-4-(methylamino)pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3R,4R)-3-hydroxy-4-(methylamino)pyrrolidin-1-yl]-3,4,6,10b-tetrahydro-1H-pyrazino[2,1-a]isoindol-2-yl]quinoline-8-carbonitrile;

5-[(4R,10bS)-4-methyl-8-[(4aR,7aR)-3,4,4a,5,7,7a-hexahydro-2H-pyrrolo[3,4-b][1,4]oxazin-6-yl]-3,4,6,10b-tetrahydro-1H-pyrazino[2,1-a]isoindol-2-yl]quinoline-8-carbonitrile;

5-[(4R,10bS)-4-methyl-8-[trans-(3R,4R)-4-amino-3-hydroxy-3-methyl-pyrrolidin-1-yl]-3,4,6,10b-tetrahydro-1H-pyrazino[2,1-a]isoindol-2-yl]quinoline-8-carbonitrile;

5-[(4R,10bS)-8-[(3R,4R)-4-amino-3-hydroxy-3-methyl-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3S,4R)-3-amino-4-fluoro-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3R,4S)-3-amino-4-fluoro-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3R,4R)-3-amino-4-fluoro-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3S,4S)-3-amino-4-fluoro-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3R)-3-(methoxymethyl)piperazin-1-yl]-4-methyl-3,4,6,10b-tetrahydro-1H-pyrazino[2,1-a]isoindol-2-yl]quinoline-8-carbonitrile;

5-[(4R,10bS)-8-(4-amino-4-methyl-1-piperidyl)-4-methyl-3,4,6,10b-tetrahydro-1H-pyrazino[2,1-a]isoindol-2-yl]quinoline-8-carbonitrile;

5-[(4R,10bS)-8-(3,4a,5,6,7,7a-hexahydro-2H-pyrrolo[3,4-b][1,4]oxazin-4-yl)-4-methyl-3,4,6,10b-tetrahydro-1H-pyrazino[2,1-a]isoindol-2-yl]quinoline-8-carbonitrile;

5-[(4R,10bS)-8-[(6S)-6-hydroxy-1,4-diazepan-1-yl]-4-methyl-3,4,6,10b-tetrahydro-1H-pyrazino[2,1-a]isoindol-2-yl]quinoline-8-carbonitrile;

5-[(4R,10bS)-8-[(6R)-6-hydroxy-1,4-diazepan-1-yl]-4-methyl-3,4,6,10b-tetrahydro-1H-pyrazino[2,1-a]isoindol-2-yl]quinoline-8-carbonitrile;

5-[(4R,10bS)-8-(6-amino-1,4-oxazepan-4-yl)-4-methyl-3,4,6,10b-tetrahydro-1H-pyrazino[2,1-a]isoindol-2-yl]quinoline-8-carbonitrile;

5-[(4R,10bS)-8-[(6R)-6-amino-1,4-oxazepan-4-yl]-4-methyl-3,4,6,10b-tetrahydro-1H-pyrazino[2,1-a]isoindol-2-yl]quinoline-8-carbonitrile;

5-[(4R,10bS)-8-[(6S)-6-amino-1,4-oxazepan-4-yl]-4-methyl-3,4,6,10b-tetrahydro-1H-pyrazino[2,1-a]isoindol-2-yl]quinoline-8-carbonitrile;

5-[(4R,10bS)-8-(6-hydroxy-6-methyl-1,4-diazepan-1-yl)-4-methyl-3,4,6,10b-tetrahydro-1H-pyrazino[2,1-a]isoindol-2-yl]quinoline-8-carbonitrile;

5-[(4R,10bS)-8-[(6S)-6-hydroxy-6-methyl-1,4-diazepan-1-yl]-4-methyl-3,4,6,10b-tetrahydro-1H-pyrazino[2,1-a]isoindol-2-yl]quinoline-8-carbonitrile;

5-[(4R,10bS)-8-[(6R)-6-hydroxy-6-methyl-1,4-diazepan-1-yl]-4-methyl-3,4,6,10b-tetrahydro-1H-pyrazino[2,1-a]isoindol-2-yl]quinoline-8-carbonitrile;

5-[(4R,10bS)-4-methyl-8-(1,4-oxazepan-6-ylamino)-3,4,6,10b-tetrahydro-1H-pyrazino[2,1-a]isoindol-2-yl]quinoline-8-carbonitrile;

5-[(4R,10bS)-4-methyl-8-[[(6R)-1,4-oxazepan-6-yl]amino]-3,4,6,10b-tetrahydro-1H-pyrazino[2,1-a]isoindol-2-yl]quinoline-8-carbonitrile;

5-[(4R,10bS)-4-methyl-8-[[(6S)-1,4-oxazepan-6-yl]amino]-3,4,6,10b-tetrahydro-1H-pyrazino[2,1-a]isoindol-2-yl]quinoline-8-carbonitrile;

5-[(4R,10bS)-4-methyl-8-(morpholin-3-ylmethylamino)-3,4,6,10b-tetrahydro-1H-pyrazino[2,1-a]isoindol-2-yl]quinoline-8-carbonitrile;

5-[(4R,10bS)-4-methyl-8-[[(2S)-morpholin-2-yl]methylamino]-3,4,6,10b-tetrahydro-1H-pyrazino[2,1-a]isoindol-2-yl]quinoline-8-carbonitrile;

5-[(4R,10bS)-4-methyl-8-[[(2R)-morpholin-2-yl]methylamino]-3,4,6,10b-tetrahydro-1H-pyrazino[2,1-a]isoindol-2-yl]quinoline-8-carbonitrile;

5-[(4R,10bS)-8-[[(3S,4R)-4-methoxypyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3R,4S)-4-methoxypyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3S,4S)-4-methoxypyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3R,4R)-4-methoxypyrrolidin-3-yl]amino]-4,9-dimethyl-3,4,6,10b-tetrahydro-1H-pyrazino[2,1-a]isoindol-2-yl]quinoline-8-carbonitrile;

5-[(4R,10bS)-8-[[(3S,4S)-4-methoxypyrrolidin-3-yl]methyl-amino]-4-methyl-3,4,6,10b-tetrahydro-1H-pyrazino[2,1-a]isoindol-2-yl]quinoline-8-carbonitrile;

5-[(4R,10bS)-4-methyl-8-[[(3R)-3-piperidyl]amino]-3,4,6,10b-tetrahydro-1H-pyrazino[2,1-a]isoindol-2-yl]quinoline-8-carbonitrile;

5-[(4R,10bS)-8-[[(3S,4R)-3-methoxy-4-piperidyl]amino]-4-methyl-3,4,6,10b-tetrahydro-1H-pyrazino[2,1-a]isoindol-2-yl]quinoline-8-carbonitrile;

5-[(4R,10bS)-4-methyl-8-(2-morpholinoethylamino)-3,4,6,10b-tetrahydro-1H-pyrazino[2,1-a]isoindol-2-yl]quinoline-8-carbonitrile;

5-[(4R,10bS)-8-[2-[(3S)-3-hydroxypyrrolidin-1-yl]ethylamino]-4-methyl-3,4,6,10b-tetrahydro-1H-pyrazino[2,1-a]isoindol-2-yl]quinoline-8-carbonitrile;

5-[(4R,10bS)-8-[(3-fluoroazetidin-3-yl)methylamino]-4-methyl-3,4,6,10b-tetrahydro-1H-pyrazino[2,1-a]isoindol-2-yl]quinoline-8-carbonitrile;

5-[(4R,10bS)-8-[[(2S,4S)-4-fluoropyrrolidin-2-yl]methylamino]-4-methyl-3,4,6,10b-tetrahydro-1H-pyrazino[2,1-a]isoindol-2-yl]quinoline-8-carbonitrile;

5-[(4R,10bS)-8-[(8aS)-3-oxo-1,5,6,7,8,8a-hexahydroimidazo[1,5-a]pyrazin-2-yl]-4-methyl-3,4,6,10b-tetrahydro-1H-pyrazino[2,1-a]isoindol-2-yl]quinoline-8-carbonitrile;

5-[(4R,10bS)-8-[(8aR)-3-oxo-1,5,6,7,8,8a-hexahydroimidazo[1,5-a]pyrazin-2-yl]-4-methyl-3,4,6,10b-tetrahydro-1H-pyrazino[2,1-a]isoindol-2-yl]quinoline-8-carbonitrile;

5-[(4R,10bS)-8-[(3S,4S)-4-fluoropyrrolidin-3-yl]oxy-4-methyl-3,4,6,10b-tetrahydro-1H-pyrazino[2,1-a]isoindol-2-yl]quinoline-8-carbonitrile;

5-[(4R,10bS)-8-[[(2S,4S)-4-fluoropyrrolidin-2-yl]methoxy]-4-methyl-3,4,6,10b-tetrahydro-1H-pyrazino[2,1-a]isoindol-2-yl]quinoline-8-carbonitrile;

(4R,10bS)—N-[(3S,4R)-4-fluoropyrrolidin-3-yl]-4-methyl-2-(8-methyl-5-quinolyl)-3,4,6,10b-tetrahydro-1H-pyrazino[2,1-a]isoindol-8-amine;

(4R,10bS)—N-[(3S,4R)-4-fluoropyrrolidin-3-yl]-4-methyl-2-(8-methylquinoxalin-5-yl)-3,4,6,10b-tetrahydro-1H-pyrazino[2,1-a]isoindol-8-amine;

(4R,10bS)—N-[(3S,4R)-4-fluoropyrrolidin-3-yl]-4-methyl-2-[8-(trifluoromethyl)quinoxalin-5-yl]-3,4,6,10b-tetrahydro-1H-pyrazino[2,1-a]isoindol-8-amine;

7-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]-1,3-benzothiazole-4-carbonitrile;

(4R,10bS)-2-(8-chloro-5-quinolyl)-N-[(3S,4R)-4-fluoropyrrolidin-3-yl]-4-methyl-3,4,6,10b-tetrahydro-1H-pyrazino[2,1-a]isoindol-8-amine;

5-[(4R,10bS)-7-[2-[(3S)-3-hydroxypyrrolidin-1-yl]ethylamino]-4-methyl-3,4,6,10b-tetrahydro-1H-pyrazino[2,1-a]isoindol-2-yl]quinoline-8-carbonitrile;

5-[(4R,10bS)-7-[[(3S,4R)-4-fluoropyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[(3R,4R)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile;

5-[(4R,10bS)-8-[(3S,4S)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile;

5-[(4R,10bS)-8-(2,6-diazaspiro[3.3]heptan-2-yl)-9-fluoro-4-methyl-3,4,6,10b-tetrahydro-1H-pyrazino[2,1-a]isoindol-2-yl]quinoline-8-carbonitrile;

5-[(4R,10bS)-9-fluoro-4-methyl-8-(9-oxa-3,7-diazabicyclo[3.3.1]nonan-3-yl)-3,4,6,10b-tetrahydro-1H-pyrazino[2,1-a]isoindol-2-yl]quinoline-8-carbonitrile;

5-[(4R,10bS)-4-methyl-8-(piperazine-1-carbonyl)-3,4,6,10b-tetrahydro-1H-pyrazino[2,1-a]isoindol-2-yl]quinoline-8-carbonitrile;

5-[(4R,10bS)-8-[(1S,4S)-2,5-diazabicyclo[2.2.1]heptane-2-carbonyl]-4-methyl-3,4,6,10b-tetrahydro-1H-pyrazino[2,1-a]isoindol-2-yl]quinoline-8-carbonitrile;

5-[(4R,10bS)-8-(4-amino-4-methyl-piperidine-1-carbonyl)-4-methyl-3,4,6,10b-tetrahydro-1H-pyrazino[2,1-a]isoindol-2-yl]quinoline-8-carbonitrile;

5-[(4R,10bS)-8-(3,8-diazabicyclo[3.2.1]octane-3-carbonyl)-4-methyl-3,4,6,10b-tetrahydro-1H-pyrazino[2,1-a]isoindol-2-yl]quinoline-8-carbonitrile;

5-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]-2-deuterio-quinoline-8-carbonitrile;

5-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]-2-deuterio-quinoline-8-carbonitrile;

5-[(4R,10bS)-8-(3-amino-3-methyl-azetidin-1-yl)-4-methyl-3,4,6,10b-tetrahydro-1H-pyrazino[2,1-a]isoindol-2-yl]-2-deuterio-quinoline-8-carbonitrile;

5-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]-2-deuterio-quinoline-8-carbonitrile;

4-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-3-amino-4-methoxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R)-3-aminopyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-4-methyl-8-[(3R)-3-methylpiperazin-1-yl]-3,4,6,10b-tetrahydro-1H-pyrazino[2,1-a]isoindol-2-yl]pyrazolo[1,5-a]pyridine-7-carbonitrile;

4-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4S)-3-amino-4-fluoro-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-(4-amino-4-methyl-1-piperidyl)-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(6R)-6-amino-1,4-oxazepan-4-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]pyrazolo[1,5-a]pyridine-7-carbonitrile;

4-[(4R,10bS)-8-[(3R)-3-amino-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4R)-4-amino-3-methoxy-1-piperidyl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4S)-4-amino-3-methoxy-1-piperidyl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4S)-3-amino-4-methoxy-1-piperidyl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4R)-4-amino-3-hydroxy-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4R)-3-amino-4-hydroxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-3-amino-4-hydroxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]-3-fluoro-pyrazolo[1,5-a]pyridine-7-carbonitrile; and 4-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]-3-fluoro-pyrazolo[1,5-a]pyridine-7-carbonitrile;

or a pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^6$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compound of formula (I) is shown in Scheme 1 below.

Scheme 1

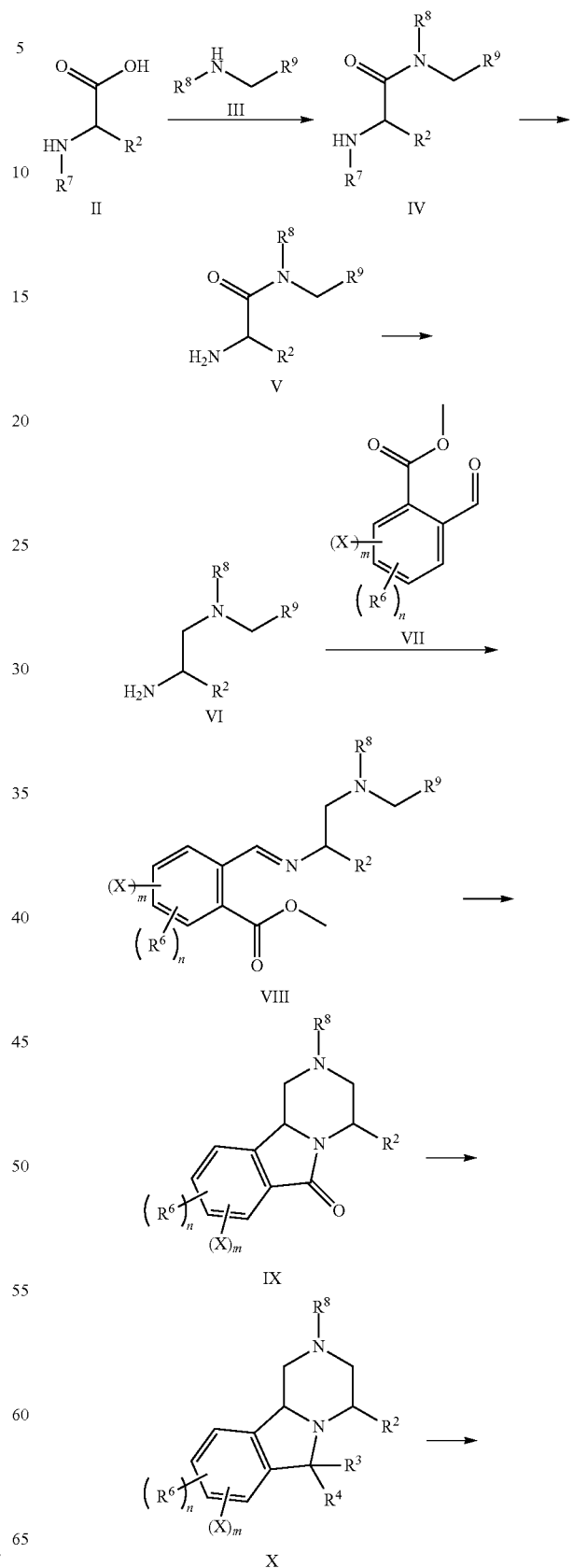

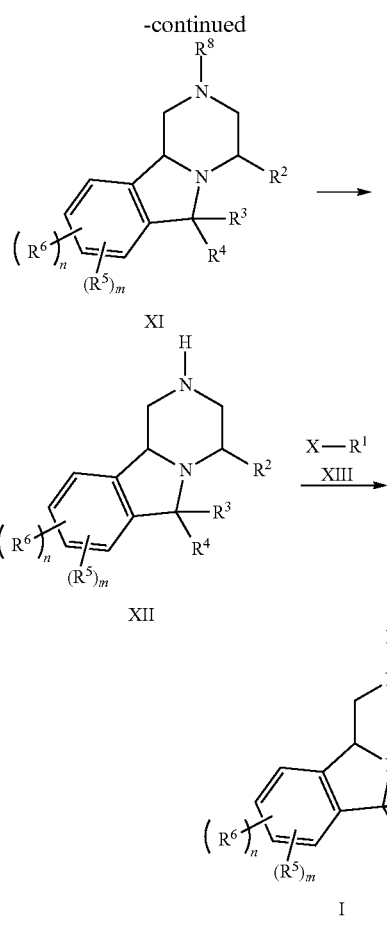

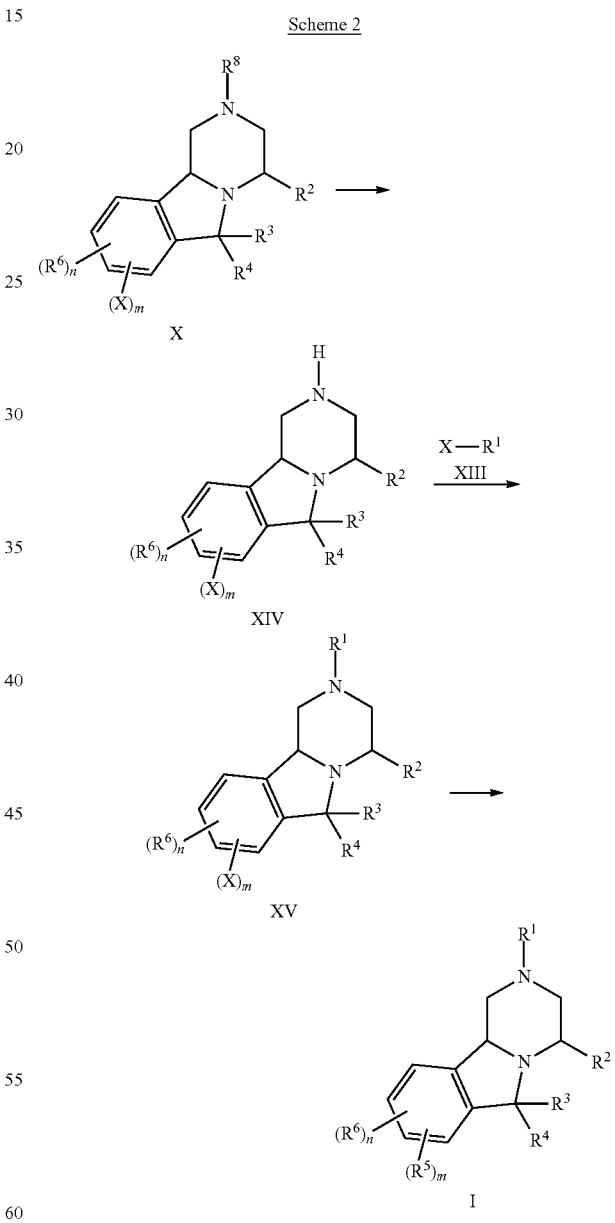

Scheme 2 selective deprotection of $R^8$ group under typical conditions (e.g. removal of benzyl protecting group by hydrogenation over catalytic amount of Palladium on carbon), the resulting compound of formula (XII) can be submitted to nucleophilic aromatic substitution conditions (e.g. heating with halide (XIII) in the presence of DIEPA in DMSO), or Buchwald-Hartwig amination conditions (e.g. heating with halide (XIII) in the presence of a catalyst, such as Ruphos Pd-G2, and a base, such as $Cs_2CO_3$, to afford compound of formula (I). In some embodiment, the compound of formula (XII) may contain a protecting group, e.g. Boc, which will be removed before affording the final compound of formula (I).

wherein X is halogen or leaving group, for example, OTf or OMs; m is 0, 1, 2, or 3; n is 1, 2, 3 or 4; m+n≤4; $R^7$ and $R^8$ are protecting groups, for example, $R^7$ is Boc and R is benzyl; $R^9$ is alkylsilyl, for example, trimethylsilyl.

The amide coupling of protected amino acid (II) and silylamine (III) can be achieved using coupling reagents, such as HATU and DIPEA, to afford intermediate (IV). After $R^7$ is removed by selective deprotection, the amide bond in the resulting intermediate (V) can be reduced under reductive conditions, such as treatment of LAH, to afford diamine (VI). Imine (VIII), which can be formed by condensation of aldehyde (VII) and diamine (VI) under typical dehydration conditions, is cyclized under photo-redox conditions, which is catalyzed by blue light and Ir-based catalyst, such as [Ir(dtbbpy)(ppy)$_2$][PF6], to afford tricyclic lactam (IX). When treated with reducing reagent, such as LAH, lactam (IX) can be reduced to compound of formula (X), in which both $R^3$ and $R^4$ are hydrogen atoms. Alternatively, lactam (IX) can also be treated with dimethyl titanocene, then reduced by hydrogenation to install an alkyl group at $R^3$ or $R^4$. Compound of formula (X) can be used as a common intermediate for further functionalization under metal catalyzed coupling conditions, such as Buchwald-Hartwig amination, Suzuki coupling, Negishi coupling, Stille coupling, or Pd-catalyzed C=O insertion. For example, under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as Ruphos Pd-G2, and a base, such as $Cs_2CO_3$, compound of formula (XI) can be generated from compound of formula (X). After After $R^8$ is removed from formula (X) by selective deprotection, the resulting compound of formula (XIV) can react with halide (XIII) to afford compound of formula (XV) by nucleophilic aromatic substitution in the presence of abase, such as DIEPA. Compound of formula (I can be obtained from compound of formula (XV) via metal catalyzed coupling conditions: Buchwald-Hartwig amination in the presence of a catalyst, such as Ruphos Pd-G2, and a base, such as Cs₂CO₃; Suzuki coupling with boronic acid, boronic ester, or potassium trifluoroborate, in the presence of a palladium catalyst, such as tetrakis(triphenylphosphine)palladium(0) or [1,1'-bis(diphenylphosphino)ferrocene]dichloropalladium (II), complex with dichloromethane and a base, such as potassium carbonate in solvent; Stille coupling with organotin reagent, in the presence of a palladium(0) catalyst, such as tetrakis(triphenylphosphine)palladium(0); or Negishi coupling with organozinc reagent in the presence of a palladium(0) catalyst, such as tetrakis(triphenylphosphine) palladium(0) or [1,1'-bis(diphenylphosphino)ferrocene]dichloropalladium (II). In some embodiment, the compound of formula (XII) may contain a protecting group, e.g. Boc, which will be removed before affording the final compound of formula (I).

Compounds of this invention can be obtained as mixtures of diastereomers or enantiomers, which can be separated by methods well known in the art, e.g. (chiral) HPLC or SFC.

This invention also relates to a process for the preparation of a compound of formula (I), (Ia) or (Ib) comprising any of the following steps:

a) the substitution reaction of compound of formula (XII),

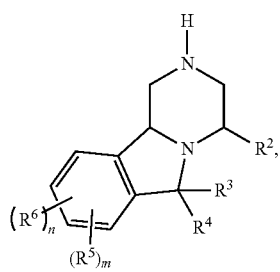

(XII)

and halide (XIII) in the presence of a base;

b) the Buchwald-Hartwig amination reaction of compound of formula (XII),

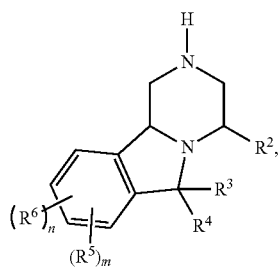

(XII)

and halide (XIII) in the presence of a catalyst and abase;

c) the Buchwald-Hartwig amination reaction of compound of formula (XV),

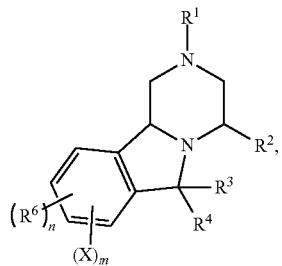

(XV)

and halide (XIII) in the presence of a catalyst and a base;

d) the Suzuki coupling reaction of compound of formula (XV),

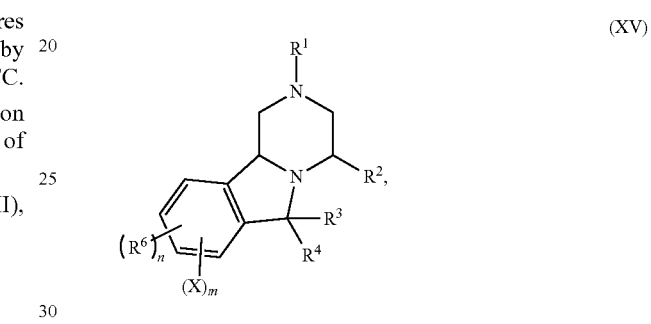

(XV)

and boronic reagent in the presence of a catalyst and a base;

e) the Stille coupling reaction of compound of formula (XV),

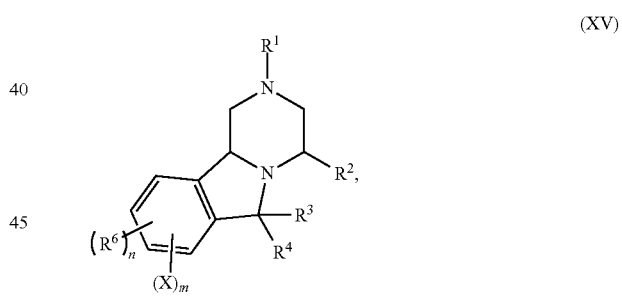

(XV)

and organotin reagent in the presence of a catalyst;

f) the Negishi coupling reaction of compound of formula (XV),

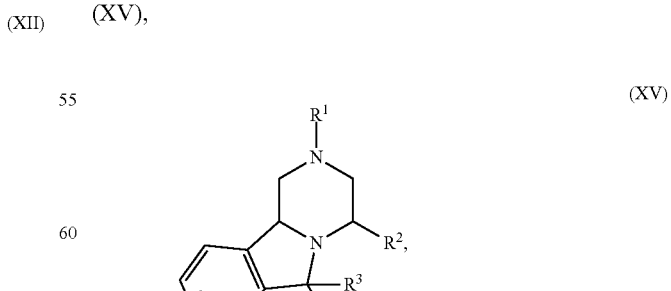

(XV)

and organozinc reagent in the presence of a catalyst;

wherein, in step a), the base can be, for example, DIPEA;

in step b) and c), the catalyst can be, for example, Ruphos Pd-G2; the base can be, for example, $Cs_2CO_3$;

in step d), the catalyst can be, for example, tetrakis(triphenylphosphine)palladium(0) or [1,1'-bis(diphenylphosphino)ferrocene]dichloropalladium (II); the base can be, for example, $K_2CO_3$;

in step e), the catalyst can be, for example, tetrakis(triphenylphosphine)palladium(0);

in step f), the catalyst can be, for example, tetrakis(triphenylphosphine)palladium(0) or [1,1'-bis(diphenylphosphino)ferrocene]dichloropalladium (II).

A compound of formula (I), (Ia) or (Ib) when manufactured according to the above process with achiral or chiral starting materials is also an object of the invention.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:

ACN: acetonitrile
$Boc_2O$: di-tert-butyl dicarbonate
$Tf_2O$: triflic anhydride
DCM: dichloromethane
DDI drug-drug-interaction
DIPEA diethylisopropylamine
DMA dimethylacetamide
EA or EtOAc: ethyl acetate
FA: formic acid
HATU 1-[Bis(dimethylamino)methylene]-1H-1,2,3-triazolo[4,5-b]pyridinium 3-oxid hexafluorophosphate
HLM human liver microsome
hr hour
hrs hours
$IC_{50}$: half inhibition concentration
LCMS liquid chromatography-mass spectrometry
LYSA lyophilisation solubility assay
MS: mass spectrometry
PE: petroleum ether
prep-HPLC: preparative high performance liquid chromatography
rt: rt
RT: retention time
RuPhos Pd G2: chloro(2-dicyclohexylphosphino-2',6'-diisopropoxy-1,1'-biphenyl)[2-(2'-amino-1,1'-biphenyl)]palladium(II) 2nd generation
SFC: supercritical fluid chromatography
TFA: trifluoroacetic acid
v/v volume ratio

GENERAL EXPERIMENTAL CONDITIONS

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 µm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 µm, OBD™ 30×100 mm) column, SunFire™ Prep-C18 (5 µm, OBD™ 30×100 mm) column, Phenomenex Synergi-C18 (10 µm, 25×150 mm) or Phenomenex Gemini-C18 (10 µm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 µm, 30×250 mm), AS (10 µm, 30×250 mm) or AD (10 µm, 30×250 mm) using Mettler Toledo Multigram III system SFC, Waters 80Q preparative SFC or Thar 80 preparative SFC, solvent system: C02 and IPA (0.5% TEA in IPA) or C02 and MeOH (0.1% $NH_3.H_2O$ in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;

Acidic condition II: A: 0.0375% TFA in $H_2O$; B: 0.01875% TFA in acetonitrile;

Basic condition I: A: 0.1% $NH_3.H_2O$ in $H_2O$; B: acetonitrile;

Basic condition II: A: 0.025% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

PREPARATIVE EXAMPLES

The following examples are intended to illustrate the meaning of the present invention but should by no means represent a limitation within the meaning of the present invention:

Example 1

5-[(4R,10bS)-4-methyl-8-piperazin-1-yl-3,4,6,10b-tetrahydro-1H-pyrazino[2,1-a]isoindol-2-yl]quinoline-8-carbonitrile

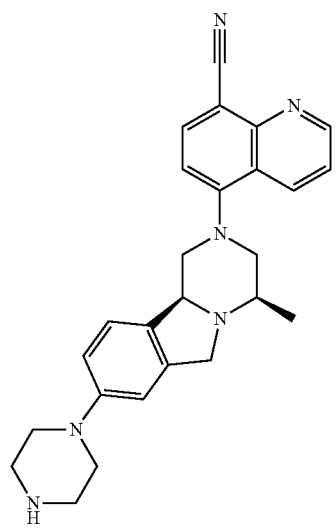 [SMILES: C[C@@H]1CN(c2ccc(C#N)c3ncccc23)C[C@@H]2c3ccc(N4CCNCC4)cc3CN12]

The title compound was prepared according to the following scheme:

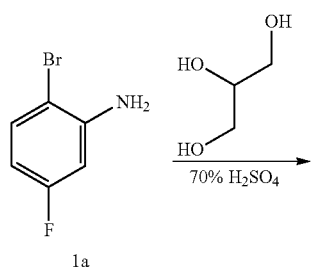

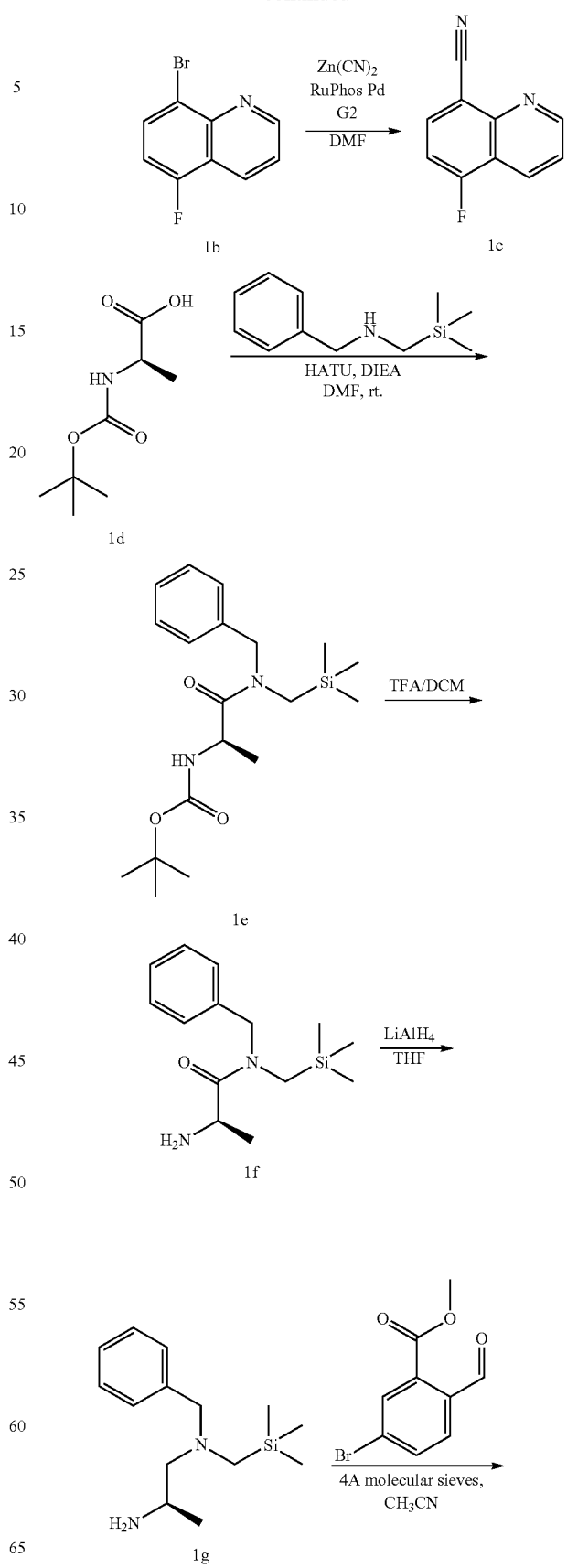

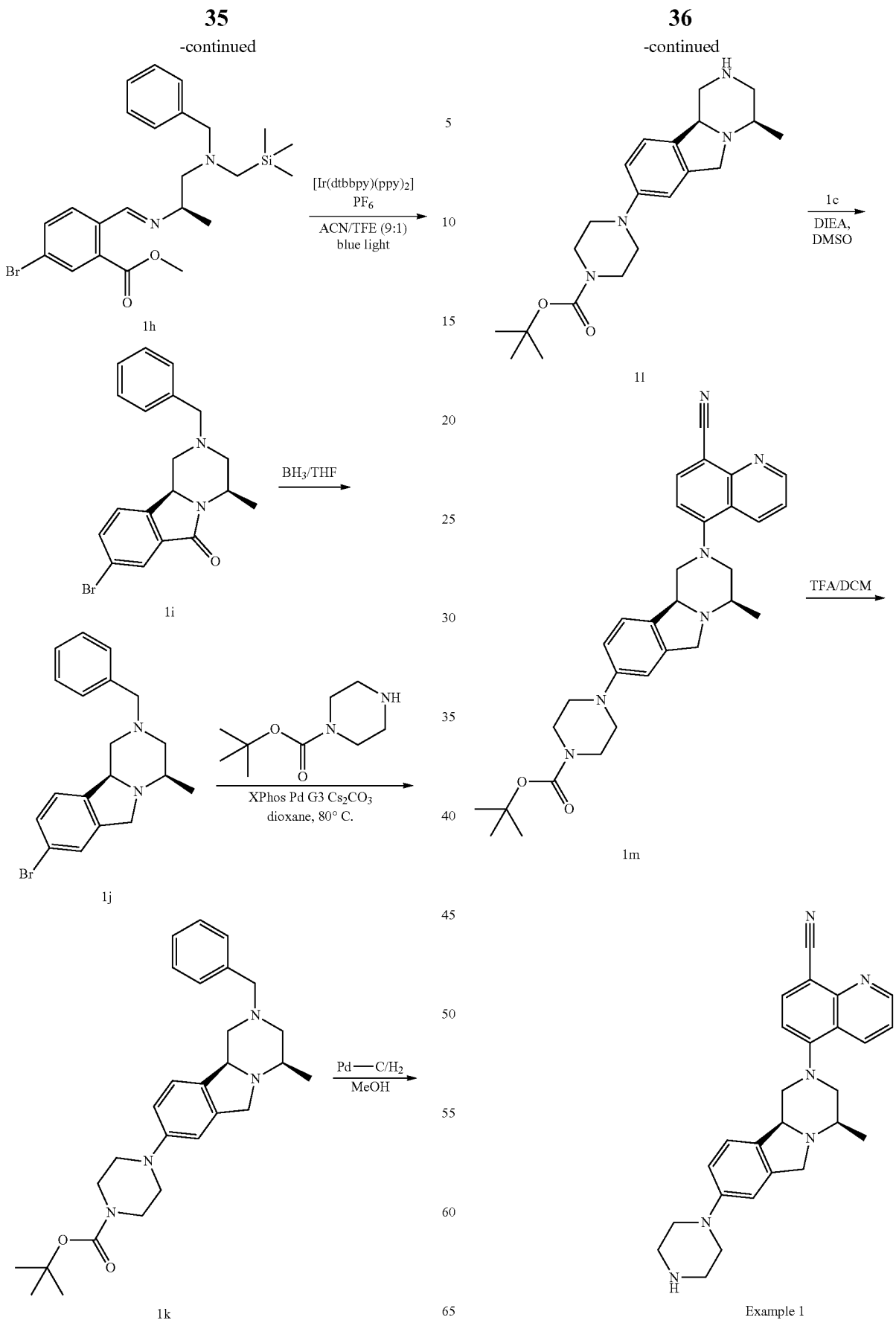

Step 1: Preparation of 8-bromo-5-fluoro-quinoline (Compound 1b)

In a 100 mL pear-shaped flask, 2-bromo-5-fluoroaniline (2.0 g, 10.5 mmol), propane-1,2,3-triol (969 mg, 10.5 mmol) and sodium 3-nitrobenzenesulfonate (2.4 g, 10.5 mmol) were combined with 70% $H_2SO_4$ (20 mL) to afford a dark brown solution, which was heated to 150° C. and stirred for 3 hrs. After cooled to room temperature, the reaction mixture was poured into ice-water, and neutralized with sodium hydroxide solution. The resultant mixture was filtered. The filter cake was dissolved in EtOAc and filtered. The resultant filtrate was concentrated in vacuo. The crude material was purified by flash chromatography (silica gel, 40 g, 0% to 30% EtOAc in PE) to afford compound 1b (2.0 g, 84% yield). MS: calc'd 226 and 228 [(M+H)$^+$], measured 226 and 228 [(M+H)$^+$].

Step 2: Preparation of 5-fluoroquinoline-8-carbonitrile (Compound 1c)

To a solution of 8-bromo-5-fluoroquinoline (compound 1b, 4.9 g, 21.7 mmol) in DMF (30 mL) was added dicyanozinc (5.0 g, 43.4 mmol) and RuPhos Pd G2 (CAS: 1375325-68-0, Sigma-Aldrich, Catalog: 753246, 842 mg, 1.1 mmol). The reaction mixture was stirred at 100° C. for 3 hrs, then cooled to room temperature. The reaction mixture was filtered and the filtrate was diluted with water (50 ml), then extracted with EA (80 mL) for three times. The combined organic layer was washed with brine, dried over $Na_2SO_4$, filtered and concentrated in vacuo. The residue was purified by flash chromatography (silica gel, 40 g, 0% to 70% EtOAc in PE) to afford compound 1c (3.0 g, 80% yield). MS: calc'd 173 [(M+H)$^+$], measured 173 [(M+H)$^+$]. $^1$H NMR (400 MHz, METHANOL-d$_4$) δ ppm 9.11 (dd, J=4.28, 1.71 Hz, 1H), 8.64 (dd, J=8.56, 1.71 Hz, 1H), 8.29 (dd, J=8.19, 5.62 Hz, 1H), 7.76 (dd, J=8.56, 4.28 Hz, 1H), 7.49 (dd, J=9.35, 8.25 Hz, 1H).

Step 3: Preparation of tert-butyl N-[(1R)-2-[benzyl(trimethylsilylmethyl)amino]-1-methyl-2-oxo-ethyl] carbamate (Compound 1e)

To a solution of (2R)-2-(tert-butoxycarbonylamino)propanoic acid (10.0 g, 52.9 mmol) in DMF (40 mL) was added N-benzyl-1-(trimethylsilyl)methanamine (10.2 g, 52.9 mmol), HATU (20.1 g, 52.9 mmol) and DIEA (13.6 g, 18.4 mL, 105.8 mmol). The reaction mixture was stirred at room temperature overnight. The reaction was quenched with water (150 mL), and extracted with DCM (100 mL) for three times. The combined organic layer was washed with brine, dried over $Na_2SO_4$, filtered and concentrated in vacuo. The residue was purified by flash chromatography (silica gel, 40 g, 0% to 30% EtOAc in PE) to afford compound 1e (13.1 g, 68% yield). MS: calc'd 365 [(M+H)$^+$], measured 365 [(M+H)$^+$].

Step 4: Preparation of (2R)-2-amino-N-benzyl-N-(trimethylsilylmethyl)-propanamide (Compound 1f)

To a solution of tert-butyl N-[(1R)-2-[benzyl(trimethylsilylmethyl)amino]-1-methyl-2-oxo-ethyl]carbamate (compound 1e, 13.0 g, 35.7 mmol) in DCM (60 mL) was added TFA (10 mL). The resultant mixture was stirred at room temperature for 4 hrs, then concentrated in vacuo, and the residue was partitioned between sat. NaHCO$_3$(aq.) and EA. The organic layer was separated and the basic aqueous layer was extracted with EA (80 mL) twice. The combined organic layer was dried over $Na_2SO_4$, filtered and concentrated in vacuo to afford compound 1f (9.1 g, 96% yield) without further purification. MS: calc'd 265 [(M+H)$^+$], measured 265 [(M+H)$^+$].

Step 5: Preparation of (2R)—N1-benzyl-N1-(trimethylsilylmethyl)propane-1,2-diamine (Compound 1g)

To an ice-cooled solution of (2R)-2-amino-N-benzyl-N-(trimethylsilylmethyl)-propanamide (compound 1f, 9.0 g, 34.0 mmol) in anhydrous THF (100 mL) was added LiAlH$_4$ (3.9 g, 102.0 mmol) slowly. After the addition was completed, the mixture was heated under reflux overnight, then cooled to room temperature and quenched with NaOH (10 mL, 20% aq. solution) before filtered and washed with EtOAc. The combined filtrate was concentrated in vacuo to afford compound 1g (5.7 g, 67% yield) without further purification. MS: calc'd 251 [(M+H)$^+$], measured 251 [(M+H)$^+$].

Step 6: Preparation of (4R,10bS)-2-benzyl-8-bromo-4-methyl-1,3,4,10b-tetrahydropyrazino[1,2-b]isoindol-6-one (Compound 1i)

A mixture of the (2R)—N1-benzyl-N1-(trimethylsilylmethyl)propane-1,2-diamine (compound 1g, 3.0 g, 12.0 mmol), methyl 5-bromo-2-formylbenzoate (2.9 g, 12.0 mmol), and 4 A MS (5.0 g) in MeCN (80 mL) under N$_2$ was stirred overnight at room temperature. The reaction mixture was filtered and the filter cake was washed with DCM. The filtrate was concentrated in vacuo and the residue was re-dissolved in MeCN/TFE (45 mL/5 mL), followed by the addition of [Ir(dtbbpy)(ppy)$_2$][PF$_6$](CAS: 676525-77-2, TCI, Catalog: D4887, 109 mg, 120 μmol). The reaction was stirred at room temperature under the exposure of blue LEDs (synLED-16 A Discover, 12 W, wavelength 465-470 nm, purchased from SYNLED corp.) for 2 days. After the solvents were removed in vacuo, the residue was purified by flash chromatography (silica gel, 80 g, 20% to 70% EA in PE) to afford compound 1i (1.8 g, 42% yield). The stereochemistry was confirmed by NOESY. MS: calc'd 371 and 373 [(M+H)$^+$], measured 371 and 373 [(M+H)$^+$]. $^1$H NMR (400 MHz, METHANOL-d$_4$) δ ppm 7.75 (d, J=1.71 Hz, 1H), 7.63 (dd, J=8.01, 1.77 Hz, 1H), 7.19-7.35 (m, 6H), 4.43 (dd, J=10.88, 3.67 Hz, 1H), 3.67-3.86 (m, 1H), 3.56 (s, 2H), 3.41-3.45 (m, 1H), 2.79-2.87 (m, 1H), 1.86 (t, J=11.07 Hz, 1H), 1.67 (d, J=6.97 Hz, 3H), 1.64 (t, J=11.07 Hz, 1H).

Step 7: Preparation of (4R,10bS)-2-benzyl-8-bromo-4-methyl-3,4,6,10b-tetrahydro-1H-pyrazino[2,1-a]isoindole (Compound 1j)

A mixture of (4R,10bS)-2-benzyl-8-bromo-4-methyl-1,3,4,10b-tetrahydropyrazino[1,2-b]isoindol-6-one (compound 1i, 1.9 g, 5.0 mmol) and BH$_3$ solution (1M in THF, 40 mL, 40 mmol) was stirred at 80° C. for 5 hrs. HCl solution (6 N, 10 mL) was added slowly to the reaction mixture at 0° C. The resultant mixture was stirred at room temperature overnight, then basified with a NaOH solution (2 N) to pH 10. The mixture was extracted with EtOAc twice, and the combined organic layer was dried over MgSO$_4$, filtered and concentrated in vacuo. The crude material was purified by flash chromatography (silica gel, 40 g, 30% to 100% EtOAc in PE) to afford compound 1j (1.5 g, 85% yield). MS: calc'd 357 and 359 [(M+H)$^+$], measured 357 and 359 [(M+H)$^+$]. $^1$H NMR (400 MHz, METHANOL-d$_4$) δ ppm 7.49 (s, 1H), 7.32-7.43 (m, 5H), 7.26-7.32 (m, 1H), 7.05 (d, J=7.95 Hz, 1H), 4.18 (d, J=12.59 Hz, 1H), 3.71 (br d, J=10.51 Hz, 1H), 3.55 (dd, J=12.47, 2.32 Hz, 1H), 3.36-3.31 (m, 1H), 2.97-2.89 (m, 1H), 2.77-2.87 (m, 1H), 2.12 (t, J=10.64 Hz, 1H), 2.00 (t, J=10.64 Hz, 1H), 1.14 (d, J=6.48 Hz, 3H).

Step 8: Preparation of tert-butyl 4-[(4R,10bS)-2-benzyl-4-methyl-3,4,6,10b-tetrahydro-1H-pyrazino[2,1-a]isoindol-8-yl]piperazine-1-carboxylate (Compound 1k)

To a solution of (4R,10bS)-2-benzyl-8-bromo-4-methyl-3,4,6,10b-tetrahydro-1H-pyrazino[2,1-a]isoindole (compound 1j, 0.4 g, 1.1 mmol) in dioxane (15 mL) was added tert-butyl piperazine-1-carboxylate (209 mg, 1.1 mmol), Cs$_2$CO$_3$ (365 mg, 1.1 mmol) and XPhos Pd G3 (CAS: 1445085-55-1, BePharm, Catalog: D449923, 94.8 mg, 0.1 mmol). The reaction mixture was stirred at 80° C. overnight, then cooled to room temperature, diluted with water (50 mL) and extracted with EA (50 mL) for three times. The combined organic layer was washed with brine, dried over Na$_2$SO$_4$, filtered and concentrated in vacuo. The residue was purified by flash chromatography (silica gel, 40 g, 0% to 100% EtOAc in PE) to afford compound 1k (420 mg, 81.1% yield). MS: calc'd 463 [(M+H)$^+$], measured 463 [(M+H)$^+$].

Step 9: Preparation of tert-butyl 4-[(4R,10bS)-4-methyl-1,2,3,4,6,10b-hexahydropyrazino[2,1-a]isoindol-8-yl]piperazine-1-carboxylate (Compound 1l)

A mixture of tert-butyl 4-[(4R,10bS)-2-benzyl-4-methyl-3,4,6,10b-tetrahydro-1H-pyrazino[2,1-a]isoindol-8-yl]piperazine-1-carboxylate (compound 1k, 240 mg, 519 μmol) and Pd—C (16.6 mg, 156 μmol) in MeOH (20 mL) was hydrogenated with a hydrogen balloon at room temperature for 5 hrs. After the catalyst was filtered off, the filtrate was concentrated in vacuo to afford compound 1l (181 mg, 94% yield) which was used directly for the next step without further purification. MS: calc'd 373 [(M+H)$^+$], measured 373 [(M+H)$^+$].

Step 10: Preparation of tert-butyl 4-[(4R,10bS)-2-(8-cyano-5-quinolyl)-4-methyl-3,4,6,10b-tetrahydro-1H-pyrazino[2,1-a]isoindol-8-yl]piperazine-1-carboxylate (Compound 1m)

To a solution of 5-fluoroquinoline-8-carbonitrile (compound 1c, 20.1 mg, 112 μmol) in DMSO (3 mL) was added tert-butyl 4-[(4R,10bS)-4-methyl-1,2,3,4,6,10b-hexahydropyrazino[2,1-a]isoindol-8-yl]piperazine-1-carboxylate (compound 1l, 42 mg, 112 μmol) and DIEA (73 mg, 560 μmol). The reaction mixture was stirred at 120° C. for 5 hrs. After cooled to room temperature, the reaction was quenched with water (30 mL) and extracted with EA (50 mL) twice. The combined organic layer was washed with brine, dried over Na$_2$SO$_4$, filtered and concentrated in vacuo. The residue was purified by flash chromatography (silica gel, 24 g, 0% to 100% EtOAc in PE) to afford compound 1m (41 mg, 68% yield). MS: calc'd 525 [(M+H)$^+$], measured 525 [(M+H)$^+$].

Step 11: Preparation of 5-[(4R,10bS)-4-methyl-8-piperazin-1-yl-3,4,6,10b-tetrahydro-1H-pyrazino[2,1-a]isoindol-2-yl]quinoline-8-carbonitrile (Example 1)

To a solution of tert-butyl 4-[(4R,10bS)-2-(8-cyano-5-quinolyl)-4-methyl-3,4,6,10b-tetrahydro-1H-pyrazino[2,1-a]isoindol-8-yl]piperazine-1-carboxylate (compound 1m, 100 mg) in DCM (10 mL) was added TFA (2 mL). The reaction mixture was stirred at room temperature for 30 min, then concentrated to afford a crude product, which was purified by prep-HPLC to afford Example 1 (33 mg, 77%). MS: calc'd 425 [(M+H)$^+$], measured 425 [(M+H)$^+$]. $^1$H NMR (400 MHz, METHANOL-d$_4$) δ ppm 9.02 (dd, J=4.22, 1.53 Hz, 1H), 8.73 (dd, J=8.56, 1.59 Hz, 1H), 8.18 (d, J=8.07 Hz, 1H), 7.71 (dd, J=8.56, 4.28 Hz, 1H), 7.35 (d, J=8.07 Hz, 1H), 7.14 (d, J=8.31 Hz, 1H), 7.06 (s, 1H), 6.88 (dd, J=8.25, 2.02 Hz, 1H), 4.29 (d, J=12.10 Hz, 1H), 4.10 (br d, J=10.51 Hz, 1H), 3.89 (br d, J=11.49 Hz, 1H), 3.70 (br d, J=11.86 Hz, 1H), 3.46 (br d, J=11.74 Hz, 1H), 3.34-3.38 (m, 1H), 3.07-3.19 (m, 4H), 2.94-3.05 (m, 5H), 2.73-2.92 (m, 1H), 1.28 (d, J=6.48 Hz, 3H).

Example 2

5-[(4S,10bR)-4-methyl-8-piperazin-1-yl-3,4,6,10b-tetrahydro-1H-pyrazino[2,1-a]isoindol-2-yl]quinoline-8-carbonitrile

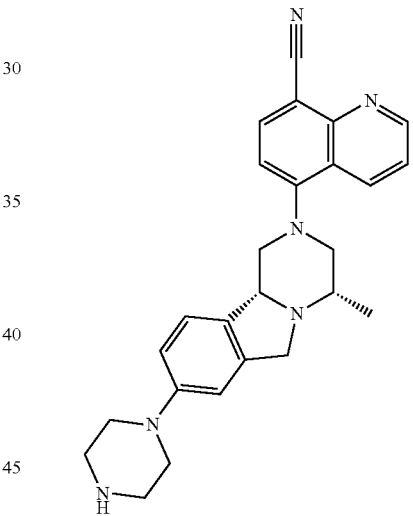

The title compound was prepared in analogy to the preparation of Example 1 by using (2S)-2-(tert-butoxycarbonylamino)propanoic acid instead of (2R)-2-(tert-butoxycarbonylamino)propanoic acid (compound 1d). Example 2 (12 mg) was obtained. MS: calc'd 425 [(M+H)$^+$], measured 425 [(M+H)$^+$]. $^1$H NMR (400 MHz, METHANOL-d$_4$) δ ppm 9.02 (dd, J=4.28, 1.59 Hz, 1H), 8.72 (dd, J=8.56, 1.47 Hz, 1H), 8.19 (d, J=7.95 Hz, 1H), 7.72 (dd, J=8.56, 4.28 Hz, 1H), 7.35 (d, J=8.07 Hz, 1H), 7.14 (d, J=8.31 Hz, 1H), 7.05 (s, 1H), 6.87 (dd, J=8.31, 1.96 Hz, 1H), 4.23-4.25 (m, 1H), 4.28 (d, J=12.10 Hz, 1H), 4.09 (br d, J=10.51 Hz, 1H), 3.88 (br d, J=11.37 Hz, 1H), 3.70 (br d, J=11.98 Hz, 1H), 3.45 (br d, J=11.25 Hz, 1H), 3.34-3.38 (m, 1H), 3.07-3.18 (m, 4H), 2.96-3.06 (m, 5H), 2.79-2.91 (m, 1H), 1.28 (d, J=6.36 Hz, 3H).

Example 3

5-(8-piperazin-1-yl-3,4,6,10b-tetrahydro-1H-pyrazino[2,1-a]isoindol-2-yl)quinoline-8-carbonitrile

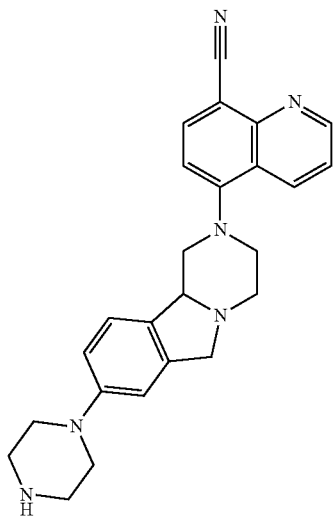 [SMILES: N#Cc1ccc(N2CCN3Cc4cc(N5CCNCC5)ccc4C3C2)c2cccnc12]

The title compound was prepared in analogy to the preparation of Example 1 by using 2-(tert-butoxycarbonylamino)acetic acid instead of (2R)-2-(tert-butoxycarbonylamino)-propanoic acid (compound 1d). Example 3 (19.7 mg) was obtained. MS: calc'd 411 [(M+H)$^+$], measured 411 [(M+H)$^+$]. $^1$H NMR (400 MHz, METHANOL-d$_4$) δ ppm 9.05 (dd, J=4.28, 1.59 Hz, 1H), 8.71 (dd, J=8.62, 1.53 Hz, 1H), 8.21 (d, J=8.07 Hz, 1H), 7.72 (dd, J=8.68, 4.28 Hz, 1H), 7.42 (dd, J=8.25, 4.71 Hz, 2H), 7.23 (s, 1H), 7.13 (dd, J=8.44, 2.08 Hz, 1H), 5.31 (dd, J=8.50, 4.46 Hz, 1H), 4.91-4.96 (m, 1H), 4.76-4.84 (m, 1H), 3.95-4.06 (m, 1H), 3.87 (br d, J=15.41 Hz, 1H), 3.78 (br d, J=13.33 Hz, 1H), 3.37-3.64 (m, 11H).

Example 4

7-(8-piperazin-1-yl-3,4,6,10b-tetrahydro-1H-pyrazino[2,1-a]isoindol-2-yl)-1,3-benzothiazole-4-carbonitrile

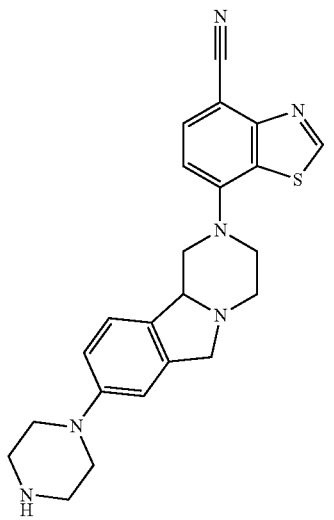 [SMILES: N#Cc1ccc(N2CCN3Cc4cc(N5CCNCC5)ccc4C3C2)c2scnc12]

The title compound was prepared in analogy to the preparation of Example 3 by using 7-fluoro-1,3-benzothiazole-4-carbonitrile instead of 5-fluoroquinoline-8-carbonitrile (compound 1c). Example 4 (15 mg) was obtained. MS: calc'd 417 [(M+H)$^+$], measured 417 [(M+H)$^+$]. $^1$H NMR (400 MHz, METHANOL-d$_4$) δ ppm 9.46 (s, 1H), 7.95 (d, J=8.19 Hz, 1H), 7.45 (d, J=8.44 Hz, 1H), 7.26 (d, J=8.19 Hz, 1H), 7.21 (s, 1H), 7.13 (dd, J=8.44, 2.20 Hz, 1H), 5.19 (br s, 1H), 4.81 (s, 2H), 4.00-4.10 (m, 1H), 3.76-3.92 (m, 1H), 3.55-3.65 (m, 2H), 3.45-3.53 (m, 5H), 3.37-3.44 (m, 5H).

Example 5

4-[(4R,10bS)-4-methyl-8-piperazin-1-yl-3,4,6,10b-tetrahydro-1H-pyrazino[2,1-a]isoindol-2-yl]pyrazolo[1,5-a]pyridine-7-carbonitrile

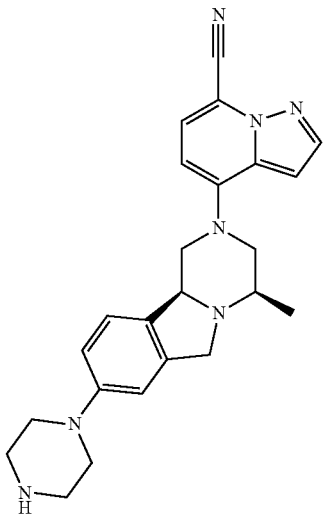 [SMILES: C[C@@H]1CN(c2ccc(C#N)n3nccc23)C[C@@H]2c3ccc(N4CCNCC4)cc3CN12]

The title compound was prepared according to the following scheme:

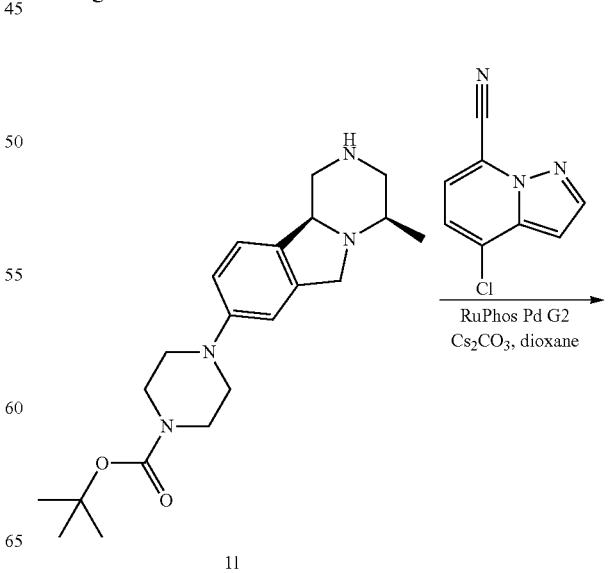

-continued

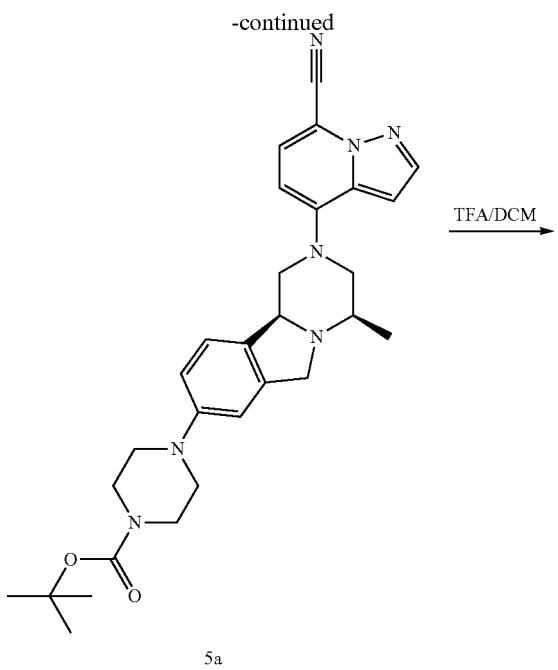

5a compound 5a (15 mg, 26% yield). MS: calc'd 514 [(M+H)+], measured 514 [(M+H)+].

Step 2: Preparation of 4-[(4R,10bS)-4-methyl-8-piperazin-1-yl-3,4,6,10b-tetrahydro-1H-pyrazino[2,1-a]isoindol-2-yl]pyrazolo[1,5-a]pyridine-7-carbonitrile (Example 5)

To a solution of tert-butyl 4-[(4R,10bS)-2-(7-cyanopyrazolo[1,5-a]pyridin-4-yl)-4-methyl-3,4,6,10b-tetrahydro-1H-pyrazino[2,1-a]isoindol-8-yl]piperazine-1-carboxylate (compound 5a, 15 mg, 29.2 μmol) in DCM (3 mL) was added TFA (1 mL). The reaction was stirred at room temperature for 30 min, then concentrated to afford a crude product, which was purified by prep-HPLC to afford Example 5 (3.3 mg, 27% yield). MS: calc'd 414 [(M+H)+], measured 414 [(M+H)+]. $^1$H NMR (400 MHz, METHANOL-$d_4$) δ ppm 7.96 (d, J=2.32 Hz, 1H), 7.39 (d, J=8.07 Hz, 1H), 7.09 (d, J=8.31 Hz, 1H), 6.94 (s, 1H), 6.83 (d, J=2.45 Hz, 1H), 6.79 (dd, J=8.31, 2.08 Hz, 1H), 6.59 (d, J=8.07 Hz, 1H), 4.08-4.24 (m, 2H), 3.67-3.88 (m, 2H), 3.55 (br d, J=13.33 Hz, 1H), 2.97-3.13 (m, 5H), 2.85-2.96 (m, 5H), 2.73 (dd, J=12.35, 10.51 Hz, 1H), 1.18 (d, J=6.48 Hz, 3H).

Example 6

7-[(4R,10bS)-4-methyl-8-piperazin-1-yl-3,4,6,10b-tetrahydro-1H-pyrazino[2,1-a]isoindol-2-yl]-1,3-benzothiazole-4-carbonitrile Example 5

Step 1: Preparation of tert-butyl 4-[(4R,10bS)-2-(7-cyanopyrazolo[1,5-a]pyridin-4-yl)-4-methyl-3,4,6,10b-tetrahydro-1H-pyrazino[2,1-a]isoindol-8-yl]piperazine-1-carboxylate (Compound 5a)

To a solution of tert-butyl 4-[(4R,10bS)-4-methyl-1,2,3,4,6,10b-hexahydropyrazino[2,1-a]isoindol-8-yl]piperazine-1-carboxylate (compound 11, 42.0 mg, 113 μmol) in dioxane (5 mL) was added 4-chloropyrazolo[1,5-a]pyridine-7-carbonitrile (20 mg, 113 μmol), RuPhos Pd G2 (CAS: 1375325-68-0, Sigma-Aldrich, Catalog: 753246; 8.7 mg, 11.3 μmol) and $Cs_2CO_3$ (110 mg, 338 μmol). The reaction mixture was stirred at 90° C. for 20 hrs, then cooled to room temperature, diluted with water (20 mL), and extracted with EA (30 mL) for three times. The combined organic layer was washed with brine, dried over $Na_2SO_4$, filtered and concentrated in vacuo. The residue was purified by flash chromatography (silica gel, 24 g, 0% to 100% EtOAc in PE) to afford The title compound was prepared in analogy to the preparation of Example 1 by using 7-fluoro-1,3-benzothiazole-4-carbonitrile instead of 5-fluoroquinoline-8-carbonitrile (compound 1c). Example 6 (15 mg) was obtained. MS: calc'd 431 [(M+H)+], measured 431 [(M+H)+]. $^1$H NMR (400 MHz, METHANOL-$d_4$) δ ppm 9.44 (s, 1H), 7.92 (d, J=8.31 Hz, 1H), 7.21 (d, J=8.31 Hz, 1H), 7.18 (d, J=8.19 Hz, 1H), 7.05 (d, J=1.47 Hz, 1H), 6.90 (dd, J=8.31, 2.08 Hz, 1H), 4.28 (d, J=12.35 Hz, 1H), 4.22 (br d, J=11.13 Hz, 1H), 3.90 (br d, J=10.39 Hz, 1H), 3.79 (br d, J=11.74 Hz, 1H), 3.67 (br d, J=12.10 Hz, 1H), 3.10-3.21 (m, 5H), 2.94-3.07 (m, 5H), 2.83-2.92 (m, 1H), 1.30 (d, J=6.24 Hz, 3H).

Example 7

8-[(4R,10bS)-4-methyl-8-piperazin-1-yl-3,4,6,10b-tetrahydro-1H-pyrazino[2,1-a]isoindol-2-yl]quinoxaline-5-carbonitrile

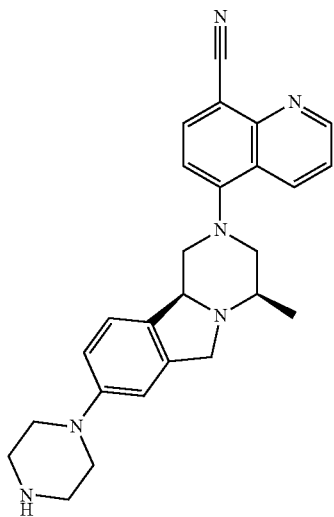

The title compound was prepared in analogy to the preparation of Example 5 by using 8-bromoquinoxaline-5-carbonitrile instead of 4-chloropyrazolo[1,5-a]pyridine-7-carbonitrile. Example 7 (3.3 mg) was obtained. MS: calc'd 426 [(M+H)⁺], measured 426 [(M+H)⁺]. ¹H NMR (400 MHz, METHANOL-d₄) δ ppm 8.85 (dd, J=11.25, 1.71 Hz, 2H), 8.04 (d, J=8.31 Hz, 1H), 7.21 (d, J=8.31 Hz, 1H), 7.06 (d, J=8.07 Hz, 1H), 6.94 (s, 1H), 6.78 (dd, J=8.25, 2.02 Hz, 1H), 4.58 (br d, J=11.13 Hz, 1H), 4.10-4.21 (m, 2H), 3.90 (br d, J=10.88 Hz, 1H), 3.55 (br d, J=12.72 Hz, 1H), 3.13-3.18 (m, 1H), 3.02-3.06 (m, 4H), 2.98 (t, J=11.07 Hz, 1H), 2.88-2.93 (m, 4H), 2.78-2.86 (m, 1H), 1.17 (d, J=6.48 Hz, 3H).

Example 8

5-[(4R,10bS)-4-methyl-7-piperazin-1-yl-3,4,6,10b-tetrahydro-1H-pyrazino[2,1-a]isoindol-2-yl]quinoline-8-carbonitrile

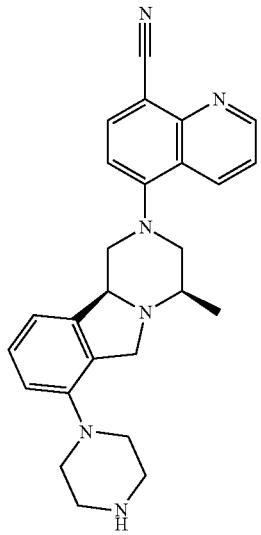 [SMILES: C[C@@H]1CN(c2ccc(C#N)c3ncccc23)C[C@@H]2c3cccc(N4CCNCC4)c3CN12]

The title compound was prepared in analogy to the preparation of Example 1 by using methyl 2-bromo-6-formyl-benzoate instead of 5-bromo-2-formylbenzoate. Example 8 (19.6 mg) was obtained. MS: calc'd 425 [(M+H)⁺], measured 425 [(M+H)⁺]. ¹H NMR (400 MHz, METHANOL-d₄) δ ppm 9.02 (dd, J=4.28, 1.59 Hz, 1H), 8.74 (dd, J=8.56, 1.59 Hz, 1H), 8.19 (d, J=7.95 Hz, 1H), 7.71 (dd, J=8.56, 4.28 Hz, 1H), 7.36 (d, J=8.07 Hz, 1H), 7.23 (t, J=7.70 Hz, 1H), 6.91 (d, J=7.70 Hz, 2H), 4.31 (d, J=11.98 Hz, 1H), 4.15 (br d, J=10.27 Hz, 1H), 3.93 (br d, J 20=10.76 Hz, 1H), 3.69 (dd, J=11.98, 2.20 Hz, 1H), 3.42-3.53 (m, 1H), 3.35-3.38 (m, 1H), 2.90-3.13 (m, 9H), 2.85 (dd, J=11.86, 10.27 Hz, 1H), 1.30 (d, J=6.36 Hz, 4H).

Example 9

5-[(4R,10bS)-4-methyl-8-(4-piperidyl)-3,4,6,10b-tetrahydro-1H-pyrazino[2,1-a]isoindol-2-yl]quinoline-8-carbonitrile

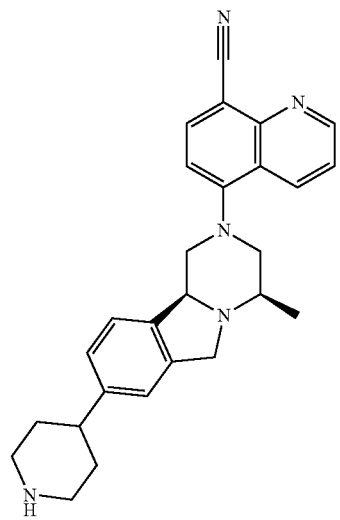 [SMILES: C[C@@H]1CN(c2ccc(C#N)c3ncccc23)C[C@@H]2c3ccc(C4CCNCC4)cc3CN12]

The title compound was prepared according to the following scheme:

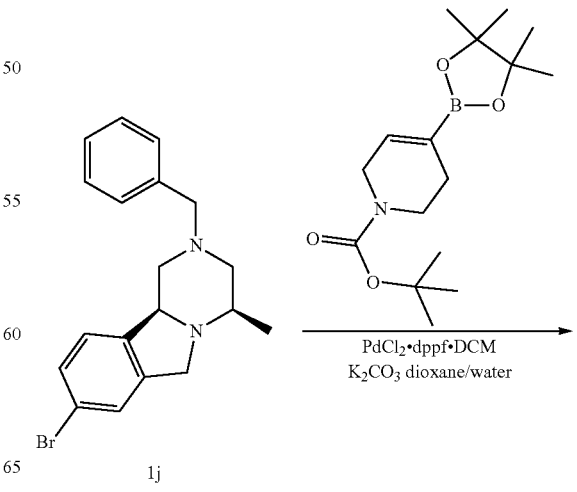

-continued

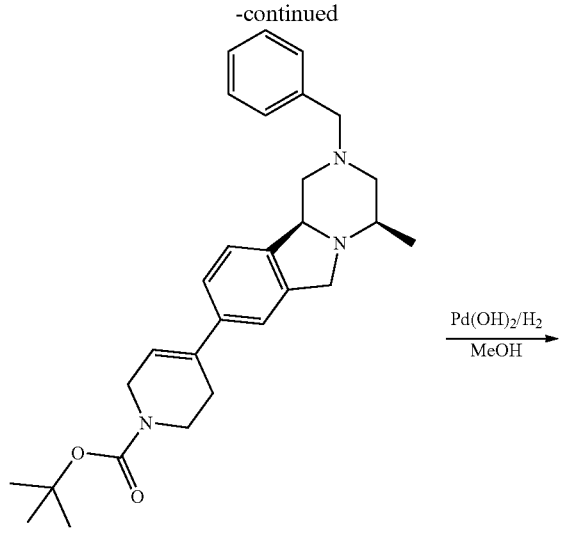

9a

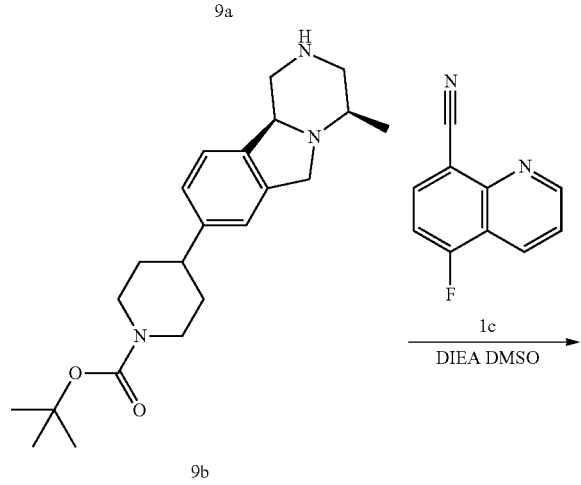

9b

9c

-continued

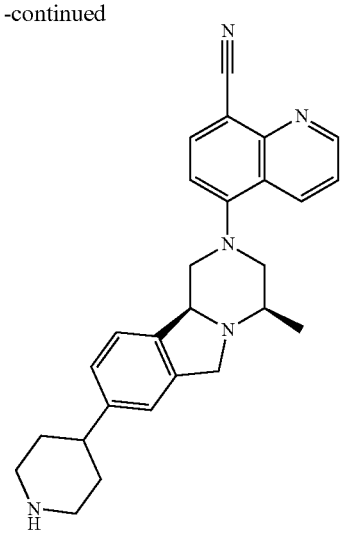

Example 9

Step 1: Preparation of tert-butyl 4-[(4R,10bS)-2-benzyl-4-methyl-3,4,6,10b-tetrahydro-1H-pyrazino[2,1-a]isoindol-8-yl]-3,6-dihydro-2H-pyridine-1-carboxylate (Compound 9a)

To a 10 mL microwave vial was added tert-butyl 4-(4,4,5,5-tetramethyl-1,3,2-dioxaborolan-2-yl)-3,6-dihydro-2H-pyridine-1-carboxylate (130 mg, 420 μmol), (4R,10bS)-2-benzyl-8-bromo-4-methyl-3,4,6,10b-tetrahydro-1H-pyrazino[2,1-a]isoindole (compound 1j, 100 mg, 280 μmol), PdCl$_2$(dppf).DCM adduct (20.5 mg, 28 μmol), and K$_2$CO$_3$ (77.4 mg, 560 μmol) in dioxane (4 mL) and water (0.4 mL). The reaction mixture was heated in the microwave at 100° C. for 30 min, then cooled to room temperature, diluted with water (50 mL) and extracted with DCM (30 mL) for three times. The combined organic layer was washed with brine, dried over Na$_2$SO$_4$, filtered and concentrated in vacuo. The residue was purified by flash chromatography (silica gel, 40 g, 0% to 30% EtOAc in PE) to afford compound 9a (83 mg, 64% yield). MS: calc'd 460 [(M+H)$^+$], measured 460 [(M+H)$^+$].

Step 2: Preparation of tert-butyl 4-[(4R,10bS)-4-methyl-1,2,3,4,6,10b-hexahydropyrazino[2,1-a]isoindol-8-yl]piperidine-1-carboxylate (Compound 9b)

A mixture of tert-butyl 4-[(4R,10bS)-2-benzyl-4-methyl-3,4,6,10b-tetrahydro-1H-pyrazino[2,1-a]isoindol-8-yl]-3,6-dihydro-2H-pyridine-1-carboxylate (compound 9a, 83 mg, 180 μmol) and Pd(OH)$_2$ (10 mg) in MeOH (20 mL) was hydrogenated with a hydrogen balloon at room temperature for 30 min. After the catalyst was filtered off, the filtrate was concentrated in vacuo to afford compound 9b (62 mg, 75% yield) which was directly used for the next step without further purification. MS: calc'd 372 [(M+H)$^+$], measured 372 [(M+H)$^+$].

Step 3: Preparation of tert-butyl 4-[(4R,10bS)-2-(8-cyano-5-quinolyl)-4-methyl-3,4,6,10b-tetrahydro-1H-pyrazino[2,1-a]isoindol-8-yl]piperidine-1-carboxylate (Compound 9c)

To a solution of 5-fluoroquinoline-8-carbonitrile (compound 1c, 19 mg, 113 μmol) in DMSO (2 mL) was added tert-butyl 4-((4R,10bS)-4-methyl-1,2,3,4,6,10b-hexahydropyrazino[2,1-a]isoindol-8-yl)piperidine-1-carboxylate (compound 9b, 42 mg, 113 μmol) and DIEA (73 mg, 565 μmol). The reaction mixture was stirred at 120° C. for 5 hrs, then cooled to room temperature, diluted with water (10 mL), and extracted with EA (15 mL) twice. The combined organic layer was washed with brine, dried over Na₂SO₄, filtered and concentrated in vacuo. The residue was purified by flash chromatography (silica gel, 24 g, 0% to 100% EtOAc in PE) to afford compound 9c (40 mg, 68% yield). MS: calc'd 524 [(M+H)⁺], measured 524 [(M+H)⁺].

Step 4: Preparation of 5-[(4R,10bS)-4-methyl-8-(4-piperidyl)-3,4,6,10b-tetrahydro-1H-pyrazino[2,1-a]isoindol-2-yl]quinoline-8-carbonitrile (Example 9)

To a solution of tert-butyl 4-((4R,10bS)-2-(8-cyanoquinolin-5-yl)-4-methyl-1,2,3,4,6,10b-hexahydropyrazino[2,1-a]isoindol-8-yl)piperidine-1-carboxylate (compound 9c, 40 mg, 76.4 μmol) in DCM (3 mL) was added TFA (1 mL). The reaction was stirred at room temperature for 30 min, then concentrated to afford a crude product, which was purified by prep-HPLC to afford Example 9 (12 mg, 38% yield). MS: calc'd 424 [(M+H)⁺], measured 424 [(M+H)⁺]. ¹H NMR (400 MHz, METHANOL-d₄) δ ppm 9.07 (dd, J=4.22, 1.65 Hz, 1H), 8.81 (dd, J=8.62, 1.53 Hz, 1H), 8.22 (d, J=7.95 Hz, 1H), 7.76 (dd, J=8.56, 4.28 Hz, 1H), 7.47-7.53 (m, 2H), 7.35-7.45 (m, 2H), 5.34-5.38 (m, 1H), 4.98 (br d, J=13.69 Hz, 1H), 4.68 (br d, J=13.94 Hz, 1H), 4.33 (br s, 1H), 3.85-4.15 (m, 1H), 3.65-3.72 (m, 1H), 3.54 (br d, J=12.72 Hz, 2H), 3.12-3.24 (m, 3H), 2.96-3.09 (m, 1H), 1.87-2.15 (m, 5H), 1.56 (d, J=6.72 Hz, 3H).

Example 10

5-[(4R,10bS)-8-[(2R)-2-(hydroxymethyl)piperazin-1-yl]-4-methyl-3,4,6,10b-tetrahydro-1H-pyrazino[2,1-a]isoindol-2-yl]quinoline-8-carbonitrile The title compound was prepared according to the following scheme:

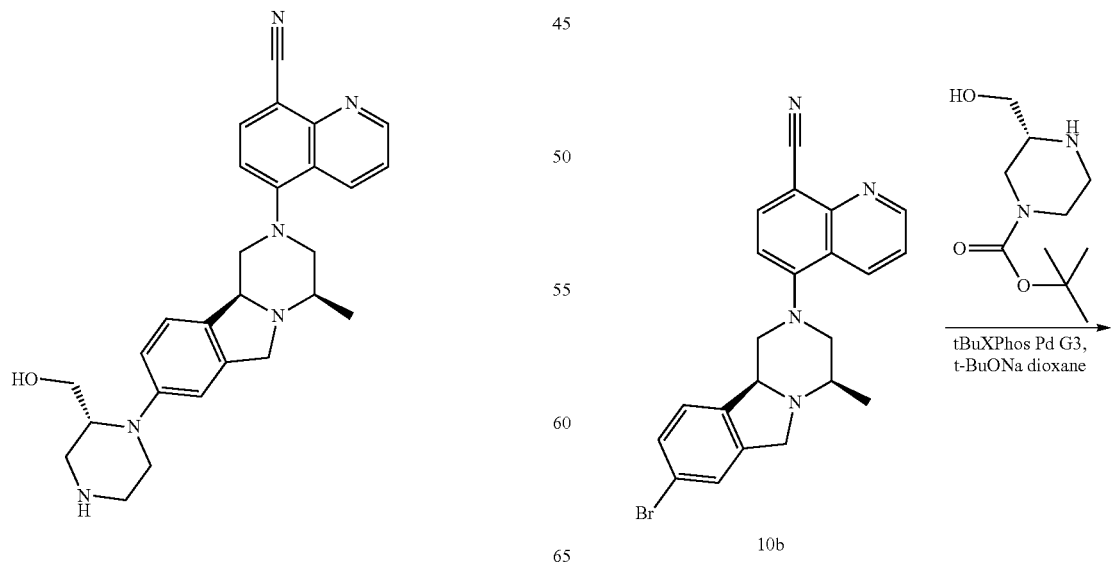

-continued

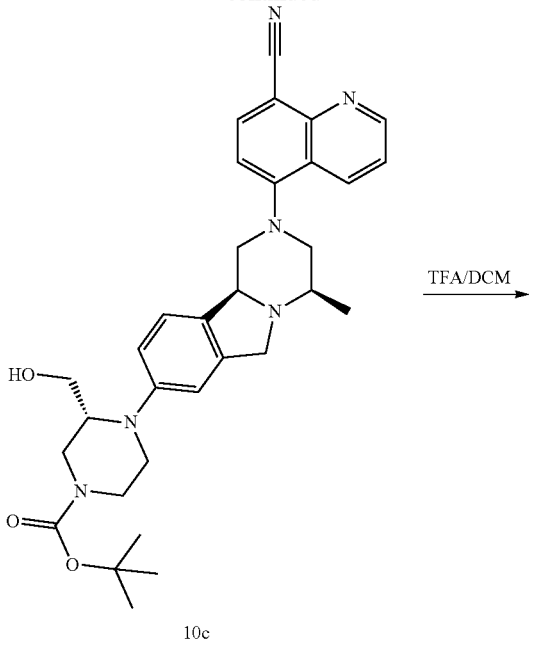

10c

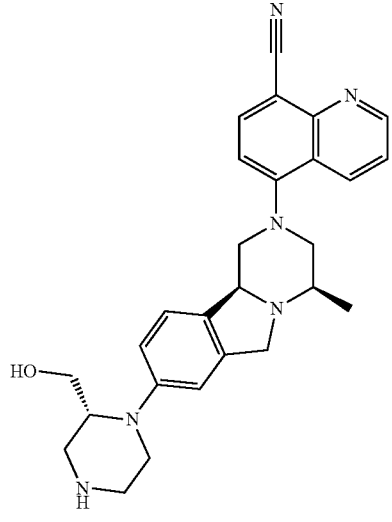

Example 10

Step 1: Preparation of (4R,10bS)-8-bromo-4-methyl-1,2,3,4,6,10b-hexahydropyrazino[2,1-a]isoindole (Compound 10a)

To a stirred solution of (4R,10bS)-2-benzyl-8-bromo-4-methyl-3,4,6,10b-tetrahydro-1H-pyrazino[2,1-a]isoindole (compound 1j, 900 mg, 2.4 mmol) in DCE (30 mL) at room temperature was added 1-chloroethyl carbonochloridate (1.7 g, 12.1 mmol). The reaction mixture was heated under reflux overnight and cooled to room temperature before concentrated in vacuo. The residue was dissolved in MeOH (20 mL) and heated under reflux for additional 2 hrs, then cooled to room temperature and concentrated in vacuo. The residue was diluted with water (10 mL), basified with aq. NaHCO$_3$, and extracted with EtOAc twice. The combined organic layer was washed with brine, dried over Na$_2$SO$_4$, filtered and concentrated in vacuo to afford compound 10a (660 mg, 98% yield), which used directly to the next step. MS: calc'd 267 and 269 [(M+H)$^+$], measured 267 and 269 [(M+H)$^+$].

Step 2: Preparation of 5-[(4R,10bS)-8-bromo-4-methyl-3,4,6,10b-tetrahydro-1H-pyrazino[2,1-a]isoindol-2-yl]quinoline-8-carbonitrile (compound 10b)

To a solution of 5-fluoroquinoline-8-carbonitrile (compound 1c, 258 mg, 1.5 mmol) in DMSO (10 mL) was added (4R,10bS)-8-bromo-4-methyl-1,2,3,4,6,10b-hexahydropyrazino[2,1-a]isoindole (compound 10a, 400 mg, 1.5 mmol) and DIEA (1.3 mL, 7.5 mmol). The reaction mixture was stirred at 120° C. for 5 hrs, then cooled to room temperature, quenched with water (50 mL), and extracted with EA (80 mL) twice. The combined organic layer was washed with brine, dried over Na$_2$SO$_4$, filtered and concentrated in vacuo. The residue was purified by flash chromatography to afford compound 10b (450 mg, 72% yield). MS: calc'd 419 and 421 [(M+H)$^+$], measured 419 and 421 [(M+H)$^+$].

Step 3: Preparation of tert-butyl (3R)-4-[(4R,10bS)-2-(8-cyano-5-quinolyl)-4-methyl-3,4,6,10b-tetrahydro-1H-pyrazino[2,1-a]isoindol-8-yl]-3-(hydroxymethyl)-piperazine-1-carboxylate (Compound 10c)

To a solution of 5-[(4R,10bS)-8-bromo-4-methyl-3,4,6,10b-tetrahydro-1H-pyrazino[2,1-a]isoindol-2-yl]quinoline-8-carbonitrile (compound 10b, 70 mg, 167 µmol) in dioxane (10 mL) was added tert-butyl (3R)-3-(hydroxymethyl)piperazine-1-carboxylate (CAS: 278788-66-2, Accela ChemBio, Catalog: SY017685, 43.2 mg, 200 µmol), t-BuONa (32.1 mg, 334 µmol) and tBuXPhos Pd G3 (CAS: 1447963-75-8, Sigma-Aldrich, Catalog: 762229, 13.3 mg, 16.7 µmol). The reaction mixture was stirred at 90° C. overnight, then cooled to room temperature, diluted with water (50 mL) and extracted with EA (30 mL) for three times. The combined organic layer was washed with brine, dried over Na$_2$SO$_4$, filtered and concentrated in vacuo. The residue was purified by flash chromatography (silica gel, 40 g, 30% to 100% EtOAc in PE) to afford compound 10c (21 mg, 23% yield). MS: calc'd 555 [(M+H)$^+$], measured 555 [(M+H)$^+$].

Step 4: Preparation of 5-[(4R,10bS)-8-[(2R)-2-(hydroxymethyl)piperazin-1-yl]-4-methyl-3,4,6,10b-tetrahydro-1H-pyrazino[2,1-a]isoindol-2-yl]quinoline-8-carbonitrile (Example 10)

To a solution of tert-butyl (3R)-4-[(4R,10bS)-2-(8-cyano-5-quinolyl)-4-methyl-3,4,6,10b-tetrahydro-1H-pyrazino[2,1-a]isoindol-8-yl]-3-(hydroxymethyl)-piperazine-1-carboxylate (compound 10c, 21 mg, 38 µmol) in DCM (2 mL) was added TFA (1 mL). The reaction mixture was stirred at room temperature for 30 min, then concentrated to afford a crude product, which was purified by prep-HPLC to afford Example 10 (8 mg, 46% yield). MS: calc'd 455 [(M+H)$^+$], measured 455 [(M+H)$^+$]. $^1$H NMR (400 MHz, METHANOL-d$_4$) δ ppm 9.01 (dd, J=4.16, 1.47 Hz, 1H), 8.73 (dd, J=8.62, 1.53 Hz, 1H), 8.19 (d, J=7.95 Hz, 1H), 7.73 (dd, J=8.56, 4.28 Hz, 1H), 7.35 (d, J=8.07 Hz, 1H), 7.14 (d, J=8.19 Hz, 1H), 7.07 (s, 1H), 6.90 (br d, J=8.19 Hz, 1H), 4.28 (d, J=12.23 Hz, 1H), 4.09 (br d, J=10.51 Hz, 1H), 3.87 (br d, J=10.76 Hz, 1H), 3.61-3.78 (m, 3H), 3.41-3.49 (m, 2H), 3.14-3.25 (m, 2H), 2.97-3.13 (m, 5H), 2.80-2.93 (m, 2H), 1.28 (d, J=6.36 Hz, 3H).

Example 11

5-[(4R,10S)-8-[(2S)-2-(hydroxymethyl)piperazin-1-yl]-4-methyl-3,4,6,10b-tetrahydro-1H-pyrazino[2,1-a]isoindol-2-yl]quinoline-8-carbonitrile

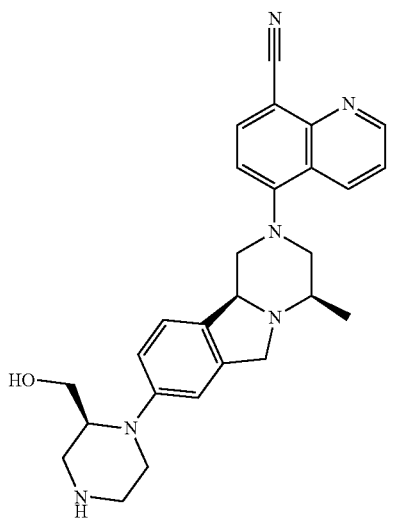 [SMILES: C[C@@H]1CN(c2ccc(C#N)c3ncccc23)C[C@@H]2c3ccc(N4CCNC[C@H]4CO)cc3CN12]

The title compound was prepared in analogy to the preparation of Example 10 by using tert-butyl (3S)-3-(hydroxymethyl)piperazine-1-carboxylate (CAS: 314741-40-7, Accela ChemBio, Catalog: SY020478) instead of tert-butyl (3R)-3-(hydroxymethyl)piperazine-1-carboxylate. Example 11 (24 mg) was obtained. MS: calc'd 455 [(M+H)$^+$], measured 455 [(M+H)$^+$]. $^1$H NMR (400 MHz, METHANOL-d$_4$) δ ppm 9.02 (dd, J=4.16, 1.47 Hz, 1H), 8.73 (dd, J=8.62, 1.53 Hz, 1H), 8.19 (d, J=7.95 Hz, 1H), 7.71 (dd, J=8.56, 4.28 Hz, 1H), 7.35 (d, J=8.07 Hz, 1H), 7.14 (d, J=8.19 Hz, 1H), 7.07 (s, 1H), 6.90 (br d, J=8.19 Hz, 1H), 4.28 (d, J=12.23 Hz, 1H), 4.09 (br d, J=10.51 Hz, 1H), 3.89 (br d, J=10.76 Hz, 1H), 3.61-3.78 (m, 3H), 3.41-3.49 (m, 2H), 3.14-3.25 (m, 2H), 2.96-3.12 (m, 5H), 2.80-2.93 (m, 2H), 1.28 (d, J=6.36 Hz, 3H).

Example 12

5-[(4R,10bS)-8-[(3S)-3-(hydroxymethyl)piperazin-1-yl]-4-methyl-3,4,6,10b-tetrahydro-1H-pyrazino[2,1-a]isoindol-2-yl]quinoline-8-carbonitrile

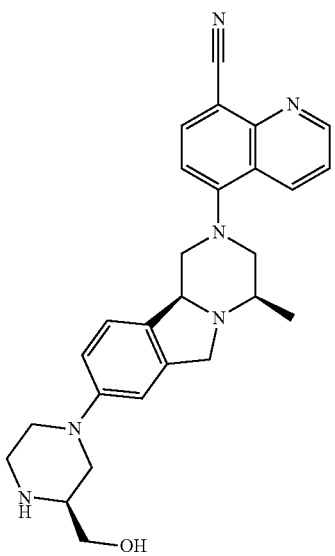 [SMILES: C[C@@H]1CN(c2ccc(C#N)c3ncccc23)C[C@@H]2c3ccc(N4CCN[C@H](CO)C4)cc3CN12]

The title compound was prepared in analogy to the preparation of Example 10 by using tert-butyl (2S)-2-(hydroxymethyl)piperazine-1-carboxylate (CAS: 1030377-21-9, Accela ChemBio, Catalog: SY018056) instead of tert-butyl (3R)-3-(hydroxymethyl)piperazine-1-carboxylate. Example 12 (8.6 mg) was obtained. MS: calc'd 455 [(M+H)$^+$], measured 455 [(M+H)$^+$]. $^1$H NMR (400 MHz, METHANOL-d$_4$) δ ppm 9.07 (dd, J=4.28, 1.59 Hz, 1H), 8.80 (dd, J=8.62, 1.53 Hz, 1H), 8.22 (d, J=7.95 Hz, 1H), 7.75 (dd, J=8.56, 4.28 Hz, 1H), 7.35-7.47 (m, 2H), 7.24 (s, 1H), 7.13 (dd, J=8.50, 2.14 Hz, 1H), 5.24-5.31 (m, 1H), 4.95 (br d, J=13.57 Hz, 1H), 4.65 (br d, J=13.69 Hz, 1H), 4.34 (br s, 1H), 3.82-3.95 (m, 4H), 3.72-3.80 (m, 1H), 3.67 (br s, 1H), 3.46-3.56 (m, 3H), 3.34-3.39 (m, 1H), 2.96-3.24 (m, 3H), 1.56 (d, J=6.72 Hz, 3H).

Example 13

5-[(4R,10bS)-4-methyl-8-(3-oxa-7,9-diazabicyclo[3.3.1]nonan-7-yl)-3,4,6,10b-tetrahydro-1H-pyrazino[2,1-a]isoindol-2-yl]quinoline-8-carbonitrile

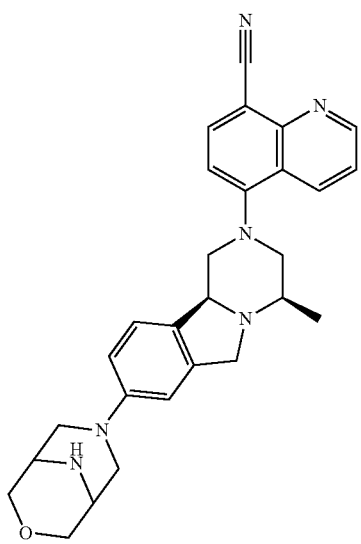 [SMILES: C[C@@H]1CN(c2ccc(C#N)c3ncccc23)C[C@@H]2c3ccc(N4CC5COCC(C4)N5)cc3CN12]

The title compound was prepared in analogy to the preparation of Example 10 by using tert-butyl 3-oxa-7,9-diazabicyclo[3.3.1]nonane-9-carboxylate (CAS: 1251010-45-3, PharmaBlock, Catalog: PB07078) instead of tert-butyl (3R)-3-(hydroxymethyl)piperazine-1-carboxylate. Example 13 (8.2 mg) was obtained. MS: calc'd 467 [(M+H)$^+$], measured 467 [(M+H)$^+$]. $^1$H NMR (400 MHz, METHANOL-$d_4$) δ ppm 9.02 (dd, J=4.28, 1.59 Hz, 1H), 8.73 (dd, J=8.56, 1.59 Hz, 1H), 8.18 (d, J=7.95 Hz, 1H), 7.71 (dd, J=8.62, 4.22 Hz, 1H), 7.34 (d, J=8.07 Hz, 1H), 7.13 (d, J=8.31 Hz, 1H), 7.01 (d, J=1.71 Hz, 1H), 6.83 (dd, J=8.31, 2.20 Hz, 1H), 4.29 (d, J=12.23 Hz, 1H), 4.10 (br d, J=10.27 Hz, 1H), 3.92-4.02 (m, 4H), 3.77-3.91 (m, 3H), 3.71 (br d, J=12.23 Hz, 1H), 3.46 (br d, J=11.49 Hz, 1H), 3.09-3.19 (m, 2H), 2.96-3.09 (m, 1H), 2.93-3.07 (m, 3H), 2.82-2.92 (m, 1H), 1.28 (d, J=6.36 Hz, 3H).

Example 14

5-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]quinoline-8-carbonitrile

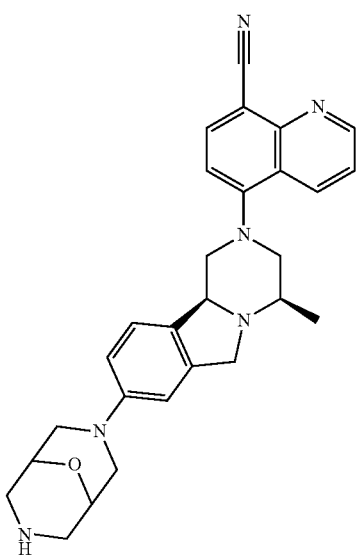 [SMILES: C[C@@H]1CN(c2ccc(C#N)c3ncccc23)C[C@@H]2c3ccc(N4CC5CNCC(C4)O5)cc3CN12]

The title compound was prepared in analogy to the preparation of Example 10 by using tert-butyl 9-oxa-3,7-diazabicyclo[3.3.1]nonane-3-carboxylate (CAS: 478647-20-0, WuXi Pharma, Catalog: WX120052) instead of tert-butyl (3R)-3-(hydroxymethyl)piperazine-1-carboxylate. Example 14 (7.2 mg) was obtained. MS: calc'd 467 [(M+H)$^+$], measured 467 [(M+H)$^+$]. $^1$H NMR (400 MHz, METHANOL-$d_4$) δ ppm 9.02 (dd, J=4.22, 1.53 Hz, 1H), 8.71 (dd, J=8.56, 1.47 Hz, 1H), 8.18 (d, J=7.95 Hz, 1H), 7.72 (dd, J=8.56, 4.28 Hz, 1H), 7.33 (d, J=8.07 Hz, 1H), 7.14 (d, J=8.31 Hz, 1H), 7.09 (s, 1H), 6.90 (dd, J=8.25, 2.02 Hz, 1H), 4.29 (d, J=12.23 Hz, 1H), 4.08 (br d, J=10.15 Hz, 1H), 3.87 (br s, 3H), 3.77 (br dd, J=11.68, 6.17 Hz, 2H), 3.69 (br d, J=12.10 Hz, 1H), 3.45 (br d, J=11.74 Hz, 1H), 3.24-3.35 (m, 3H), 3.09-3.23 (m, 4H), 3.02 (t, J=10.88 Hz, 1H), 2.85 (t, J=11.07 Hz, 1H), 1.27 (d, J=6.48 Hz, 3H).

Example 15

5-[(4R,10bS)-8-(6-hydroxy-1,4-diazepan-1-yl)-4-methyl-3,4,6,10b-tetrahydro-1H-pyrazino[2,1-a]isoindol-2-yl]quinoline-8-carbonitrile

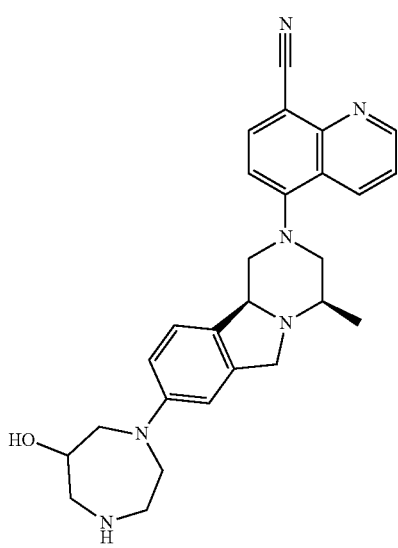 [SMILES: C[C@@H]1CN(c2ccc(C#N)c3ncccc23)C[C@@H]2c3ccc(N4CCNCC(O)C4)cc3CN12]

The title compound was prepared in analogy to the preparation of Example 10 by using tert-butyl 6-hydroxy-1,4-diazepane-1-carboxylate (CAS: 956317-40-1, WuXi Pharma, Catalog: WX604354) instead of tert-butyl (3R)-3-(hydroxymethyl)piperazine-1-carboxylate. Example 15 (7.2 mg) was obtained. MS: calc'd 455 [(M+H)$^+$], measured 455 [(M+H)$^+$]. $^1$H NMR (400 MHz, METHANOL-d$_4$) δ ppm 9.00 (d, J=3.06 Hz, 1H), 8.69 (d, J=8.56 Hz, 1H), 8.15 (d, J=8.07 Hz, 1H), 7.69 (dd, J=8.56, 4.28 Hz, 1H), 7.30 (d, J=8.07 Hz, 1H), 7.04 (d, J=8.31 Hz, 1H), 6.87 (s, 1H), 6.68 (d, J=8.31 Hz, 1H), 4.23 (br d, J=12.23 Hz, 1H), 3.98-4.13 (m, 2H), 3.76-3.94 (m, 2H), 3.54-3.74 (m, 2H), 3.33-3.49 (m, 4H), 2.92-3.08 (m, 3H), 2.69-2.89 (m, 3H), 1.26 (d, J=6.36 Hz, 3H).

Example 16

5-[(4R,10bS)-8-[trans-3-amino-4-methoxy-pyrrolidin-1-yl]-4-methyl-3,4,6,10b-tetrahydro-1H-pyrazino[2,1-a]isoindol-2-yl]quinoline-8-carbonitrile

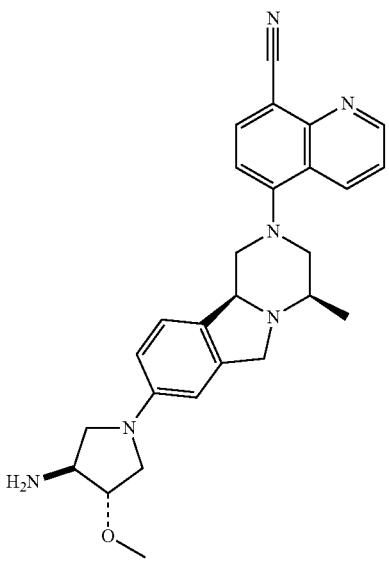 [SMILES: CO[C@H]1CN(c2ccc3c(c2)CN2[C@H](C)CN(c4ccc(C#N)c5ncccc45)C[C@H]32)C[C@@H]1N]

The title compound was prepared in analogy to the preparation of Example 10 by using trans-3-(boc-amino)-4-methoxypyrrolidine (CAS: 128739-92-4, PharmaBlock, Catalog: PBN20121069) instead of tert-butyl (3R)-3-(hydroxymethyl)piperazine-1-carboxylate. Example 16 (58 mg) was obtained. MS: calc'd 455 [(M+H)$^+$], measured 455 [(M+H)$^+$]. $^1$H NMR (400 MHz, METHANOL-d$_4$) δ ppm 9.01 (dd, J=4.22, 1.65 Hz, 1H), 8.72 (dd, J=8.56, 1.59 Hz, 1H), 8.17 (d, J=7.95 Hz, 1H), 7.70 (dd, J=8.62, 4.22 Hz, 1H), 7.34 (d, J=8.19 Hz, 1H), 7.07 (d, J=8.07 Hz, 1H), 6.64 (d, J=1.47 Hz, 1H), 6.46 (dd, J=8.25, 2.02 Hz, 1H), 4.26 (d, J=12.10 Hz, 1H), 4.08 (br d, J=10.51 Hz, 1H), 3.86 (br d, J=11.13 Hz, 1H), 3.77-3.83 (m, 1H), 3.64-3.74 (m, 2H), 3.49-3.57 (m, 2H), 3.45-3.49 (m, 1H), 3.44 (s, 3H), 3.35-3.40 (m, 1H), 3.25 (dd, J=10.51, 2.81 Hz, 1H), 3.06-3.17 (m, 1H), 2.96-3.04 (m, 1H), 2.80-2.92 (m, 1H), 1.28 (d, J=6.48 Hz, 3H).

Example 16A and 16B: 5-[(4R,10bS)-8-[(3S,4S)-3-amino-4-methoxy-pyrrolidin-1-yl]-4-methyl-3,4,6,10b-tetrahydro-1H-pyrazino[2,1-a]isoindol-2-yl]quinoline-8-carbonitrile and 5-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]quinoline-8-carbonitrile
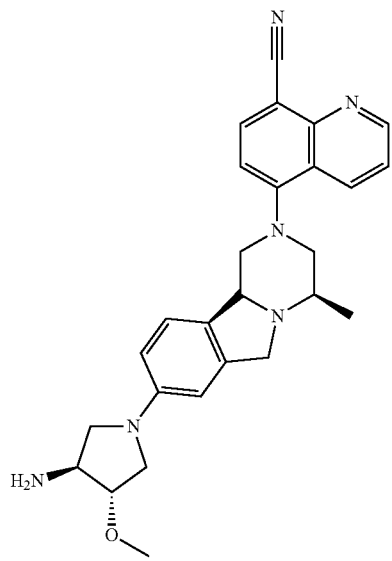
-continued
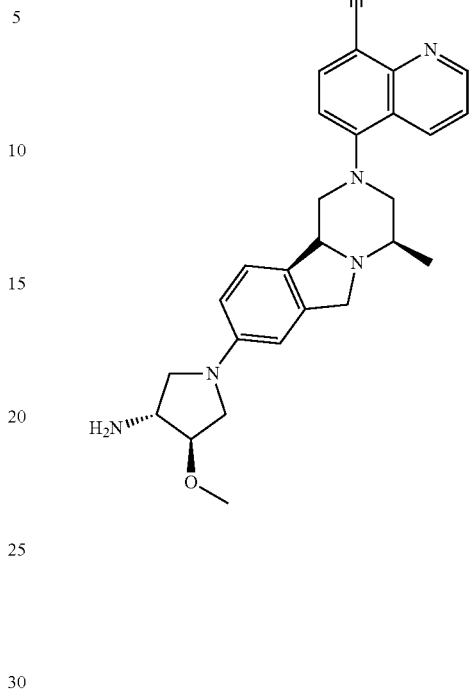
Preparation of Example 16A & 16B
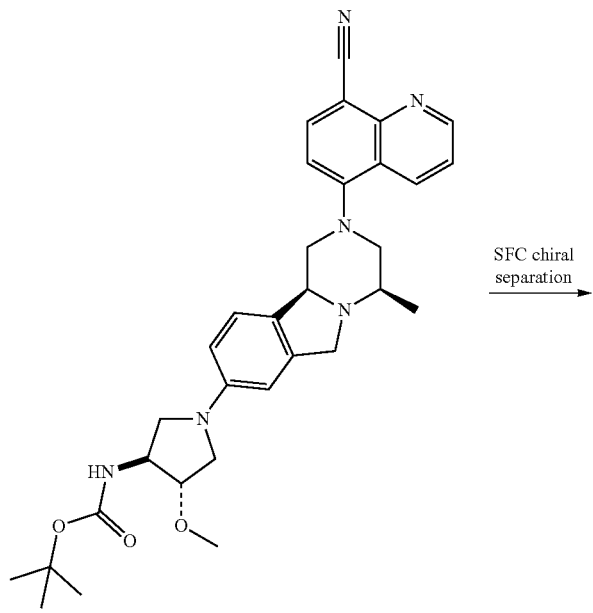
16c
SFC chiral separation →

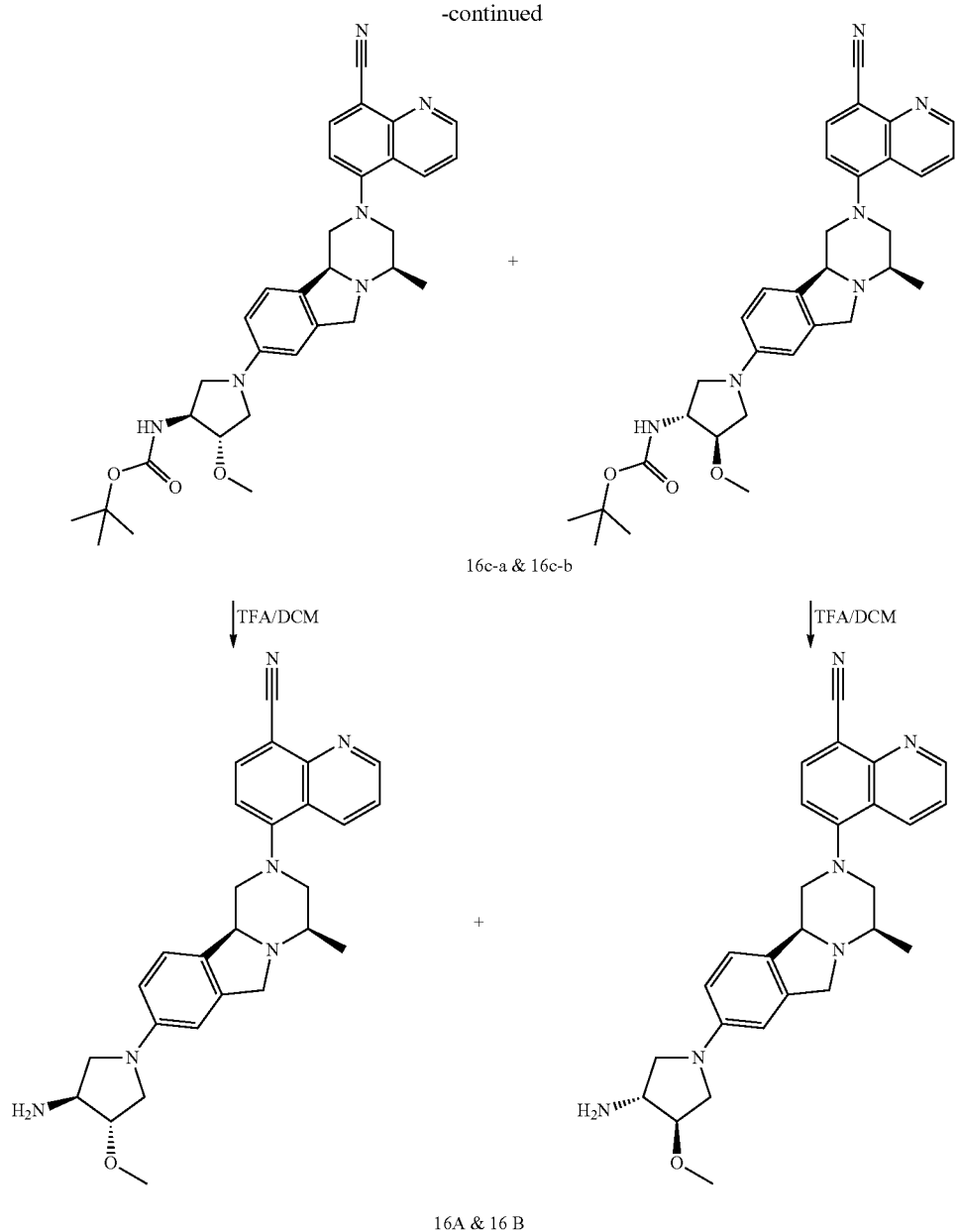

16c-a & 16c-b

16A & 16 B

Intermediate 16c (162 mg) was resolved by SFC to give two single isomers: 16c-a (faster eluting, 62 mg, yield: 38%) MS: calc'd 555 (M+H)$^+$, measured 555 (M+H)+; and compound 16c-b (slower eluting, 76 mg, yield: 47%) MS: calc'd 555 (M+H)$^+$, measured 555 (M+H)$^+$, with 40% Ethanol (0.25% NH$_3$H$_2$O)/CO$_2$ on OJ (5 μm, 250×20 mm) column.

To a solution of compound 16c-a (62 mg, 112 μmol) in DCM (4 mL) was added TFA (1 mL). The reaction mixture was stirred at room temperature for 30 min, then concentrated to afford a crude product, which was purified by prep-HPLC to afford Example 16A (42 mg, 82% yield). MS: calc'd 455 [(M+H)$^+$], measured 455 [(M+H)$^+$]. $^1$H NMR (400 MHz, METHANOL-d$_4$) δ ppm 9.01 (dd, J=4.22, 1.65 Hz, 1H), 8.72 (dd, J=8.56, 1.59 Hz, 1H), 8.17 (d, J=7.95 Hz, 1H), 7.70 (dd, J=8.62, 4.22 Hz, 1H), 7.34 (d, J=8.19 Hz, 1H), 7.07 (d, J=8.07 Hz, 1H), 6.64 (d, J=1.47 Hz, 1H), 6.46 (dd, J=8.25, 2.02 Hz, 1H), 4.26 (d, J=12.10 Hz, 1H), 4.08 (br d, J=10.51 Hz, 1H), 3.86 (br d, J=11.13 Hz, 1H), 3.77-3.83 (m, 1H), 3.64-3.74 (m, 2H), 3.49-3.57 (m, 2H), 3.45-3.49 (m, 1H), 3.44 (s, 3H), 3.35-3.40 (m, 1H), 3.25 (dd, J=10.51, 2.81 Hz, 1H), 3.06-3.17 (m, 1H), 2.96-3.04 (m, 1H), 2.80-2.92 (m, 1H), 1.28 (d, J=6.48 Hz, 3H).

Example 16B was prepared in analogy to Example 16A (51 mg, 82% yield). MS: calc'd 455 [(M+H)$^+$], measured 455 [(M+H)$^+$]. $^1$H NMR (400 MHz, METHANOL-d$_4$) δ ppm 9.01 (dd, J=4.28, 1.59 Hz, 1H), 8.72 (dd, J=8.68, 1.59 Hz, 1H), 8.18 (d, J=8.07 Hz, 1H), 7.71 (dd, J=8.56, 4.28 Hz, 1H), 7.34 (d, J=8.07 Hz, 1H), 7.06 (d, J=8.19 Hz, 1H), 6.64 (s, 1H), 6.46 (dd, J=8.25, 2.02 Hz, 1H), 4.26 (d, J=12.10 Hz, 1H), 4.08 (br d, J=10.27 Hz, 1H), 3.86 (br d, J=11.25 Hz, 1H), 3.78-3.83 (m, 1H), 3.63-3.75 (m, 2H), 3.49-3.58 (m, 2H), 3.40-3.47 (m, 1H), 3.44 (s, 3H), 3.35-3.38 (m, 1H), 3.24 (dd, J=10.51, 2.81 Hz, 1H), 3.07-3.17 (m, 1H), 2.96-3.04 (m, 1H), 2.78-2.93 (m, 1H), 1.28 (d, J=6.48 Hz, 3H).

Example 17

5-[(4R,10bS)-8-[cis-3-amino-4-methoxy-pyrrolidin-1-yl]-4-methyl-3,4,6,10b-tetrahydro-1H-pyrazino[2,1-a]isoindol-2-yl]quinoline-8-carbonitrile

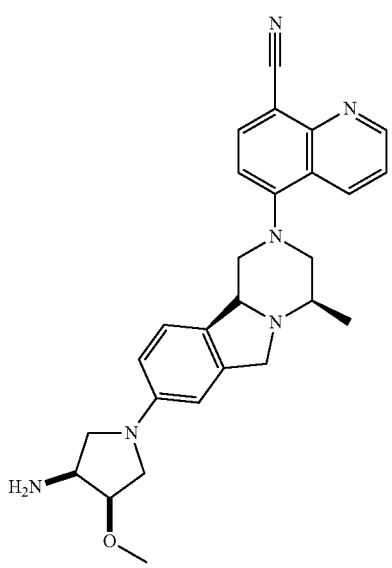

The title compound was prepared in analogy to the preparation of Example 10 by using cis-3-(boc-amino)-4-methoxypyrrolidine (CAS: 128739-89-9, PharmaBlock, Catalog: PBXA8055) instead of tert-butyl (3R)-3-(hydroxymethyl)piperazine-1-carboxylate. Example 17 (36 mg) was obtained. MS: calc'd 455 [(M+H)$^+$], measured 455 [(M+H)$^+$]. $^1$H NMR (400 MHz, METHANOL-d$_4$) δ ppm 9.02 (dd, J=4.28, 1.59 Hz, 1H), 8.72 (dd, J=8.62, 1.53 Hz, 1H), 8.18 (d, J=7.95 Hz, 1H), 7.71 (dd, J=8.56, 4.28 Hz, 1H), 7.33 (d, J=8.07 Hz, 1H), 7.05 (d, J=8.07 Hz, 1H), 6.60 (s, 1H), 6.42 (dd, J=8.25, 1.90 Hz, 1H), 4.25 (d, J=12.23 Hz, 1H), 4.07 (br d, J=10.27 Hz, 1H), 3.91 (br d, J=2.93 Hz, 1H), 3.85 (br d, J=11.00 Hz, 1H), 3.67 (br d, J=12.10 Hz, 1H), 3.55-3.63 (m, 1H), 3.39-3.54 (m, 8H), 2.96-3.11 (m, 2H), 2.79-2.91 (m, 1H), 1.27 (d, J=6.48 Hz, 3H).

Example 18

5-[(4R,10bS)-8-(5-amino-2-oxa-7-azaspiro[3.4]octan-7-yl)-4-methyl-3,4,6,10b-tetrahydro-1H-pyrazino[2,1-a]isoindol-2-yl]quinoline-8-carbonitrile

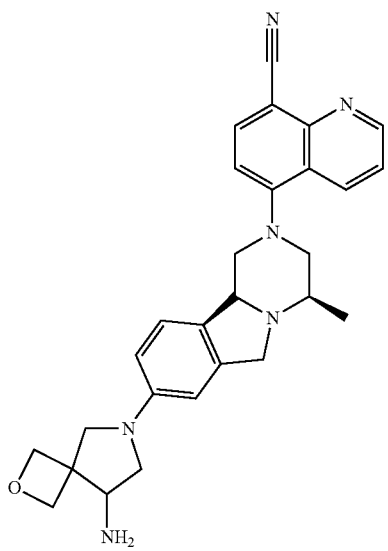

The title compound was prepared in analogy to the preparation of Example 10 by using tert-butyl N-(2-oxa-7-azaspiro[3.4]octan-5-yl)carbamate (CAS: 1422496-61-4, PharmaBlock, Catalog: PBLG1162) instead of tert-butyl (3R)-3-(hydroxymethyl)piperazine-1-carboxylate. Example 18 (12 mg) was obtained. MS: calc'd 467 [(M+H)$^+$], measured 467 [(M+H)$^+$]. $^1$H NMR (400 MHz, METHANOL-d$_4$) δ ppm 9.01 (dd, J=4.28, 1.59 Hz, 1H), 8.73 (dd, J=8.56, 1.59 Hz, 1H), 8.17 (d, J=7.95 Hz, 1H), 7.69 (dd, J=8.62, 4.22 Hz, 1H), 7.34 (d, J=8.07 Hz, 1H), 7.08 (d, J=8.19 Hz, 1H), 6.65 (s, 1H), 6.47 (dd, J=8.13, 1.90 Hz, 1H), 4.96 (d, J=6.72 Hz, 1H), 4.54-4.68 (m, 3H), 4.27 (d, J=12.23 Hz, 1H), 4.09 (br d, J=10.03 Hz, 1H), 3.87 (br d, J=11.49 Hz, 1H), 3.58-3.78 (m, 4H), 3.42-3.56 (m, 3H), 3.07-3.17 (m, 1H), 2.94-3.04 (m, 1H), 2.80-2.92 (m, 1H), 1.28 (d, J=6.36 Hz, 3H).

Example 19

5-[(4R,10bS)-8-[3-amino-3-(hydroxymethyl)pyrrolidin-1-yl]-4-methyl-3,4,6,10b-tetrahydro-1H-pyrazino[2,1-a]isoindol-2-yl]quinoline-8-carbonitrile

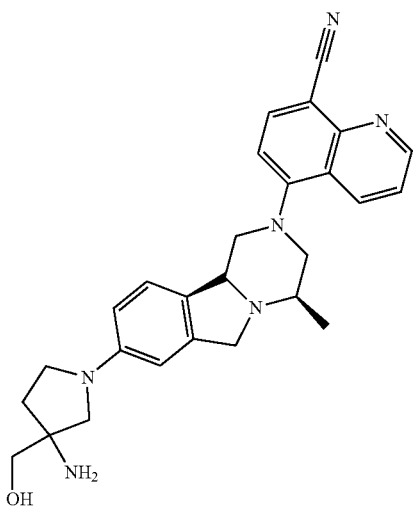

The title compound was prepared in analogy to the preparation of Example 10 by using tert-butyl N-[3-(hydroxymethyl)pyrrolidin-3-yl]carbamate (CAS: No, PharmaBlock, Catalog: PBXA7029-1) instead of tert-butyl (3R)-3-(hydroxymethyl)piperazine-1-carboxylate. Example 19 (7.7 mg) was obtained. MS: calc'd 455 [(M+H)$^+$], measured 455 [(M+H)$^+$]. $^1$H NMR (400 MHz, METHANOL-d$_4$) δ ppm 9.06 (dd, J=4.28, 1.59 Hz, 1H), 8.79 (dd, J=8.56, 1.34 Hz, 1H), 8.21 (d, J=7.95 Hz, 1H), 7.75 (dd, J=8.56, 4.28 Hz, 1H), 7.41 (br d, J=5.62 Hz, 1H), 7.36 (d, J=8.44 Hz, 1H), 6.82 (s, 1H), 6.71 (dd, J=8.44, 2.08 Hz, 1H), 5.27 (br s, 1H), 4.93 (br d, J=13.57 Hz, 1H), 4.62 (br d, J=13.82 Hz, 1H), 4.33 (br s, 1H), 3.78 (s, 2H), 3.75-3.82 (m, 1H), 3.60-3.72 (m, 2H), 3.54 (s, 2H), 3.43-3.52 (m, 2H), 2.85-3.00 (m, 1H), 2.30-2.40 (m, 1H), 2.19-2.30 ((m, 1H), 1.55 (d, J=6.72 Hz, 3H).

Example 20

5-[(4R,10bS)-8-[(3R)-3-aminopyrrolidin-1-yl]-4-methyl-3,4,6,10b-tetrahydro-1H-pyrazino[2,1-a]isoindol-2-yl]quinoline-8-carbonitrile

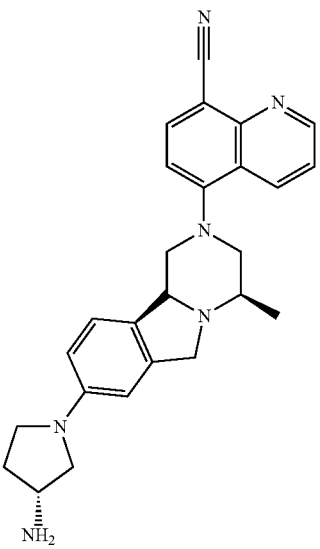

The title compound was prepared in analogy to the preparation of Example 10 by using tert-butyl N-[(3R)-pyrrolidin-3-yl]carbamate (CAS: 122536-77-0, Accela ChemBio, Catalog: SY006424) instead of tert-butyl (3R)-3-(hydroxymethyl)piperazine-1-carboxylate. Example 20 (8.6 mg) was obtained. MS: calc'd 425 [(M+H)$^+$], measured 425 [(M+H)$^+$]. $^1$H NMR (400 MHz, METHANOL-d$_4$) δ ppm 9.06 (dd, J=4.28, 1.59 Hz, 1H), 8.80 (d, J=8.68 Hz, 1H), 8.21 (d, J=7.83 Hz, 1H), 7.75 (dd, J=8.56, 4.28 Hz, 1H), 7.40 (br s, 1H), 7.36 (d, J=8.44 Hz, 1H), 6.82 (s, 1H), 6.72 (dd, J=8.38, 2.02 Hz, 1H), 5.27 (br s, 1H), 4.95 (br d, J=12.80 Hz, 1H), 4.62 (br d, J=13.94 Hz, 1H), 4.32 (br s, 1H), 4.08 (br s, 1H), 3.56-3.87 (m, 5H), 3.39-3.54 (m, 2H), 2.85-3.10 (m, 1H), 2.45-2.58 (m, 1H), 2.15-2.26 (m, 1H), 1.55 (d, J=6.72 Hz, 3H).

Example 21

5-[(4R,10bS)-8-[trans-3-amino-4-hydroxy-pyrrolidin-1-yl]-4-methyl-3,4,6,10b-tetrahydro-1H-pyrazino[2,1-a]isoindol-2-yl]quinoline-8-carbonitrile

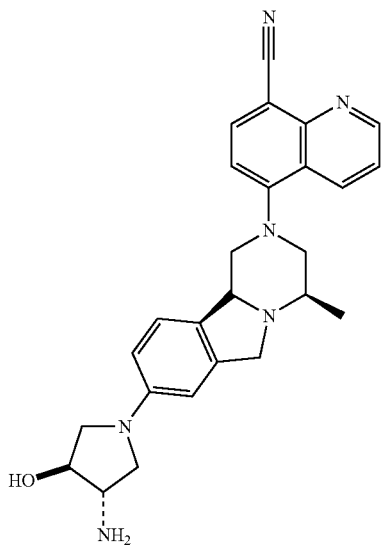

The title compound was prepared in analogy to the preparation of Example 10 by using trans-3-(boc-amino)-4-hydroxypyrrolidine (CAS: 870632-89-6, PharmaBlock, Catalog: PB07572) instead of tert-butyl (3R)-3-(hydroxymethyl)piperazine-1-carboxylate. Example 21 (8.6 mg) was obtained. MS: calc'd 441 [(M+H)$^+$], measured 441 [(M+H)$^+$]. $^1$H NMR (400 MHz, METHANOL-d$_4$) δ ppm 9.01 (dd, J=4.28, 1.59 Hz, 1H), 8.72 (dd, J=8.56, 1.59 Hz, 1H), 8.18 (d, J=8.07 Hz, 1H), 7.70 (dd, J=8.62, 4.34 Hz, 1H), 7.33 (d, J=8.07 Hz, 1H), 7.05 (d, J=8.07 Hz, 1H), 6.61 (s, 1H), 6.31-6.53 (m, 1H), 4.26 (d, J=12.23 Hz, 1H), 4.01-4.17 (m, 2H), 3.85 (br d, J=11.13 Hz, 1H), 3.57-3.75 (m, 3H), 3.45 (br d, J=11.86 Hz, 1H), 3.34-3.40 (m, 2H), 3.12-3.20 (m, 1H), 3.05-3.12 (m, 1H), 3.00 (br t, J=12.00 Hz, 1H), 2.86 (br t, J=11.07 Hz, 1H), 1.27 (d, J=6.36 Hz, 3H).

Example 22

5-[(4R,10bS)-8-(3-aminoazetidin-1-yl)-4-methyl-3,4,6,10b-tetrahydro-1H-pyrazino[2,1-a]isoindol-2-yl]quinoline-8-carbonitrile

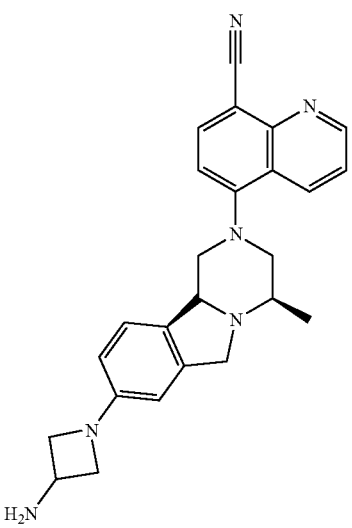

The title compound was prepared in analogy to the preparation of Example 10 by using tert-butyl N-(azetidin-3-yl)carbamate instead of tert-butyl (3R)-3-(hydroxymethyl)piperazine-1-carboxylate. Example 22 (34 mg) was obtained. MS: calc'd 411 [(M+H)$^+$], measured 411 [(M+H)$^+$]. $^1$H NMR (400 MHz, METHANOL-d$_4$) δ ppm 8.89 (dd, J=4.28, 1.59 Hz, 1H), 8.58 (dd, J=8.56, 1.59 Hz, 1H), 8.02 (d, J=7.95 Hz, 1H), 7.55 (dd, J=8.56, 4.28 Hz, 1H), 7.18 (d, J=8.07 Hz, 1H), 7.03 (d, J=8.07 Hz, 1H), 6.48 (d, J=1.59 Hz, 1H), 6.31 (dd, J=8.07, 2.08 Hz, 1H), 4.24 (d, J=12.59 Hz, 1H), 4.04-4.16 (m, 3H), 3.63-3.84 (m, 4H), 3.27-3.44 (m, 3H), 2.87 (t, J=11.13 Hz, 1H), 2.74-2.82 (m, 1H), 1.18 (d, J=6.24 Hz, 3H).

Example 23

5-[(4R,10bS)-8-[(3S,4S)-3-methoxy-4-(methyl-amino)pyrrolidin-1-yl]-4-methyl-3,4,6,10b-tetra-hydro-1H-pyrazino[2,1-a]isoindol-2-yl]quinoline-8-carbonitrile

Example 24

5-[(4R,10bS)-4-methyl-8-(5-oxa-2,8-diazaspiro[3.5]nonan-8-yl)-3,4,6,10b-tetrahydro-1H-pyrazino[2,1-a]isoindol-2-yl]quinoline-8-carbonitrile

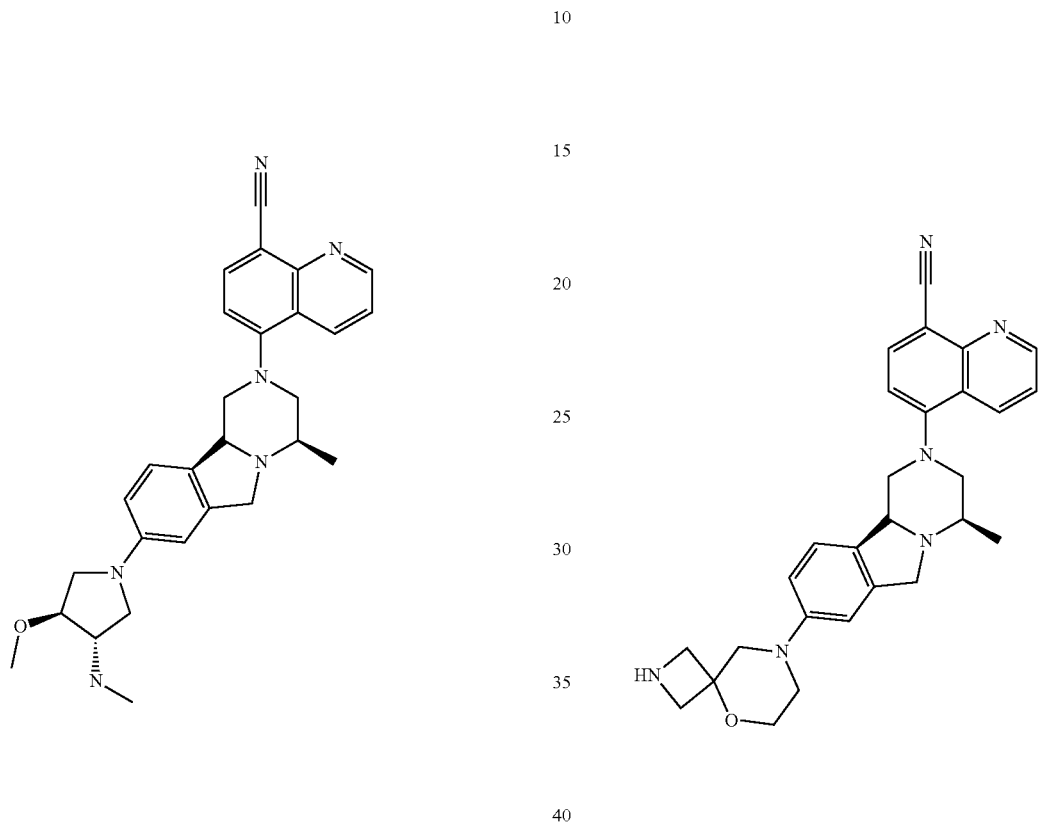

The title compound was prepared in analogy to the preparation of Example 10 by using tert-butyl N-[(3S,4S)-4-methoxypyrrolidin-3-yl]-N-methyl-carbamate (CAS: 174727-04-9, PharmaBlock, Catalog: PBN20121070) instead of tert-butyl (3R)-3-(hydroxymethyl)piperazine-1-carboxylate. Example 23 (34 mg) was obtained. MS: calc'd 469 [(M+H)$^+$], measured 469 [(M+H)$^+$]. $^1$H NMR (400 MHz, METHANOL-$d_4$) δ ppm 9.02 (d, J=3.06 Hz, 1H), 8.71 (d, J=8.68 Hz, 1H), 8.19 (d, J=7.95 Hz, 1H), 7.72 (dd, J=8.56, 4.28 Hz, 1H), 7.18-7.47 (m, 1H), 7.06 (d, J=8.19 Hz, 1H), 6.65 (s, 1H), 6.47 (br d, J=8.19 Hz, 1H), 4.26 (d, J=11.98 Hz, 1H), 4.07 (br d, J=9.78 Hz, 1H), 3.88-3.95 (m, 1H), 3.85 (br d, J=11.37 Hz, 1H), 3.62-3.71 (m, 2H), 3.56 (dd, J=9.72, 6.17 Hz, 1H), 3.43-3.46 (m, 1H), 3.44 (s, 3H), 3.23-3.33 (m, 3H), 3.17 (dd, J=9.78, 3.67 Hz, 1H), 3.00 (t, J=11.00 Hz, 1H), 2.86 (br t, J=11.07 Hz, 1H), 2.46 (s, 3H), 1.27 (d, J=6.36 Hz, 3H).

The title compound was prepared in analogy to the preparation of Example 10 by using tert-butyl 5-oxa-2,8-diazaspiro[3.5]nonane-2-carboxylate (CAS: 1251011-05-8, PharmaBlock, Catalog: PBN20111063) instead of tert-butyl (3R)-3-(hydroxymethyl)piperazine-1-carboxylate. Example 24 (16 mg) was obtained. MS: calc'd 467 [(M+H)$^+$], measured 467 [(M+H)$^+$]. $^1$H NMR (400 MHz, METHANOL-$d_4$) δ ppm 9.04 (dd, J=1.65, 4.22 Hz, 1H), 8.78 (dd, J=1.59, 8.56 Hz, 1H), 8.19 (d, J=7.95 Hz, 1H), 7.73 (dd, J=4.28, 8.56 Hz, 1H), 7.32-7.46 (m, 2H), 7.20 (s, 1H), 7.09 (dd, J=2.26, 8.50 Hz, 1H), 5.28 (br s, 1H), 4.93 (br d, J=13.69 Hz, 1H), 4.62 (br d, J=13.82 Hz, 1H), 4.32 (br s, 1H), 4.04-4.19 (m, 4H), 3.51-4.03 (m, 4H), 3.40 (s, 2H), 3.14-3.21 (m, 1H), 2.90-3.23 (m, 1H), 1.54 (d, J=6.85 Hz, 3H).

Example 25

5-[(4R,10bS)-8-[2-(dimethylamino)ethoxy]-4-methyl-3,4,6,10b-tetrahydro-1H-pyrazino[2,1-a]isoindol-2-yl]quinoline-8-carbonitrile

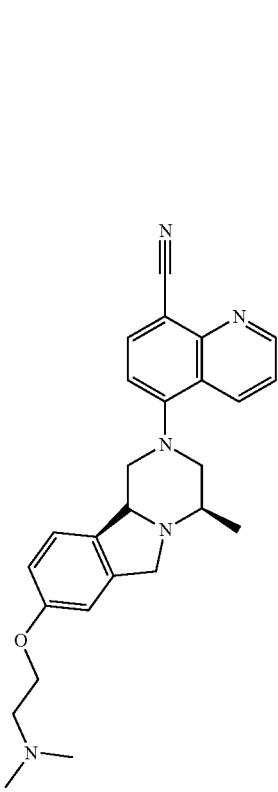

The title compound was prepared in analogy to the preparation of Example 10 by using N,N-dimethylethanolamine (CAS: 108-01-0, Aldrich, Catalog: 471453) instead of tert-butyl (3R)-3-(hydroxymethyl)piperazine-1-carboxylate. Example 25 (9.4 mg) was obtained. MS: calc'd 428 [(M+H)$^+$], measured 428 [(M+H)$^+$]. $^1$H NMR (400 MHz, METHANOL-d$_4$) δ ppm 8.99 (dd, J=1.65, 4.22 Hz, 1H), 8.71 (dd, J=1.6, 8.6 Hz, 1H), 8.15 (d, J=7.95 Hz, 1H), 7.67 (dd, J=4.22, 8.62 Hz, 1H), 7.32 (d, J=8.1 Hz, 1H), 7.15 (d, J=8.19 Hz, 1H), 7.00 (d, J=1.96 Hz, 1H), 6.83 (dd, J=2.32, 8.19 Hz, 1H), 4.28 (d, J=12.35 Hz, 1H), 4.04-4.13 (m, 3H), 3.82-3.92 (m, 1H), 3.69 (br d, J=12.23 Hz, 1H), 3.40-3.48 (m, 1H), 3.33-3.38 (m, 1H), 2.93-3.05 (m, 1H), 2.71-2.88 (m, 3H), 2.35 (s, 6H), 1.25 (d, J=6.5 Hz, 3H).

Example 26

5-[(4R,10bS)-8-[2-(dimethylamino)ethylamino]-4-methyl-3,4,6,10b-tetrahydro-1H-pyrazino[2,1-a]isoindol-2-yl]quinoline-8-carbonitrile The title compound was prepared in analogy to the preparation of Example 10 by using 2-dimethylaminoethylamine (CAS: 108-00-9, TCI, Catalog: D0719) instead of tert-butyl (3R)-3-(hydroxymethyl)piperazine-1-carboxylate. Example 26 (19 mg) was obtained. MS: calc'd 427 [(M+H)$^+$], measured 427 [(M+H)$^+$]. $^1$H NMR (400 MHz, METHANOL-d$_4$) δ ppm 8.98 (dd, J=1.59, 4.28 Hz, 1H), 8.70 (dd, J=1.59, 8.56 Hz, 1H), 8.15 (d, J=8.07 Hz, 1H), 7.66 (dd, J=4.22, 8.62 Hz, 1H), 7.31 (d, J=8.07 Hz, 1H), 7.00 (d, J=7.95 Hz, 1H), 6.69 (d, J=1.83 Hz, 1H), 6.52 (dd, J=2.02, 8.13 Hz, 1H), 4.22 (d, J=12.10 Hz, 1H), 4.04 (br d, J=10.03 Hz, 1H), 3.84 (br d, J=11.25 Hz, 1H), 3.63 (br d, J=11.98 Hz, 1H), 3.33-3.38 (m, 1H), 3.43 (br d, J=11.49 Hz, 1H), 3.23 (t, J=6.66 Hz, 2H), 2.98 (t, J=10.88 Hz, 1H), 2.83 (dd, J=10.33, 11.80 Hz, 1H), 2.58 (t, J=6.66 Hz, 2H), 2.31 (s, 6H), 1.25 (d, J=6.48 Hz, 3H).

Example 27

5-[(4R,10bS)-8-(azetidin-3-yloxy)-4-methyl-3,4,6,10b-tetrahydro-1H-pyrazino[2,1-a]isoindol-2-yl]quinoline-8-carbonitrile

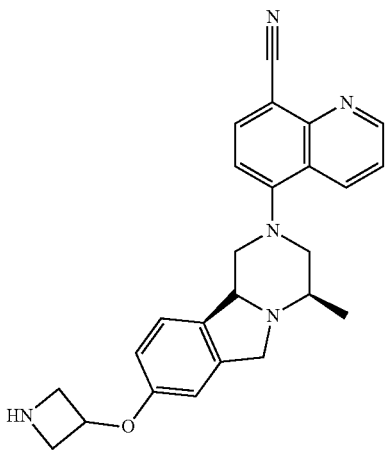

The title compound was prepared in analogy to the preparation of Example 10 by using tert-butyl 3-hydroxyazetidine-1-carboxylate (CAS: 141699-55-0, PharmaBlock, Catalog: PB00001) instead of tert-butyl (3R)-3-(hydroxymethyl)piperazine-1-carboxylate. Example 27 (13 mg) was obtained. MS: calc'd 412 [(M+H)$^+$], measured 412 [(M+H)$^+$]. $^1$H NMR (400 MHz, METHANOL-d$_4$) δ ppm 8.90 (dd, J=1.7, 4.2 Hz, 1H), 8.64 (dd, J=1.7, 8.6 Hz, 1H), 8.04 (d, J=8.1 Hz, 1H), 7.59 (dd, J=4.2, 8.6 Hz, 1H), 7.27 (dd, J=8.2, 18.3 Hz, 2H), 6.94 (d, J=2.2 Hz, 1H), 6.78 (dd, J=2.3, 8.4 Hz, 1H), 5.15-5.02 (m, 1H), 4.92 (dd, J=3.7, 11.0 Hz, 1H), 4.69 (d, J=13.6 Hz, 1H), 4.43-4.54 (m, 2H), 4.33 (d, J=13.6 Hz, 1H), 4.03-4.11 (m, 2H), 3.94-4.02 (m, 1H), 3.80-3.87 (m, 1H), 3.45-3.55 (m, 1H), 2.96-3.13 (m, 2H), 1.37 (d, J=6.6 Hz, 3H).

Example 28

5-[(4R,10S)-8-(azetidin-3-ylamino)-4-methyl-3,4,6,10b-tetrahydro-1H-pyrazino[2,1-a]isoindol-2-yl]quinoline-8-carbonitrile

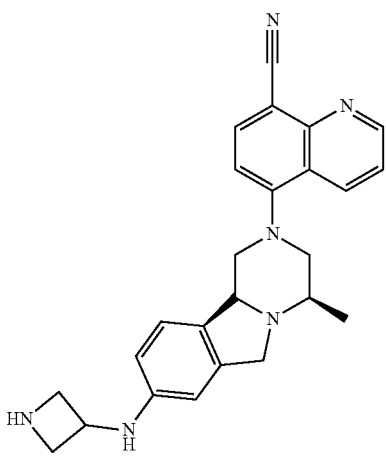

The title compound was prepared in analogy to the preparation of Example 10 by using tert-butyl 3-aminoazetidine-1-carboxylate (CAS: 193269-78-2, PharmaBlock, Catalog: PB00002) instead of tert-butyl (3R)-3-(hydroxymethyl)piperazine-1-carboxylate. Example 28 (30 mg) was obtained. MS: calc'd 411 [(M+H)$^+$], measured 411 [(M+H)$^+$]. $^1$H NMR (400 MHz, METHANOL-d$_4$). δ ppm 9.03 (dd, J=1.7, 4.2 Hz, 1H), 8.76 (dd, J=1.6, 8.6 Hz, 1H), 8.18 (d, J=7.9 Hz, 1H), 7.72 (dd, J=4.3, 8.6 Hz, 1H), 7.37 (d, J=8.1 Hz, 1H), 7.23 (d, J=8.3 Hz, 1H), 6.73 (d, J=1.8 Hz, 1H), 6.61 (dd, J=2.1, 8.3 Hz, 1H), 4.93-4.96 (m, 1H), 4.71 (d, J=13.3 Hz, 1H), 4.51-4.62 (m, 1H), 4.39-4.49 (m, 2H), 4.34 (d, J=13.4 Hz, 1H), 3.97-4.13 (m, 3H), 3.84-3.95 (m, 1H), 3.51-3.6.5 (m, 1H), 3.03-3.24 (m, 2H), 1.47 (d, J=6.7 Hz, 3H).

Example 29

5-[(4R,10bS)-8-(azetidin-3-yl)-4-methyl-3,4,6,10b-tetrahydro-1H-pyrazino[2,1-a]isoindol-2-yl]quinoline-8-carbonitrile

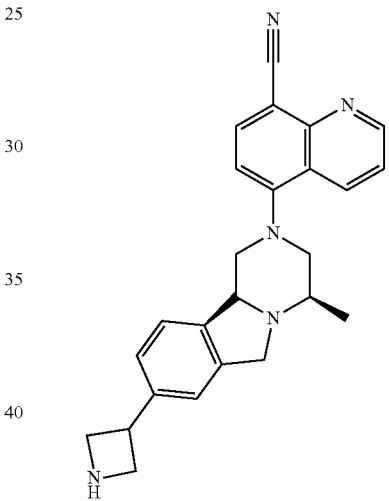

The title compound was prepared according to the following scheme:

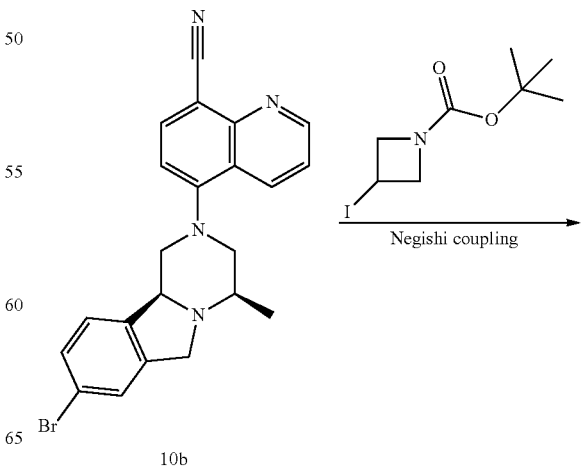

10b

-continued

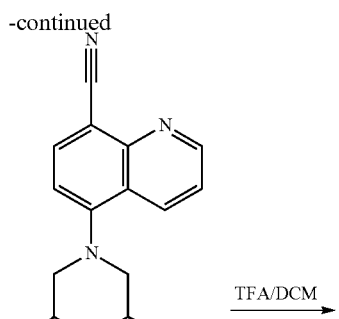

29a

TFA/DCM →

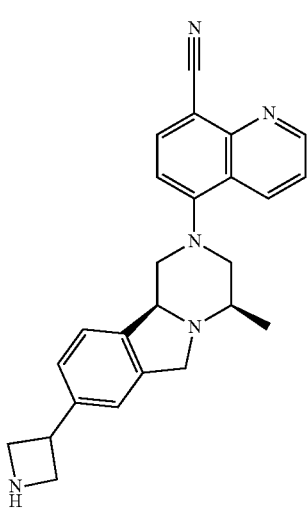

Example 29

Step 1: Preparation of tert-butyl 3-[(4R,10S)-2-(8-cyano-5-quinolyl)-4-methyl-3,4,6,10b-tetrahydro-1H-pyrazino[2,1-a]isoindol-8-yl]azetidine-1-carboxylate (Compound 29a)

To a suspension of zinc (156 mg, 2.4 mmol) in DMF (3 mL) was added 1,2-dibromoethane (44.8 mg, 238 μmol). The resultant mixture was heated at 60° C. for 10 min, and then cooled to room temperature. Chlorotrimethylsilane (25.9 mg, 238 μmol) was added to the mixture, stirred at 60° C. for 10 min, then cooled to room temperature. A solution of tert-butyl 3-iodoazetidine-1-carboxylate (CAS: 254454-54-1, PharmaBlock, Catalog: PB00430, 675 mg, 2.4 mmol) in DMF (1 mL) was then added and the mixture was stirred at room temperature for 1 hr. 5-[(4R,10bS)-8-bromo-4-methyl-3,4,6,10b-tetrahydro-1H-pyrazino[2,1-a]isoindol-2-yl]quinoline-8-carbonitrile (compound 10b, 500 mg, 1.2 mmol) and Pd(PPh$_3$)$_2$Cl$_2$ (83.7 mg, 0.1 mmol) were added sequentially and the reaction mixture was heated to 80° C. for 4 hrs, then cooled to room temperature and partitioned between EA and sat.NH$_4$Cl solution. The aqueous layer was extracted with EA twice, and the combined organic layer was washed with water and brine, dried over Na$_2$SO$_4$, filtered and concentrated in vacuo. The residue was purified by flash chromatography to afford compound 29a (202 mg, 34% yield). MS: calc'd 4% [(M+H)$^+$], measured 4% [(M+H)$^+$].

Step 2: Preparation of 5-[(4R,10bS)-8-(azetidin-3-yl)-4-methyl-3,4,6,10b-tetrahydro-1H-pyrazino[2,1-a]isoindol-2-yl]quinoline-8-carbonitrile (Example 29)

To a solution of tert-butyl 3-[(4R,10bS)-2-(8-cyano-5-quinolyl)-4-methyl-3,4,6,10b-tetrahydro-1H-pyrazino[2,1-a]isoindol-8-yl]azetidine-1-carboxylate (compound 29a, 42 mg, 85 μmol) in DCM (2 mL) was added TFA (1 mL). The reaction mixture was stirred at room temperature for 30 min, then concentrated to afford a crude product, which was purified by pre-HPLC to afford Example 29 (23 mg, 68% yield). MS: calc'd 396 [(M+H)$^+$], measured 396 [(M+H)$^+$]. $^1$H NMR (400 MHz, METHANOL-d$_4$) δ ppm 9.02 (dd, J=1.71, 4.28 Hz, 1H), 8.79 (dd, J=1.59, 8.56 Hz, 1H), 8.17 (d, J=8.07 Hz, 1H), 7.73 (dd, J=4.28, 8.56 Hz, 1H), 7.61 (s, 1H), 7.54-7.58 (m, 1H), 7.43-7.52 (m, 1H), 7.39 (d, J=8.07 Hz, 1H), 5.41 (br dd, J=3.85, 11.19 Hz, 1H), 5.01 (d, J=13.82 Hz, 1H), 4.72 (d, J=13.94 Hz, 1H), 4.20-4.46 (m, 6H), 3.99 (br s, 1H), 3.68 (br d, J=12.% Hz, 1H), 3.33-3.36 (m, 1H), 3.10-3.25 (m, 1H), 1.56 (d, J=6.72 Hz, 3H).

Example 30

5-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]quinoline-8-carbonitrile

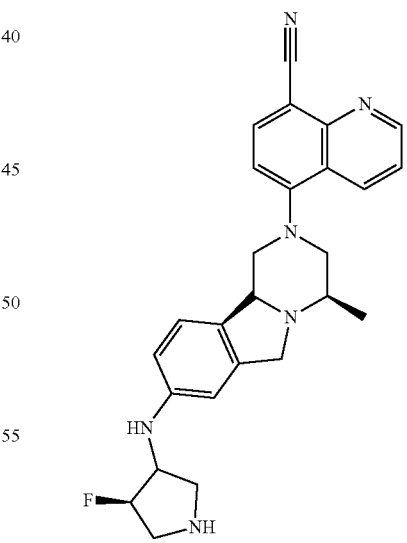

The title compound was prepared in analogy to the preparation of Example 10 by using tert-butyl (3S,4R)-3-amino-4-fluoropyrrolidine-1-carboxylate (CAS: 1174020-30-4, PharmaBlock, Catalog: PB07374) instead of tert-butyl (3R)-3-(hydroxymethyl)piperazine-1-carboxylate. Example 30 (46 mg) was obtained. MS: calc'd 443 [(M+H)$^+$], measured 443 [(M+H)$^+$]. $^1$H NMR (400 MHz, METHANOL-d$_4$)

δ ppm 9.02 (dd, J=1.6, 4.3 Hz, 1H), 8.76 (dd, J=1.6, 8.6 Hz, 1H), 8.16 (d, J=7.9 Hz, 1H), 7.71 (dd, J=4.3, 8.6 Hz, 1H), 7.37 (d, J=8.1 Hz, 1H), 7.26 (d, J=8.3 Hz, 1H), 6.92 (d, J=1.8 Hz, 1H), 6.81 (dd, J=2.1, 8.3 Hz, 1H), 5.21-5.44 (m, 1H), 5.12 (dd, J=3.9, 11.0 Hz, 1H), 4.82 (d, J=13.6 Hz, 1H), 4.38-4.55 (m, 2H), 4.10-4.26 (m, 1H), 3.85-3.97 (m, 1H), 3.56-3.84 (m, 4H), 3.20-3.30 (m, 2H), 3.12 (dd, J=11.2, 13.1 Hz, 1H), 1.51 (d, J=6.7 Hz, 3H).

Example 31

5-[(4R,10bS)-8-[[(3S,4S)-4-fluoropyrrolidin-3-yl]amino]-4-methyl-3,4,6,10b-tetrahydro-1H-pyrazino[2,1-a]isoindol-2-yl]quinoline-8-carbonitrile

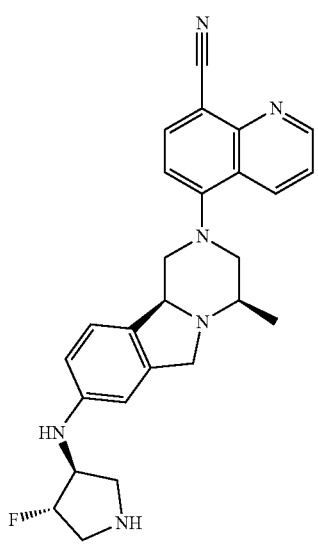 [SMILES: C[C@@H]1CN(c2ccc(C#N)c3ncccc23)C[C@@H]2c3ccc(N[C@H]4CNC[C@@H]4F)cc3CN12]

The title compound was prepared in analogy to the preparation of Example 10 by using tert-butyl (3S,4S)-3-amino-4-fluoropyrrolidine-1-carboxylate (CAS: 1009075-43-7, PharmaBlock, Catalog: PB07376) instead of tert-butyl (3R)-3-(hydroxymethyl)piperazine-1-carboxylate. Example 31 (46 mg) was obtained. MS: calc'd 443 [(M+H)+], measured 443 [(M+H)+]. ¹H NMR (400 MHz, METHANOL-d₄) δ ppm 9.01 (d, J=4.03 Hz, 1H), 8.71 (d, J=8.19 Hz, 1H), 8.17 (d, J=8.07 Hz, 1H), 7.70 (dd, J=4.22, 8.62 Hz, 1H), 7.33 (d, J=7.95 Hz, 1H), 7.03 (d, J=8.19 Hz, 1H), 6.75 (s, 1H), 6.59 (br d, J=8.07 Hz, 1H), 4.77-5.02 (m, 1H), 4.24 (d, J=12.23 Hz, 1H), 4.06 (br d, J=10.27 Hz, 1H), 3.89-4.00 (m, 1H), 3.85 (br d, J=11.13 Hz, 1H), 3.66 (br d, J=11.86 Hz, 1H), 3.41-3.52 (m, 2H), 2.93-3.17 (m, 3H), 2.85 (t, J=11.13 Hz, 1H), 2.75 (dd, J=4.28, 11.98 Hz, 1H), 1.27 (d, J=6.36 Hz, 3H).

Example 32

5-[(4R,10bS)-8-[[(3R,4S)-4-fluoropyrrolidin-3-yl]amino]-4-methyl-3,4,6,10b-tetrahydro-1H-pyrazino[2,1-a]isoindol-2-yl]quinoline-8-carbonitrile

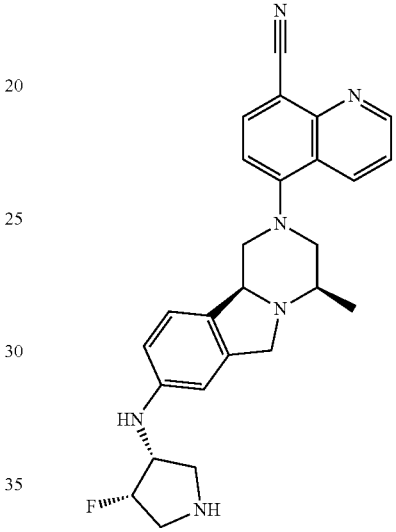

The title compound was prepared in analogy to the preparation of Example 10 by using tert-butyl (3R,4S)-3-amino-4-fluoropyrrolidine-1-carboxylate (CAS: 1009075-48-2, PharmaBlock, Catalog: PB07375) instead of tert-butyl (3R)-3-(hydroxymethyl)piperazine-1-carboxylate. Example 32 (26 mg) was obtained. MS: calc'd 443 [(M+H)+], measured 443 [(M+H)+]. ¹H NMR (400 MHz, METHANOL-d₄) δ ppm 9.00 (dd, J=1.28, 4.22 Hz, 1H), 8.72 (dd, J=1.6, 8.6 Hz, 1H), 8.16 (d, J=8.07 Hz, 1H), 7.69 (dd, J=4.28, 8.56 Hz, 1H), 7.32 (d, J=8.07 Hz, 1H), 7.01 (d, J=8.07 Hz, 1H), 6.80 (s, 1H), 6.63 (br d, J=8.07 Hz, 1H), 5.00-5.22 (m, 1H), 4.22 (d, J=12.23 Hz, 1H), 3.89-4.09 (m, 2H), 3.84 (br d, J=11.37 Hz, 1H), 3.64 (br d, J=11.86 Hz, 1H), 3.43 (br d, J=11.49 Hz, 1H), 3.12 (t, J=13.51 Hz, 1H), 2.94-3.04 (m, 1H), 2.84 (t, J=11.13 Hz, 1H), 2.71 (t, J=10.27 Hz, 1H), 1.25 (d, J=6.48 Hz, 3H).

Example 33

5-[(4R,10bS)-8-[[(3R,4R)-4-fluoropyrrolidin-3-yl]amino]-4-methyl-3,4,6,10b-tetrahydro-1H-pyrazino[2,1-a]isoindol-2-yl]quinoline-8-carbonitrile

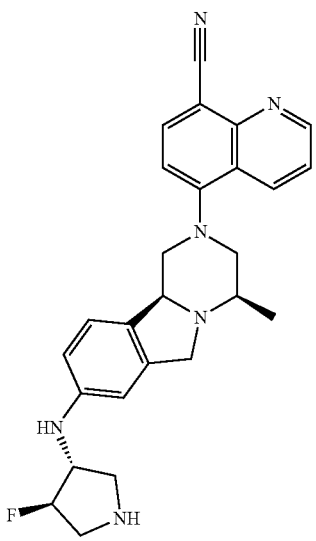 [SMILES: C[C@@H]1CN(c2ccc(C#N)c3ncccc23)C[C@@H]2c3ccc(N[C@@H]4CNC[C@H]4F)cc3CN12]

The title compound was prepared in analogy to the preparation of Example 10 by using tert-butyl (3R,4R)-3-amino-4-fluoropyrrolidine-1-carboxylate (CAS: 1441392-27-3, PharmaBlock, Catalog: PB07377) instead of tert-butyl (3R)-3-(hydroxymethyl)piperazine-1-carboxylate. Example 33 (38 mg) was obtained. MS: calc'd 443 [(M+H)$^+$], measured 443 [(M+H)$^+$]. $^1$H NMR (400 MHz, METHANOL-d$_4$) δ ppm 8.99 (dd, J=1.59, 4.16 Hz, 1H), 8.70 (dd, J=1.65, 8.62 Hz, 1H), 8.15 (d, J=7.95 Hz, 1H), 7.68 (dd, J=4.28, 8.56 Hz, 1H), 7.31 (d, J=8.19 Hz, 1H), 7.02 (d, J=8.19 Hz, 1H), 6.73 (d, J=1.59 Hz, 1H), 6.57 (dd, J=1.96, 8.07 Hz, 1H), 4.77-5.02 (m, 1H), 4.22 (d, J=12.35 Hz, 1H), 4.04 (br d, J=10.39 Hz, 1H), 3.93 (td, J=5.64, 18.43 Hz, 1H), 3.83 (br d, J=10.88 Hz, 1H), 3.63 (br d, J=11.98 Hz, 1H), 3.36-3.49 (m, 2H), 2.91-3.17 (m, 3H), 2.77-2.88 (m, 1H), 2.73 (dd, J=4.40, 12.10 Hz, 1H), 1.25 (d, J=6.36 Hz, 3H).

Example 34

5-[(4R,10bS)-8-[[(3R,4R)-4-methoxypyrrolidin-3-yl]amino]-4-methyl-3,4,6,10b-tetrahydro-1H-pyrazino[2,1-a]isoindol-2-yl]quinoline-8-carbonitrile

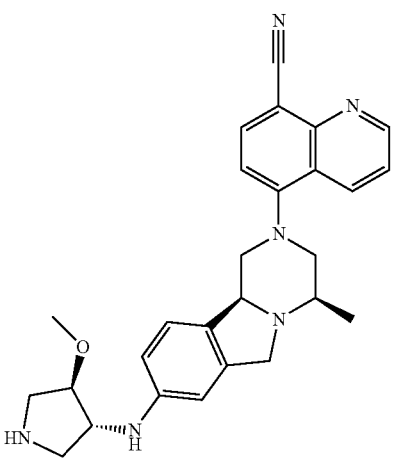 [SMILES: CO[C@@H]1CNC[C@H]1Nc1ccc2c(c1)CN1[C@H](C)CN(c3ccc(C#N)c4ncccc34)C[C@H]21]

The title compound was prepared in analogy to the preparation of Example 10 by using tert-butyl (3R,4R)-3-amino-4-methoxypyrrolidine-1-carboxylate (CAS: 1400562-12-0, PharmaBlock, Catalog: PBXA3109) instead of tert-butyl (3R)-3-(hydroxymethyl)piperazine-1-carboxylate. Example 34 (46 mg) was obtained. MS: calc'd 455 [(M+H)$^+$], measured 455 [(M+H)$^+$]. $^1$H NMR (400 MHz, METHANOL-d$_4$) δ ppm 8.69 (dd, J=1.59, 8.56 Hz, 1H), 8.14 (d, J=7.95 Hz, 1H), 7.67 (dd, J=4.28, 8.56 Hz, 1H), 7.30 (d, J=8.07 Hz, 1H), 7.00 (d, J=8.07 Hz, 1H), 6.71 (d, J=1.59 Hz, 1H), 6.55 (dd, J=2.02, 8.13 Hz, 1H), 4.20 (d, J=12.10 Hz, 1H), 4.03 (br d, J=10.15 Hz, 1H), 3.83 (br d, J=11.25 Hz, 1H), 3.74-3.79 (m, 1H), 3.66-3.71 (m, 1H), 3.63 (br d, J=11.86 Hz, 1H), 3.39-3.46 (m, 1H), 3.35 (s, 3H), 3.27-3.31 (m, 1H), 2.90-3.04 (m, 3H), 2.82 (dd, J=10.45, 11.68 Hz, 1H), 2.67 (dd, J=3.91, 11.98 Hz, 1H), 1.24 (d, J=6.48 Hz, 3H).

Example 35

5-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]quinoline-8-carbonitrile

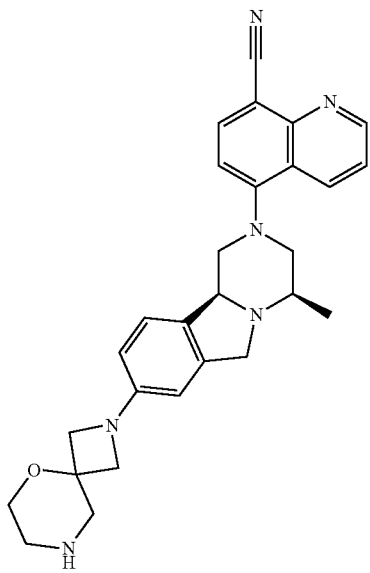 [SMILES: C[C@@H]1CN(c2ccc(C#N)c3ncccc23)C[C@@H]2c3ccc(N4CC5(CNCCO5)C4)cc3CN12]

The title compound was prepared in analogy to the preparation of Example 10 by using tert-butyl 5-oxa-2,8-diazaspiro[3.5]nonane-8-carboxylate (CAS: 1251005-61-4, PharmaBlock, Catalog: PBN20111065-5G) instead of tert-butyl (3R)-3-(hydroxymethyl)piperazine-1-carboxylate. Example 35 (16 mg) was obtained. MS: calc'd 467 [(M+H)$^+$], measured 467 [(M+H)$^+$]. $^1$H NMR (400 MHz, METHANOL-$d_4$) δ ppm 8.89 (dd, J=1.7, 4.2 Hz, 1H), 8.61 (dd, J=1.6, 8.6 Hz, 1H), 8.06 (d, J=8.1 Hz, 1H), 7.57 (dd, J=4.2, 8.5 Hz, 1H), 7.22 (d, J=8.1 Hz, 1H), 6.98 (d, J=7.9 Hz, 1H), 6.48 (d, J=1.3 Hz, 1H), 6.29 (dd, J=2.0, 7.9 Hz, 1H), 4.15 (d, J=12.3 Hz, 1H), 3.97 (br d, J=10.5 Hz, 1H), 3.69-3.84 (m, 3H), 3.44-3.61 (m, 5H), 3.34 (br d, J=11.6 Hz, 1H), 3.23-3.28 (m, 1H), 2.84-2.96 (m, 3H), 2.67-2.78 (m, 3H), 1.16 (d, J=6.4 Hz, 3H).

Example 36

5-[(4R,10bS)-8-(2,6-diazaspiro[3.3]heptan-2-yl)-4-methyl-3,4,6,10b-tetrahydro-1H-pyrazino[2,1-a]isoindol-2-yl]quinoline-8-carbonitrile

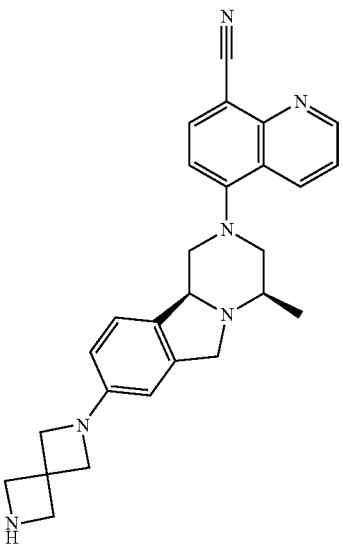 [SMILES: C[C@@H]1CN(c2ccc(C#N)c3ncccc23)C[C@@H]2c3ccc(N4CC5(CNC5)C4)cc3CN12]

The title compound was prepared in analogy to the preparation of Example 10 by using tert-butyl 2,6-diazaspiro[3.3]heptane-2-carboxylate oxalate (CAS: 1041026-70-3, PharmaBlock, Catalog: PB03883-1G) instead of tert-butyl (3R)-3-(hydroxymethyl)piperazine-1-carboxylate. Example 36 (19.2 mg) was obtained. MS: calc'd 437 [(M+H)$^+$], measured 437 [(M+H)$^+$]. $^1$H NMR (400 MHz, METHANOL-$d_4$) δ ppm 9.01 (dd, J=1.5, 4.2 Hz, 1H), 8.71 (dd, J=1.3, 8.6 Hz, 1H), 8.17 (d, J=7.9 Hz, 1H), 7.70 (dd, J=4.3, 8.6 Hz, 1H), 7.33 (d, J=8.1 Hz, 1H), 7.07 (d, J=8.1 Hz, 1H), 6.55 (s, 1H), 6.37 (dd, J=1.7, 7.9 Hz, 1H), 4.25 (d, J=12.3 Hz, 1H), 4.06 (br d, J=10.1 Hz, 1H), 3.92 (s, 4H), 3.78-3.88 (m, 1H), 3.77 (s, 4H), 3.65 (br d, J=12.5 Hz, 1H), 3.34-3.48 (m, 2H), 2.99 (t, J=10.9 Hz, 1H), 2.84 (br t, J=11.1 Hz, 1H), 1.27 (d, J=6.4 Hz, 3H).

83

Example 37

5-[(4R,10bS)-8-(1,6-diazaspiro[3.3]heptan-6-yl)-4-methyl-3,4,6,10b-tetrahydro-1H-pyrazino[2,1-a]isoindol-2-yl]quinoline-8-carbonitrile

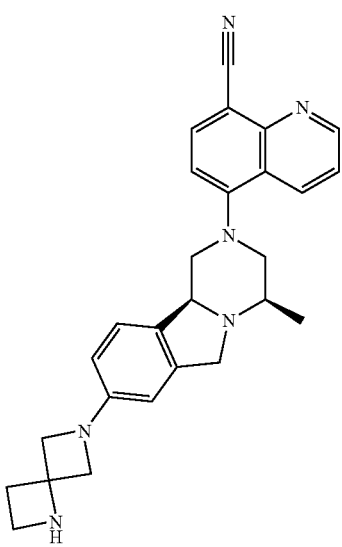 [SMILES: C[C@@H]1CN(c2ccc(C#N)c3ncccc23)C[C@@H]2c3ccc(N4CC5(CCN5)C4)cc3CN12]

The title compound was prepared in analogy to the preparation of Example 10 by using tert-butyl 1,6-diazaspiro[3.3]heptane-1-carboxylate (CAS: 1330763-95-5, PharmaBlock, Catalog: PBN2011926-1G) instead of tert-butyl (3R)-3-(hydroxymethyl)piperazine-1-carboxylate. Example 37 (8.8 mg) was obtained. MS: calc'd 437 [(M+H)$^+$], measured 437 [(M+H)$^+$]. $^1$H NMR (400 MHz, METHANOL-d$_4$) δ ppm 9.03 (dd, J=1.7, 4.2 Hz, 1H), 8.75 (dd, J=1.6, 8.6 Hz, 1H), 8.18 (d, J=8.1 Hz, 1H), 7.71 (dd, J=4.3, 8.6 Hz, 1H), 7.36 (d, J=8.1 Hz, 1H), 7.22 (d, J=8.2 Hz, 1H), 6.66 (d, J=1.7 Hz, 1H), 6.49 (dd, J=2.1, 8.1 Hz, 1H), 4.50-4.64 (m, 2H), 4.35 (d, J=10.0 Hz, 2H), 4.13 (d, J=9.7 Hz, 2H), 4.08 (br d, J=12.7 Hz, 1H), 3.95-4.03 (m, 2H), 3.86-3.93 (m, 1H), 3.71-3.80 (m, 1H), 3.52-3.59 (m, 1H), 2.98-3.11 (m, 2H), 2.79-2.91 (m, 2H), 1.39 (d, J=6.6 Hz, 3H).

84

Example 38

5-[(4R,10bS)-4-methyl-8-(6-methyl-2,6-diazaspiro[3.3]heptan-2-yl)-3,4,6,10b-tetrahydro-1H-pyrazino[2,1-a]isoindol-2-yl]quinoline-8-carbonitrile

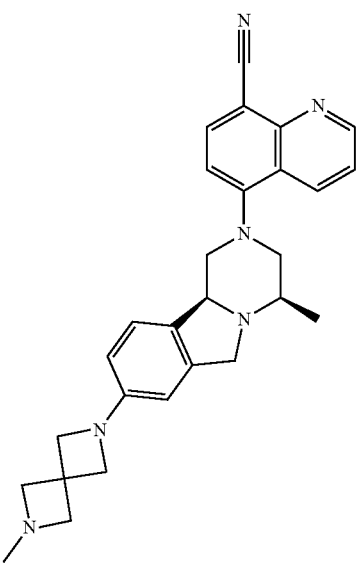 [SMILES: C[C@@H]1CN(c2ccc(C#N)c3ncccc23)C[C@@H]2c3ccc(N4CC5(CN(C)C5)C4)cc3CN12]

The title compound was prepared in analogy to the preparation of Example 10 by using 2-methyl-2,6-diazaspiro[3.3]heptane (CAS: 1203567-11-6, PharmaBlock, Catalog: PBLJ2831) instead of tert-butyl (3R)-3-(hydroxymethyl)piperazine-1-carboxylate. Example 38 (16.0 mg) was obtained. MS: calc'd 451 [(M+H)$^+$], measured 451 [(M+H)$^+$]. $^1$H NMR (400 MHz, METHANOL-d$_4$) δ ppm 9.06 (dd, J=1.6, 4.3 Hz, 1H), 8.80 (dd, J=1.5, 8.6 Hz, 1H), 8.21 (d, J=7.9 Hz, 1H), 7.75 (dd, J=4.3, 8.6 Hz, 1H), 7.35-7.47 (m, 2H), 7.19 (s, 1H), 7.08 (dd, J=2.2, 8.4 Hz, 1H), 5.24-5.36 (m, 1H), 4.94 (d, J=13.8 Hz, 1H), 4.64 (br d, J=13.7 Hz, 1H), 4.26-4.41 (m, 1H), 4.15 (s, 2H), 3.78-3.86 (m, 2H), 3.55-3.73 (m, 3H), 3.26-3.32 (m, 5H), 2.78 (s, 3H), 1.56 (d, J=6.7 Hz, 3H).

Example 39

5-[(4R,10bS)-8-(3-amino-3-methyl-azetidin-1-yl)-4-methyl-3,4,6,10b-tetrahydro-1H-pyrazino[2,1-a]isoindol-2-yl]quinoline-8-carbonitrile

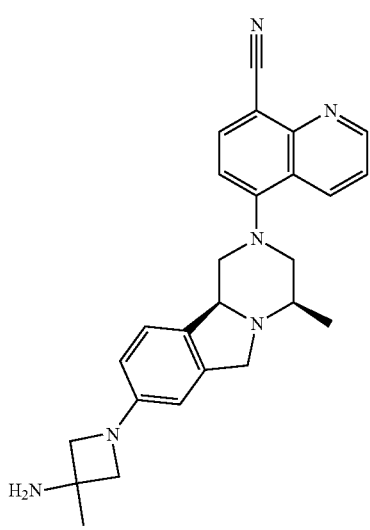 [SMILES: C[C@@H]1CN(c2ccc(C#N)c3ncccc23)C[C@@H]2c3ccc(N4CC(C)(N)C4)cc3CN12]

The title compound was prepared in analogy to the preparation of Example 10 by using tert-butyl N-(3-methylazetidin-3-yl)carbamate (CAS: 1018443-01-0, PharmaBlock, Catalog: PB03046) instead of tert-butyl (3R)-3-(hydroxymethyl)-piperazine-1-carboxylate. Example 39 (30 mg) was obtained. MS: calc'd 425 [(M+H)$^+$], measured 425 [(M+H)$^+$]. $^1$H NMR (400 MHz, METHANOL-d$_4$) δ ppm 9.04 (dd, J=1.6, 4.3 Hz, 1H), 8.76 (dd, J=1.6, 8.6 Hz, 1H), 8.18 (d, J=7.9 Hz, 1H), 7.71 (dd, J=4.3, 8.6 Hz, 1H), 7.37 (d, J=8.1 Hz, 1H), 7.25 (d, J=8.1 Hz, 1H), 6.66 (d, J=1.7 Hz, 1H), 6.51 (dd, J=2.1, 8.1 Hz, 1H), 4.73-4.81 (m, 1H), 4.64 (d, J=13.2 Hz, 1H), 4.22 (d, J=13.1 Hz, 1H), 3.99-4.09 (m, 2H), 3.87-3.97 (m, 4H), 3.53-3.65 (m, 1H), 3.02-3.16 (m, 2H), 1.70 (s, 3H), 1.43 (d, J=6.6 Hz, 3H).

Example 40A and 40B

5-[(4R,10bS)-8-[(3S,4S)-3-amino-4-hydroxy-pyrrolidin-1-yl]-4-methyl-3,4,6,10b-tetrahydro-1H-pyrazino[2,1-a]isoindol-2-yl]quinoline-8-carbonitrile and 5-[(4R,10bS)-8-[(3R,4R)-3-amino-4-hydroxy-pyrrolidin-1-yl]-4-methyl-3,4,6,10b-tetrahydro-1H-pyrazino[2,1-a]isoindol-2-yl]quinoline-8-carbonitrile

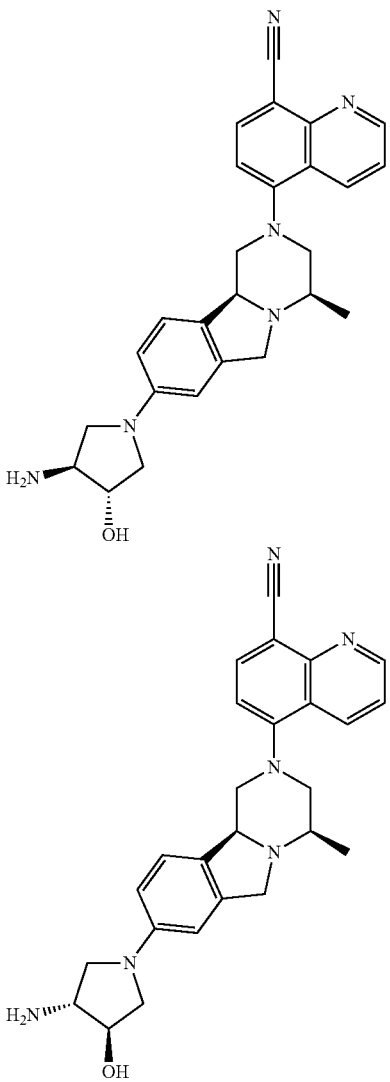

The title compound was prepared in analogy to the preparation of Example 16A and 16B by using trans-3-(boc-amino)-4-hydroxypyrrolidine (CAS: 870632-89-6, PharmaBlock, Catalog: PB07572) instead of trans-3-(boc-amino)-4-methoxypyrrolidine. Example 40A (38 mg) was obtained. MS: calc'd 441 [(M+H)$^+$], measured 441 [(M+H)$^+$]. $^1$H NMR (400 MHz, METHANOL-d$_4$) δ ppm 9.07 (dd, J=1.3, 4.1 Hz, 1H), 8.79 (d, J=8.3 Hz, 1H), 8.21 (d, J=8.2 Hz, 1H), 7.75 (dd, J=4.3, 8.6 Hz, 1H), 7.30-7.48 (m, 2H), 6.82 (s, 1H), 6.71 (dd, J=1.5, 8.3 Hz, 1H), 5.14-5.40 (m, 1H), 4.89-4.96

(m, 2H), 4.55-4.66 (m, 1H), 4.43-4.51 (m, 1H), 4.20-4.37 (m, 1H), 3.74-3.89 (m, 4H), 3.42-3.52 (m, 2H), 3.15-3.29 (m, 2H), 1.55 (d, J=6.7 Hz, 3H). Example 40B (40 mg) was obtained. MS: calc'd 441 [(M+H)$^+$], measured 441 [(M+H)$^+$]. $^1$H NMR (400 MHz, METHANOL-d$_4$) δ ppm 9.07 (dd, J=1.3, 4.1 Hz, 1H), 8.79 (d, J=8.3 Hz, 1H), 8.21 (d, J=8.2 Hz, 1H), 7.75 (dd, J=4.3, 8.6 Hz, 1H), 7.30-7.48 (m, 2H), 6.82 (s, 1H), 6.71 (dd, J=1.5, 8.3 Hz, 1H), 5.14-5.40 (m, 1H), 4.89-4.96 (m, 2H), 4.55-4.66 (m, 1H), 4.43-4.51 (m, 1H), 4.20-4.37 (m, 1H), 3.74-3.89 (m, 4H), 3.42-3.52 (m, 2H), 3.15-3.29 (m, 2H), 1.55 (d, J=6.7 Hz, 3H).

Example 41

5-[(4R,10bS)-8-(3a-methoxy-1,2,3,4,6,6a-hexahydropyrrolo[3,4-c]pyrrol-5-yl)-4-methyl-3,4,6,10b-tetrahydro-1H-pyrazino[2,1-a]isoindol-2-yl]quinoline-8-carbonitrile

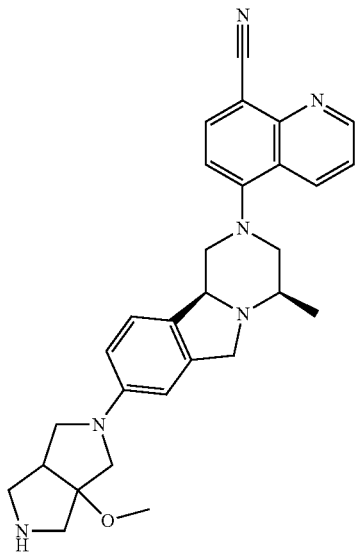 [SMILES: COC12CNCC1CN(c1ccc3c(c1)CN1[C@H](C)CN(c4ccc(C#N)c5ncccc45)C[C@H]31)C2]

The title compound was prepared in analogy to the preparation of Example 10 by using tert-butyl 3a-methoxy-1,2,3,4,6,6a-hexahydropyrrolo[3,4-c]pyrrole-5-carboxylate instead of tert-butyl (3R)-3-(hydroxymethyl)piperazine-1-carboxylate. Example 41 (8.8 mg) was obtained. MS: calc'd 481 [(M+H)$^+$], measured 481 [(M+H)$^+$]. $^1$H NMR (400 MHz, METHANOL-d$_4$) δ ppm 9.07 (dd, J=1.6, 4.3 Hz, 1H), 8.80 (br d, J=8.3 Hz, 1H), 8.21 (br d, J=7.8 Hz, 1H), 7.75 (dd, J=4.3, 8.6 Hz, 1H), 7.23-7.49 (m, 2H), 6.75 (s, 1H), 6.65 (dd, J=2.0, 8.4 Hz, 1H), 5.13-5.36 (m, 1H), 4.90-4.96 (m, 1H), 4.49-4.65 (m, 1H), 4.23-4.39 (m, 1H), 3.74-3.83 (m, 2H), 3.57-3.68 (m, 1H), 3.47-3.56 (m, 2H), 3.23-3.43 (m, 9H), 2.91-3.06 (m, 2H), 1.55 (d, J=6.7 Hz, 3H).

Example 42

5-[(4R,10bS)-8-[(3S,4S)-3-hydroxy-4-(methylamino)pyrrolidin-1-yl]-4-methyl-3,4,6,10b-tetrahydro-1H-pyrazino[2,1-a]isoindol-2-yl]quinoline-8-carbonitrile

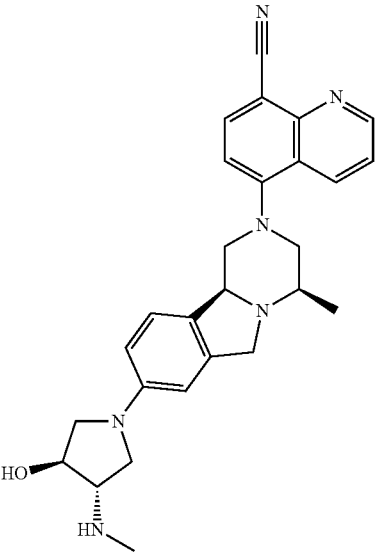 [SMILES: CN[C@H]1CN(c2ccc3c(c2)CN2[C@H](C)CN(c4ccc(C#N)c5ncccc45)C[C@H]32)C[C@@H]1O]

The title compound was prepared in analogy to the preparation of Example 10 by using tert-butyl N-[(3S,4S)-4-hydroxypyrrolidin-3-yl]-N-methyl-carbamate instead of tert-butyl (3R)-3-(hydroxymethyl)piperazine-1-carboxylate. Example 42 (46 mg) was obtained. MS: calc'd 455 [(M+H)$^+$], measured 455 [(M+H)$^+$]. $^1$H NMR (400 MHz, METHANOL-d$_4$) δ ppm 9.04 (dd, J=1.7, 4.2 Hz, 1H), 8.76 (dd, J=1.6, 8.6 Hz, 1H), 8.19 (d, J=7.9 Hz, 1H), 7.72 (dd, J=4.2, 8.6 Hz, 1H), 7.37 (d, J=8.1 Hz, 1H), 7.27 (d, J=8.2 Hz, 1H), 6.79 (d, J=1.7 Hz, 1H), 6.65 (dd, J=2.2, 8.4 Hz, 1H), 4.75-4.86 (m, 1H), 4.67 (d, J=13.2 Hz, 1H), 4.55-4.62 (m, 1H), 4.26 (d, J=13.2 Hz, 1H), 3.88-4.02 (m, 2H), 3.69-3.86 (m, 3H), 3.51-3.64 (m, 2H), 3.20-3.28 (m, 1H), 3.04-3.17 (m, 2H), 2.88 (s, 3H), 1.45 (d, J=6.6 Hz, 3H).

Example 43

5-[(4R,10bS)-4-methyl-8-[(3R,4R)-3-hydroxy-4-(methylamino)pyrrolidin-1-yl]-3,4,6,10b-tetrahydro-1H-pyrazino[2,1-a]isoindol-2-yl]quinoline-8-carbonitrile

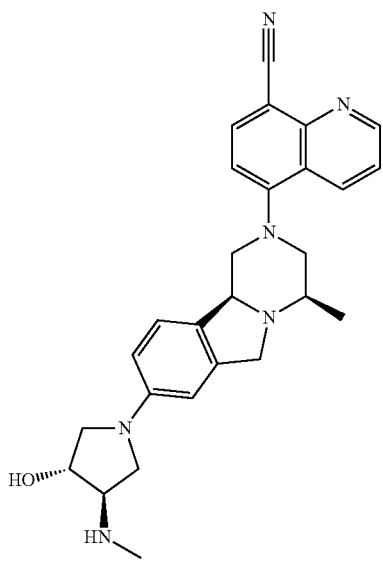 [SMILES: CN[C@@H]1CN(c2ccc3c(c2)CN2[C@H](C)CN(c4ccc(C#N)c5ncccc45)C[C@H]32)C[C@H]1O]

The title compound was prepared in analogy to the preparation of Example 10 by using tert-butyl N-[(3S,4S)-4-hydroxypyrrolidin-3-yl]-N-methyl-carbamate instead of tert-butyl (3R)-3-(hydroxymethyl)piperazine-1-carboxylate. Example 43 (45 mg) was obtained. MS: calc'd 455 [(M+H)$^+$], measured 455 [(M+H)$^+$]. $^1$H NMR (400 MHz, METHANOL-d$_4$) δ ppm 9.04 (dd, J=1.6, 4.3 Hz, 1H), 8.76 (dd, J=1.6, 8.6 Hz, 1H), 8.18 (d, J=7.9 Hz, 1H), 7.72 (dd, J=4.2, 8.6 Hz, 1H), 7.37 (d, J=7.9 Hz, 1H), 7.28 (d, J=8.3 Hz, 1H), 6.79 (d, J=1.8 Hz, 1H), 6.65 (dd, J=2.1, 8.4 Hz, 1H), 4.82-4.90 (m, 1H), 4.66-4.75 (m, 1H), 4.55-4.64 (m, 1H), 4.31 (d, J=13.2 Hz, 1H), 3.95-4.09 (m, 1H), 3.88-3.94 (m, 1H), 3.69-3.86 (m, 3H), 3.52-3.63 (m, 2H), 3.22-3.28 (m, 1H), 3.04-3.20 (m, 2H), 2.88 (s, 3H), 1.46 (d, J=6.7 Hz, 3H).

Example 44

5-[(4R,10bS)-4-methyl-8-[(4aR,7aR)-3,4,4a,5,7,7a-hexahydro-2H-pyrrolo[3,4-b][1,4]oxazin-6-yl]-3,4,6,10b-tetrahydro-1H-pyrazino[2,1-a]isoindol-2-yl]quinoline-8-carbonitrile

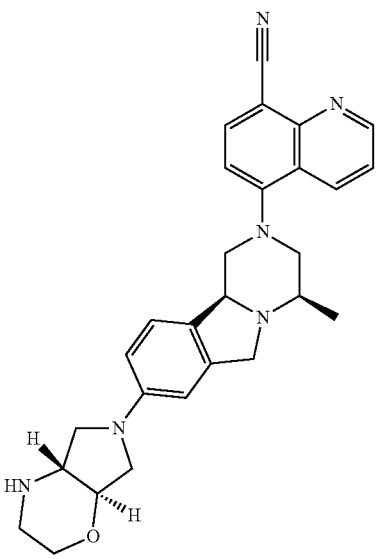 [SMILES: C[C@@H]1CN(c2ccc(C#N)c3ncccc23)C[C@@H]2c3ccc(N4C[C@H]5NCCO[C@@H]5C4)cc3CN12]

The title compound was prepared in analogy to the preparation of Example 10 by using tert-butyl-(4aR,7aR)-3,4a,5,6,7,7a-hexahydro-2H-pyrrolo[3,4-b][1,4]oxazine-4-carboxylate instead of tert-butyl (3R)-3-(hydroxymethyl)piperazine-1-carboxylate. Example 44 (8.8 mg) was obtained. MS: calc'd 467 [(M+H)$^+$], measured 467 [(M+H)$^+$]. $^1$H NMR (400 MHz, METHANOL-d$_4$) δ ppm 9.03 (dd, J=1.6, 4.3 Hz, 1H), 8.75 (dd, J=1.7, 8.6 Hz, 1H), 8.18 (d, J=7.9 Hz, 1H), 7.71 (dd, J=4.2, 8.6 Hz, 1H), 7.36 (d, J=8.1 Hz, 1H), 7.21 (d, J=8.3 Hz, 1H), 6.70 (d, J=1.6 Hz, 1H), 6.54 (dd, J=2.0, 8.3 Hz, 1H), 4.47-4.68 (m, 2H), 4.15-4.25 (m, 1H), 4.11 (d, J=13.2 Hz, 1H), 3.86-4.03 (m, 3H), 3.74-3.84 (m, 1H), 3.64-3.73 (m, 2H), 3.52-3.60 (m, 1H), 3.38-3.47 (m, 1H), 3.23-3.37 (m, 4H), 2.95-3.12 (m, 2H), 1.40 (d, J=6.5 Hz, 3H).

Example 45

5-[(4R,10bS)-4-methyl-8-[trans-(3R,4R)-4-amino-3-hydroxy-3-methyl-pyrrolidin-1-yl]-3,4,6,10b-tetrahydro-1H-pyrazino[2,1-a]isoindol-2-yl]quinoline-8-carbonitrile

Example 45A and 45B

5-[(4R,10bS)-8-[(3R,4R)-4-amino-3-hydroxy-3-methyl-pyrrolidin-1-yl]-4-methyl-3,4,6,10b-tetrahydro-1H-pyrazino[2,1-a]isoindol-2-yl]quinoline-8-carbonitrile and 5-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]quinoline-8-carbonitrile

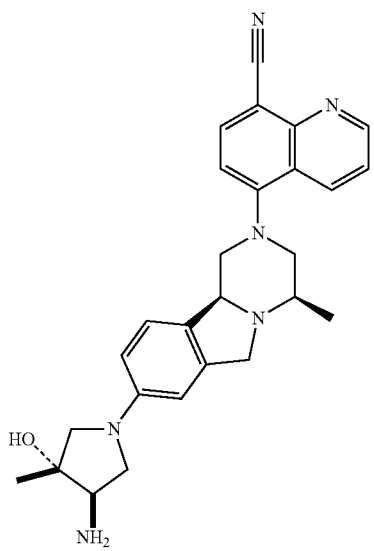 [SMILES: C[C@@H]1CN(c2ccc(C#N)c3ncccc23)C[C@@H]2c3ccc(N4C[C@@H](N)[C@](C)(O)C4)cc3CN12]

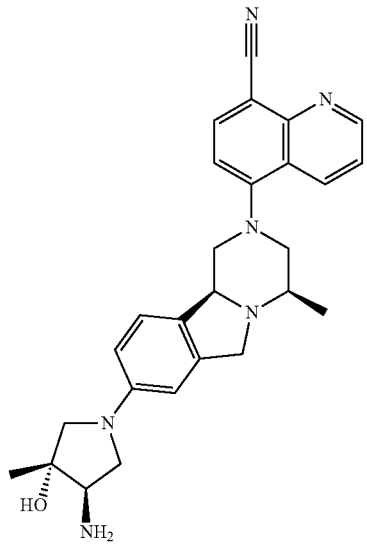

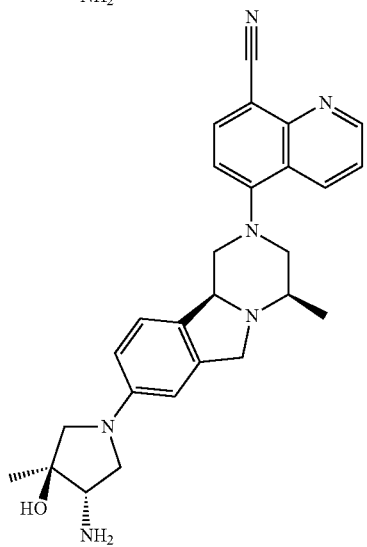

The title compound was prepared in analogy to the preparation of Example 10 by using tert-butyl N-[trans-4-hydroxy-4-methyl-pyrrolidin-3-yl]carbamate instead of tert-butyl (3R)-3-(hydroxymethyl)piperazine-1-carboxylate. Example 45 (26 mg) was obtained. MS: calc'd 455 [(M+H)+], measured 455 [(M+H)+]. ¹H NMR (400 MHz, METHANOL-d₄) δ ppm 9.04 (dd, J=1.6, 4.3 Hz, 1H), 8.76 (dd, J=1.6, 8.6 Hz, 1H), 8.18 (d, J=8.1 Hz, 1H), 7.72 (dd, J=4.3, 8.6 Hz, 1H), 7.37 (d, J=7.9 Hz, 1H), 7.25 (d, J=8.3 Hz, 1H), 6.73 (d, J=1.6 Hz, 1H), 6.59 (dd, J=2.1, 8.3 Hz, 1H), 4.76 (br d, J=7.9 Hz, 1H), 4.64 (d, J=13.1 Hz, 1H), 4.22 (d, J=13.1 Hz, 1H), 3.81-4.02 (m, 3H), 3.67-3.75 (m, 1H), 3.54-3.63 (m, 2H), 3.46-3.51 (m, 1H), 3.38 (d, J=10.4 Hz, 1H), 3.03-3.17 (m, 2H), 1.51 (s, 3H), 1.44 (d, J=6.6 Hz, 3H).

The title compound was prepared in analogy to the preparation of Example 16A and 16B by using tert-butyl N-[trans-4-hydroxy-4-methyl-pyrrolidin-3-yl]carbamate instead of trans-3-(boc-amino)-4-methoxypyrrolidine. Example 45A (18 mg) was obtained. MS: calc'd 455 [(M+H)+], measured 455 [(M+H)+]. ¹H NMR (400 MHz, METHANOL-d₄) δ ppm ¹H NMR (400 MHz, CD3OD, 299 K) δ (ppm) 9.04 (dd, J=1.6, 4.3 Hz, 1H), 8.76 (dd, J=1.6, 8.6 Hz, 1H), 8.18 (d, J=8.1 Hz, 1H), 7.72 (dd, J=4.3, 8.6 Hz, 1H), 7.37 (d, J=7.9 Hz, 1H), 7.25 (d, J=8.3 Hz, 1H), 6.73 (d, J=1.6 Hz, 1H), 6.59 (dd, J=2.1, 8.3 Hz, 1H), 4.76 (br d, J=7.9 Hz, 1H), 4.64 (d, J=13.1 Hz, 1H), 4.22 (d, J=13.1 Hz, 1H), 3.81-4.02 (m, 3H), 3.67-3.75 (m, 1H), 3.54-3.63 (m, 2H), 3.46-3.51 (m, 1H), 3.38 (d, J=10.4 Hz, 1H), 3.03-3.17 (m, 2H), 1.51 (s, 3H), 1.44 (d, J=6.6 Hz, 3H). Example 45B (19 mg) was obtained. MS: calc'd 455 [(M+H)$^+$], measured 455 [(M+H)$^+$]. $^1$H NMR (400 MHz, METHANOL-d$_4$) δ ppm 9.04 (dd, J=1.6, 4.3 Hz, 1H), 8.76 (dd, J=1.7, 8.6 Hz, 1H), 8.19 (d, J=7.9 Hz, 1H), 7.72 (dd, J=4.3, 8.6 Hz, 1H), 7.37 (d, J=8.1 Hz, 1H), 7.26 (d, J=8.3 Hz, 1H), 6.74 (d, J=1.7 Hz, 1H), 6.59 (dd, J=2.2, 8.3 Hz, 1H), 4.76-4.84 (m, 1H), 4.67 (d, J=13.2 Hz, 1H), 4.25 (d, J=13.2 Hz, 1H), 3.83-3.98 (m, 3H), 3.65-3.73 (m, 1H), 3.55-3.64 (m, 2H), 3.46-3.53 (m, 1H), 3.38 (d, J=10.5 Hz, 1H), 3.00-3.20 (m, 2H), 1.51 (s, 3H), 1.45 (d, J=6.6 Hz, 3H).

Example 46

5-[(4R,10bS)-8-[(3S,4R)-3-amino-4-fluoro-pyrrolidin-1-yl]-4-methyl-3,4,6,10b-tetrahydro-1H-pyrazino[2,1-a]isoindol-2-yl]quinoline-8-carbonitrile

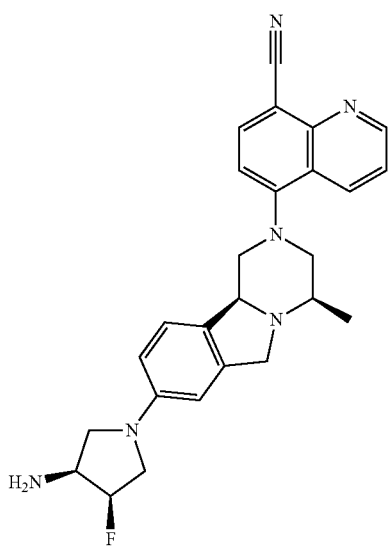

The title compound was prepared in analogy to the preparation of Example 10 by using tert-butyl N-[(3S,4R)-4-fluoropyrrolidin-3-yl]carbamate (CAS: 1033718-89-6, PharmaBlock, Catalog: PB09206) instead of tert-butyl-(3R)-3-(hydroxymethyl)-piperazine-1-carboxylate.
Example 46 (35 mg) was obtained. MS: calc'd 443 [(M+H)$^+$], measured 443 [(M+H)$^+$]. $^1$H NMR (400 MHz, METHANOL-d$_4$) δ ppm 9.05 (dd, J=1.6, 4.3 Hz, 1H), 8.78 (dd, J=1.7, 8.6 Hz, 1H), 8.19 (d, J=8.1 Hz, 1H), 7.73 (dd, J=4.3, 8.6 Hz, 1H), 7.39 (d, J=8.1 Hz, 1H), 7.33 (d, J=8.4 Hz, 1H), 6.80 (d, J=1.8 Hz, 1H), 6.66 (dd, J=2.2, 8.4 Hz, 1H), 5.38-5.63 (m, 1H), 5.05-5.16 (m, 1H), 4.83 (d, J=13.6 Hz, 1H), 4.48 (d, J=13.6 Hz, 1H), 4.12-4.25 (m, 2H), 3.68-3.97 (m, 4H), 3.60-3.66 (m, 1H), 3.44-3.53 (m, 1H), 3.19-3.28 (m, 1H), 3.08-3.17 (m, 1H), 1.51 (d, J=6.7 Hz, 3H).

Example 47

5-[(4R,10bS)-8-[(3R,4S)-3-amino-4-fluoro-pyrrolidin-1-yl]-4-methyl-3,4,6,10b-tetrahydro-1H-pyrazino[2,1-a]isoindol-2-yl]quinoline-8-carbonitrile

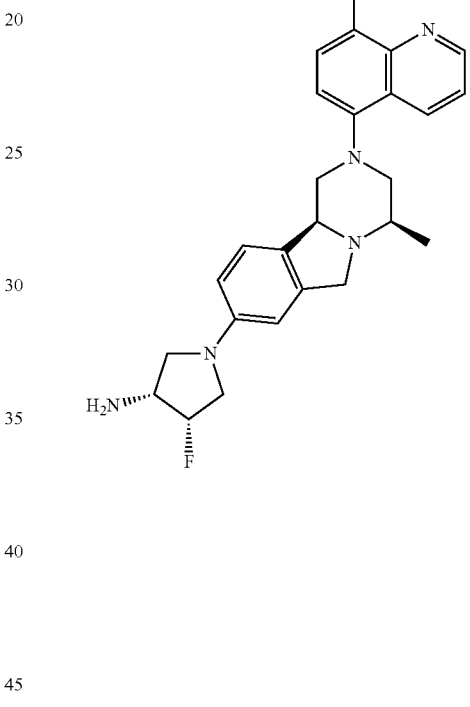

The title compound was prepared in analogy to the preparation of Example 10 by using tert-butyl N-[(3R,4S)-4-fluoropyrrolidin-3-yl]carbamate (CAS: 1033718-91-0, PharmaBlock, Catalog: PB09204) instead of tert-butyl-(3R)-3-(hydroxymethyl)piperazine-1-carboxylate. Example 47 (31 mg) was obtained. MS: calc'd 443 [(M+H)$^+$], measured 443 [(M+H)$^+$]. $^1$H NMR (400 MHz, METHANOL-d$_4$) δ ppm 9.04 (dd, J=1.7, 4.2 Hz, 1H), 8.77 (dd, J=1.7, 8.6 Hz, 1H), 8.19 (d, J=8.1 Hz, 1H), 7.73 (dd, J=4.3, 8.6 Hz, 1H), 7.38 (d, J=7.9 Hz, 1H), 7.30 (d, J=8.4 Hz, 1H), 6.78 (d, J=1.8 Hz, 1H), 6.64 (dd, J=2.2, 8.4 Hz, 1H), 5.38-5.61 (m, 1H), 5.05-5.16 (m, 1H), 4.73 (d, J=13.3 Hz, 1H), 4.33 (d, J=13.2 Hz, 1H), 4.09-4.23 (m, 1H), 3.97-4.07 (m, 1H), 3.65-3.95 (m, 4H), 3.59-3.63 (m, 1H), 3.42-3.53 (m, 1H), 3.04-3.22 (m, 2H), 1.47 (d, J=6.6 Hz, 3H).

Example 48

5-[(4R,10bS)-8-[(3R,4R)-3-amino-4-fluoro-pyrrolidin-1-yl]-4-methyl-3,4,6,10b-tetrahydro-1H-pyrazino[2,1-a]isoindol-2-yl]quinoline-8-carbonitrile

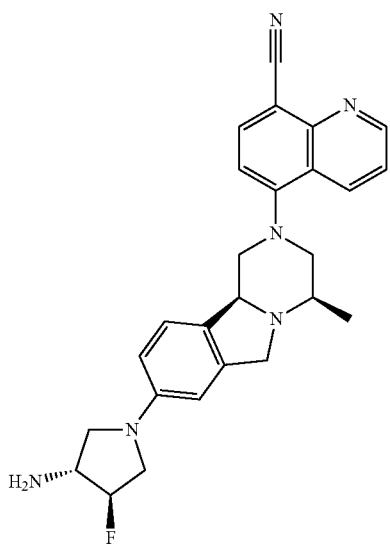

The title compound was prepared in analogy to the preparation of Example 10 by using tert-butyl ((3R,4R)-4-fluoropyrrolidin-3-yl)carbamate hydrochloride (CAS: 2097061-04-4, BePharm, Catalog: BD00765464) instead of tert-butyl (3R)-3-(hydroxymethyl)piperazine-1-carboxylate. Example 48 (8.8 mg) was obtained. MS: calc'd 443 [(M+H)$^+$], measured 443 [(M+H)$^+$]. $^1$H NMR (400 MHz, METHANOL-d$_4$) δ ppm 9.03 (dd, J=1.6, 4.3 Hz, 1H), 8.75 (dd, J=1.6, 8.6 Hz, 1H), 8.18 (d, J=7.9 Hz, 1H), 7.71 (dd, J=4.3, 8.6 Hz, 1H), 7.36 (d, J=7.9 Hz, 1H), 7.26 (d, J=8.2 Hz, 1H), 6.81 (d, J=1.7 Hz, 1H), 6.66 (dd, J=2.1, 8.4 Hz, 1H), 5.28-5.48 (m, 1H), 4.65-4.73 (m, 1H), 4.61 (d, J=13.0 Hz, 1H), 4.06-4.23 (m, 2H), 3.75-4.01 (m, 4H), 3.45-3.67 (m, 3H), 3.01-3.15 (m, 2H), 1.42 (d, J=6.5 Hz, 3H).

Example 49

5-[(4R,10bS)-8-[(3S,4S)-3-amino-4-fluoro-pyrrolidin-1-yl]-4-methyl-3,4,6,10b-tetrahydro-1H-pyrazino[2,1-a]isoindol-2-yl]quinoline-8-carbonitrile

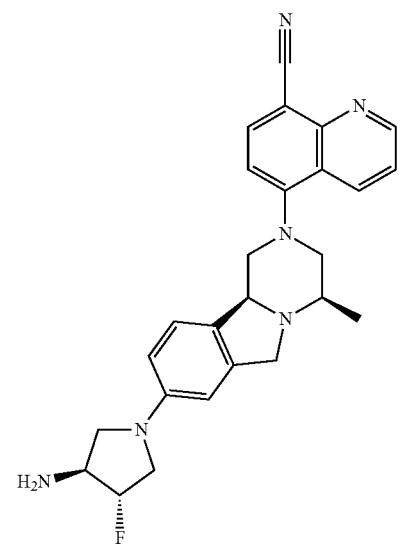

The title compound was prepared in analogy to the preparation of Example 10 by using tert-butyl N-[(3S,4S)-4-fluoropyrrolidin-3-yl]carbamate (CAS: 213388-72-8, PharmaBlock, Catalog: PB09205) instead of tert-butyl (3R)-3-(hydroxymethyl)piperazine-1-carboxylate. Example 49 (58 mg) was obtained. MS: calc'd 443 [(M+H)$^+$], measured 443 [(M+H)$^+$]. $^1$H NMR (400 MHz, METHANOL-d$_4$) δ ppm 9.03 (dd, J=1.6, 4.3 Hz, 1H), 8.75 (dd, J=1.6, 8.6 Hz, 1H), 8.18 (d, J=7.9 Hz, 1H), 7.71 (dd, J=4.3, 8.6 Hz, 1H), 7.36 (d, J=7.9 Hz, 1H), 7.26 (d, J=8.2 Hz, 1H), 6.81 (d, J=1.7 Hz, 1H), 6.66 (dd, J=2.1, 8.4 Hz, 1H), 5.28-5.48 (m, 1H), 4.65-4.73 (m, 1H), 4.61 (d, J=13.0 Hz, 1H), 4.06-4.23 (m, 2H), 3.75-4.01 (m, 4H), 3.45-3.67 (m, 3H), 3.01-3.15 (m, 2H), 1.42 (d, J=6.5 Hz, 3H).

Example 50

5-[(4R,10bS)-8-[(3R)-3-(methoxymethyl)piperazin-1-yl]-4-methyl-3,4,6,10b-tetrahydro-1H-pyrazino[2,1-a]isoindol-2-yl]quinoline-8-carbonitrile

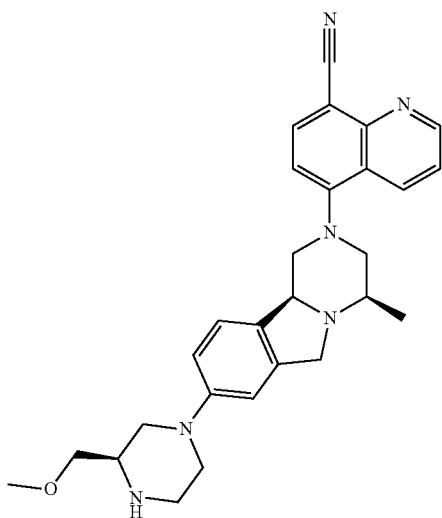

The title compound was prepared in analogy to the preparation of Example 10 by using tert-butyl (2R)-2-(methoxymethyl)piperazine-1-carboxylate (CAS: 1023301-73-6, PharmaBlock, Catalog: PBU12178) instead of tert-butyl (3R)-3-(hydroxymethyl)piperazine-1-carboxylate. Example 50 (5.4 mg) was obtained. MS: calc'd 469 [(M+H)$^+$], measured 469 [(M+H)$^+$]. $^1$H NMR (400 MHz, METHANOL-d$_4$) δ ppm 8.91 (dd, J=1.6, 4.3 Hz, 1H), 8.64 (dd, J=1.7, 8.6 Hz, 1H), 8.05 (d, J=7.9 Hz, 1H), 7.60 (dd, J=4.3, 8.6 Hz, 1H), 7.25 (dd, J=5.3, 8.2 Hz, 2H), 7.08 (d, J=1.8 Hz, 1H), 6.94 (dd, J=2.2, 8.4 Hz, 1H), 4.85-4.91 (m, 2H), 4.65 (d, J=13.4 Hz, 1H), 4.27 (d, J=13.4 Hz, 1H), 3.89-4.01 (m, 1H), 3.78-3.86 (m, 1H), 3.67-3.76 (m, 2H), 3.45-3.64 (m, 4H), 3.36-3.42 (m, 1H), 3.30-3.38 (m, 2H), 3.22-3.26 (m, 1H), 2.85-3.11 (m, 4H), 1.36 (d, J=6.7 Hz, 3H).

Example 51

5-[(4R,10bS)-8-(4-amino-4-methyl-1-piperidyl)-4-methyl-3,4,6,10b-tetrahydro-1H-pyrazino[2,1-a]isoindol-2-yl]quinoline-8-carbonitrile The title compound was prepared in analogy to the preparation of Example 10 by using tert-butyl N-(4-methylpiperidin-4-yl)carbamate (CAS: 163271-08-7, PharmaBlock, Catalog: PB02909) instead of tert-butyl (3R)-3-(hydroxymethyl)piperazine-1-carboxylate. Example 51 (40 mg) was obtained. MS: calc'd 453 [(M+H)$^+$], measured 453 [(M+H)]. $^1$H NMR (400 MHz, METHANOL-d$_4$) δ ppm 9.05 (dd, J=1.6, 4.3 Hz, 1H), 8.79 (dd, J=1.7, 8.6 Hz, 1H), 8.19 (d, J=7.9 Hz, 1H), 7.74 (dd, J=4.3, 8.6 Hz, 1H), 7.38 (dd, J=8.3, 17.4 Hz, 2H), 7.18 (d, J=1.8 Hz, 1H), 7.06 (dd, J=2.2, 8.6 Hz, 1H), 6.94 (dd, J=2.2, 8.4 Hz, 1H), 5.16-5.26 (m, 1H), 4.87 (d, J=13.6 Hz, 1H), 4.58 (d, J=13.6 Hz, 1H), 4.23-4.34 (m, 1H), 3.87-4.00 (m, 1H), 3.55-3.69 (m, 3H), 3.24-3.31 (m, 1H), 3.07-3.21 (m, 3H), 1.79-2.04 (m, 4H), 1.54 (d, J=6.7 Hz, 3H), 1.47 (s, 3H).

Example 52

5-[(4R,10bS)-8-(3,4a,5,6,7,7a-hexahydro-2H-pyrrolo[3,4-b][1,4]oxazin-4-yl)-4-methyl-3,4,6,10b-tetrahydro-1H-pyrazino[2,1-a]isoindol-2-yl]quinoline-8-carbonitrile

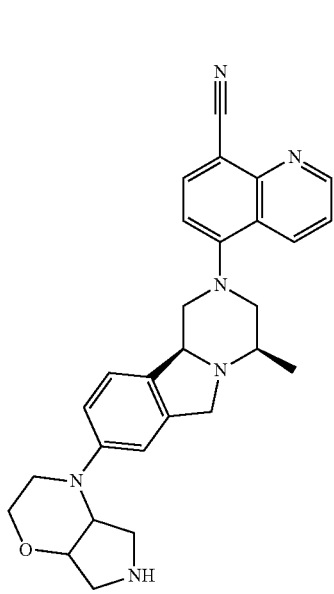

The title compound was prepared in analogy to the preparation of Example 10 by using tert-butyl octahydropyrrolo[3,4-b]morpholine-6-carboxylate (CAS: 1360364-21-1, PharmaBlock, Catalog: PBCS1406244) instead of tert-butyl (3R)-3-(hydroxymethyl)piperazine-1-carboxylate. Example 52 (18 mg) was obtained. MS: calc'd 467 [(M+H)$^+$], measured 467 [(M+H)$^+$]. $^1$H NMR (400 MHz, METHANOL-d$_4$) δ ppm 9.03 (dd, J=1.6, 4.3 Hz, 1H), 8.75 (dd, J=1.6, 8.6 Hz, 1H), 8.18 (d, J=7.9 Hz, 1H), 7.71 (dd, J=4.3, 8.6 Hz, 1H), 7.36 (d, J=8.1 Hz, 1H), 7.33 (d, J=8.1 Hz, 1H), 7.25 (s, 1H), 7.09 (dd, J=1.5, 7.9 Hz, 1H), 4.54 (br d, J=12.7 Hz, 2H), 4.09-4.18 (m, 1H), 4.01-4.08 (m, 1H), 3.89-4.00 (m, 2H), 3.79-3.89 (m, 1H), 3.59-3.74 (m, 3H), 3.51-3.58 (m, 1H), 3.18-3.31 (m, 2H), 2.87-3.13 (m, 5H), 1.38 (d, J=6.4 Hz, 3H).

Example 53A and 53B

5-[(4R,10bS)-8-[(6S)-6-hydroxy-1,4-diazepan-1-yl]-4-methyl-3,4,6,10b-tetrahydro-1H-pyrazino[2,1-a]isoindol-2-yl]quinoline-8-carbonitrile and 5-[(4R,10bS)-8-[(6R)-6-hydroxy-1,4-diazepan-1-yl]-4-methyl-3,4,6,10b-tetrahydro-1H-pyrazino[2,1-a]isoindol-2-yl]quinoline-8-carbonitrile

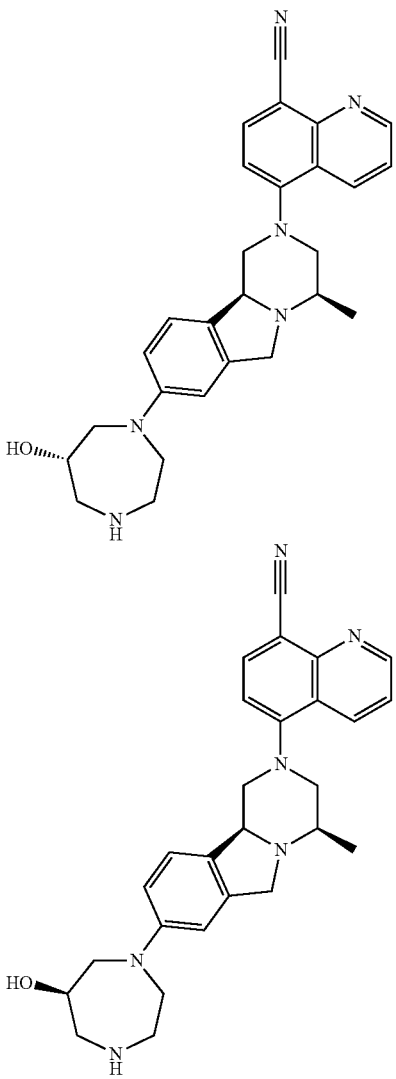

The title compound was prepared in analogy to the preparation of Example 16A and 16B by using tert-butyl 6-hydroxy-1,4-diazepane-1-carboxylate (CAS: 956317-40-1, WUXI APPTEC, Catalog: WX604354) instead of trans-3-(boc-amino)-4-methoxypyrrolidine. Example 53A (19.8 mg) was obtained. MS: calc'd 455 [(M+H)$^+$], measured 455 [(M+H)$^+$]. $^1$H NMR (400 MHz, METHANOL-d$_4$) δ ppm 8.91 (dd, J=1.6, 4.3 Hz, 1H), 8.66 (dd, J=1.5, 8.6 Hz, 1H), 8.05 (d, J=8.1 Hz, 1H), 7.61 (dd, J=4.3, 8.7 Hz, 1H), 7.36-7.17 (m, 2H), 6.94 (d, J=1.3 Hz, 1H), 6.83 (dd, J=2.3, 8.6 Hz, 1H), 5.17 (br d, J=7.7 Hz, 1H), 4.73-4.81 (m, 1H), 4.50 (br d, J=13.7 Hz, 1H), 4.27-4.34 (m, 1H), 4.15-4.26 (m, 1H), 3.70-3.86 (m, 3H), 3.47-3.66 (m, 3H), 3.36-3.45 (m, 1H), 3.13-3.28 (m, 5H), 1.44 (d, J=6.7 Hz, 3H). Example 53B (23.3 mg) was obtained. MS: calc'd 455 [(M+H)+], measured 455 [(M+H)+]. ¹H NMR (400 MHz, METHANOL-d₄) δ ppm 8.91 (dd, J=1.6, 4.2 Hz, 1H), 8.66 (dd, J=1.5, 8.6 Hz, 1H), 8.05 (d, J=7.9 Hz, 1H), 7.61 (dd, J=4.3, 8.6 Hz, 1H), 7.17-7.34 (m, 2H), 6.95 (d, J=1.3 Hz, 1H), 6.83 (dd, J=2.3, 8.6 Hz, 1H), 5.10-5.22 (m, 1H), 4.78-4.82 (m, 1H), 4.50 (br d, J=13.7 Hz, 1H), 4.28-4.35 (m, 1H), 4.14-4.27 (m, 1H), 3.70-3.86 (m, 3H), 3.46-3.66 (m, 3H), 3.35-3.44 (m, 1H), 3.12-3.29 (m, 5H), 1.44 (d, J=6.7 Hz, 3H).

Example 54

5-[(4R,10bS)-8-(6-amino-1,4-oxazepan-4-yl)-4-methyl-3,4,6,10b-tetrahydro-1H-pyrazino[2,1-a]isoindol-2-yl]quinoline-8-carbonitrile

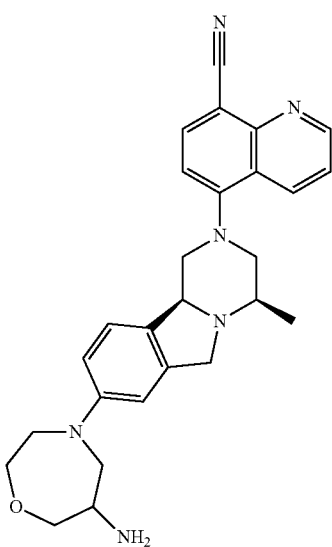

The title compound was prepared in analogy to the preparation of Example 10 by using tert-butyl N-(1,4-oxazepan-6-yl)carbamate (CAS: 1782916-90-8, PharmaBlock, Catalog: PB95734) instead of tert-butyl (3R)-3-(hydroxymethyl)piperazine-1-carboxylate. Example 54 (8.1 mg) was obtained. MS: calc'd 455 [(M+H)+], measured 455 [(M+H)+]. ¹H NMR (400 MHz, METHANOL-d4) δ ppm 9.04 (dd, J=1.6, 4.3 Hz, 1H), 8.77 (dd, J=1.7, 8.6 Hz, 1H), 8.19 (d, J=8.1 Hz, 1H), 7.72 (dd, J=4.3, 8.6 Hz, 1H), 7.37 (d, J=8.1 Hz, 1H), 7.28 (d, J=8.4 Hz, 1H), 7.02 (d, J=2.0 Hz, 1H), 6.87 (dd, J=2.3, 8.4 Hz, 1H), 4.80-4.87 (m, 1H), 4.69 (d, J=13.2 Hz, 1H), 4.28 (d, J=13.1 Hz, 1H), 4.13-4.21 (m, 1H), 3.71-4.08 (m, 7H), 3.45-3.68 (m, 4H), 3.01-3.20 (m, 2H), 1.46 (d, J=6.6 Hz, 3H).

Example 54A and 54B

5-[(4R,10bS)-8-[(6R)-6-amino-1,4-oxazepan-4-yl]-4-methyl-3,4,6,10b-tetrahydro-1H-pyrazino[2,1-a]isoindol-2-yl]quinoline-8-carbonitrile and 5-[(4R,10bS)-8-[(6S)-6-amino-1,4-oxazepan-4-yl]-4-methyl-3,4,6,10b-tetrahydro-1H-pyrazino[2,1-a]isoindol-2-yl]quinoline-8-carbonitrile

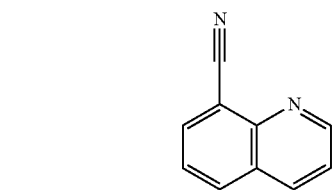
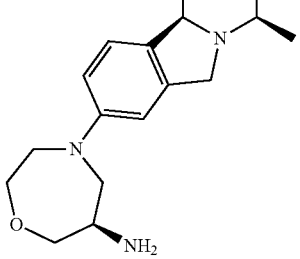
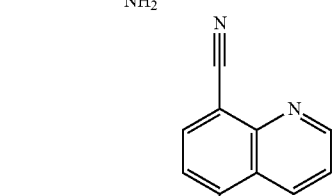
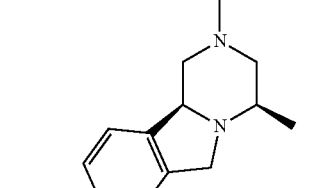
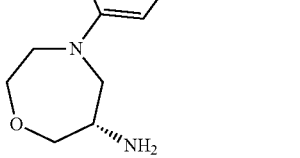

The title compound was prepared in analogy to the preparation of Example 16A and 16B by using tert-butyl N-(1,4-oxazepan-6-yl)carbamate (CAS: 1782916-90-8, PharmaBlock, Catalog: PB95734) instead of trans-3-(boc-amino)-4-methoxypyrrolidine. Example 54A (29 mg) was obtained. MS: calc'd 455 [(M+H)+], measured 455 [(M+H)+]. ¹H NMR (400 MHz, METHANOL-d₄) δ ppm 9.04 (dd, J=1.6, 4.3 Hz, 1H), 8.77 (dd, J=1.7, 8.6 Hz, 1H), 8.19 (d, J=8.1 Hz, 1H), 7.72 (dd, J=4.3, 8.6 Hz, 1H), 7.37 (d, J=8.1 Hz, 1H), 7.28 (d, J=8.4 Hz, 1H), 7.02 (d, J=2.0 Hz, 1H), 6.87 (dd, J=2.3, 8.4 Hz, 1H), 4.80-4.87 (m, 1H), 4.69 (d, J=13.2 Hz, 1H), 4.28 (d, J=13.1 Hz, 1H), 4.13-4.21 (m, 1H), 3.71-4.08 (m, 7H), 3.45-3.68 (m, 4H), 3.01-3.20 (m, 2H), 1.46 (d, J=6.6 Hz, 3H). Example 54B (36 mg) was obtained. MS: calc'd 455 [(M+H)⁺], measured 455 [(M+H)⁺]. ¹H NMR (400 MHz, METHANOL-d₄) δ ppm 9.04 (dd, J=1.6, 4.3 Hz, 1H), 8.77 (dd, J=1.7, 8.6 Hz, 1H), 8.19 (d, J=7.9 Hz, 1H), 7.72 (dd, J=4.2, 8.6 Hz, 1H), 7.38 (d, J=8.1 Hz, 1H), 7.28 (d, J=8.4 Hz, 1H), 7.01 (d, J=2.0 Hz, 1H), 6.86 (dd, J=2.4, 8.5 Hz, 1H), 4.74-4.83 (m, 1H), 4.66 (d, J=13.1 Hz, 1H), 4.25 (d, J=13.2 Hz, 1H), 4.12-4.21 (m, 1H), 3.73-4.08 (m, 7H), 3.45-3.67 (m, 4H), 3.01-3.19 (m, 2H), 1.44 (d, J=6.6 Hz, 3H).

Example 55

5-[(4R,10S)-8-(6-hydroxy-6-methyl-1,4-diazepan-1-yl)-4-methyl-3,4,6,10b-tetrahydro-1H-pyrazino[2,1-a]isoindol-2-yl]quinoline-8-carbonitrile

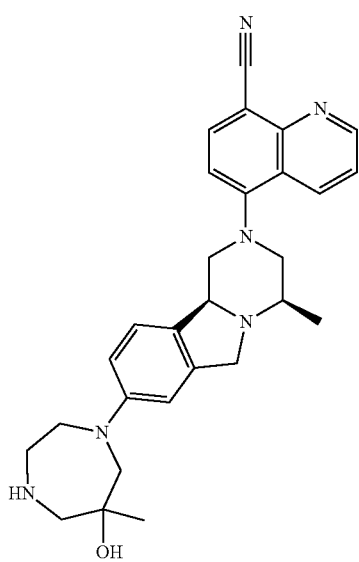

The title compound was prepared in analogy to the preparation of Example 10 by using tert-butyl 6-hydroxy-6-methyl-1,4-diazepane-1-carboxylate (PharmaBlock, Catalog: PB96918) instead of tert-butyl (3R)-3-(hydroxymethyl)piperazine-1-carboxylate. Example 55 (42 mg) was obtained. MS: calc'd 469 [(M+H)⁺], measured 469 [(M+H)⁺]. ¹H NMR (400 MHz, METHANOL-d) δ ppm 9.03 (dd, J=1.7, 4.2 Hz, 1H), 8.73 (dd, J=1.6, 8.6 Hz, 1H), 8.17 (d, J=8.1 Hz, 1H), 7.70 (dd, J=4.2, 8.6 Hz, 1H), 7.33 (d, J=8.1 Hz, 1H), 7.18 (d, J=8.4 Hz, 1H), 7.05 (d, J=1.8 Hz, 1H), 6.88 (dd, J=2.3, 8.4 Hz, 1H), 4.48 (br d, J=12.6 Hz, 2H), 3.96-4.09 (m, 2H), 3.81-3.90 (m, 2H), 3.61-3.73 (m, 3H), 3.49-3.55 (m, 1H), 3.38-3.44 (m, 1H), 3.25-3.33 (m, 2H), 3.10-3.17 (m, 1H), 2.95-3.05 (m, 2H), 1.38 (s, 3H), 1.38 (d, J=6.7 Hz, 3H).

Example 55A and 55B

5-[(4R,10bS)-8-[(6S)-6-hydroxy-6-methyl-1,4-diazepan-1-yl]-4-methyl-3,4,6,10b-tetrahydro-1H-pyrazino[2,1-a]isoindol-2-yl]quinoline-8-carbonitrile and 5-[(4R,10bS)-8-[(6R)-6-hydroxy-6-methyl-1,4-diazepan-1-yl]-4-methyl-3,4,6,10b-tetrahydro-1H-pyrazino[2,1-a]isoindol-2-yl]quinoline-8-carbonitrile

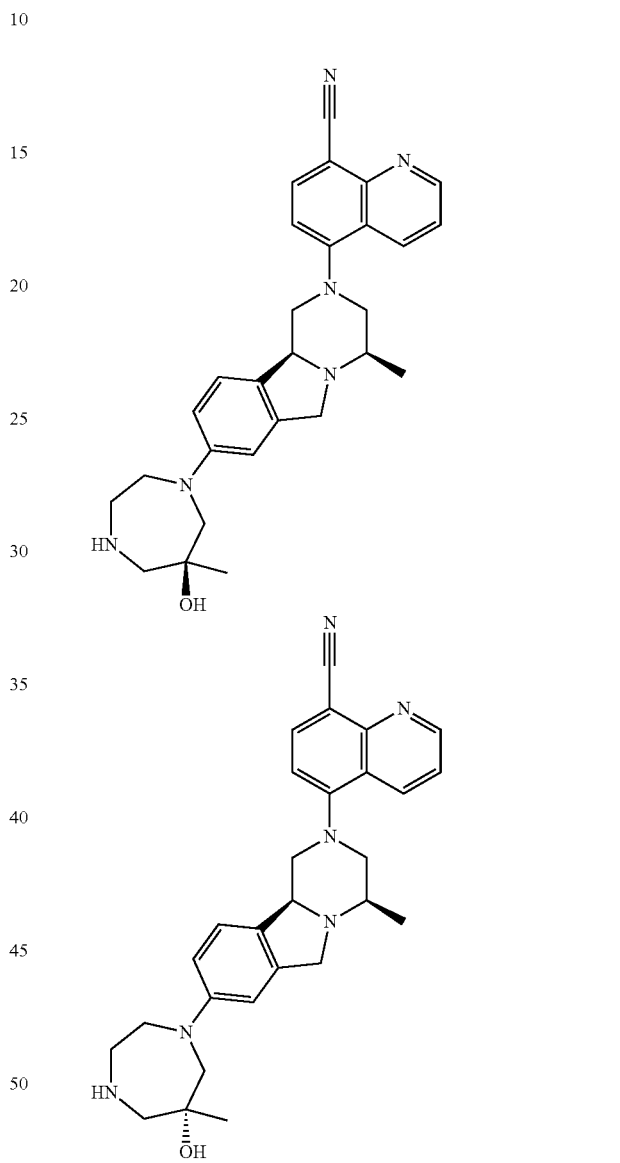

The title compound was prepared in analogy to the preparation of Example 16A and 16B by using tert-butyl 6-hydroxy-6-methyl-1,4-diazepane-1-carboxylate (PharmaBlock, Catalog: PB96918) instead of trans-3-(boc-amino)-4-methoxypyrrolidine. Example 55A (26 mg) was obtained. MS: calc'd 469 [(M+H)⁺], measured 469 [(M+H)⁺]. ¹H NMR (400 MHz, METHANOL-d₄) δ ppm 9.03 (dd, J=1.7, 4.2 Hz, 1H), 8.73 (dd, J=1.6, 8.6 Hz, 1H), 8.17 (d, J=8.1 Hz, 1H), 7.70 (dd, J=4.2, 8.6 Hz, 1H), 7.33 (d, J=8.1 Hz, 1H), 7.18 (d, J=8.4 Hz, 1H), 7.05 (d, J=1.8 Hz, 1H), 6.88 (dd, J=2.3, 8.4 Hz, 1H), 4.48 (br d, J=12.6 Hz, 2H), 3.96-4.09 (m, 2H), 3.81-3.90 (m, 2H), 3.61-3.73 (m, 3H), 3.49-3.55 (m, 1H), 3.38-3.44 (m, 1H), 3.25-3.32 (m, 2H), 3.10-3.17 (m, 1H), 2.95-3.05 (m, 2H), 1.38 (s, 3H), 1.38 (d, J=6.7 Hz, 3H). Example 55B (23.8 mg) was obtained. MS: calc'd 469 [(M+H)+], measured 469 [(M+H)+]. $^1$H NMR (400 MHz, METHANOL-$d_4$) δ ppm $^1$H NMR (400 MHz, CD3OD, 298 K) δ (ppm)=9.05 (dd, J=1.6, 4.3 Hz, 1H), 8.77 (dd, J=1.7, 8.6 Hz, 1H), 8.19 (d, J=7.9 Hz, 1H), 7.73 (dd, J=4.3, 8.6 Hz, 1H), 7.37 (d, J=8.1 Hz, 1H), 7.25 (d, J=8.6 Hz, 1H), 7.07 (d, J=2.1 Hz, 1H), 6.94 (dd, J=2.3, 8.5 Hz, 1H), 4.70 (d, J=13.2 Hz, 1H), 4.32 (d, J=13.3 Hz, 1H), 3.95-4.13 (m, 2H), 3.80-3.94 (m, 2H), 3.54-3.75 (m, 3H), 3.38-3.44 (m, 1H), 3.23-3.32 (m, 3H), 3.01-3.21 (m, 3H), 1.47 (d, J=6.7 Hz, 3H), 1.38 (s, 3H).

Example 56

5-[(4R,10bS)-4-methyl-8-(1,4-oxazepan-6-ylamino)-3,4,6,10b-tetrahydro-1H-pyrazino[2,1-a]isoindol-2-yl]quinoline-8-carbonitrile

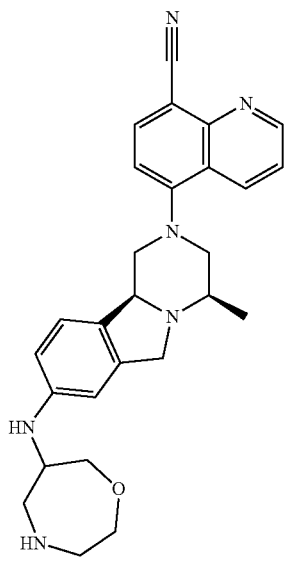

The title compound was prepared in analogy to the preparation of Example 10 by using tert-butyl 6-amino-1,4-oxazepane-4-carboxylate (CAS: 1170390-54-1, WUXI APPTEC, Catalog: WX601045) instead of tert-butyl (3R)-3-(hydroxymethyl)piperazine-1-carboxylate. Example 56 (49.4 mg) was obtained. MS: calc'd 455 [(M+H)+], measured 455 [(M+H)+]. $^1$H NMR (400 MHz, METHANOL-$d_4$) δ ppm 9.03 (dd, J=1.6, 4.3 Hz, 1H), 8.75 (dd, J=1.7, 8.6 Hz, 1H), 8.17 (d, J=7.9 Hz, 1H), 7.71 (dd, J=4.3, 8.6 Hz, 1H), 7.36 (d, J=8.1 Hz, 1H), 7.20 (d, J=8.3 Hz, 1H), 6.85 (d, J=1.8 Hz, 1H), 6.72 (dd, J=2.1, 8.3 Hz, 1H), 4.76-4.86 (m, 1H), 4.65 (d, J=13.1 Hz, 1H), 4.25 (d, J=13.1 Hz, 1H), 3.85-4.15 (m, 6H), 3.76-3.85 (m, 1H), 3.54-3.62 (m, 1H), 3.38-3.51 (m, 4H), 3.01-3.17 (m, 2H), 1.45 (d, J=6.6 Hz, 3H).

Example 56A and 56B

5-[(4R,10bS)-4-methyl-8-[[(6R)-1,4-oxazepan-6-yl]amino]-3,4,6,10b-tetrahydro-1H-pyrazino[2,1-a]isoindol-2-yl]quinoline-8-carbonitrile and 5-[(4R,10bS)-4-methyl-8-[[(6S)-1,4-oxazepan-6-yl]amino]-3,4,6,10b-tetrahydro-1H-pyrazino[2,1-a]isoindol-2-yl]quinoline-8-carbonitrile

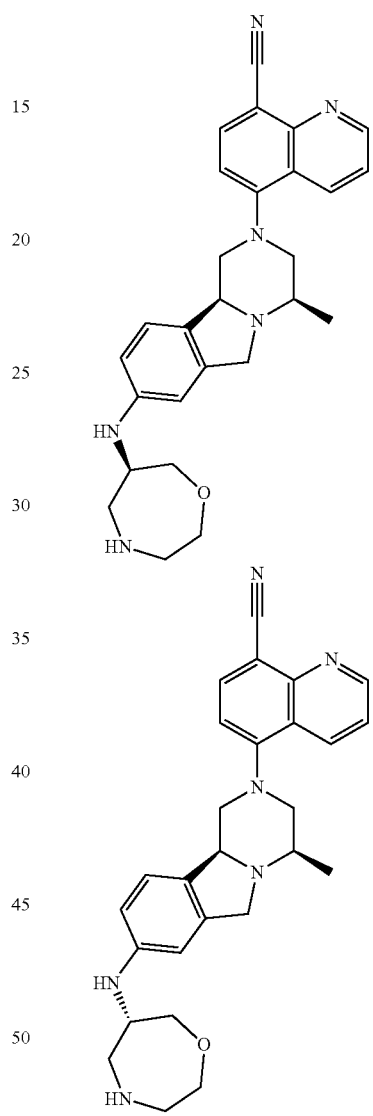

The title compound was prepared in analogy to the preparation of Example 16A and 16B by using tert-butyl 6-amino-1,4-oxazepane-4-carboxylate (CAS: 1170390-54-1, WUXI APPTEC, Catalog: WX601045) instead of trans-3-(boc-amino)-4-methoxypyrrolidine. Example 56A (24 mg) was obtained. MS: calc'd 455 [(M+H)+], measured 455 [(M+H)+]. $^1$H NMR (400 MHz, METHANOL-$d_4$) δ ppm 9.03 (dd, J=1.6, 4.3 Hz, 1H), 8.75 (dd, J=1.7, 8.6 Hz, 1H), 8.17 (d, J=7.9 Hz, 1H), 7.71 (dd, J=4.3, 8.6 Hz, 1H), 7.36 (d, J=8.1 Hz, 1H), 7.20 (d, J=8.3 Hz, 1H), 6.85 (d, J=1.8 Hz, 1H), 6.72 (dd, J=2.1, 8.3 Hz, 1H), 4.76-4.86 (m, 1H), 4.65 (d, J=13.1 Hz, 1H), 4.25 (d, J=13.1 Hz, 1H), 3.85-4.15 (m, 6H), 3.76-3.85 (m, 1H), 3.54-3.62 (m, 1H), 3.38-3.51 (m, 4H), 3.01-3.17 (m, 2H), 1.45 (d, J=6.6 Hz, 3H). Example 56B (28 mg) was obtained. MS: calc'd 455 [(M+H)+], measured 455 [(M+H)+]. ¹H NMR (400 MHz, METHANOL-d₄) δ ppm ¹H NMR (400 MHz, CD3OD, 298 K) δ (ppm) 9.03 (dd, J=1.7, 4.2 Hz, 1H), 8.75 (dd, J=1.7, 8.6 Hz, 1H), 8.18 (d, J=8.1 Hz, 1H), 7.71 (dd, J=4.2, 8.6 Hz, 1H), 7.36 (d, J=8.1 Hz, 1H), 7.18 (d, J=8.2 Hz, 1H), 6.83 (d, J=1.7 Hz, 1H), 6.69 (dd, J=2.1, 8.3 Hz, 1H), 4.60-4.69 (m, 1H), 4.56 (d, J=13.1 Hz, 1H), 3.94-4.15 (m, 5H), 3.74-3.92 (m, 3H), 3.52-3.59 (m, 1H), 3.39-3.48 (m, 4H), 2.94-3.12 (m, 2H), 1.40 (d, J=6.6 Hz, 3H).

Example 57

5-[(4R,10bS)-4-methyl-8-(morpholin-3-ylmethylamino)-3,4,6,10b-tetrahydro-1H-pyrazino[2,1-a]isoindol-2-yl]quinoline-8-carbonitrile

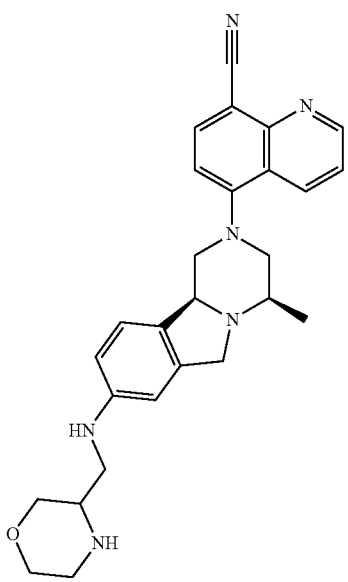 [SMILES: C[C@@H]1CN(c2ccc(C#N)c3ncccc23)C[C@@H]2c3ccc(NCC4COCCN4)cc3CN12]

The title compound was prepared in analogy to the preparation of Example 10 by using tert-butyl 3-(aminomethyl)morpholine-4-carboxylate (CAS: 475106-18-4, BePharm, Catalog: BD28817) instead of tert-butyl (3R)-3-(hydroxymethyl)piperazine-1-carboxylate. Example 57 (17.5 mg) was obtained. MS: calc'd 455 [(M+H)+], measured 455 [(M+H)+]. ¹H NMR (400 MHz, METHANOL-d₄) δ ppm 9.01 (dd, J=1.6, 4.3 Hz, 1H), 8.75 (dd, J=1.7, 8.6 Hz, 1H), 8.15 (d, J=7.9 Hz, 1H), 7.70 (dd, J=4.3, 8.6 Hz, 1H), 7.35 (d, J=7.9 Hz, 1H), 7.23 (d, J=8.3 Hz, 1H), 6.85 (d, J=1.8 Hz, 1H), 6.73 (dd, J=2.1, 8.4 Hz, 1H), 5.02-5.12 (m, 1H), 4.78 (d, J=13.6 Hz, 1H), 4.44 (d, J=13.6 Hz, 1H), 4.15-4.21 (m, 1H), 4.07-4.14 (m, 1H), 3.96-4.03 (m, 1H), 3.86-3.92 (m, 1H), 3.73-3.82 (m, 1H), 3.50-3.67 (m, 3H), 3.40-3.45 (m, 2H), 3.32-3.38 (m, 1H), 3.16-3.26 (m, 2H), 3.05-3.14 (m, 1H), 1.49 (d, J=6.7 Hz, 3H).

Example 58

5-[(4R,10bS)-4-methyl-8-[[(2S)-morpholin-2-yl]methylamino]-3,4,6,10b-tetrahydro-1H-pyrazino[2,1-a]isoindol-2-yl]quinoline-8-carbonitrile

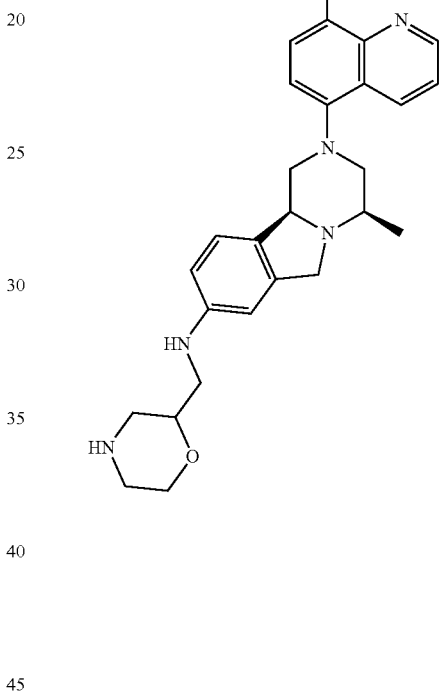

The title compound was prepared in analogy to the preparation of Example 10 by using tert-butyl N-[(2S)-morpholin-2-ylmethyl]carbamate (CAS: 875551-59-0, PharmaBlock, Catalog: PBN20121323) instead of tert-butyl (3R)-3-(hydroxymethyl)piperazine-1-carboxylate. Example 58 (28 mg) was obtained. MS: calc'd 455 [(M+H)+], measured 455 [(M+H)+]. ¹H NMR (400 MHz, METHANOL-d₄) δ ppm 8.88 (dd, J=1.7, 4.2 Hz, 1H), 8.60 (dd, J=1.6, 8.6 Hz, 1H), 8.05 (d, J=7.9 Hz, 1H), 7.56 (dd, J=4.3, 8.6 Hz, 1H), 7.21 (d, J=8.1 Hz, 1H), 6.89 (d, J=8.1 Hz, 1H), 6.60 (d, J=1.7 Hz, 1H), 6.43 (dd, J=2.1, 8.1 Hz, 1H), 4.11 (d, J=12.1 Hz, 1H), 3.94 (br d, J=10.1 Hz, 1H), 3.69-3.83 (m, 2H), 3.45-3.62 (m, 3H), 3.31-3.41 (m, 1H), 3.27-3.30 (m, 1H), 2.94-3.10 (m, 2H), 2.79-2.91 (m, 2H), 2.64-2.78 (m, 3H), 2.38-2.55 (m, 1H), 1.15 (d, J=6.4 Hz, 3H).

Example 59

5-[(4R,10bS)-4-methyl-8-[[(2R)-morpholin-2-yl]methylamino]-3,4,6,10b-tetrahydro-1H-pyrazino[2,1-a]isoindol-2-yl]quinoline-8-carbonitrile

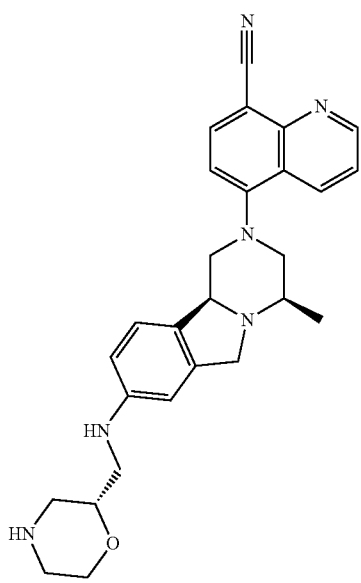 [SMILES: C[C@@H]1CN(c2ccc(C#N)c3ncccc23)C[C@@H]2c3ccc(NC[C@H]4CNCCO4)cc3CN12]

The title compound was prepared in analogy to the preparation of Example 10 by using tert-butyl N-[(2R)-morpholin-2-ylmethyl]carbamate (CAS: 186202-57-3, PharmaBlock, Catalog: PBN20121322) instead of tert-butyl (3R)-3-(hydroxymethyl)piperazine-1-carboxylate. Example 59 (8.8 mg) was obtained. MS: calc'd 455 [(M+H)$^+$], measured 455 [(M+H)$^+$]. $^1$H NMR (400 MHz, METHANOL-d$_4$) δ ppm 8.88 (dd, J=1.7, 4.2 Hz, 1H), 8.60 (dd, J=1.6, 8.6 Hz, 1H), 8.05 (d, J=7.9 Hz, 1H), 7.56 (dd, J=4.3, 8.6 Hz, 1H), 7.21 (d, J=8.1 Hz, 1H), 6.89 (d, J=8.1 Hz, 1H), 6.60 (d, J=1.7 Hz, 1H), 6.43 (dd, J=2.1, 8.1 Hz, 1H), 4.11 (d, J=12.1 Hz, 1H), 3.94 (br d, J=10.1 Hz, 1H), 3.69-3.83 (m, 2H), 3.45-3.62 (m, 3H), 3.31-3.41 (m, 1H), 3.27-3.30 (m, 1H), 2.94-3.10 (m, 2H), 2.79-2.91 (m, 2H), 2.64-2.78 (m, 3H), 2.38-2.55 (m, 1H), 1.15 (d, J=6.4 Hz, 3H).

Example 60

5-[(4R,10bS)-8-[[(3S,4R)-4-methoxypyrrolidin-3-yl]amino]-4-methyl-3,4,6,10b-tetrahydro-1H-pyrazino[2,1-a]isoindol-2-yl]quinoline-8-carbonitrile

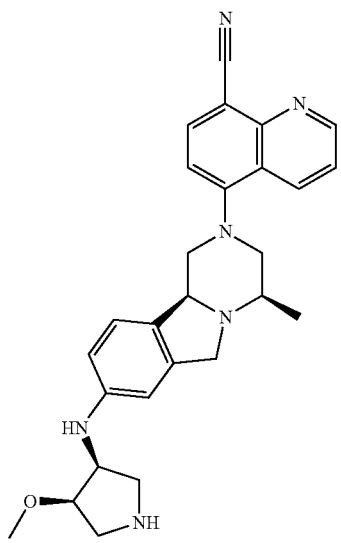 [SMILES: CO[C@@H]1CNC[C@@H]1Nc1ccc2c(c1)CN1[C@H](C)CN(c3ccc(C#N)c4ncccc34)C[C@H]21]

The title compound was prepared in analogy to the preparation of Example 10 by using (3S,4R)-tert-butyl 3-amino-4-methoxypyrrolidine-1-carboxylate (CAS: 148260-95-1, BePharm, Catalog: BD260807) instead of tert-butyl (3R)-3-(hydroxymethyl)piperazine-1-carboxylate. Example 60 (70 mg) was obtained. MS: calc'd 455 [(M+H)$^+$], measured 455 [(M+H)$^+$]. $^1$H NMR (400 MHz, METHANOL-d$_4$) δ ppm 9.03 (dd, J=1.7, 4.2 Hz, 1H), 8.75 (dd, J=1.7, 8.6 Hz, 1H), 8.18 (d, J=8.1 Hz, 1H), 7.71 (dd, J=4.3, 8.6 Hz, 1H), 7.36 (d, J=8.1 Hz, 1H), 7.19 (d, J=8.3 Hz, 1H), 6.89 (d, J=1.7 Hz, 1H), 6.75 (dd, J=2.1, 8.3 Hz, 1H), 4.68-4.77 (m, 1H), 4.61 (d, J=13.1 Hz, 1H), 4.29-4.39 (m, 1H), 4.11-4.21 (m, 2H), 3.81-3.95 (m, 2H), 3.52-3.69 (m, 3H), 3.42-3.46 (m, 1H), 3.42 (s, 3H), 3.03-3.22 (m, 3H), 1.42 (d, J=6.6 Hz, 3H).

Example 61

5-[(4R,10bS)-8-[[(3R,4S)-4-methoxypyrrolidin-3-yl]amino]-4-methyl-3,4,6,10b-tetrahydro-1H-pyrazino[2,1-a]isoindol-2-yl]quinoline-8-carbonitrile

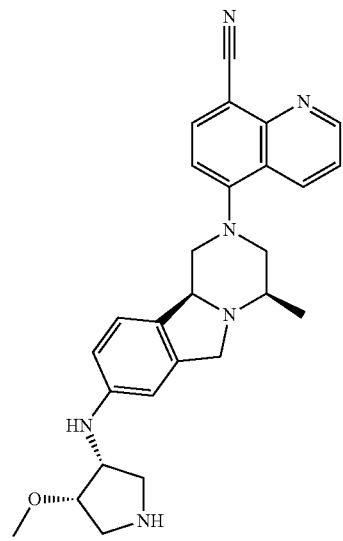 [SMILES: CO[C@H]1CNC[C@H]1Nc1ccc2c(c1)CN1[C@H](C)CN(c3ccc(C#N)c4ncccc34)C[C@H]21]

The title compound was prepared in analogy to the preparation of Example 10 by using (3R,4S)-tert-butyl 3-amino-4-methoxypyrrolidine-1-carboxylate (CAS: 148260-94-0, BePharm, Catalog: BD285562) instead of tert-butyl (3R)-3-(hydroxymethyl)piperazine-1-carboxylate. Example 61 (61 mg) was obtained. MS: calc'd 455 [(M+H)$^+$], measured 455 [(M+H)$^+$]. $^1$H NMR (400 MHz, METHANOL-d$_4$) δ ppm 9.03 (dd, J=1.6, 4.3 Hz, 1H), 8.74 (dd, J=1.6, 8.6 Hz, 1H), 8.18 (d, J=7.9 Hz, 1H), 7.70 (dd, J=4.2, 8.6 Hz, 1H), 7.35 (d, J=8.1 Hz, 1H), 7.16 (d, J=8.2 Hz, 1H), 6.88 (d, J=1.8 Hz, 1H), 6.73 (dd, J=2.1, 8.2 Hz, 1H), 4.48-4.59 (m, 2H), 4.28-4.38 (m, 1H), 4.10-4.17 (m, 1H), 4.05 (d, J=13.0 Hz, 1H), 3.85-3.93 (m, 1H), 3.69-3.79 (m, 1H), 3.58-3.67 (m, 2H), 3.51-3.57 (m, 1H), 3.41-3.45 (m, 1H), 3.42 (s, 3H), 3.13-3.22 (m, 1H), 2.96-3.09 (m, 2H), 1.39 (d, J=6.5 Hz, 3H).

Example 62

5-[(4R,10bS)-8-[[(3S,4S)-4-methoxypyrrolidin-3-yl]amino]-4-methyl-3,4,6,10b-tetrahydro-1H-pyrazino[2,1-a]isoindol-2-yl]quinoline-8-carbonitrile

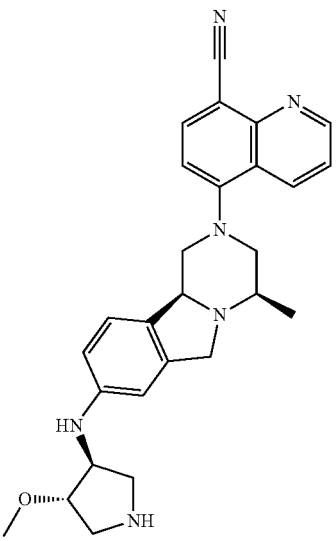 [SMILES: CO[C@H]1CNC[C@@H]1Nc1ccc2c(c1)CN1[C@H](C)CN(c3ccc(C#N)c4ncccc34)C[C@H]21]

The title compound was prepared in analogy to the preparation of Example 10 by using tert-butyl (3S,4S)-3-amino-4-methoxypyrrolidine-1-carboxylate (CAS: 1001635-01-3, BePharm, Catalog: BD260806) instead of tert-butyl (3R)-3-(hydroxymethyl)piperazine-1-carboxylate. Example 62 (58 mg) was obtained. MS: calc'd 455 [(M+H)$^+$], measured 455 [(M+H)$^+$]. $^1$H NMR (400 MHz, METHANOL-d$_4$) δ ppm 9.04 (dd, J=1.7, 4.2 Hz, 1H), 8.77 (dd, J=1.7, 8.6 Hz, 1H), 8.19 (d, J=8.1 Hz, 1H), 7.73 (dd, J=4.3, 8.6 Hz, 1H), 7.38 (d, J=8.1 Hz, 1H), 7.25 (d, J=8.2 Hz, 1H), 6.84 (d, J=1.8 Hz, 1H), 6.72 (dd, J=2.1, 8.3 Hz, 1H), 4.93-5.03 (m, 1H), 4.74 (d, J=13.4 Hz, 1H), 4.38 (d, J=13.3 Hz, 1H), 4.20 (br d, J=5.4 Hz, 1H), 4.02-4.12 (m, 2H), 3.87-3.95 (m, 1H), 3.67-3.75 (m, 1H), 3.58-3.65 (m, 1H), 3.50-3.54 (m, 2H), 3.48 (s, 3H), 3.37 (d, J=2.1 Hz, 1H), 3.06-3.24 (m, 2H), 1.48 (d, J=6.7 Hz, 3H).

Example 63
5-[(4R,10bS)-8-[[(3R,4R)-4-methoxypyrrolidin-3-yl]amino]-4,9-dimethyl-3,4,6,10b-tetrahydro-1H-pyrazino[2,1-a]isoindol-2-yl]quinoline-8-carbonitrile
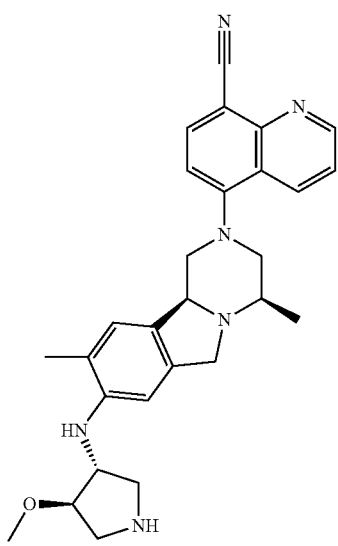 [SMILES: CO[C@@H]1CNC[C@H]1Nc1cc2c(cc1C)[C@H]1CN(c3ccc(C#N)c4ncccc34)C[C@@H](C)N1C2]
The title compound was prepared according to the following scheme:
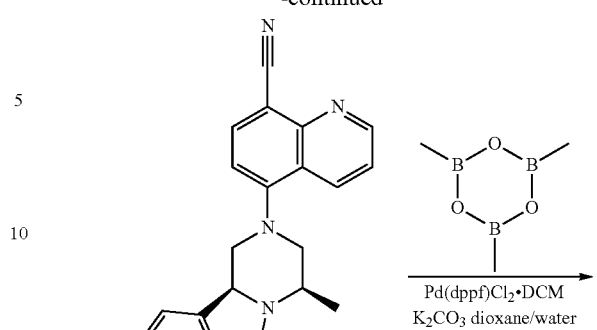
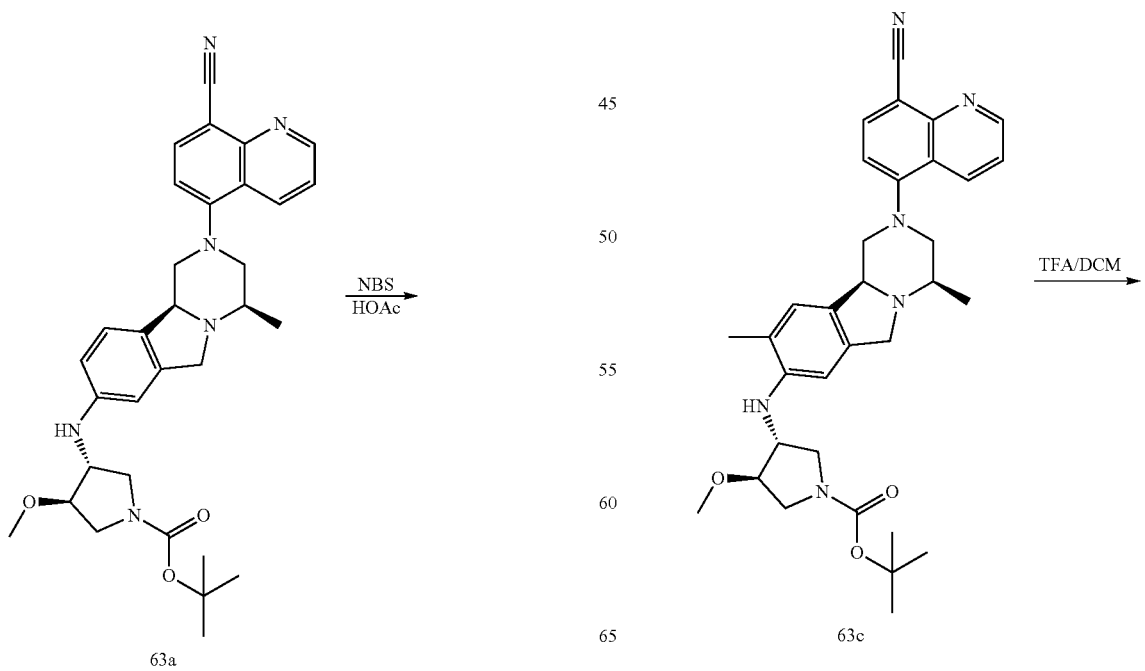

-continued

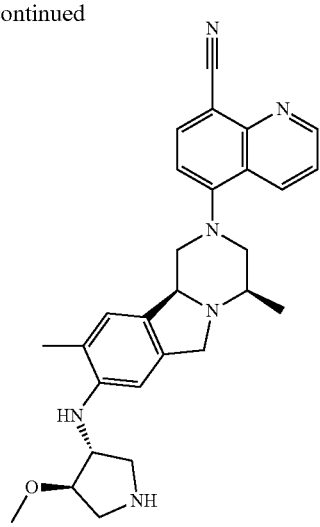

Example 63

Step 1: Preparation of tert-butyl (3R,4R)-3-[[(4R,10bS)-9-bromo-2-(8-cyano-5-quinolyl) 4-methyl-3,4,6,10b-tetrahydro-1H-pyrazino[2,1-a]isoindol-8-yl]amino]-4-methoxy-pyrrolidine-1-carboxylate (Compound 63b)

To a solution of tert-butyl (3R,4R)-3-[[(4R,10bS)-2-(8-cyano-5-quinolyl)-4-methyl-3,4,6,10b-tetrahydro-1H-pyrazino[2,1-a]isoindol-8-yl]amino]-4-methoxy-pyrrolidine-1-carboxylate (compound 63a, 200 mg, 361 μmol) in Acetic Acid (5 mL) was added NBS (64.2 mg, 361 μmol). The resultant mixture was stirred at room temperature for 2 hrs. The reaction was quenched with aqueous NaHCO₃. The aqueous layer was extracted with EtOAc (10 mL) for three times. The combined organic layers were washed with water, brine, dried over Na₂SO₄ and concentrated in vacuo. The residue was purified by flash chromatography (silica gel, 12 g, 0% to 100% EtOAc in PE) to afford compound 63b (98 mg, 42.9% yield). MS: calc'd 633 [(M+H)$^+$], measured 633 [(M+H)$^+$].

Step 2: Preparation of tert-butyl (3R,4R)-3-[[(4R,10bS)-2-(8-cyano-5-quinolyl)-4,9-dimethyl-3,4,6,10b-tetrahydro-1H-pyrazino[2,1-a]isoindol-4-yl]amino]-4-methoxy-pyrrolidine-1-carboxylate (Compound 63c)

To a solution of tert-butyl (3R,4R)-3-[[(4R,10bS)-9-bromo-2-(8-cyano-5-quinolyl)-4-methyl-3,4,6,10b-tetrahydro-1H-pyrazino[2,1-a]isoindol-8-yl]amino]-4-methoxy-pyrrolidine-1-carboxylate (compound 63b, 98 mg, 155 μmol) in dioxane (5 mL) and water (1 mL) was added 2,4,6-trimethyl-1,3,5,2,4,6-trioxatriborinane (38.8 mg, 309 μmol), K₂CO₃ (42.8 mg, 309 μmol) and Pd(dppf)Cl—CH₂Cl₂ adduct (11.3 mg, 15.5 μmol). The resultant mixture was stirred at 90° C. for 2 hrs. Then the mixture was cooled to room temperature, diluted with water (20 mL) and extracted with EA (20 mL) for three times. The combined organic layer was washed with brine, dried over Na₂SO₄, filtered and concentrated in vacuo. The residue was purified by flash chromatography (silica gel, 20 g, 30% to 100% EtOAc in PE) to afford compound 63c (53 mg, 60.3% yield). MS: calc'd 569 [(M+H)$^+$], measured 569 [(M+H)$^+$].

Step 3: Preparation of 5-[(4R,10bS)-8-[[(3R,4R)-4-methoxypyrrolidin-3-yl]amino]-4,9-dimethyl-3,4,6,10b-tetrahydro-1H-pyrazino[2,1-a]isoindol-2-yl]quinoline-8-carbonitrile (Example 63)

To a solution of tert-butyl (3R,4R)-3-[[(4R,10bS)-2-(8-cyano-5-quinolyl)-4,9-dimethyl-3,4,6,10b-tetrahydro-1H-pyrazino[2,1-a]isoindol-8-yl]amino]-4-methoxy-pyrrolidine-1-carboxylate (compound 63c, 53 mg, 93.2 μmol) in DCM (10 ml) was added TFA (5 ml). The reaction mixture was stirred at room temperature for 2 hrs, then concentrated to afford a crude product which was purified by pre-HPLC to afford Example 63 (32 mg, 58.9% yield). MS: calc'd 469 [(M+H)$^+$], measured 469 [(M+H)$^+$]. $^1$H NMR (400 MHz, METHANOL-d₄) δ ppm 9.03 (dd, J=1.7, 4.2 Hz, 1H), 8.75 (dd, J=1.6, 8.6 Hz, 1H), 8.18 (d, J=8.1 Hz, 1H), 7.71 (dd, J=4.3, 8.6 Hz, 1H), 7.36 (d, J=8.1 Hz, 1H), 7.10 (s, 1H), 6.82 (s, 1H), 4.53-4.67 (m, 2H), 4.27 (br d, J=5.5 Hz, 1H), 4.08-4.17 (m, 2H), 3.90 (br d, J=12.1 Hz, 1H), 3.70-3.83 (m, 2H), 3.52-3.59 (m, 3H), 3.50 (s, 3H), 3.42-3.49 (m, 1H), 3.02-3.12 (m, 2H), 2.20 (s, 3H), 1.41 (d, J=6.6 Hz, 3H).

Example 64

5-[(4R,10bS)-8-[[(3S,4S)-4-methoxypyrrolidin-3-yl]-methyl-amino]-4-methyl-3,4,6,10b-tetrahydro-1H-pyrazino[2,1-a]isoindol-2-yl]quinoline-8-carbonitrile

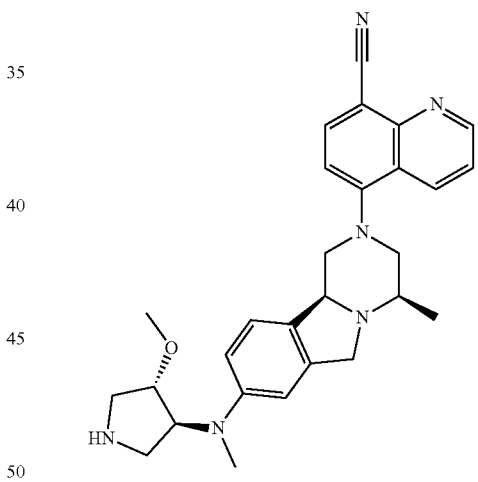

The title compound was prepared in analogy to the preparation of Example 10 by using tert-butyl (3S,4S)-3-methoxy-4-(methylamino)pyrrolidine-1-carboxylate (CAS: 960316-16-9, PharmaBlock, Catalog: PBXA7014) instead of tert-butyl (3R)-3-(hydroxymethyl)piperazine-1-carboxylate. Example 64 (25 mg) was obtained. MS: calc'd 469 [(M+H)$^+$], measured 469 [(M+H)$^+$]. $^1$H NMR (400 MHz, METHANOL-d₄) δ ppm 9.04 (dd, J=1.7, 4.3 Hz, 1H), 8.77 (dd, J=1.7, 8.6 Hz, 1H), 8.19 (d, J=7.9 Hz, 1H), 7.73 (dd, J=4.2, 8.6 Hz, 1H), 7.38 (d, J=7.9 Hz, 1H), 7.33 (d, J=8.3 Hz, 1H), 7.16 (d, J=1.8 Hz, 1H), 7.03 (dd, J=2.2, 8.3 Hz, 1H), 4.82-4.87 (m, 1H), 4.71 (d, J=13.2 Hz, 1H), 4.40-4.47 (m, 1H), 4.31 (d, J=13.1 Hz, 1H), 4.14-4.21 (m, 1H), 3.88-4.04 (m, 2H), 3.51-3.69 (m, 2H), 3.37-3.48 (m, 2H), 3.36 (s, 3H), 3.06-3.19 (m, 2H), 2.91 (s, 3H), 1.46 (d, J=6.7 Hz, 3H).

Example 65

5-[(4R,10bS)-4-methyl-8-[[(3R)-3-piperidyl]amino]-3,4,6,10b-tetrahydro-1H-pyrazino[2,1-a]isoindol-2-yl]quinoline-8-carbonitrile

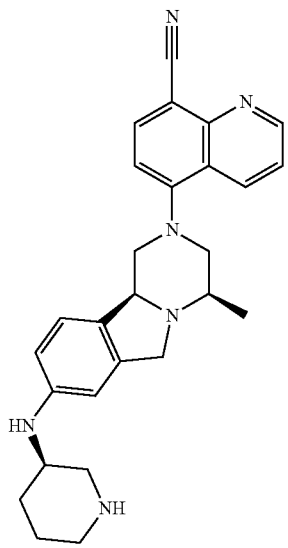 [SMILES: C[C@@H]1CN(c2ccc(C#N)c3ncccc23)C[C@@H]2c3ccc(N[C@@H]4CCCNC4)cc3CN12]

The title compound was prepared in analogy to the preparation of Example 10 by using tert-butyl (3R)-3-aminopiperidine-1-carboxylate (CAS: 188111-79-7, BePharm, Catalog: BD0329) instead of tert-butyl (3R)-3-(hydroxymethyl)piperazine-1-carboxylate. Example 65 (27 mg) was obtained. MS: calc'd 439 [(M+H)$^+$], measured 439 [(M+H)$^+$]. $^1$H NMR (400 MHz, METHANOL-d$_4$) δ ppm 9.05 (dd, J=1.7, 4.2 Hz, 1H), 8.77 (dd, J=1.7, 8.6 Hz, 1H), 8.19 (d, J=7.9 Hz, 1H), 7.73 (dd, J=4.3, 8.6 Hz, 1H), 7.38 (d, J=7.9 Hz, 1H), 7.32 (d, J=8.4 Hz, 1H), 7.16 (d, J=1.7 Hz, 1H), 7.03 (dd, J=2.1, 8.5 Hz, 1H), 4.72 (d, J=13.3 Hz, 1H), 4.33 (d, J=13.4 Hz, 1H), 3.96-4.06 (m, 1H), 3.90-3.96 (m, 1H), 3.46-3.66 (m, 3H), 3.25-3.31 (m, 2H), 3.06-3.20 (m, 4H), 1.93-2.14 (m, 2H), 1.70-1.86 (m, 2H), 1.46 (d, J=6.6 Hz, 3H).

Example 66

5-[(4R,10bS)-8-[[(3S,4R)-3-methoxy-4-piperidyl]amino]-4-methyl-3,4,6,10b-tetrahydro-1H-pyrazino[2,1-a]isoindol-2-yl]quinoline-8-carbonitrile

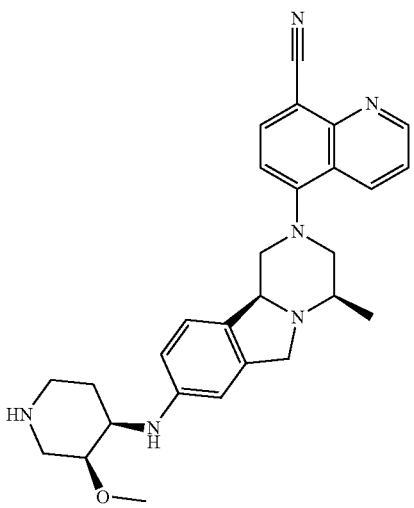 [SMILES: CO[C@H]1CNCC[C@H]1Nc1ccc2c(c1)CN1[C@H](C)CN(c3ccc(C#N)c4ncccc34)C[C@H]21]

The title compound was prepared in analogy to the preparation of Example 10 by using tert-butyl (3S,4R)-4-amino-3-methoxypiperidine-1-carboxylate (CAS: 1171125-92-0, PharmaBlock, Catalog: PBN20120813) instead of tert-butyl (3R)-3-(hydroxymethyl)piperazine-1-carboxylate. Example 66 (28 mg) was obtained. MS: calc'd 469 [(M+H)$^+$], measured 469 [(M+H)$^+$]. $^1$H NMR (400 MHz, METHANOL-d$_4$) δ ppm 8.87 (dd, J=1.6, 4.3 Hz, 1H), 8.58 (dd, J=1.7, 8.6 Hz, 1H), 8.02 (d, J=7.9 Hz, 1H), 7.55 (dd, J=4.3, 8.6 Hz, 1H), 7.19 (d, J=8.1 Hz, 1H), 6.90 (d, J=8.1 Hz, 1H), 6.67 (d, J=1.5 Hz, 1H), 6.50 (dd, J=2.0, 8.1 Hz, 1H), 4.10 (d, J=12.1 Hz, 1H), 3.92 (br d, J=10.4 Hz, 1H), 3.73 (br d, J=11.0 Hz, 1H), 3.52 (br d, J=11.7 Hz, 1H), 3.42-3.49 (m, 1H), 3.29-3.34 (m, 2H), 3.24 (s, 3H), 3.13-3.20 (m, 2H), 2.81-2.96 (m, 2H), 2.65-2.76 (m, 1H), 2.44-2.61 (m, 2H), 1.48-1.67 (m, 2H), 1.14 (d, J=6.5 Hz, 3H).

Example 67

5-[(4R,10bS)-4-methyl-8-(2-morpholinoethyl-amino)-3,4,6,10b-tetrahydro-1H-pyrazino[2,1-a]isoindol-2-yl]quinoline-8-carbonitrile

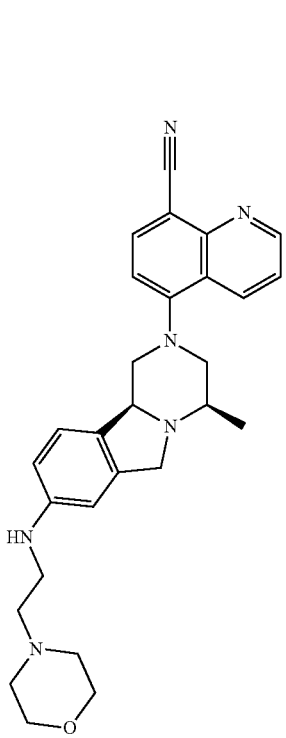 [SMILES: C[C@@H]1CN(c2ccc(C#N)c3ncccc23)C[C@@H]2c3ccc(NCCN4CCOCC4)cc3CN12]

The title compound was prepared in analogy to the preparation of Example 10 by using 2-morpholinoethanamine (CAS: 2038-03-1, BePharm, Catalog: BD89767) instead of tert-butyl (3R)-3-(hydroxymethyl)piperazine-1-carboxylate. Example 67 (29 mg) was obtained. MS: calc'd 469 [(M+H)$^+$], measured 469 [(M+H)$^+$]. $^1$H NMR (400 MHz, METHANOL-d$_4$) δ ppm 8.87 (dd, J=1.7, 4.2 Hz, 1H), 8.57 (dd, J=1.7, 8.6 Hz, 1H), 8.02 (d, J=8.1 Hz, 1H), 7.55 (dd, J=4.2, 8.6 Hz, 1H), 7.18 (d, J=8.1 Hz, 1H), 6.88 (d, J=8.1 Hz, 1H), 6.59 (d, J=1.7 Hz, 1H), 6.42 (dd, J=2.1, 8.1 Hz, 1H), 4.10 (d, J=12.2 Hz, 1H), 3.91 (br d, J=10.3 Hz, 1H), 3.68-3.76 (m, 1H), 3.57-3.64 (m, 4H), 3.51 (br d, J=11.6 Hz, 1H), 3.31 (br d, J=11.6 Hz, 1H), 3.16-3.19 (m, 1H), 3.13 (t, J=6.5 Hz, 2H), 2.86 (t, J=10.9 Hz, 1H), 2.67-2.74 (m, 1H), 2.50 (t, J=6.5 Hz, 2H), 2.37-2.45 (m, 4H), 1.14 (d, J=6.4 Hz, 3H).

Example 68

5-[(4R,10bS)-8-[2-[(3S)-3-hydroxypyrrolidin-1-yl]ethylamino]-4-methyl-3,4,6,10b-tetrahydro-1H-pyrazino[2,1-a]isoindol-2-yl]quinoline-8-carbonitrile

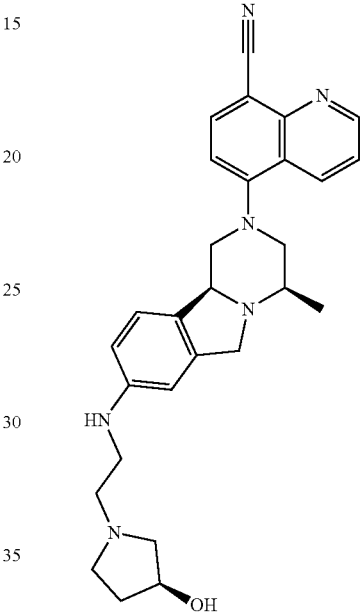

The title compound was prepared in analogy to the preparation of Example 10 by using (3S)-1-(2-aminoethyl)pyrrolidin-3-ol (CAS: 540787-75-5, BePharm, Catalog: BD45313) instead of tert-butyl (3R)-3-(hydroxymethyl)piperazine-1-carboxylate. Example 68 (13 mg) was obtained. MS: calc'd 469 [(M+H)$^+$], measured 469 [(M+H)$^+$]. $^1$H NMR (400 MHz, METHANOL-d$_4$) δ ppm 8.87 (dd, J=1.6, 4.3 Hz, 1H), 8.58 (dd, J=1.6, 8.6 Hz, 1H), 8.03 (d, J=7.9 Hz, 1H), 7.55 (dd, J=4.3, 8.6 Hz, 1H), 7.19 (d, J=8.1 Hz, 1H), 6.89 (d, J=8.1 Hz, 1H), 6.60 (d, J=1.6 Hz, 1H), 6.43 (dd, J=2.0, 8.1 Hz, 1H), 4.20-4.31 (m, 1H), 4.10 (d, J=12.2 Hz, 1H), 3.92 (br d, J=10.3 Hz, 1H), 3.72 (br d, J=11.2 Hz, 1H), 3.52 (br d, J=12.0 Hz, 1H), 3.32 (br d, J=11.6 Hz, 1H), 3.16-3.20 (m, 1H), 3.13 (t, J=6.6 Hz, 2H), 2.86 (t, J=10.9 Hz, 1H), 2.59-2.77 (m, 5H), 2.38-2.51 (m, 2H), 1.99-2.12 (m, 1H), 1.59-1.72 (m, 1H), 1.14 (d, J=6.4 Hz, 3H).

Example 69

5-[(4R,10bS)-8-[(3-fluoroazetidin-3-yl)methyl-amino]-4-methyl-3,4,6,10b-tetrahydro-1H-pyrazino[2,1-a]isoindol-2-yl]quinoline-8-carbonitrile

Example 70

5-[(4R,10bS)-8-[[(2S,4S)-4-fluoropyrrolidin-2-yl]methylamino]-4-methyl-3,4,6,10b-tetrahydro-1H-pyrazino[2,1-a]isoindol-2-yl]quinoline-8-carbonitrile

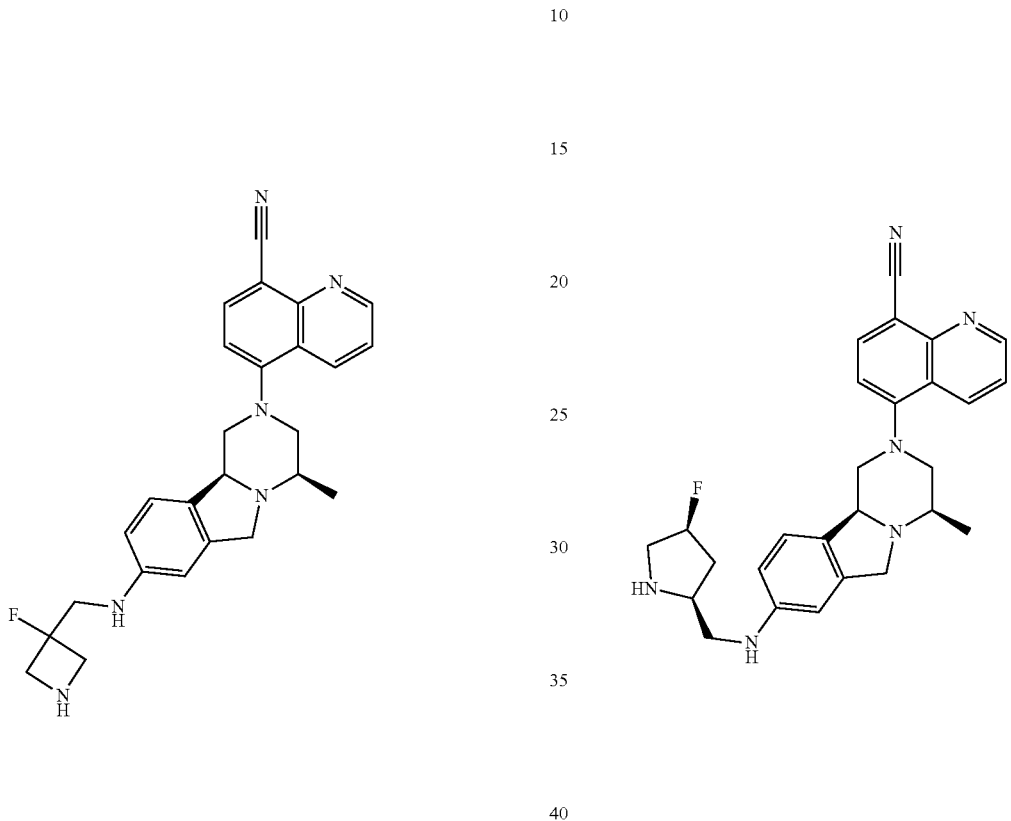

The title compound was prepared in analogy to the preparation of Example 10 by using tert-butyl 3-(aminomethyl)-3-fluoroazetidine-1-carboxylate (CAS: 1083181-23-0, PharmaBlock, Catalog: PBN20120081) instead of tert-butyl (3R)-3-(hydroxymethyl)piperazine-1-carboxylate. Example 69 (10 mg) was obtained. MS: calc'd 443 [(M+H)$^+$], measured 443 [(M+H)$^+$]. $^1$H NMR (400 MHz, METHANOL-d$_4$) δ ppm 9.04 (dd, J=1.6, 4.3 Hz, 1H), 8.76 (dd, J=1.7, 8.6 Hz, 1H), 8.18 (d, J=7.9 Hz, 1H), 7.72 (dd, J=4.3, 8.6 Hz, 1H), 7.37 (d, J=7.9 Hz, 1H), 7.22 (d, J=8.3 Hz, 1H), 6.90 (d, J=1.7 Hz, 1H), 6.77 (dd, J=2.1, 8.3 Hz, 1H), 4.95-5.02 (m, 1H), 4.75 (d, J=13.3 Hz, 1H), 4.24-4.46 (m, 5H), 4.06-4.18 (m, 1H), 3.86-3.95 (m, 1H), 3.69 (d, J=19.8 Hz, 2H), 3.55-3.64 (m, 1H), 3.16-3.25 (m, 1H), 3.04-3.13 (m, 1H), 1.49 (d, J=6.6 Hz, 3H).

The title compound was prepared in analogy to the preparation of Example 10 by using tert-butyl (2S,4S)-2-(aminomethyl)-4-fluoropyrrolidine-1-carboxylate (CAS: 1033245-12-3, PharmaBlock, Catalog: PB05325) instead of tert-butyl (3R)-3-(hydroxymethyl)piperazine-1-carboxylate. Example 70 (28 mg) was obtained. MS: calc'd 457 [(M+H)$^+$], measured 457 [(M+H)$^+$]. $^1$H NMR (400 MHz, METHANOL-d$_4$) δ ppm 9.03 (dd, J=1.6, 4.3 Hz, 1H), 8.76 (dd, J=1.7, 8.6 Hz, 1H), 8.17 (d, J=7.9 Hz, 1H), 7.72 (dd, J=4.3, 8.6 Hz, 1H), 7.37 (d, J=7.9 Hz, 1H), 7.24 (d, J=8.3 Hz, 1H), 6.87 (d, J=1.7 Hz, 1H), 6.74 (dd, J=2.1, 8.3 Hz, 1H), 5.39-5.58 (m, 1H), 4.97-5.04 (m, 1H), 4.76 (d, J=13.4 Hz, 1H), 4.40 (d, J=13.4 Hz, 1H), 4.04-4.17 (m, 2H), 3.84-3.96 (m, 1H), 3.68-3.78 (m, 1H), 3.40-3.65 (m, 4H), 3.17-3.27 (m, 1H), 3.06-3.14 (m, 1H), 2.51-2.73 (m, 1H), 2.12-2.31 (m, 1H), 1.49 (d, J=6.6 Hz, 3H).

Example 71

5-[(4R,10bS)-8-[(8aS)-3-oxo-1,5,6,7,8,8a-hexahydroimidazo[1,5-a]pyrazin-2-yl]-4-methyl-3,4,6,10b-tetrahydro-1H-pyrazino[2,1-a]isoindol-2-yl]quinoline-8-carbonitrile

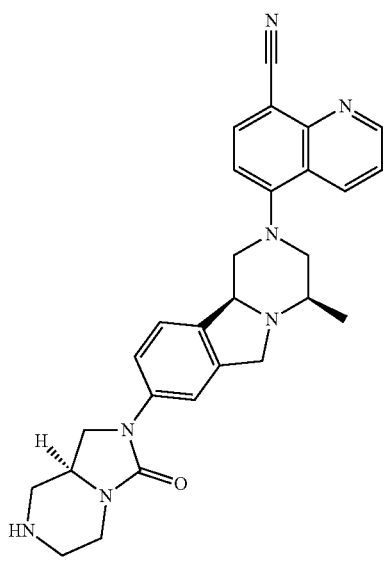

The title compound was prepared in analogy to the preparation of Example 10 by using tert-butyl (8aR)-3-oxo-1,2,5,6,8,8a-hexahydroimidazo[1,5-a]pyrazine-7-carboxylate instead of tert-butyl (3R)-3-(hydroxymethyl)piperazine-1-carboxylate. Example 71 (38 mg) was obtained. MS: calc'd 480 [(M+H)$^+$], measured 480 [(M+H)$^+$]. $^1$H NMR (400 MHz, METHANOL-$d_4$) δ ppm 9.03 (dd, J=1.7, 4.2 Hz, 1H), 8.77 (dd, J=1.6, 8.6 Hz, 1H), 8.18 (d, J=7.9 Hz, 1H), 7.86 (d, J=1.3 Hz, 1H), 7.72 (dd, J=4.3, 8.6 Hz, 1H), 7.51 (dd, J=2.0, 8.4 Hz, 1H), 7.33-7.47 (m, 1H), 4.92-5.01 (m, 1H), 4.77 (d, J=13.3 Hz, 1H), 4.38 (d, J=13.3 Hz, 1H), 4.06-4.22 (m, 3H), 3.93-4.06 (m, 2H), 3.68-3.74 (m, 1H), 3.54-3.65 (m, 2H), 3.41-3.47 (m, 1H), 3.29 (br d, J=3.3 Hz, 1H), 3.00-3.22 (m, 4H), 1.47 (d, J=6.6 Hz, 3H).

Example 72

5-[(4R,10bS)-8-[(8aR)-3-oxo-1,5,6,7,8,8a-hexahydroimidazo[1,5-a]pyrazin-2-yl]-4-methyl-3,4,6,10b-tetrahydro-1H-pyrazino[2,1-a]isoindol-2-yl]quinoline-8-carbonitrile

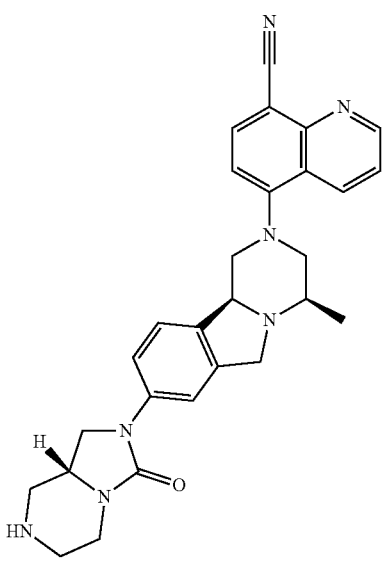 [SMILES: C[C@@H]1CN(c2ccc(C#N)c3ncccc23)C[C@@H]2c3ccc(N4C[C@H]5CNCCN5C4=O)cc3CN12]

The title compound was prepared in analogy to the preparation of Example 10 by using tert-butyl (8aS)-3-oxo-1,2,5,6,8,8a-hexahydroimidazo[1,5-a]pyrazine-7-carboxylate instead of tert-butyl (3R)-3-(hydroxymethyl)piperazine-1-carboxylate. Example 72 (8.8 mg) was obtained. MS: calc'd 480 [(M+H)$^+$], measured 480 [(M+H)$^+$]. $^1$H NMR (400 MHz, METHANOL-$d_4$) δ ppm 9.02 (dd, J=1.6, 4.3 Hz, 1H), 8.74 (dd, J=1.7, 8.6 Hz, 1H), 8.18 (d, J=8.1 Hz, 1H), 7.75 (d, J=1.5 Hz, 1H), 7.70 (dd, J=4.2, 8.6 Hz, 1H), 7.44 (dd, J=2.0, 8.3 Hz, 1H), 7.27-7.38 (m, 2H), 4.41-4.54 (m, 2H), 4.04-4.15 (m, 3H), 3.90-4.01 (m, 2H), 3.49-3.70 (m, 4H), 3.37-3.44 (m, 1H), 3.24-3.30 (m, 1H), 3.03-3.14 (m, 3H), 2.87-3.01 (m, 1H), 1.36 (d, J=6.5 Hz, 3H).

Example 73

5-[(4R,10bS)-8-[(3S,4S)-4-fluoropyrrolidin-3-yl]oxy-4-methyl-3,4,6,10b-tetrahydro-1H-pyrazino[2,1-a]isoindol-2-yl]quinoline-8-carbonitrile

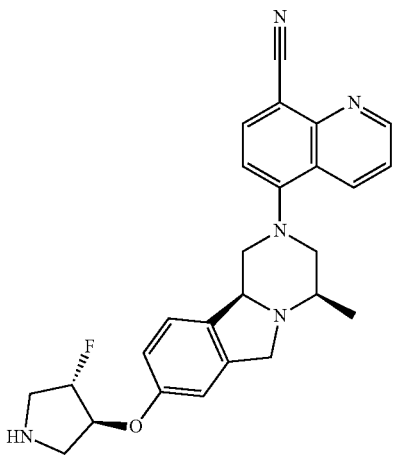 [SMILES: C[C@@H]1CN(c2ccc(C#N)c3ncccc23)C[C@@H]2c3ccc(O[C@H]4CNC[C@@H]4F)cc3CN12]

The title compound was prepared in analogy to the preparation of Example 10 by using tert-butyl (3S,4S)-3-fluoro-4-hydroxypyrrolidine-1-carboxylate (CAS: 1174020-51-9, PharmaBlock, Catalog: PB08192) instead of tert-butyl (3R)-3-(hydroxymethyl)piperazine-1-carboxylate. Example 73 (18 mg) was obtained. MS: calc'd 444 [(M+H)$^+$], measured 444 [(M+H)$^+$]. $^1$H NMR (400 MHz, METHANOL-d$_4$) δ ppm 9.02 (dd, J=1.5, 4.2 Hz, 1H), 8.73 (dd, J=1.5, 8.6 Hz, 1H), 8.17 (d, J=8.1 Hz, 1H), 7.69 (dd, J=4.2, 8.6 Hz, 1H), 7.34 (d, J=7.9 Hz, 1H), 7.28 (d, J=8.1 Hz, 1H), 7.14 (s, 1H), 6.97 (br d, J=8.4 Hz, 1H), 5.37-5.57 (m, 1H), 5.25-5.34 (m, 1H), 4.41 (d, J=12.6 Hz, 1H), 4.28 (br d, J=10.1 Hz, 1H), 3.62-3.95 (m, 6H), 3.49 (br d, J=8.9 Hz, 2H), 3.03 (t, J=11.1 Hz, 1H), 2.90 (t, J=11.7 Hz, 1H), 1.32 (d, J=6.2 Hz, 3H).

Example 74

5-[(4R,10bS)-8-[[(2S,4S)-4-fluoropyrrolidin-2-yl]methoxy]-4-methyl-3,4,6,10b-tetrahydro-1H-pyrazino[2,1-a]isoindol-2-yl]quinoline-8-carbonitrile

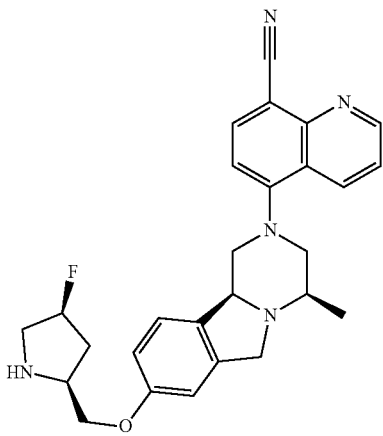 [SMILES: C[C@@H]1CN(c2ccc(C#N)c3ncccc23)C[C@@H]2c3ccc(OC[C@@H]4C[C@H](F)CN4)cc3CN12]

The title compound was prepared in analogy to the preparation of Example 10 by using tert-butyl (2S,4S)-4-fluoro-2-(hydroxymethyl)pyrrolidine-1-carboxylate (CAS: 317356-27-7, PharmaBlock, Catalog: PB05324) instead of tert-butyl (3R)-3-(hydroxymethyl)piperazine-1-carboxylate. Example 74 (12 mg) was obtained. MS: calc'd 458 [(M+H)$^+$], measured 458 [(M+H)$^+$]. $^1$H NMR (400 MHz, METHANOL-d$_4$) δ ppm 9.02 (dd, J=1.6, 4.3 Hz, 1H), 8.74 (dd, J=1.6, 8.6 Hz, 1H), 8.17 (d, J=8.1 Hz, 1H), 7.70 (dd, J=4.3, 8.6 Hz, 1H), 7.35 (d, J=8.1 Hz, 1H), 7.29 (d, J=8.3 Hz, 1H), 7.12 (d, J=2.1 Hz, 1H), 6.96 (dd, J=2.3, 8.3 Hz, 1H), 5.35-5.63 (m, 1H), 4.36-4.53 (m, 3H), 4.14-4.32 (m, 2H), 3.99 (d, J=12.8 Hz, 1H), 3.88-3.95 (m, 1H), 3.71-3.81 (m, 1H), 3.42-3.67 (m, 3H), 2.92-3.09 (m, 2H), 2.60-2.81 (m, 1H), 2.16-2.34 (m, 1H), 1.36 (d, J=6.6 Hz, 3H).

Example 75

(4R,10bS)—N-[(3S,4R)-4-fluoropyrrolidin-3-yl]-4-methyl-2-(8-methyl-5-quinolyl)-3,4,6,10b-tetrahydro-1H-pyrazino[2,1-a]isoindol-8-amine

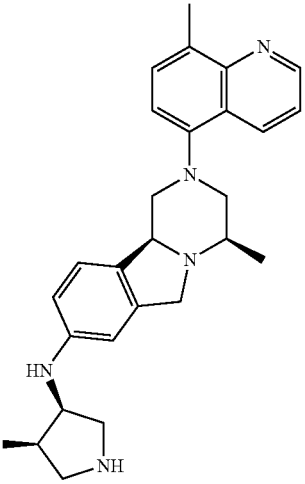

The title compound was prepared according to the following scheme:

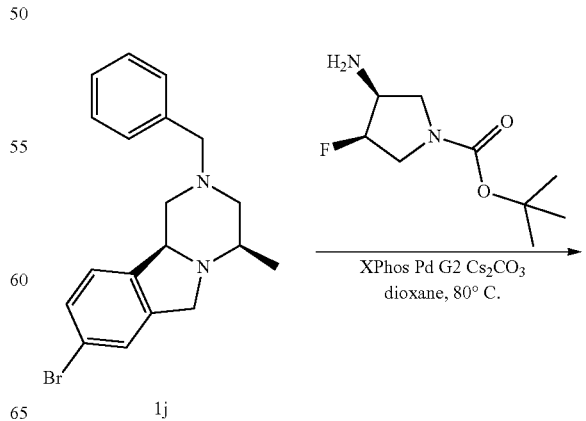

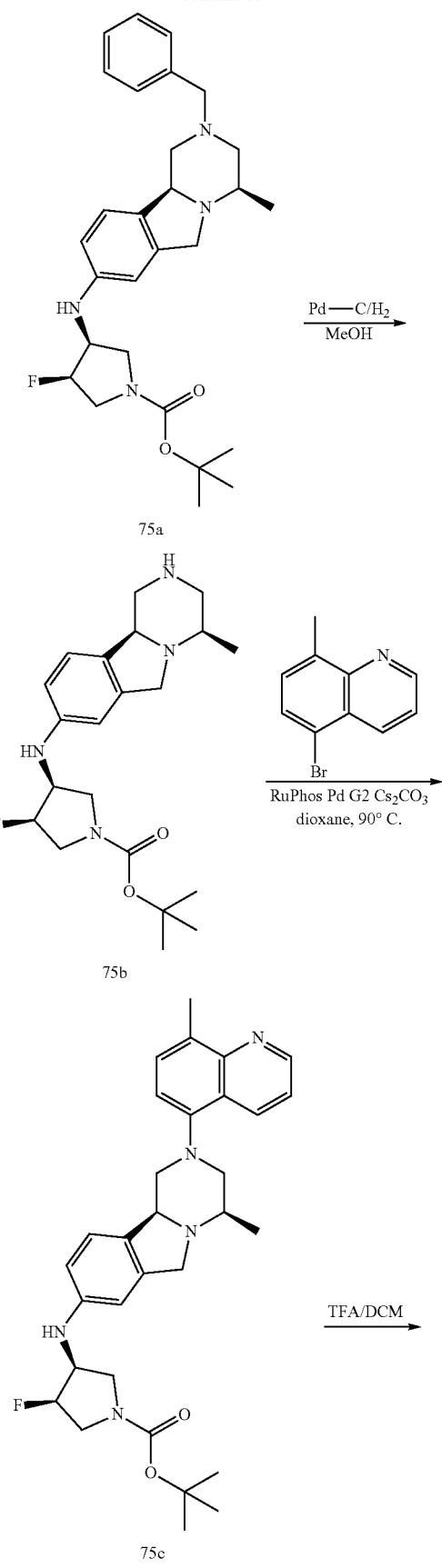

Example 75

Step 1: Preparation of ter-butyl (3S,4R)-3-(((4R,10bS)-2-benzyl-4-methyl-1,2,3,4,6,10b-hexahydro-pyrazino[2,1-a]isoindol-8-yl)amino)-4-fluoropyrrolidine-1-carboxylate (Compound 75a)

To a solution of tert-butyl (3S,4R)-3-amino-4-fluoropyrrolidine-1-carboxylate (366 mg, 1.8 mmol) in dioxane (15 mL) was added (4R,10bS)-2-benzyl-8-bromo-4-methyl-1,2,3,4,6,10b-hexahydropyrazino[2,1-a]isoindole (compound 1j, 640 mg, 1.8 mmol), $Cs_2CO_3$ (1.7 g, 5.4 mmol) and XPhos Pd G2 (152 mg, 179 μmol). The reaction mixture was stirred at 85° C. overnight. The mixture was cooled to room temperature, diluted with water (50 mL) and extracted with EA (80 mL) for three times. The combined organic layer was washed with brine, dried over $Na_2SO_4$, filtered and concentrated in vacuo. The residue was purified by flash chromatography (silica gel, 40 g, 0% to 100% EtOAc in DCM) to afford compound 75a (710 mg, 82.5% yield). MS: calc'd 481 [(M+H)$^+$], measured 481 [(M+H)$^+$].

Step 2: Preparation of tert-butyl (3R,4S)-3-fluoro-4-(((4R,10bS)-4-methyl-1,2,3,4,6,10b-hexahydropyrazino[2,1-a]isoindol-8-yl)amino)pyrrolidine-1-carboxylate (Compound 75b)

A mixture of tert-butyl (3S,4R)-3-(((4R,10bS)-2-benzyl-4-methyl-1,2,3,4,6,10b-hexahydropyrazino[2,1-a]isoindol-8-yl)amino)-4-fluoropyrrolidine-1-carboxylate (compound 75a, 710 mg, 1.5 mmol) and Pd—C (100 mg) in MeOH (80 mL) was hydrogenated by a hydrogen balloon at room temperature for 5 hrs. After the catalyst was filtered off, the filtrate was concentrated in vacuo to afford compound 75b (490 mg, 84.9% yield) which was used directly for the next step without further purification. MS: calc'd 391 [(M+H)$^+$], measured 391 [(M+H)$^+$].

Step 3: Preparation of tert-butyl (3R,4S)-3-fluoro-4-(((4R,10bS)-4-methyl-2-(8-methylquinolin-5-yl)-1,2,3,4,6,10b-hexahydropyrazino[2,1-a]isoindol-8-yl)-amino)-pyrrolidine-1-carboxylate (Compound 75c)

To a solution of 5-bromo-8-methylquinoline (CAS: 74316-55-5, BePharm, Catalog: BD239383, 34.1 mg, 154

µmol) in dioxane (5 mL) was added tert-butyl (3R,4S)-3-fluoro-4-(((4R,10bS)-4-methyl-1,2,3,4,6,10b-hexahydropyrazino[2,1-a]isoindol-8-yl)amino)pyrrolidine-1-carboxylate (compound 75b, 60 mg, 154 µmol), RuPhos Pd G2 (11.9 mg, 15.4 µmol) and $Cs_2CO_3$ (150 mg, 461 µmol). The reaction mixture was stirred at 90° C. for 20 hrs. The mixture was cooled to room temperature, diluted with water (20 mL) and extracted with EA (20 mL) for three times. The combined organic layer was washed with brine, dried over $Na_2SO_4$, filtered and concentrated in vacuo. The residue was purified by flash chromatography (silica gel, 20 g, 0% to 100% EtOAc in PE) to afford compound 75c (39 mg, 47.7% yield). MS: calc'd 532 [(M+H)$^+$], measured 532 [(M+H)$^+$].

Step 4: (4R,10bS)—N-[(3S,4R)-4-fluoropyrrolidin-3-yl]-4-methyl-2-(8-methyl-5-quinolyl)-3,4,6,10b-tetrahydro-1H-pyrazino[2,1-a]isoindol-8-amine (Example 75)

To a solution of tert-butyl (3R,4S)-3-fluoro-4-(((4R,10bS)-4-methyl-2-(8-methylquinolin-5-yl)-1,2,3,4,6,10b-hexahydropyrazino[2,1-a]isoindol-8-yl)amino)pyrrolidine-1-carboxylate (compound 75c, 39 mg, 73.4 µmol) in DCM (8 mL) was added TFA (2 mL). The reaction mixture was stirred at room temperature for 2 hrs, then concentrated to afford a crude product, which was purified by pre-HPLC to afford Example 75 (10 mg, 32% yield). MS: calc'd 432 [(M+H)$^+$], measured 432 [(M+H)$^+$]. $^1$H NMR (400 MHz, METHANOL-$d_4$) δ ppm 8.80 (dd, J=1.7, 4.3 Hz, 1H), 8.68 (dd, J=1.5, 8.5 Hz, 1H), 7.50 (dd, J=4.3, 8.4 Hz, 1H), 7.45 (dd, J=0.7, 7.7 Hz, 1H), 7.16 (d, J=7.6 Hz, 1H), 7.13 (d, J=8.4 Hz, 1H), 6.83 (d, J=1.7 Hz, 1H), 6.70 (dd, J=2.1, 8.4 Hz, 1H), 5.15-5.34 (m, 1H), 4.99-5.08 (m, 1H), 4.75 (d, J=13.7 Hz, 1H), 4.31-4.47 (m, 2H), 4.06-4.19 (m, 1H), 3.54-3.74 (m, 4H), 3.31 (br d, J=12.3 Hz, 1H), 3.03-3.18 (m, 2H), 2.85-2.98 (m, 1H), 2.61 (s, 3H), 1.40 (d, J=6.7 Hz, 3H).

Example 76

(4R,10bS)—N-[(3S,4R)-4-fluoropyrrolidin-3-yl]-4-methyl-2-(8-methylquinoxalin-5-yl)-3,4,6,10b-tetrahydro-1H-pyrazino[2,1-a]isoindol-8-amine

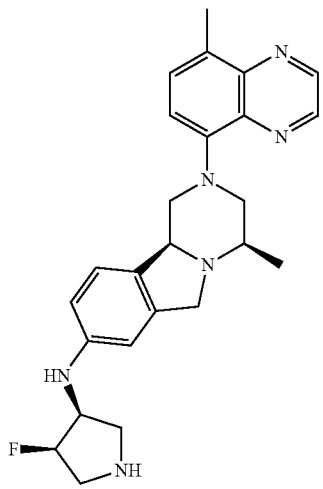 [SMILES: Cc1ccc(N2C[C@@H](C)N3Cc4cc(N[C@H]5CNC[C@H]5F)ccc4[C@H]3C2)c2nccnc12]

The title compound was prepared in analogy to the preparation of Example 75 by using 5-Bromo-8-methylquinoxaline (CAS: 1360599-43-4, BePharm, Catalog: BD00771201) instead of 5-bromo-8-methylquinoline. Example 76 (11 mg) was obtained. MS: calc'd 433 [(M+H)$^+$], measured 433 [(M+H)$^+$]. $^1$H NMR (400 MHz, METHANOL-$d_4$) δ ppm 8.84-8.98 (m, 2H), 7.53-7.69 (m, 1H), 7.31 (d, J=7.8 Hz, 1H), 7.22 (d, J=8.3 Hz, 1H), 6.92 (d, J=1.6 Hz, 1H), 6.80 (dd, J=2.1, 8.2 Hz, 1H), 5.25-5.45 (m, 1H), 4.81-4.87 (m, 1H), 4.68 (d, J=13.3 Hz, 1H), 4.40-4.56 (m, 1H), 4.18-4.33 (m, 2H), 3.88-4.03 (m, 2H), 3.62-3.83 (m, 3H), 3.25 (t, J=11.2 Hz, 1H), 2.95-3.10 (m, 2H), 2.71 (s, 3H), 1.45 (d, J=6.5 Hz, 3H).

Example 77

(4R,10bS)—N-[(3S,4R)-4-fluoropyrrolidin-3-yl]-4-methyl-2-[8-(trifluoromethyl)quinoxalin-5-yl]-3,4,6,10b-tetrahydro-1H-pyrazino[2,1-a]isoindol-8-amine

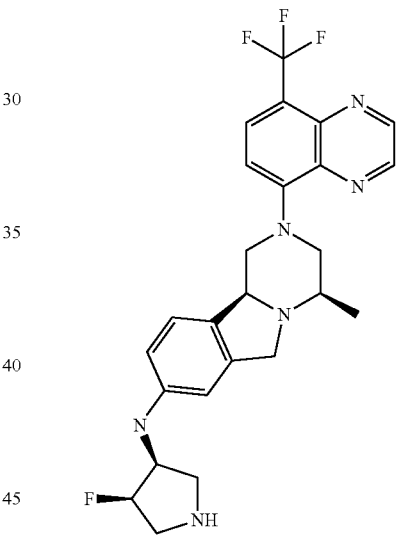

The title compound was prepared in analogy to the preparation of Example 75 by using 5-bromo-8-(trifluoromethyl)quinoxaline instead of 5-bromo-8-methylquinoline. Example 77 (21.2 mg) was obtained. MS: calc'd 487 [(M+H)$^+$], measured 487 [(M+H)$^+$]. $^1$H NMR (400 MHz, METHANOL-$d_4$) δ ppm 8.86-9.04 (m, 2H), 8.11 (d, J=8.4 Hz, 1H), 7.37 (d, J=8.2 Hz, 1H), 7.24 (d, J=8.3 Hz, 1H), 6.91 (d, J=1.7 Hz, 1H), 6.79 (dd, J=2.1, 8.3 Hz, 1H), 5.20-5.44 (m, 1H), 4.69-4.75 (m, 1H), 4.64 (d, J=13.2 Hz, 1H), 4.38-4.59 (m, 2H), 4.17-4.29 (m, 2H), 3.84-3.94 (m, 1H), 3.65-3.83 (m, 3H), 3.25 (t, J=11.2 Hz, 1H), 3.09-3.20 (m, 2H), 1.45 (d, J=6.6 Hz, 3H).

Example 78

7-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]-1,3-benzothiazole-4-carbonitrile

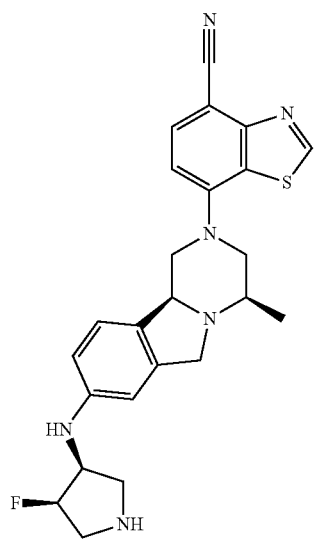 [SMILES: C[C@@H]1CN(c2ccc(C#N)c3ncsc23)C[C@@H]2c3ccc(N[C@H]4CNC[C@H]4F)cc3CN12]

The title compound was prepared according to the following scheme:

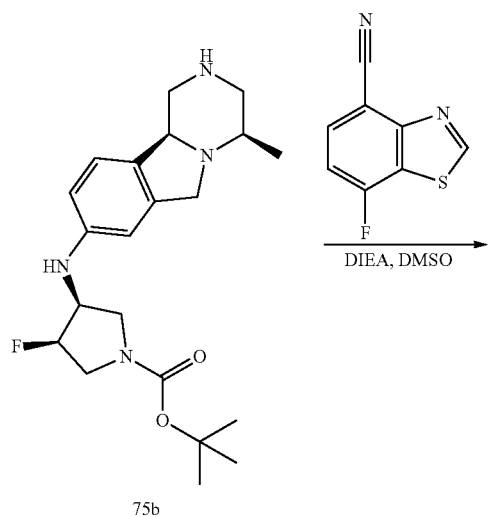

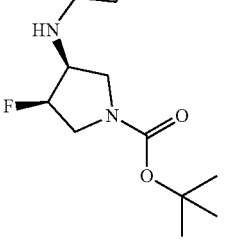

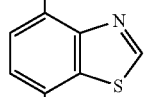

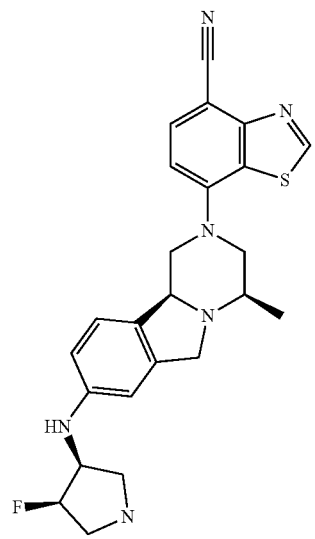

Example 78

Step 1: Preparation of tert-butyl (3S,4R)-3-[[(4R,10bS)-2-(4-cyano-1,3-benzothiazol-7-yl)-4-methyl-3,4,6,10b-tetrahydro-1H-pyrazino[2,1-a]isoindol-8-yl]-amino]-4-fluoro-pyrrolidine-1-carboxylate (Compound 78a)

To a solution of 7-fluorobenzo[d]thiazole-4-carbonitrile (27.4 mg, 154 μmol) in DMSO (2 ml) was added tert-butyl (3S,4R)-3-[[(4R,10bS)-4-methyl-1,2,3,4,6,10b-hexahydropyrazino[2,1-a]isoindol-8-yl]amino]-4-fluoro-pyrrolidine-1-carboxylate (compound 75b, 60 mg, 154 μmol) and DIEA (99.3 mg, 768 μmol). The resultant mixture was stirred at 120° C. overnight. After cooled to room temperature, the reaction was quenched with water (20 mL) and extracted with EA (20 mL) twice. The combined organic layer was washed with brine, dried over Na₂SO₄, filtered and concentrated in vacuo. The residue was purified by flash chromatography (silica gel, 20 g, 0% to 100% EtOAc in PE) to afford compound 78a (29 mg, 34.4% yield). MS: calc'd 549 [(M+H)⁺], measured 549 [(M+H)⁺].

Step 2: Preparation of 7-[(4R,10bS)-8-[[(3S,4R)-4-fluoropyrrolidin-3-yl]-amino]-4-methyl-3,4,6,10b-tetrahydro-1H-pyrazino[2,1-a]isoindol-2-yl]-1,3-benzothiazole-4-carbonitrile (Example 78)

To a solution of tert-butyl (3S,4R)-3-[[(4R,10bS)-2-(4-cyano-1,3-benzothiazol-7-yl)-4-methyl-3,4,6,10b-tetrahydro-1H-pyrazino[2,1-a]isoindol-8-yl]amino]-4-fluoropyrrolidine-1-carboxylate (compound 78a, 20 mg, 36.5 μmol) in DCM (8 mL) was added TFA (2 mL). The reaction mixture was stirred at room temperature for 2 hrs, then concentrated to afford a crude product, which was purified by pre-HPLC to afford Example 78 (11 mg, 67% yield). MS: calc'd 449 [(M+H)⁺], measured 449 [(M+H)⁺]. ¹H NMR (400 MHz, METHANOL-d₄) δ ppm 9.33 (s, 1H), 7.81 (d, J=8.2 Hz, 1H), 7.13 (dd, J=4.0, 8.2 Hz, 2H), 6.81 (d, J=1.6 Hz, 1H), 6.68 (dd, J=2.0, 8.3 Hz, 1H), 5.11-5.34 (m, 1H), 4.46-4.57 (m, 2H), 4.29-4.45 (m, 1H), 4.02-4.15 (m, 2H), 3.77 (br d, J=12.7 Hz, 1H), 3.52-3.71 (m, 4H), 2.96-3.16 (m, 3H), 1.35 (d, J=6.5 Hz, 3H).

Example 79

(4R,10b)-2-(8-chloro-5-quinolyl)-N-[(3S,4R)-4-fluoropyrrolidin-3-yl]-4-methyl-3,4,6,10b-tetrahydro-1H-pyrazino[2,1-a]isoindol-8-amine The title compound was prepared in analogy to the preparation of Example 75 by using 5-Bromo-8-chloroquinoline (CAS: 927800-41-7, BePharm, Catalog: BD38263) instead of 5-bromo-8-methylquinoline. Example 79 (12 mg) was obtained. MS: calc'd 452 [(M+H)⁺], measured 452 [(M+H)⁺]. ¹H NMR (400 MHz, METHANOL-d₄) δ ppm 8.99 (dd, J=1.6, 4.3 Hz, 1H), 8.78-8.88 (m, 1H), 7.87 (d, J=8.1 Hz, 1H), 7.71 (dd, J=4.2, 8.5 Hz, 1H), 7.34 (d, J=8.2 Hz, 1H), 7.23 (d, J=8.2 Hz, 1H), 6.93 (d, J=1.7 Hz, 1H), 6.80 (dd, J=2.1, 8.3 Hz, 1H), 5.22-5.44 (m, 1H), 4.94-5.02 (m, 1H), 4.76 (d, J=13.4 Hz, 1H), 4.32-4.55 (m, 2H), 4.08 (br d, J=7.0 Hz, 1H), 3.61-3.85 (m, 4H), 3.45 (br d, J=12.0 Hz, 1H), 3.25 (t, J=11.2 Hz, 1H), 3.00-3.18 (m, 2H), 1.48 (d, J=6.7 Hz, 3H).

Example 80

5-[(4R,10bS)-7-[2-[(3S)-3-hydroxypyrrolidin-1-yl]ethylamino]-4-methyl-3,4,6,10b-tetrahydro-1H-pyrazino[2,1-a]isoindol-2-yl]quinoline-8-carbonitrile The title compound was prepared in analogy to the preparation of Example 68. Example 80 (12 mg) was obtained. MS: calc'd 469 [(M+H)⁺], measured 469 [(M+H)⁺]. ¹H NMR (400 MHz, METHANOL-d₄) δ ppm 8.97-9.05 (m, 1H), 8.73-8.78 (m, 1H), 8.17 (d, J=8.1 Hz, 1H), 7.71 (dd, J=4.3, 8.6 Hz, 1H), 7.37 (d, J=8.1 Hz, 1H), 7.28 (t, J=7.8 Hz, 1H), 6.70-6.83 (m, 2H), 4.96-5.01 (m, 1H), 4.56-4.69 (m, 2H), 4.31 (br d, J=13.0 Hz, 1H), 4.02-4.14 (m, 1H), 3.92 (br d, J=11.1 Hz, 1H), 3.41-3.76 (m, 9H), 3.07-3.22 (m, 2H), 2.24-2.36 (m, 1H), 2.03-2.15 (m, 1H), 1.49 (d, J=6.6 Hz, 3H).

Example 81

5-[(4R,10bS)-7-[[(3S,4R)-4-fluoropyrrolidin-3-yl]amino]-4-methyl-3,4,6,10b-tetrahydro-1H-pyrazino[2,1-a]isoindol-2-yl]quinoline-8-carbonitrile

Example 82

5-[(4R,10bS)-8-[(3R,4R)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile

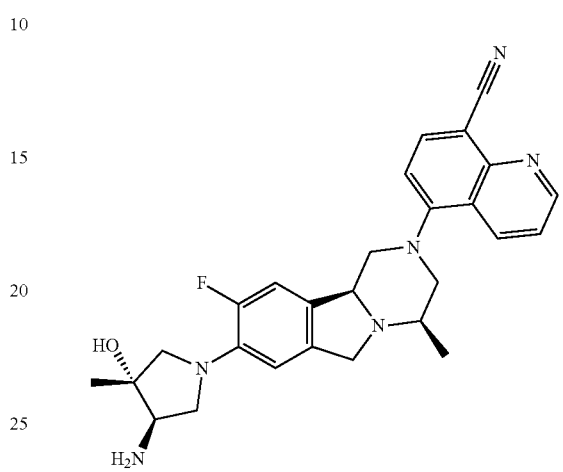

The tide compound was prepared according to the following scheme:

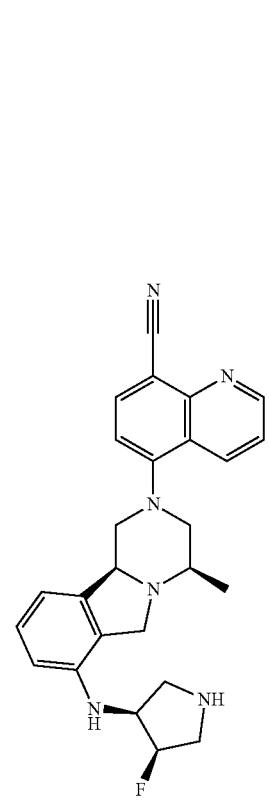 [SMILES: C[C@@H]1CN(c2ccc(C#N)c3ncccc23)C[C@@H]2c3cccc(N[C@H]4CNC[C@H]4F)c3CN12]

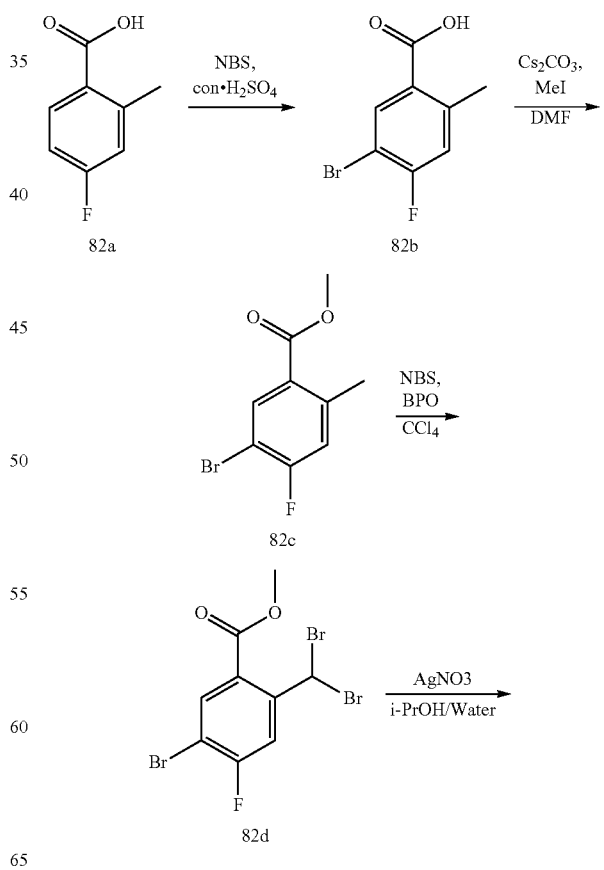

The title compound was prepared in analogy to the preparation of Example 30. Example 81 (10 mg) was obtained. MS: calc'd 443 [(M+H)$^+$], measured 443 [(M+H)$^+$]. $^1$H NMR (400 MHz, METHANOL-d$_4$) δ ppm 9.02 (dd, J=1.6, 4.3 Hz, 1H), 8.74 (dd, J=1.7, 8.6 Hz, 1H), 8.16 (d, J=7.9 Hz, 1H), 7.70 (dd, J=4.3, 8.6 Hz, 1H), 7.36 (d, J=8.1 Hz, 1H), 7.27 (t, J=7.8 Hz, 1H), 6.86 (d, J=8.2 Hz, 1H), 6.81 (d, J=7.5 Hz, 1H), 5.29 (t, J=2.9 Hz, 1H), 4.84 (br d, J=3.4 Hz, 2H), 4.64 (d, J=13.1 Hz, 1H), 4.22 (d, J=13.1 Hz, 1H), 3.88-4.01 (m, 2H), 3.68-3.84 (m, 3H), 3.59 (br d, J=12.5 Hz, 1H), 3.43 (t, J=11.2 Hz, 1H), 3.02-3.19 (m, 2H), 1.45 (d, J=6.6 Hz, 3H).

137
-continued
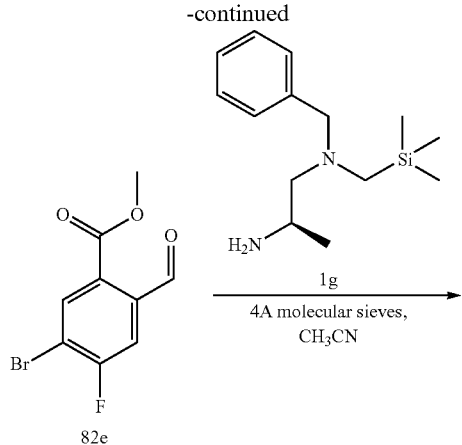
82e
138
-continued
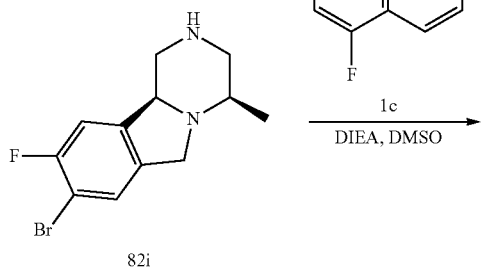
82i
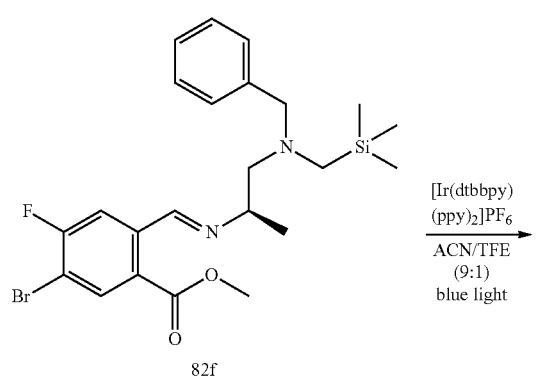
82f
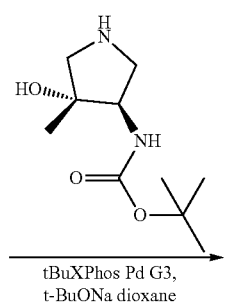
82j
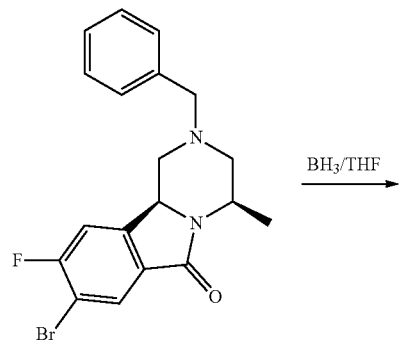
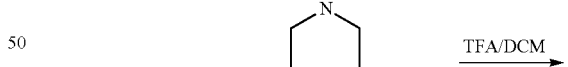
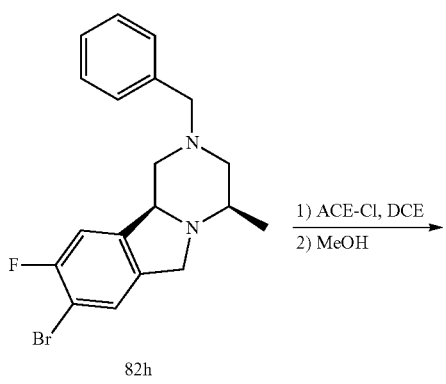
82h
82k -continued

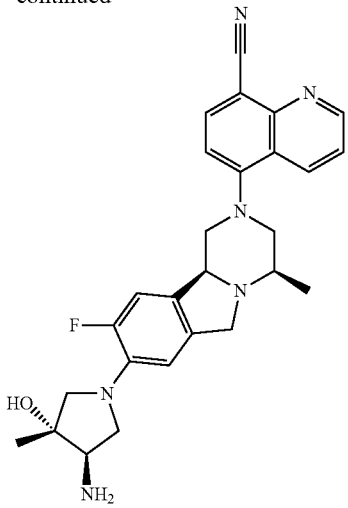

Example 82

Step 1: Preparation of 5-bromo-4-fluoro-2-methyl-benzoic acid (Compound 82b)

To the solution of 4-fluoro-2-methylbenzoic acid (compound 82a, 50.0 g, 324.38 mmol) in Con. $H_2SO_4$ (250.0 mL) was added NBS (58.0 g, 325.88 mmol) in portions at 0° C. Then the reaction mixture was stirred at 0-5° C. for 1 hr. The resultant mixture was poured into 2.5 L ice-water. The solid was collected by filtration. The collected solid was dried in air and then in vacuo to afford compound 82b (67 g, 88.6% yield). MS: calc'd 231, 233 [(M–H)⁻], measured 231, 233 [(M–H)⁻].

Step 2: Preparation of methyl 5-bromo-4-fluoro-2-methyl-benzoate (Compound 82c)

To the stirred solution of 5-bromo-4-fluoro-2-methyl-benzoic acid (compound 82b, 35.0 g, 150.2 mmol) in DMF (350 mL) was added cesium carbonate (73.5 g, 225.6 mmol) The resultant mixture was stirred for 30 minutes, followed by the addition of iodomethane (22.0 g, 155 mmol). Then the mixture was stirred at 40° C. for 15 hrs. After cooled to room temperature, the reaction was quenched with water (1.5 L) and extracted with EA (800 mL) for three times. The combined organic layer was washed with brine, dried over $Na_2SO_4$, filtered and concentrated in vacuo to afford compound 82c (35 g, crude) which was used directly for the next step without further purification. MS: calc'd 247, 249 [(M+H)⁺], measured 247, 249 [(M+H)⁺].

Step 3: Preparation of methyl 5-bromo-2-(dibromomethyl)-4-fluoro-benzoate (Compound 82d)

To the solution of methyl 5-bromo-4-fluoro-2-methyl-benzoate (compound 82c, 35.0 g, crude) in carbon tetrachloride (200 mL) was added benzoylperoxide (3.43 g, 14.2 mmol) and NBS (77.0 g, 432.6 mmol). The resultant mixture was stirred at reflux for 18 hrs. The reaction mixture was filtered through Celite and washed with CCl4. The filtrate was washed with the mixed solution of aq. $NaHCO_3$/aq. $Na_2S_2O_3$ aq. (1:1, 200 mL) and brine (200 mL) subsequently, dried over $Na_2SO_4$, filtered and concentrated in vacuo afford compound 82d (51 g, crude). MS: calc'd 405, 407 [(M+H)⁺], measured 325, 327 [(M–Br)⁺].

Step 4: Preparation of methyl 5-bromo-4-fluoro-2-formyl-benzoate (Compound 82e)

To a suspension of methyl 5-bromo-2-(dibromomethyl)-4-fluoro-benzoate (compound 82d, 10.0 g, crude) in 2-propanol (150 mL) was added a solution of silver nitrate (9.2 g, 54.16 mmol) in deionized water (20 mL) at room temperature in the absence of light under the protection of $N_2$ over about 30 mins. The resultant mixture was stirred at room temperature for another 3 hrs in the absence of light. The reaction was quenched with 5 mL brine, the resultant mixture was filtered through Celite, and the filtrate was concentrated in vacuo. The residue was re-dissolved with DCM (500 mL), washed with aq.$NaHCO_3$ (200 mL) and brine (300 mL) subsequently, dried over $Na_2SO_4$, filtered and concentrated in vacuo. The residue was purified by flash chromatography (silica gel, 120 g, 0% to 10% EtOAc in PE) to afford compound 82e (2.5 g, 31.9% yield for total three steps). MS: calc'd 261, 263 [(M+H)⁺], measured 261,263 [(M+H)⁺].

Step 5: Preparation of (4R,10bS)-2-benzyl-8-bromo-9-fluoro-4-methyl-1,3,4,10b-tetrahydropyrazino[1,2-b]isoindol-6-one (Compound 82g)

A mixture of the (2R)—N1-benzyl-N1-(trimethylsilylmethyl)propane-1,2-diamine (compound 1g, 1.0 g, 2.0 g, 8.0 mmol), methyl 5-bromo-4-fluoro-2-formyl-benzoate (compound 82e, 2.5 g, 7.6 mmol), and 4 A MS (4.5 g) in MeCN (50 mL) under N2 was stirred overnight at room temperature. The reaction mixture was filtered through Celite and washed with DCM. The filtrate was concentrated in vacuo to afford the intermediate compound 82f, and the residue was re-dissolved in MeCN/TFE (18 mL/2 mL), followed by the addition of [Ir(dtbbpy)(ppy)₂][PF₆](CAS: 676525-77-2, TCI, Catalog: D4887, 120 mg, 130 μmol). The reaction was stirred at room temperature under the exposure of blue LEDs (synLED-16 A Discover, 12 W, wavelength 465-470 nm, purchased from SYNLED corp.) for 24 hrs. After the solvents were removed in vacuo, the residue was purified by flash chromatography (silica gel, 40 g, 20% to 80% EA in PE) to afford compound 82g (0.9 g, 28.5% yield). The stereochemistry was confirmed by NOESY. MS: calc'd 389 and 391 [(M+H)⁺], measured 389,391 [(M+H)⁺]. ¹H NMR (400 MHz, CHLOROFORM-d) δ ppm 7.97 (d, J=6.0 Hz, 1H), 7.40-7.30 (m, 5H), 7.10-7.06 (m, 1H), 4.39 (dd, J=3.2, 10.8 Hz, 1H), 3.86-3.75 (m, 1H), 3.66-3.55 (m, 2H), 3.34-3.30 (m, 1H), 2.89-2.85 (m, 1H), 1.98 (t, J=11.0 Hz, 1H), 1.79 (d, J=6.8 Hz, 3H), 1.76-1.73 (m, 1H).

Step 6: Preparation of (4R,10bS)-2-benzyl-8-bromo-9-fluoro-4-methyl-3,4,6,10b-tetrahydro-1H-pyrazino[2,1-a]isoindole (Compound 82h)

A mixture of (4R,10bS)-2-benzyl-8-bromo-9-fluoro-4-methyl-1,3,4,10b-tetrahydropyrazino[1,2-b]isoindol-6-one (compound 82g, 0.9 g, 2.31 mmol) and $BH_3$ solution (1M in THF, 40 mL, 40 mmol) was heated at 80° C. with stirring on for 15 hrs. HCl solution (6 N, 10 mL) was added slowly to the reaction mixture at 0° C. The resultant mixture was stirred at room temperature overnight, then the mixture was basified with a NaOH solution (2 N) to pH 10.

The mixture was extracted with EtOAc twice. The organic phases were combined and dried over MgSO₄, filtered and concentrated in vacuo. The crude material was purified by flash chromatography (silica gel, 40 g, 30% to 100% EtOAc in PE) to afford compound 82h (0.5 g, 57.6% yield). MS: calc'd 375,377 [(M+H)⁺], measured 375,377 [(M+H)⁺].

Step 7: Preparation of (4R,10bS)-8-bromo-9-fluoro-4-methyl-1,2,3,4,6,10b-hexahydropyrazino[2,1-a]isoindole (Compound 82i)

To a stirred solution of (4R,10bS)-2-benzyl-8-bromo-9-fluoro-4-methyl-3,4,6,10b-tetrahydro-1H-pyrazino[2,1-a]isoindole (compound 82g, 0.5 g, 1.3 mmol) in DCE (15 mL) at room temperature was added 1-chloroethyl carbonochloridate (0.9 g, 6.6 mmol). The reaction mixture was heated under reflux overnight and cooled to room temperature before concentrated in vacuo. The residue was dissolved in MeOH (30 mL) and the resultant mixture was heated under reflux for additional 2 hrs. The mixture was cooled to room temperature and concentrated in vacuo. The residue was diluted with water (10 mL), and the solution was basified with aq. NaHCO₃. The resultant mixture was extracted with EtOAc (50 mL) twice. The combined organic layer was washed with brine, dried over Na₂SO₄, filtered and concentrated in vacuo to afford compound 82i (290 mg, 77.6% yield) which used directly to the next step. MS: calc'd 285, 287 [(M+H)⁺], measured 285,287 [(M+H)⁺].

Step 8: Preparation of 5-[(4R,10bS)-8-bromo-9-fluoro-4-methyl-3,4,6,10b-tetrahydro-1H-pyrazino[2,1-a]isoindol-2-yl]quinoline-8-carbonitrile (Compound 82j)

To a solution of 5-fluoroquinoline-8-carbonitrile (compound 1c, 186 mg, 1.1 mmol) in DMSO (5 mL) was added (4R,10bS)-8-bromo-9-fluoro-4-methyl-1,2,3,4,6,10b-hexahydropyrazino[2,1-a]isoindole (compound 82i, 280 mg, 1.0 mmol) and (381 mg, 3.0 mmol). The reaction mixture was stirred at 120° C. for 5 hrs. The mixture was cooled to room temperature, quenched with water (50 mL), and extracted with EA (60 mL) twice. The combined organic layer was washed with brine, dried over Na₂SO₄, filtered and concentrated in vacuo. The residue was purified by flash chromatography to afford compound 82j (150 mg, 32% yield). MS: calc'd 437 and 439 [(M+H)⁺], measured 437 and 439 [(M+H)⁺].

Step 9: Preparation of tert-butyl N-[(3R,4R)-1-[(4R,10bS)-2-(8-cyano-5-quinolyl)-9-fluoro-4-methyl-3,4,6,10b-tetrahydro-1H-pyrazino[2,1-a]isoindol-8-yl]-4-hydroxy-4-methyl-pyrrolidin-3-yl]carbamate (Compound 82k)

To a solution of 5-[(4R,10bS)-8-bromo-9-fluoro-4-methyl-3,4,6,10b-tetrahydro-1H-pyrazino[2,1-a]isoindol-2-yl]quinoline-8-carbonitrile (compound 82j, 60.0 mg, 140 µmol) in dioxane (5 mL) was added tert-butyl N-[(3R,4R)-4-hydroxy-4-methyl-pyrrolidin-3-yl]carbamate (45.0 mg, 210 µmol), Cesium carbonate (90.0 mg, 280 µmol) and tBuXPhos Pd G3 (CAS: 1447963-75-8, Sigma-Aldrich, Catalog: 762229, 24 mg, 30 µmol). The reaction mixture was stirred at 90° C. overnight. The mixture was cooled to room temperature, diluted with water (10 mL) and extracted with EA (15 mL) for three times. The combined organic layer was washed with brine, dried over Na₂SO₄, filtered and concentrated in vacuo. The residue was purified by flash chromatography (silica gel, 12 g, 30% to 100% EtOAc in PE) to afford compound 82k (50 mg, 62% yield). MS: calc'd 573 [(M+H)⁺], measured 573 [(M+H)⁺].

Step 10: Preparation of 5-[(4R,10bS)-8-[(3R,4R)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile (Example 82)

To a solution of tert-butyl N-[(3R,4R)-1-[(4R,10bS)-2-(8-cyano-5-quinolyl)-9-fluoro-4-methyl-3,4,6,10b-tetrahydro-1H-pyrazino[2,1-a]isoindol-8-yl]-4-hydroxy-4-methyl-pyrrolidin-3-yl]carbamate (compound 82k, 50.0 mg, 87 µmol) in DCM (5 mL) was added TFA (2 mL). The reaction mixture was stirred at room temperature for 2 hrs, then concentrated to afford a crude product, which was purified by pre-HPLC to afford Example 82 (5.9 mg, 14% yield). MS: calc'd 473 [(M+H)⁺], measured 473 [(M+H)⁺]. ¹H NMR (400 MHz, DMSO-d6) δ ppm 9.05 (d, J=3.2 Hz, 1H), 8.60 (d, J=8.8 Hz, 1H), 8.23 (d, J=8.4 Hz, 1H), 7.70 (dd, J=8.0, 4.0 Hz, 1H), 7.28 (br d, J=8.0 Hz, 1H) 7.00 (J=13.6 Hz, 1H), 6.62 (d, J=8.8 Hz, 1H), 4.72 (s, 1H), 4.05-4.12 (m, 2H), 3.89-3.92 (m, 1H), 3.87 (br d, J=10.4 Hz, 1H), 3.61-3.67 (m, 1H), 3.50-3.53 (m, 2H), 3.16-3.20 (m, 2H), 3.09 (br s, 1H), 2.96-3.00 (m, 1H), 2.87 (t, J=10.8 Hz, 1H), 2.69-2.74 (m, 1H), 1.20 (s, 3H), 1.13 (br d, J=6.0 Hz, 3H).

Example 83

5-[(4R,10bS)-8-[(3S,4S)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile

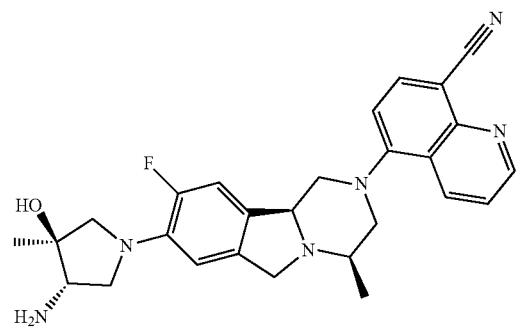 [SMILES: C[C@@H]1CN(c2ccc(C#N)c3ncccc23)C[C@@H]2c3cc(F)c(N4C[C@H](N)[C@@](C)(O)C4)cc3CN12]

The title compound was prepared in analogy to the preparation of Example 82 by using tert-butyl N-[(3S,4S)-4-hydroxy-4-methyl-pyrrolidin-3-yl]carbamate instead of tert-butyl N-[(3R,4R)-4-hydroxy-4-methyl-pyrrolidin-3-yl]carbamate. Example 83 (8.1 mg) was obtained. MS: calc'd 473 [(M+H)⁺], measured 473 [(M+H)⁺]. ¹H NMR (400 MHz, DMSO-d₆) δ ppm 9.06 (dd, J=1.6, 4.0 Hz, 1H), 8.61 (dd, J=1.6, 8.4 Hz, 1H), 8.24 (d, J=8.0 Hz, 1H), 7.70 (dd, J=4.0, 8.4 Hz, 1H), 7.28 (d, J=8.4 Hz, 1H), 7.01 (d, J=13.6 Hz, 1H), 6.62 (d, J=8.4 Hz, 1H), 4.70 (s, 1H), 4.11 (d, J=12.0 Hz, 1H), 3.87 (br d, J=9.2 Hz, 2H), 3.64-3.68 (m, 1H), 3.52 (br d, J=11.6 Hz, 1H), 3.36-3.43 (m, 2H), 3.16 (br dd, J=2.8, 9.6 Hz, 2H), 3.06-3.11 (m, 1H), 2.97-3.00 (m, 1H), 2.86 (t, J=11.2 Hz, 1H), 2.69-2.75 (m, 1H), 1.48-1.79 (m, 2H), 1.21 (s, 3H), 1.14 (d, J=6.4 Hz, 3H).

Example 84

5-[(4R,10bS)-8-(2,6-diazaspiro[3.3]heptan-2-yl)-9-fluoro-4-methyl-3,4,6,10b-tetrahydro-1H-pyrazino[2,1-a]isoindol-2-yl]quinoline-8-carbonitrile

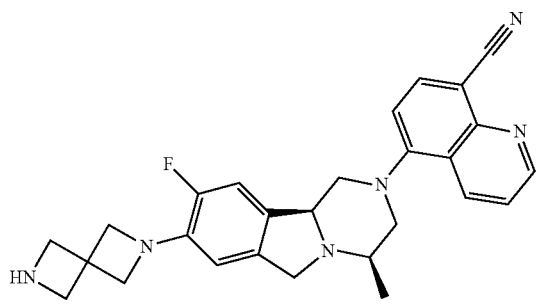 [SMILES: C[C@@H]1CN(c2ccc(C#N)c3ncccc23)C[C@@H]2c3cc(F)c(N4CC5(CNC5)C4)cc3CN12]

The title compound was prepared in analogy to the preparation of Example 82 by using tert-butyl 2,6-diazaspiro[3.3]heptane-2-carboxylate instead of tert-butyl N-[(3R,4R)-4-hydroxy-4-methyl-pyrrolidin-3-yl]carbamate.
Example 84 (10.4 mg) was obtained. MS: calc'd 455 [(M+H)$^+$], measured 455 [(M+H)$^+$]. $^1$H NMR (400 MHz, DMSO-d$_6$) δ ppm 9.12 (br d, J=2.8 Hz, 1H), 8.68 (br s, 2H), 8.28 (br d, J=8.0 Hz, 1H), 7.73 (dd, J=4.0, 8.4 Hz, 1H), 7.25-7.33 (m, 2H), 6.67 (br s, 1H), 4.75-5.25 (m, 1H), 4.31-4.60 (m, 1H), 4.17 (br t, J=5.6 Hz, 4H), 4.09 (br s, 4H), 3.68-3.92 (m, 1H), 3.45-3.59 (m, 2H), 3.19-3.27 (m, 2H), 2.86-2.96 (m, 1H), 1.33 (br s, 3H).

Example 85

5-[(4R,10bS)-9-fluoro-4-methyl-8-(9-oxa-3,7-diazabicyclo[3.3.1]nonan-3-yl)-3,4,6,10b-tetrahydro-1H-pyrazino[2,1-a]isoindol-2-yl]quinoline-8-carbonitrile

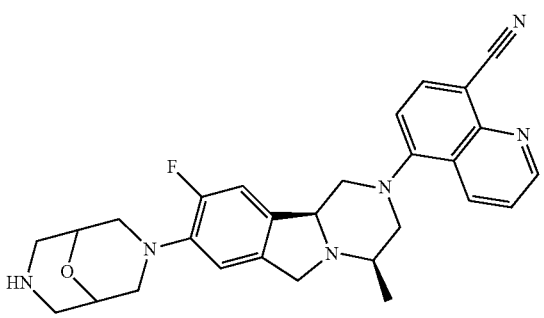 [SMILES: C[C@@H]1CN(c2ccc(C#N)c3ncccc23)C[C@@H]2c3cc(F)c(N4CC5CNCC(C4)O5)cc3CN12]

The title compound was prepared in analogy to the preparation of Example 82 by using tert-butyl 9-oxa-3,7-diazabicyclo[3.3.1]nonane-3-carboxylate instead of tert-butyl N-[(3R,4R)-4-hydroxy-4-methyl-pyrrolidin-3-yl]carbamate. Example 85 (10.4 mg) was obtained. MS: calc'd 485 [(M+H)$^+$], measured 485 [(M+H)$^+$]. $^1$H NMR (400 MHz, DMSO-d$_6$) δ ppm 9.30 (br d, J=10.8 Hz, 1H), 9.10 (dd, J=1.3, 4.2 Hz, 1H), 8.73 (br d, J=8.8 Hz, 1H), 8.30 (br d, J=8.0 Hz, 2H), 7.75 (dd, J=4.2, 8.6 Hz, 1H), 7.44 (br d, J=11.6 Hz, 1H), 7.34 (br d, J=7.2 Hz, 1H), 7.26 (br d, J=7.6 Hz, 1H), 5.22-5.38 (m, 1H), 4.79-4.91 (m, 1H), 4.43-4.59 (m, 1H), 4.10-4.28 (m, 4H), 3.64-4.00 (m, 2H), 3.37-3.43 (m, 6H), 3.19-3.27 (m, 2H), 2.93-3.10 (m, 1H), 1.37 (br d, J=6.0 Hz, 3H).

Example 86

5-[(4R,10bS)-4-methyl-8-(piperazine-1-carbonyl)-3,4,6,10b-tetrahydro-1H-pyrazino[2,1-a]isoindol-2-yl]quinoline-8-carbonitrile

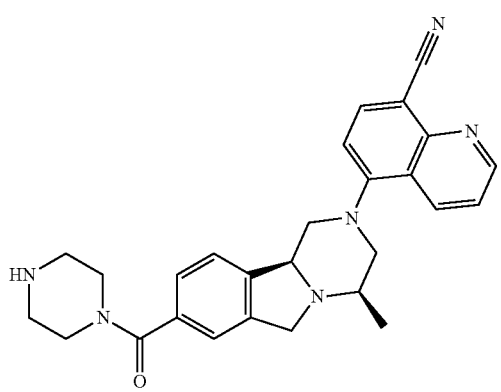 [SMILES: C[C@@H]1CN(c2ccc(C#N)c3ncccc23)C[C@@H]2c3ccc(C(=O)N4CCNCC4)cc3CN12]

The title compound was prepared according to the following scheme:

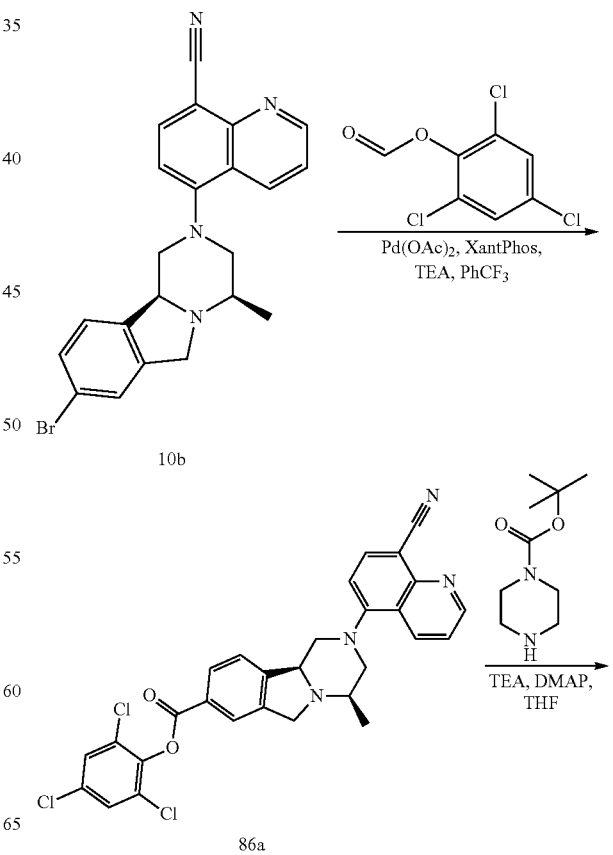

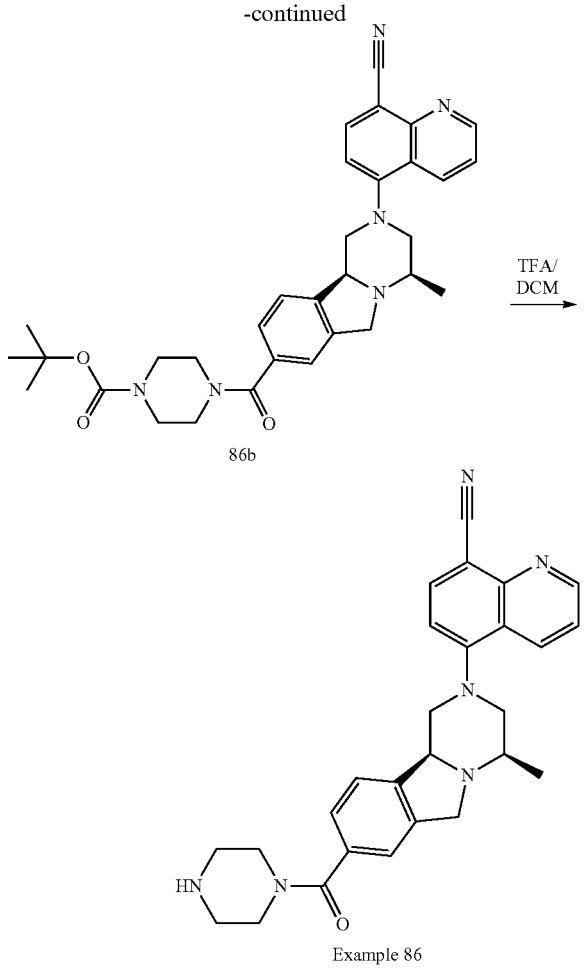

86b

TFA/
DCM
→

Example 86

Step 1: Preparation of (2,4,6-trichlorophenyl) (4R,10bS)-2-(8-cyano-5-quinolyl)-4-methyl-3,4,6,10b-tetrahydro-1H-pyrazino[2,1-a]isoindole-8-carboxylate (Compound 86a)

The mixture of 5-[(4R,10bS)-8-bromo-4-methyl-3,4,6,10b-tetrahydro-1H-pyrazino[2,1-a]isoindol-2-yl]quinoline-8-carbonitrile (compound 10b, 500 mg, 1.2 mmol), (2,4,6-trichlorophenyl) formate (1.6 g, 7.1 mmol), XantPhos (140 mg, 240 µmol), Pd(OAc)$_2$ (30.0 mg, 0.130 mmol) and triethylamine (300 mg, 3.0 mmol) in PhCF$_3$ (6.0 mL) was degassed and purged with N2 for 3 times. The resultant mixture was stirred at 60° C. for 16 hrs under N2 atmosphere. The reaction mixture was diluted with DCM/MeOH (80 mL/10 mL), filtered, and the filtrate was concentrated in vacuo. The residue was purified by Prep-TLC (PE:EA=1:1) to afford compound 86a (480 mg, 70.0% yield). MS calc'd 563 [(M+H)$^+$]; measured 563 [(M+H)$^+$].

Step 2: Preparation of tert-butyl 4-[(4R,10bS)-2-(8-cyano-5-quinolyl)-4-methyl-3,4,6,10b-tetrahydro-1H-pyrazino[2,1-a]isoindole-8-carbonyl]piperazine-1-carboxylate (Compound 86b)

To a solution of (2,4,6-trichlorophenyl) (4R,10bS)-2-(8-cyano-5-quinolyl)-4-methyl-3,4,6,10b-tetrahydro-1H-pyrazino[2,1-a]isoindole-8-carboxylate (compound 86a, 120.0 mg, 210 µmol) in THF (3 mL) was added DMAP (5.0 mg, 40 µmol), triethylamine (44.0 mg, 430 µmol) and tert-butyl piperazine-1-carboxylate (60.0 mg, 320 µmol). The resultant mixture was stirred at 50° C. for 16 hrs, then the mixture was concentrated in vacuo. The residue was purified by Prep-TLC to afford compound 86b (80 mg, 64.0% yield). MS calc'd 553 [(M+H)$^+$]; measured 553 [(M+H)$^+$]

Step 3: Preparation of 5-[(4R,10bS)-4-methyl-8-(piperazine-1-carbonyl)-3,4,6,10b-tetrahydro-1H-pyrazino[2,1-a]isoindol-2-yl]quinoline-8-carbonitrile (Example 86)

To a solution of tert-butyl 4-[(4R,10bS)-2-(8-cyano-5-quinolyl)-4-methyl-3,4,6,10b-tetrahydro-1H-pyrazino[2,1-a]isoindole-8-carbonyl]piperazine-1-carboxylate (compound 86b, 80.0 mg, 140 µmol) in DCM (5 mL) was added TFA (2 mL). The reaction mixture was stirred at room temperature for 2 hrs, then concentrated to afford a crude product, which was purified by pre-HPLC to afford Example 86 (34.5 mg, 51.0% yield). MS: calc'd 453 [(M+H)$^+$], measured 453 [(M+H)$^+$]. $^1$H NMR (400 MHz, DMSO-d$_6$) δ ppm 9.06 (dd, J=4.0, 1.6 Hz, 1H), 8.64 (dd, J=8.8, 1.6 Hz, 1H), 8.25 (d, J=8.0 Hz, 1H), 7.71 (dd, J=8.8, 4.0 Hz, 1H), 7.30-7.36 (m, 3H), 7.21 (d, J=8.0 Hz, 1H), 4.25 (d, J=12.4 Hz, 1H), 3.94-4.01 (m, 2H), 3.63 (dd, J=12.4, 1.6 Hz, 1H), 3.50-3.57 (m, 1H), 3.39-3.49 (m, 2H), 3.23-3.26 (m, 1H), 3.14-3.23 (m, 2H), 2.97 (t, J=11.2 Hz, 1H), 2.70-2.76 (m, 2H), 2.65-2.70 (m, 2H), 2.52 (d, J=2.0 Hz, 2H), 1.16 (d, J=6.4 Hz, 3H).

Example 87

5-[(4R,10bS)-8-[(1S,4S)-2,5-diazabicyclo[2.2.1]heptane-2-carbonyl]-4-methyl-3,4,6,10b-tetrahydro-1H-pyrazino[2,1-a]isoindol-2-yl]quinoline-8-carbonitrile

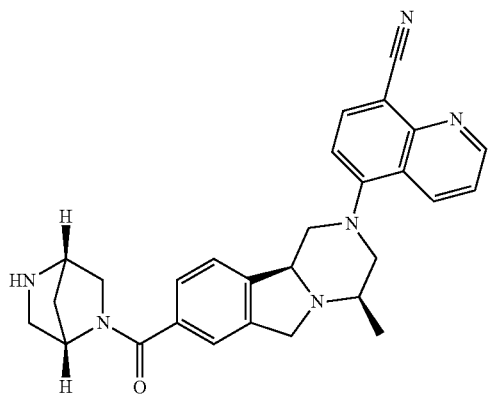 [SMILES: C[C@@H]1CN(c2ccc(C#N)c3ncccc23)C[C@@H]2c3ccc(C(=O)N4C[C@@H]5C[C@H]4CN5)cc3CN12]

The title compound was prepared in analogy to the preparation of Example 86 by using tert-butyl (1S,4S)-2,5-diazabicyclo[2.2.1]heptane-2-carboxylate instead of tert-butyl piperazine-1-carboxylate. Example 87 (46.1 mg) was obtained. MS: calc'd 465 [(M+H)$^+$], measured 465 [(M+H)$^+$]. $^1$H NMR (400 MHz, DMSO-d$_6$) δ ppm 9.07 (dd, J=4.0, 1.6 Hz, 1H), 8.64 (dd, J=8.4, 1.2 Hz, 1H), 8.26 (d, J=8.0 Hz, 1H), 7.71 (dd, J=8.4, 4.0 Hz, 1H), 7.46-7.54 (m, 1H), 7.34-7.43 (m, 2H), 7.32 (d, J=8.0 Hz, 1H), 4.33-4.76 (m, 1H), 4.24-4.32 (m, 1H), 4.12-4.22 (m, 1H), 3.99 (d, J=8.8 Hz, 2H), 3.60-3.67 (m, 2H), 3.54-3.59 (m, 1H), 3.42-3.43 (m, 1H), 3.23-3.26 (m, 1H), 3.10-3.16 (m, 1H), 2.97 (t, J=11.2 Hz, 1H), 2.73 (t, J=11.2 Hz, 1H), 2.51-2.53 (m, 2H), 1.92-2.06 (m, 1H), 1.67-1.84 (m, 1H), 1.17 (d, J=6.4 Hz, 3H).

Example 88

5-[(4R,10bS)-8-(4-amino-4-methyl-piperidine-1-carbonyl)-4-methyl-3,4,6,10b-tetrahydro-1H-pyrazino[2,1-a]isoindol-2-yl]quinoline-8-carbonitrile

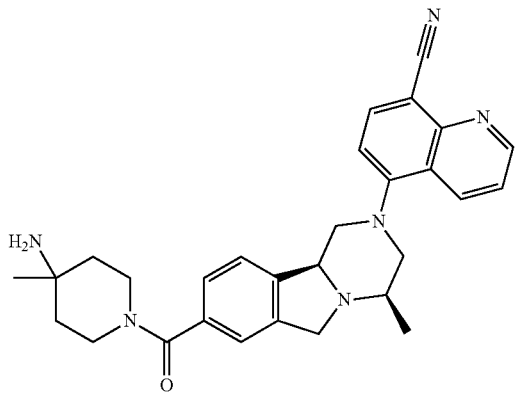 [SMILES: C[C@@H]1CN(c2ccc(C#N)c3ncccc23)C[C@@H]2c3ccc(C(=O)N4CCC(C)(N)CC4)cc3CN12]

The title compound was prepared in analogy to the preparation of Example 86 by using tert-butyl N-(4-methyl-4-piperidyl)carbamate instead of tert-butyl piperazine-1-carboxylate. Example 88 (56.1 mg) was obtained. MS: calc'd 481 [(M+H)⁺], measured 481 [(M+H)⁺]. ¹H NMR (400 MHz, DMSO-d₆) δ ppm 9.06 (d, J=3.2 Hz, 1H), 8.64 (d, J=8.0 Hz, 1H), 8.26 (d, J=8.0 Hz, 1H), 7.71 (dd, J=8.8, 4.0 Hz, 1H), 7.30-7.36 (m, 3H), 7.20 (d, J=8.0 Hz, 1H), 4.25 (d, J=12.4 Hz, 1H), 3.95-4.03 (m, 2H), 3.67-3.76 (m, 1H), 3.60-3.66 (m, 1H), 3.53-3.59 (m, 1H), 3.44 (d, J=11.6 Hz, 2H), 3.15-3.24 (m, 2H), 2.97 (t, J=11.2 Hz, 1H), 2.73 (t, J=10.8 Hz, 1H), 2.54-2.61 (m, 2H), 1.37-1.54 (m, 4H), 1.16 (d, J=6.4 Hz, 3H), 1.14 (s, 3H).

Example 89

5-[(4R,10bS)-8-(3,8-diazabicyclo[3.2.1]octane-3-carbonyl)-4-methyl-3,4,6,10b-tetrahydro-1H-pyrazino[2,1-a]isoindol-2-yl]quinoline-8-carbonitrile

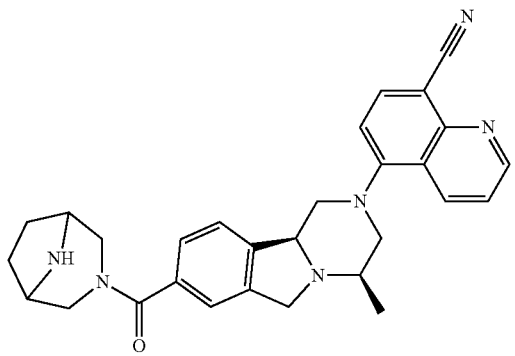 [SMILES: C[C@@H]1CN(c2ccc(C#N)c3ncccc23)C[C@@H]2c3ccc(C(=O)N4CC5CCC(C4)N5)cc3CN12]

The title compound was prepared in analogy to the preparation of Example 86 by using instead of tert-butyl piperazine-1-carboxylate. Example 89 (34.3 mg) was obtained. MS: calc'd 479 [(M+H)⁺], measured 479 [(M+H)⁺]. ¹H NMR (400 MHz, DMSO-d₆) δ ppm 9.07 (dd, J=4.0, 1.6 Hz, 1H), 8.64 (dd, J=8.4, 1.2 Hz, 1H), 8.26 (d, J=8.0 Hz, 1H), 7.71 (dd, J=8.4, 4.0 Hz, 1H), 7.45 (s, 1H), 7.30-7.37 (m, 3H), 4.44-4.59 (m, 1H), 4.27 (d, J=12.4 Hz, 1H), 3.95-4.03 (m, 2H), 3.85-3.94 (m, 1H), 3.59-3.67 (m, 1H), 3.45 (d, J=11.2 Hz, 1H), 3.15-3.28 (m, 2H), 2.95-3.01 (m, 1H), 2.84-2.93 (m, 1H), 2.69-2.79 (m, 2H), 2.51-2.53 (m, 2H), 1.86 (s, 4H), 1.16 (d, J=6.4 Hz, 3H).

Example 90

5-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]-2-deuterio-quinoline-8-carbonitrile

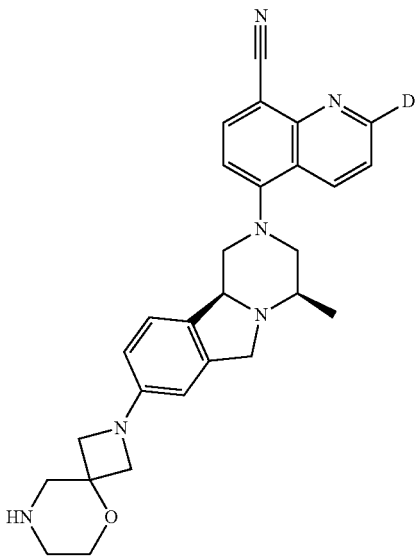 [SMILES: [2H]c1ccc2c(N3C[C@@H](C)N4Cc5cc(N6CC7(CNCCO7)C6)ccc5[C@H]4C3)ccc(C#N)c2n1]

The title compound was prepared according to the following scheme:

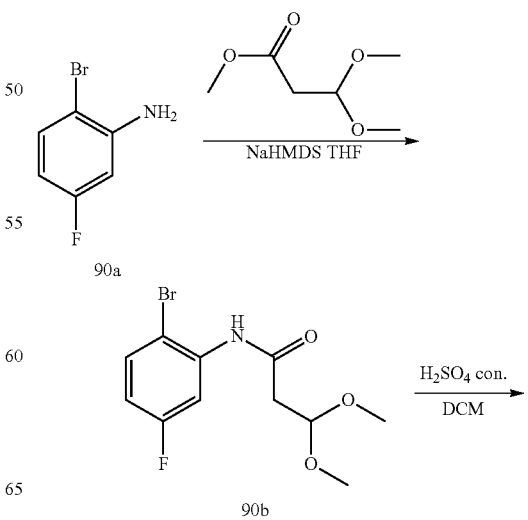

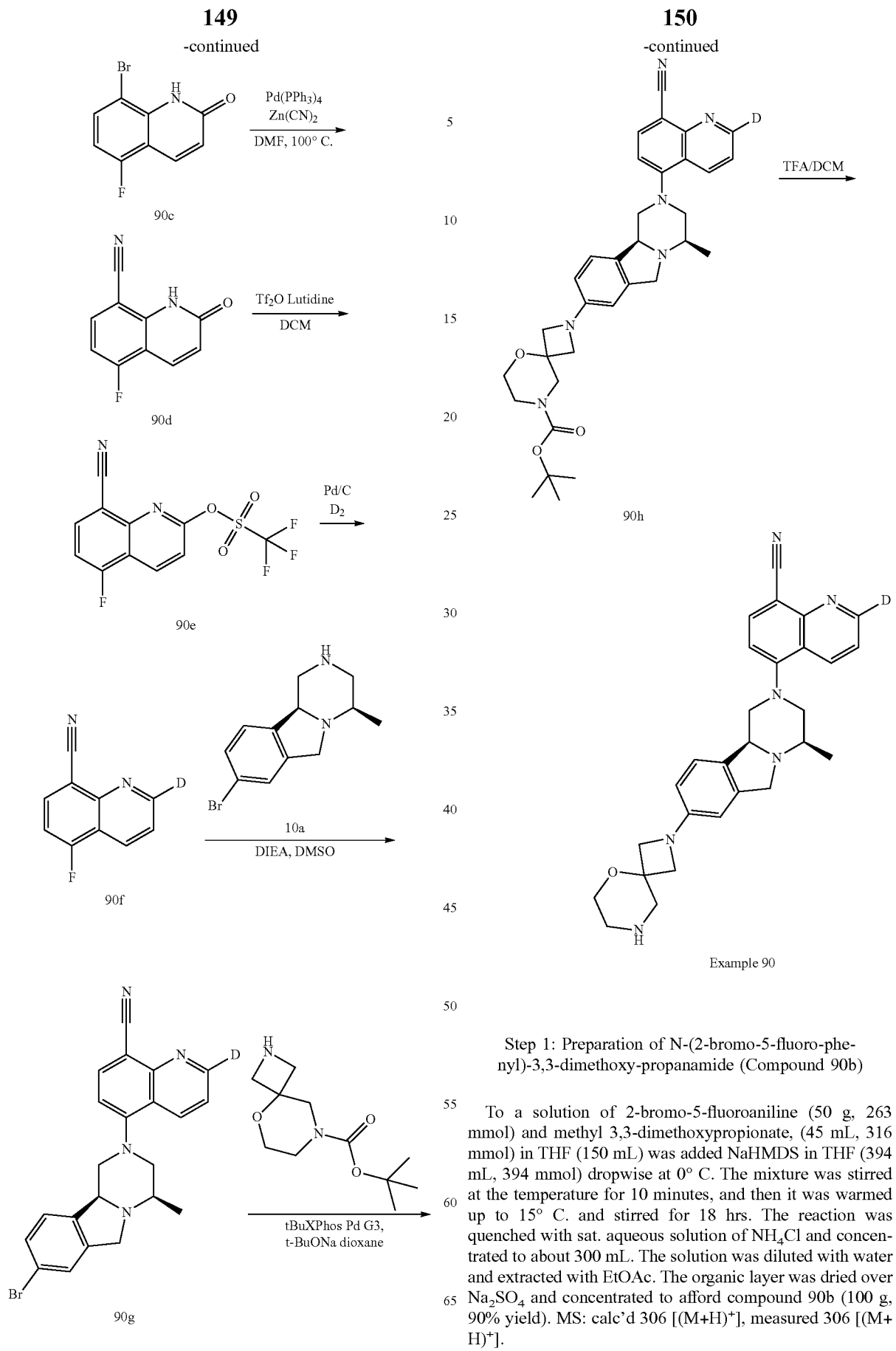

Step 1: Preparation of N-(2-bromo-5-fluoro-phenyl)-3,3-dimethoxy-propanamide (Compound 90b)

To a solution of 2-bromo-5-fluoroaniline (50 g, 263 mmol) and methyl 3,3-dimethoxypropionate, (45 mL, 316 mmol) in THF (150 mL) was added NaHMDS in THF (394 mL, 394 mmol) dropwise at 0° C. The mixture was stirred at the temperature for 10 minutes, and then it was warmed up to 15° C. and stirred for 18 hrs. The reaction was quenched with sat. aqueous solution of $NH_4Cl$ and concentrated to about 300 mL. The solution was diluted with water and extracted with EtOAc. The organic layer was dried over $Na_2SO_4$ and concentrated to afford compound 90b (100 g, 90% yield). MS: calc'd 306 [(M+H)$^+$], measured 306 [(M+H)$^+$].

Step 2: Preparation of 8-bromo-5-fluoro-1H-quinolin-2-one (Compound 90c)

A solution of N-(2-bromo-5-fluoro-phenyl)-3,3-dimethoxy-propanamide (compound 90b, 100 g, 238 mmol) in DCM (500 mL) was added to concentrated sulfuric acid (300 mL) at 0° C. The mixture was stirred at 15° C. for 2 hrs. The mixture was poured slowly into 2000 mL ice-water, and a yellow precipitate appeared. The mixture was filtered, and the wet-cake was washed with 500 mL water, 200 mL isopropyl alcohol and 300 mL PE. The solid was dried by sucking in vacuum to afford compound 90c (50 g, 86.5% yield). MS: calc'd 242 [(M+H)$^+$], measured 242 [(M+H)$^+$].

Step 3: Preparation of 5-fluoro-2-oxo-1H-quinoline-8-carbonitrile (Compound 90d)

A solution of 8-bromo-5-fluoro-1H-quinolin-2-one (compound 90c, 50 g, 206 mmol), zinc cyanide (4820 mg, 412 mmol), Pd(PPh$_3$)$_4$ (2428 mg, 21 mmol) in DMF was stirred at 120° C. for 5 hrs. The reaction mixture was diluted with water and extracted with DCM. The organic layer was dried and concentrated to give the crude product, which was purified by flash column to afford compound 90d (29 g, 74.5% yield). MS: calc'd 189 [(M+H)$^+$], measured 189 [(M+H)$^+$].

Step 4: Preparation of (8-cyano-5-fluoro-2-quinolyl) trifluoromethanesulfonate (Compound 90e)

To a solution of 5-fluoro-2-oxo-1H-quinoline-8-carbonitrile (compound 90d, 17 g, 90 mmol) and 2,6-dimethylpyridine (39 g, 361 mmol) in DCM was added trifluoromethanesulfonic anhydride (51 g, 181 mmol) dropwise at 0° C. The mixture was stirred at 0° C. for 1 hr, and then the reaction was diluted with water, extracted with DCM. The organic layer was dried and concentrated. The residue was purified by flash column to give compound 90e (23.0 g, 80% yield). MS: calc'd 321 [(M+H)$^+$], measured 321 [(M+H)$^+$].

Step 5: Preparation of 2-deuterio-5-fluoro-quinoline-8-carbonitrile (Compound 90f)

To a solution of (8-cyano-5-fluoro-2-quinolyl) trifluoromethanesulfonate (compound 90e, 23 g, 72 mmol) in THF (230 mL) and deuterium oxide (100 mL) was added potassium carbonate (20 g, 144 mmol) and Pd/C (6 g). The mixture was stirred at 40° C. for 5 hrs under deuterium atmosphere (balloon). The mixture was filtered, and the filtrate was concentrated and purified by flash column to afford compound 90f (11 g, 87.8% yield) which was used directly for the next step without further purification. MS: calc'd 174 [(M+H)$^+$], measured 174 [(M+H)$^+$].

Step 6: Preparation of 5-[(4R,10bS)-8-bromo-4-methyl-3,4,6,10b-tetrahydro-1H-pyrazino[2,1-a]isoindol-2-yl]-2-deuterio-quinoline-8-carbonitrile (Compound 90g)

To a solution of (4R,10bS)-8-bromo-4-methyl-1,2,3,4,6,10b-hexahydropyrazino-[2,1-a]isoindole (compound 10a, 660 mg, 2.8 mmol) in DMSO (20 mL) was added 2-deuterio-5-fluoro-quinoline-8-carbonitrile (compound 90f, 350 mg, 2.0 mmol) and DIEA (1.3 g, 10.1 mmol).

The resultant mixture was stirred at 120° C. overnight. After being cooled to room temperature, the reaction was quenched with water (50 mL) and extracted with EA (80 mL) twice. The combined organic layer was washed with brine, dried over Na$_2$SO$_4$, filtered and concentrated in vacuo. The residue was purified by flash chromatography (silica gel, 40 g, 0% to 100% EtOAc in PE) to afford compound 90g (810 mg, 95.3% yield). MS: calc'd 420, 422 [(M+H)$^+$], measured 420, 422 [(M+H)$^+$].

Step 2: Preparation of tert-butyl 2-[(4R,10bS)-2-(8-cyano-2-deuterio-5-quinolyl)-4-methyl-3,4,6,10b-tetrahydro-1H-pyrazino[2,1-a]isoindol-8-yl]-5-oxa-2,8-diazaspiro[3.5]nonane-8-carboxylate (Compound 90h)

To a solution of 5-[(4R,10bS)-8-bromo-4-methyl-3,4,6,10b-tetrahydro-1H-pyrazino-[2,1-a]isoindol-2-yl]-2-deuterio-quinoline-8-carbonitrile (compound 90g, 100 mg, 238 μmol) in dioxane (15 mL) was added t-BuONa (45.7 mg, 476 μmol), tert-butyl 5-oxa-2,8-diazaspiro[3.5]nonane-8-carboxylate (65.2 mg, 285 μmol) and tBuXPhos Pd G3 (9.4 mg, 11.9 μmol). The reaction mixture was stirred at 90° C. overnight. The mixture was cooled to room temperature, diluted with water (50 ml) and extracted with EA (50 mL) for three times. The combined organic layer was washed with brine, dried over Na$_2$SO$_4$ and concentrated in vacuo.

The residue was purified by flash chromatography (silica gel, 20 g, 0% to 100% EtOAc in PE) to afford compound 90h (80 mg, 59.2% yield). MS: calc'd 568 [(M+H)$^+$], measured 568 [(M+H)$^+$].

Step 3: Preparation of 5-[(4R,10bS)-4-methyl-8-(5-oxa-2,8-diazaspiro[3.5]-nonan-2-yl)-3,4,6,10b-tetrahydro-1H-pyrazino[2,1-a]isoindol-2-yl]-2-deuterio-quinoline-8-carbonitrile (Example 90)

To a solution of tert-butyl 2-[(4R,10bS)-2-(8-cyano-2-deuterio-5-quinolyl)-4-methyl-3,4,6,10b-tetrahydro-1H-pyrazino[2,1-a]isoindol-8-yl]-5-oxa-2,8-diazaspiro[3.5] nonane-8-carboxylate (compound 90h, 80 mg, 141 μmol) in DCM (8 mL) was added TFA (4 mL). The mixture was stirred at room temperature for 2 hrs. The reaction mixture was stirred at room temperature for 2 hrs, then concentrated to afford a crude product, which was purified by pre-HPLC to afford Example 90 (42 mg). MS: calc'd 468 [(M+H)$^+$], measured 468 [(M+H)$^+$]. $^1$H NMR (400 MHz, METHANOL-d$_4$) δ ppm 8.76 (d, J=8.6 Hz, 1H), 8.18 (d, J=7.9 Hz, 1H), 7.72 (d, J=8.6 Hz, 1H), 7.37 (d, J=7.9 Hz, 1H), 7.25 (d, J=8.2 Hz, 1H), 6.66 (d, J=1.8 Hz, 1H), 6.51 (dd, J=2.1, 8.2 Hz, 1H), 4.77-4.84 (m, 1H), 4.66 (d, J=13.2 Hz, 1H), 4.25 (d, J=13.2 Hz, 1H), 4.06 (d, J=8.6 Hz, 2H), 3.86-3.98 (m, 4H), 3.79 (d, J=8.4 Hz, 2H), 3.58 (br d, J=12.2 Hz, 1H), 3.54 (s, 2H), 3.23-3.29 (m, 2H), 3.01-3.17 (m, 2H), 1.44 (d, J=6.6 Hz, 3H).

Example 91

5-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]-2-deuterio-quinoline-8-carbonitrile

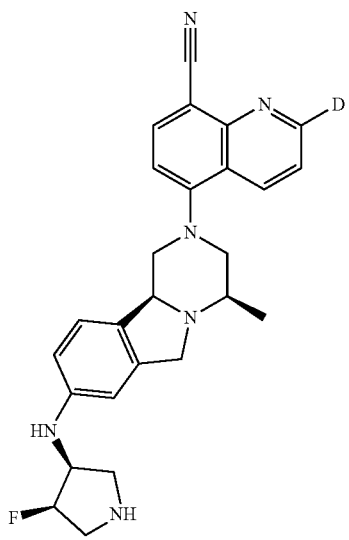 [SMILES: [2H]c1ccc2c(N3C[C@@H](C)N4Cc5cc(N[C@H]6CNC[C@H]6F)ccc5[C@H]4C3)ccc(C#N)c2n1]

The title compound was prepared in analogy to the preparation of Example 90 by using tert-butyl (3S,4R)-3-amino-4-fluoropyrrolidine-1-carboxylate instead of tert-butyl 5-oxa-2,8-diazaspiro[3.5]nonane-8-carboxylate. Example 91 (21.2 mg) was obtained. MS: calc'd 444 [(M+H)$^+$], measured 444 [(M+H)$^+$]. $^1$H NMR (400 MHz, METHANOL-d$_4$) δ ppm 8.66 (d, J=8.7 Hz, 1H), 8.07 (d, J=7.9 Hz, 1H), 7.61 (d, J=8.6 Hz, 1H), 7.27 (d, J=8.1 Hz, 1H), 7.14 (d, J=8.3 Hz, 1H), 6.84 (d, J=1.8 Hz, 1H), 6.70 (dd, J=2.2, 8.3 Hz, 1H), 5.14-5.36 (m, 1H), 4.88-4.97 (m, 1H), 4.67 (d, J=13.4 Hz, 1H), 4.28-4.48 (m, 2H), 3.95-4.10 (m, 1H), 3.74-3.84 (m, 1H), 3.45-3.72 (m, 4H), 3.07-3.18 (m, 2H), 2.95-3.05 (m, 1H), 1.39 (d, J=6.7 Hz, 3H).

Example 92

5-[(4R,10bS)-8-(3-amino-3-methyl-azetidin-1-yl)-4-methyl-3,4,6,10b-tetrahydro-1H-pyrazino[2,1-a]isoindol-2-yl]-2-deuterio-quinoline-8-carbonitrile

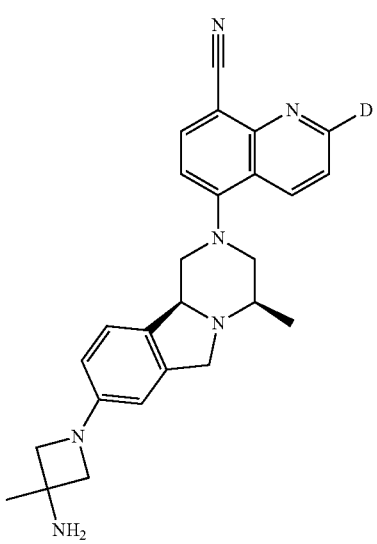 [SMILES: [2H]c1ccc2c(N3C[C@@H](C)N4Cc5cc(N6CC(C)(N)C6)ccc5[C@H]4C3)ccc(C#N)c2n1]

The title compound was prepared in analogy to the preparation of Example 90 by using tert-butyl N-(3-methylazetidin-3-yl)carbamate instead of tert-butyl 5-oxa-2,8-diazaspiro[3.5]nonane-8-carboxylate. Example 92 (21.2 mg) was obtained. MS: calc'd 426 [(M+H)$^+$], measured 426 [(M+H)$^+$]. $^1$H NMR (400 MHz, METHANOL-d$_4$) δ ppm 8.77 (d, J=8.6 Hz, 1H), 8.19 (d, J=8.1 Hz, 1H), 7.72 (d, J=8.6 Hz, 1H), 7.38 (d, J=8.1 Hz, 1H), 7.27 (d, J=8.2 Hz, 1H), 6.67 (d, J=1.8 Hz, 1H), 6.53 (dd, J=2.1, 8.2 Hz, 1H), 4.78-4.87 (m, 1H), 4.68 (d, J=13.3 Hz, 1H), 4.27 (d, J=13.3 Hz, 1H), 3.85-4.06 (m, 6H), 3.56-3.65 (m, 1H), 3.03-3.19 (m, 2H), 1.70 (s, 3H), 1.45 (d, J=6.6 Hz, 3H).

155
Example 93

5-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]-2-deuterio-quinoline-8-carbonitrile

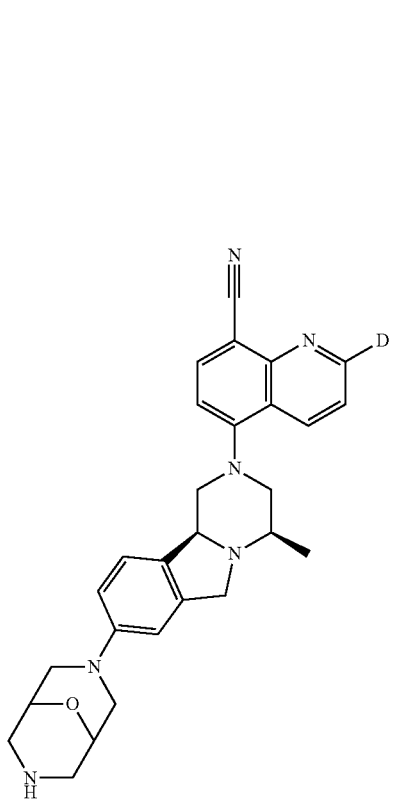 [SMILES: [2H]c1ccc2c(N3C[C@@H](C)N4Cc5cc(N6CC7CNCC(C6)O7)ccc5[C@H]4C3)ccc(C#N)c2n1]

The title compound was prepared in analogy to the preparation of Example 90 by using tert-butyl 9-oxa-3,7-diazabicyclo[3.3.1]nonane-3-carboxylate instead of tert-butyl 5-oxa-2,8-diazaspiro[3.5]nonane-8-carboxylate. Example 93 (21.2 mg) was obtained. MS: calc'd 468 [(M+H)$^+$], measured 468 [(M+H)$^+$]. $^1$H NMR (400 MHz, METHANOL-d$_4$) δ ppm 8.77 (d, J=8.7 Hz, 1H), 8.19 (d, J=7.9 Hz, 1H), 7.72 (d, J=8.6 Hz, 1H), 7.37 (d, J=7.9 Hz, 1H), 7.31 (d, J=8.3 Hz, 1H), 7.27 (d, J=1.7 Hz, 1H), 7.11 (dd, J=2.2, 8.3 Hz, 1H), 4.54-4.65 (m, 2H), 4.23-4.31 (m, 1H), 4.28 (br s, 1H), 4.12 (br d, J=12.7 Hz, 1H), 3.88-3.98 (m, 1H), 3.71-3.86 (m, 3H), 3.51-3.66 (m, 5H), 3.20-3.28 (m, 2H), 3.01-3.14 (m, 2H), 1.41 (d, J=6.5 Hz, 3H).

156
Example 94

4-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile

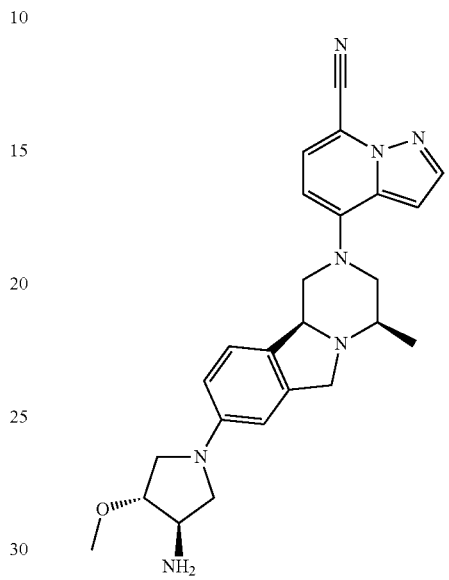

The title compound was prepared according to the following scheme:

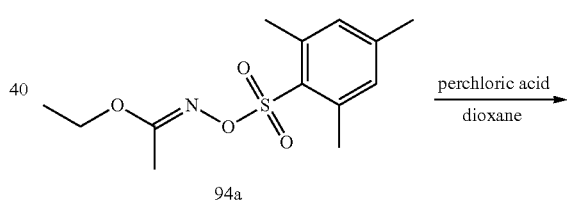

94a

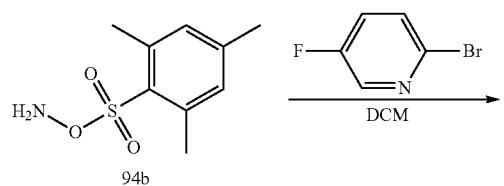

94b

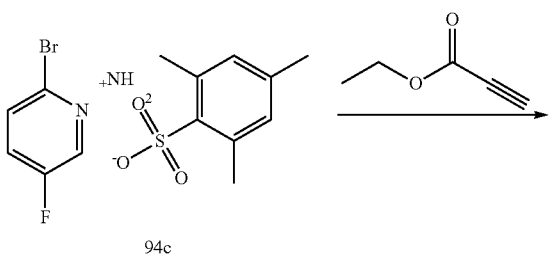

94c

-continued

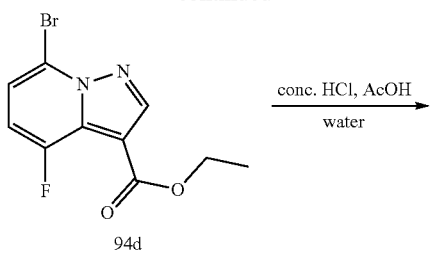
94d

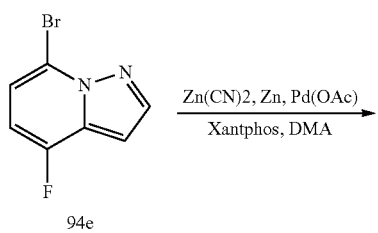
94e

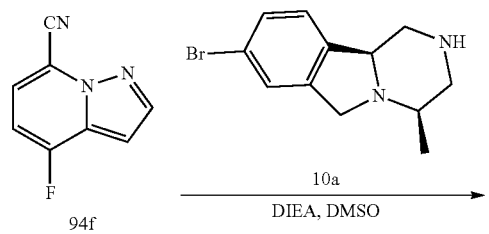
94f

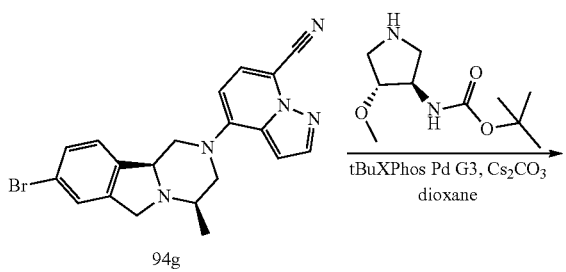
94g

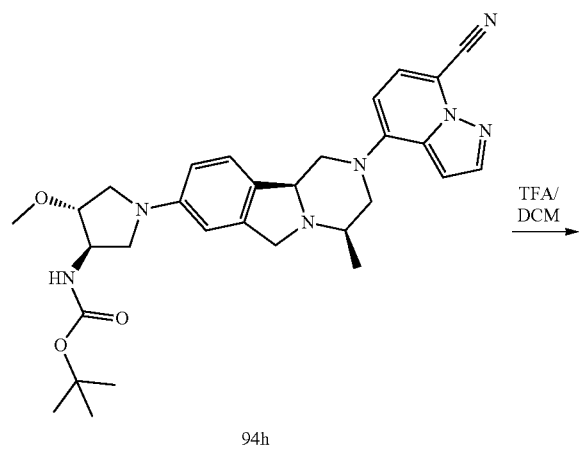
94h

-continued

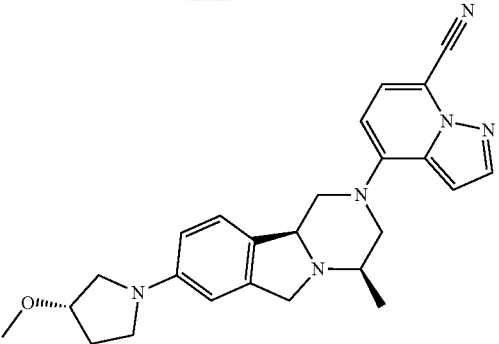

Example 94

Step 1: Preparation of amino 2,4,6-trimethylbenzenesulfonate (Compound 94b)

A solution of ethyl (1E)-N-(2,4,6-trimethylphenyl)sulfonyloxyethanimidate (compound 94a, 200 g, 700 mmol) in 1,4-dioxane (500 mL) was added perchloric acid (110 mL) dropwise in 30 min and stirred for 1 hr at 0° C. 1000 mL ice-water was added and the mixture was filtered. The filter cake was dissolved in 1.5 L EtOAc, then stirred for 30 minutes. The organic layer was concentrated (keep the temperature below 25° C.) to afford crude product. The crude product was recrystallized (petroleum/EtOAc=10/1) to afford compound 94b (110 g, 73% yield). MS: calc'd 216 [(M+H)+], measured 216 [(M+H)+].

Step 2: Preparation of 2-bromo-5-fluoro-pyridin-1-ium-1-amine 2,4,6-trimethylbenzenesulfonate (Compound 94c)

A solution of amino 2,4,6-trimethylbenzenesulfonate (compound 94b, 110 g, 511 mmol) and 2-bromo-5-fluoropyridine (60 g, 341 mmol) in DCM (1800 mL) was stirred at 10° C. for 18 hrs. The mixture was concentrated, the residue was recrystallized in EtOAc to afford compound 94c (90 g, 92% yield). MS: calc'd 191 [(M+H)+], measured 191 [(M+H)+].

Step 3: Preparation of ethyl 7-bromo-4-fluoro-pyrazolo[1,5-a]pyridine-3-carboxylate (Compound 94d)

A solution of 2-bromo-5-fluoro-pyridin-1-ium-1-amine; 2,4,6-trimethylbenzenesulfonate (compound 94c, 90 g, 230 mmol), K$_2$CO$_3$ (64 g, 460 mmol) and ethyl propiolate (28 mL, 276 mmol) in DMF (1300 mL) was stirred at 10° C. for 18 hrs. The reaction was diluted with water, extracted with EtOAc. The organic layer was dried over Na$_2$SO$_4$, filtered and the filtrate was concentrated in vacuo. The residue was purified by chromatography column to afford compound 94d (11 g, 16.7% yield). MS: calc'd 287 [(M+H)+], measured 287 [(M+H)+].

Step 4: Preparation of 7-bromo-4-fluoro-pyrazolo[1,5-a]pyridine (Compound 94e)

To a mixture of ethyl 7-bromo-4-fluoro-pyrazolo[1,5-a]pyridine-3-carboxylate (compound 94d, 8.0 g, 26.7 mmol)

in acetic acid (48 mL) and water (48 mL) was added conc. HCl (36 mL, 432 mmol). The mixture was stirred at 100° C. for 18 hrs. The mixture was diluted with water (200 mL), basified with aq. NaOH (1N) to pH=8, extracted with EA (200 mL) for three times.

The combined organic layers were washed with brine, dried over $Na_2SO_4$ and concentrated in vacuo to afford compound 94e (5 g, 86.9% yield) which was used directly for the next step. MS: calc'd 215 [(M+H)+], measured 215 [(M+H)+].

Step 5: Preparation of 4-fluoropyrazolo[1,5-a]pyridine-7-carbonitrile (Compound 94)

A mixture of 7-bromo-4-fluoro-pyrazolo[1,5-a]pyridine (compound 94e, 1000 mg, 4.6 mmol), zinc cyanide (880 mg, 7.5 mmol), zinc (31 mg, 0.5 mmol), XantPhos (1076 mg, 1.8 mmol) and $Pd(OAc)_2$ (209 mg, 0.9 mmol) in DMA (10 mL) was degassed and purged with Ar for 3 times, and then the mixture was stirred at 120° C. for 1 h under Ar atmosphere. The mixture was diluted with EA (150 mL), filtered and the filtrate was washed with water (50 mL), brine (50 mL×3), dried over $Na_2SO_4$ and concentrated in vacuo. The residue was purified by Prep-TLC (PE:EA=3:1) to afford compound 94f (600 mg, 68% yield). MS: calc'd 162 [(M+H)+], measured 162 [(M+H)+].

Step 6: Preparation of 4-((4R,10bS)-8-bromo-4-methyl-3,4,6,10b-tetrahydropyrazino-[2,1-a]isoindol-2(1H)-yl)pyrazolo[1,5-a]pyridine-7-carbonitrile (Compound 94g)

To a solution of 4-fluoropyrazolo[1,5-a]pyridine-7-carbonitrile (compound 94f, 750 mg, 4.6 mmol) in DMSO (30 mL) was added (4R,10bS)-8-bromo-4-methyl-1,2,3,4,6,10b-hexahydropyrazino[2,1-a]isoindole (compound 10a, 1.2 g, 4.6 mmol) and DIEA (3.0 g, 23.3 mmol). The reaction mixture was stirred at 100° C. for 20 hrs. After cooled to room temperature, the reaction was quenched with water (50 mL) and extracted with EA (100 mL) twice. The combined organic layer was washed with brine, dried over $Na_2SO_4$, filtered and concentrated in vacuo. The residue was purified by flash chromatography (silica gel, 80 g, 0% to 100% EtOAc in PE) to afford compound 94g (870 mg, 45.8% yield). MS: calc'd 408, 410 [(M+H)+], measured 408, 410 [(M+H)+].

Step 7: Preparation of tert-butyl ((3R,4R)-1-((4R,10bS)-2-(7-cyanopyrazolo-[1,5-a]pyridin-4-yl)-4-methyl-1,2,3,4,6,10b-hexahydropyrazino[2,1-a]isoindol-8-yl)-4-methoxypyrrolidin-3-yl)carbamate (Compound 94h)

To a solution of 4-((4R,10bS)-8-bromo-4-methyl-3,4,6,10b-tetr-ahydropyrazino[2,1-a]isoindol-2(1H)-yl)pyrazolo[1,5-a]pyridine-7-carbonitrile (compound 94g, 40 mg, 98 µmol) in dioxane (6 mL) was added tert-butyl ((3R,4R)-4-methoxypyrrolidin-3-yl)-carbamate (25.4 mg, 118 µmol), $Cs_2CO_3$ (95.8 mg, 294 µmol) and tBuXPhos Pd G3 (7.8 mg, 9.8 µmol). The reaction mixture was stirred at 90° C. overnight. The mixture was cooled to room temperature, diluted with water (30 mL) and extracted with EA (30 mL) for three times. The combined organic layer was washed with brine, dried over $Na_2SO_4$, filtered and concentrated in vacuo. The residue was purified by flash chromatography (silica gel, 12 g, 30% to 100% EtOAc in PE) to afford compound 94h (22 mg, 41.3% yield). MS: calc'd 544 [(M+H)+], measured 544 [(M+H)+].

Step 3: Preparation of 4-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]-pyrazolo[1,5-a]pyridine-7-carbonitrile (Example 94)

To a solution of tert-butyl ((3R,4R)-1-((4R,10bS)-2-(7-cyanopyrazolo[1,5-a]-pyridin-4-yl)-4-methyl-1,2,3,4,6,10b-hexahydropyrazino[2,1-a]isoindol-8-yl)-4-meth-oxypyrrolidin-3-yl)carbamate (compound 94h, 22 mg, 40.5 µmol) in DCM (10 mL) was added TFA (3 mL). The mixture was stirred at room temperature for 2 hrs. The reaction mixture was stirred at room temperature for 2 hrs, then concentrated to afford a crude product, which was purified by pre-HPLC to afford Example 94 (12 mg, 66% yield). MS: calc'd 444 [(M+H)+], measured 444 [(M+H)+]. $^1$H NMR (400 MHz, METHANOL-d$_4$) δ ppm 8.08 (d, J=2.4 Hz, 1H), 7.49 (d, J=7.9 Hz, 1H), 7.23 (d, J=8.2 Hz, 1H), 6.95 (d, J=2.4 Hz, 1H), 6.74 (d, J=1.7 Hz, 1H), 6.69 (d, J=8.1 Hz, 1H), 6.60 (dd, J=2.1, 8.3 Hz, 1H), 4.33-4.41 (m, 1H), 4.24-4.31 (m, 1H), 4.07-4.16 (m, 2H), 3.78-3.94 (m, 4H), 3.63-3.71 (m, 1H), 3.41-3.52 (m, 1H), 3.48 (s, 3H), 3.24-3.33 (m, 2H), 2.98-3.06 (m, 1H), 2.86-2.96 (m, 1H), 1.34 (d, J=6.5 Hz, 3H).

Example 95

4-[(4R,10bS)-8-[(3S,4S)-3-amino-4-methoxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile

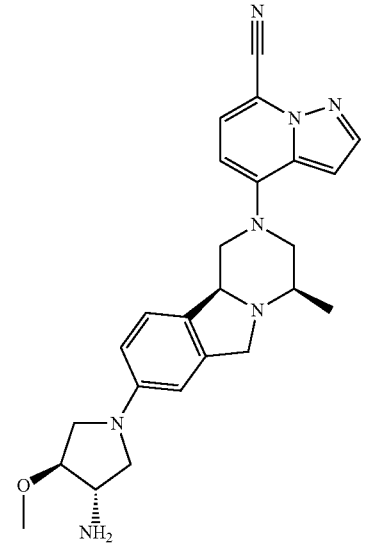 [SMILES: CO[C@H]1CN(c2ccc3c(c2)CN2[C@H](C)CN(c4ccc(C#N)n5nccc45)C[C@H]32)C[C@@H]1N]

The title compound was prepared in analogy to the preparation of Example 94 by using tert-butyl ((3S,4S)-4-methoxypyrrolidin-3-yl)-carbamate instead of tert-butyl ((3R,4R)-4-methoxypyrrolidin-3-yl)-carbamate. Example 95 (18 mg) was obtained. MS: calc'd 444 [(M+H)+], measured 444 [(M+H)+]. $^1$H NMR (400 MHz, METHANOL-d$_4$) δ ppm 8.06-8.09 (m, 1H), 7.50 (d, J=8.1 Hz, 1H), 7.26 (d, J=8.3 Hz, 1H), 6.96 (d, J=2.4 Hz, 1H), 6.75 (s, 1H), 6.70 (s, 1H), 6.57-6.65 (m, 1H), 4.46 (d, J=12.7 Hz, 1H), 4.25-4.32

(m, 2H), 4.10-4.17 (m, 1H), 3.85-3.97 (m, 5H), 3.63-3.71 (m, 1H), 3.42-3.49 (m, 2H), 3.48 (s, 3H), 2.92-3.10 (m, 2H), 1.37 (d, J=6.5 Hz, 3H).

Example 96

4-[(4R,10bS)-8-[(3R)-3-aminopyrrolidin-1-yl]-4-methyl-3,4,6,10b-tetrahydro-1H-pyrazino[2,1-a]isoindol-2-yl]pyrazolo[1,5-a]pyridine-7-carbonitrile

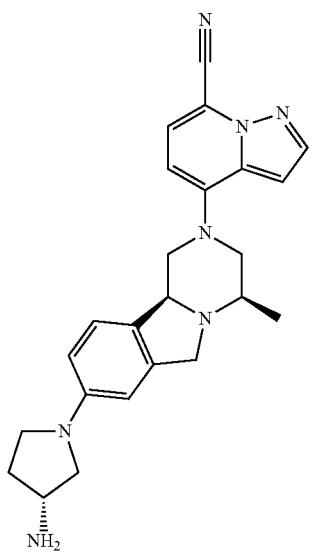 [SMILES: C[C@@H]1CN(c2ccc(C#N)n3nccc23)C[C@@H]2c3ccc(N4CC[C@@H](N)C4)cc3CN12]

The title compound was prepared in analogy to the preparation of Example 94 by using tert-butyl N-[(3R)-pyrrolidin-3-yl]carbamate instead of tert-butyl ((3R,4R)-4-methoxypyrrolidin-3-yl)-carbamate. Example 96 (5.2 mg) was obtained. MS: calc'd 414 [(M+H)$^+$], measured 414 [(M+H)$^+$]. $^1$H NMR (400 MHz, METHANOL-d$_4$) δ ppm 8.12 (d, J=2.4 Hz, 1H), 7.54 (d, J=7.9 Hz, 1H), 7.41 (br d, J=8.2 Hz, 1H), 7.03 (d, J=2.4 Hz, 1H), 6.70-6.84 (m, 3H), 4.54-4.64 (m, 1H), 4.04-4.23 (m, 3H), 3.58-3.72 (m, 2H), 3.40-3.53 (m, 2H), 2.43-2.64 (m, 1H), 2.13-2.28 (m, 1H), 1.56 (d, J=6.7 Hz, 3H).

Example 97

4-[(4R,10bS)-4-methyl-8-[(3R)-3-methylpiperazin-1-yl]-3,4,6,10b-tetrahydro-1H-pyrazino[2,1-a]isoindol-2-yl]pyrazolo[1,5-a]pyridine-7-carbonitrile

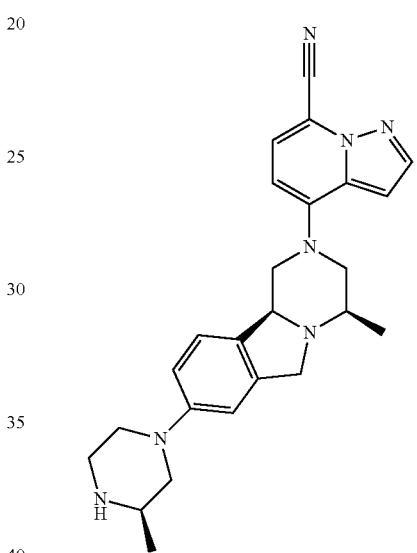

The title compound was prepared in analogy to the preparation of Example 94 by using tert-butyl (2R)-2-methylpiperazine-1-carboxylate instead of tert-butyl ((3R,4R)-4-methoxypyrrolidin-3-yl)-carbamate. Example 97 (6.0 mg) was obtained. MS: calc'd 428 [(M+H)$^+$], measured 428 [(M+H)]. $^1$H NMR (400 MHz, METHANOL-d$_4$) δ ppm 8.08 (d, J=2.4 Hz, 1H), 7.50 (d, J=8.1 Hz, 1H), 7.26 (d, J=8.6 Hz, 1H), 7.12 (d, J=1.6 Hz, 1H), 6.93-7.00 (m, 2H), 6.70 (d, J=8.1 Hz, 1H), 4.25-4.36 (m, 2H), 4.00 (br d, J=11.5 Hz, 1H), 3.69-3.91 (m, 4H), 3.47-3.58 (m, 3H), 3.20-3.27 (m, 1H), 2.96-3.09 (m, 2H), 2.74-2.91 (m, 2H), 1.42 (d, J=6.6 Hz, 3H), 1.31 (d, J=6.5 Hz, 3H).

Example 98

4-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]pyrazolo[1,5-a]pyridine-7-carbonitrile

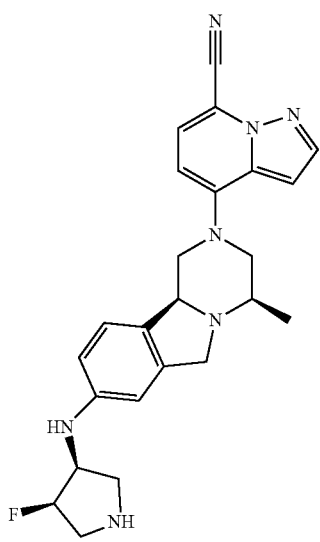 [SMILES: C[C@@H]1CN(c2ccc(C#N)n3nccc23)C[C@@H]2c3ccc(N[C@H]4CNC[C@H]4F)cc3CN12]

The title compound was prepared in analogy to the preparation of Example 94 by using tert-butyl (3S,4R)-3-amino-4-fluoro-pyrrolidine-1-carboxylate instead of tert-butyl ((3R,4R)-4-methoxypyrrolidin-3-yl)-carbamate. Example 98 (17 mg) was obtained. MS: calc'd 432 [(M+H)$^+$], measured 432 [(M+H)$^+$]. $^1$H NMR (400 MHz, METHANOL-d$_4$) δ ppm 8.09 (d, J=2.3 Hz, 1H), 7.51 (d, J=7.9 Hz, 1H), 7.21 (d, J=8.1 Hz, 1H), 6.97 (d, J=2.4 Hz, 1H), 6.87 (d, J=1.8 Hz, 1H), 6.76 (dd, J=2.2, 8.3 Hz, 1H), 6.72 (d, J=8.1 Hz, 1H), 5.24-5.45 (m, 1H), 4.47 (d, J=13.0 Hz, 1H), 4.39-4.55 (m, 1H), 4.24-4.38 (m, 2H), 3.89-4.02 (m, 2H), 3.64-3.84 (m, 3H), 3.52-3.63 (m, 1H), 3.24 (t, J=11.1 Hz, 1H), 2.96-3.11 (m, 2H), 1.39 (d, J=6.5 Hz, 3H).

Example 99

4-[(4R,10bS)-8-[(3R,4S)-3-amino-4-fluoro-pyrrolidin-1-yl]-4-methyl-3,4,6,10b-tetrahydro-1H-pyrazino[2,1-a]isoindol-2-yl]pyrazolo[1,5-a]pyridine-7-carbonitrile

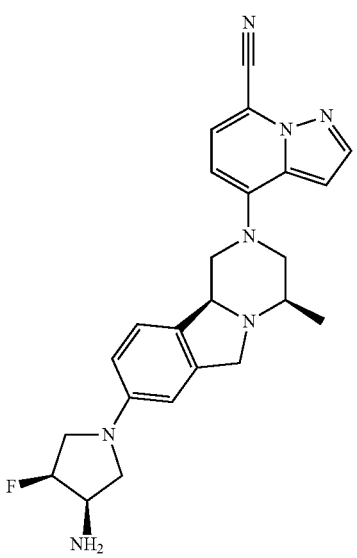 [SMILES: C[C@@H]1CN(c2ccc(C#N)n3nccc23)C[C@@H]2c3ccc(N4C[C@@H](N)[C@@H](F)C4)cc3CN12]

The title compound was prepared in analogy to the preparation of Example 94 by using tert-butyl N-[(3R,4S)-4-fluoropyrrolidin-3-yl]carbamate instead of tert-butyl ((3R,4R)-4-methoxypyrrolidin-3-yl)-carbamate. Example 99 (17 mg) was obtained. MS: calc'd 432 [(M+H)$^+$], measured 432 [(M+H)$^+$]. $^1$H NMR (400 MHz, METHANOL-d$_4$) δ ppm 8.08 (d, J=2.4 Hz, 1H), 7.50 (d, J=8.1 Hz, 1H), 7.22 (d, J=8.3 Hz, 1H), 6.95 (d, J=2.4 Hz, 1H), 6.66-6.73 (m, 2H), 6.56 (dd, J=2.3, 8.1 Hz, 1H), 5.33-5.55 (m, 1H), 4.24-4.39 (m, 2H), 4.02-4.08 (m, 1H), 3.62-3.93 (m, 5H), 3.39-3.46 (m, 2H), 2.97-3.07 (m, 1H), 2.84-2.96 (m, 1H), 2.21 (t, J=7.5 Hz, 1H), 1.32 (d, J=6.5 Hz, 3H).

Example 100

4-[(4R,10bS)-8-(4-amino-4-methyl-1-piperidyl)-4-methyl-3,4,6,10b-tetrahydro-1H-pyrazino[2,1-a]isoindol-2-yl]pyrazolo[1,5-a]pyridine-7-carbonitrile

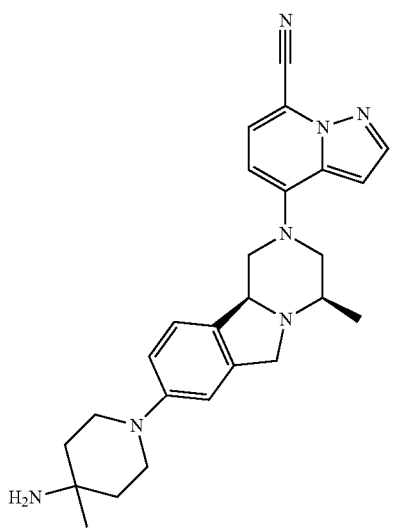 [SMILES: C[C@@H]1CN(c2ccc(C#N)n3nccc23)C[C@@H]2c3ccc(N4CCC(C)(N)CC4)cc3CN12]

The title compound was prepared in analogy to the preparation of Example 94 by using tert-butyl N-(4-methyl-4-piperidyl)carbamate instead of tert-butyl ((3R,4R)-4-methoxypyrrolidin-3-yl)-carbamate. Example 100 (9.0 mg) was obtained. MS: calc'd 442 [(M+H)$^+$], measured 442 [(M+H)$^+$]. $^1$H NMR (400 MHz, METHANOL-d$_4$) δ ppm 8.09 (d, J=2.4 Hz, 1H), 7.50 (d, J=7.9 Hz, 1H), 7.30 (d, J=8.4 Hz, 1H), 7.12 (d, J=1.7 Hz, 1H), 7.00 ((dd, J=2.2, 8.2 Hz, 1H), 6.98 (d, J=2.4 Hz, 1H), 6.73 (d, J=7.9 Hz, 1H), 4.53-4.60 (m, 1H), 4.40-4.51 (m, 1H), 4.22-4.34 (m, 1H), 4.09 (d, J=12.7 Hz, 1H), 3.90-3.99 (m, 1H), 3.61-3.70 (m, 1H), 3.52-3.60 (m, 2H), 2.98-3.17 (m, 4H), 1.88-2.03 (m, 4H), 1.47 (s, 3H), 1.42 (d, J=6.6 Hz, 3H).

Example 101

4-[(4R,10bS)-8-[(6R)-6-amino-1,4-oxazepan-4-yl]-4-methyl-3,4,6,10b-tetrahydro-1H-pyrazino[2,1-a]isoindol-2-yl]pyrazolo[1,5-a]pyridine-7-carbonitrile

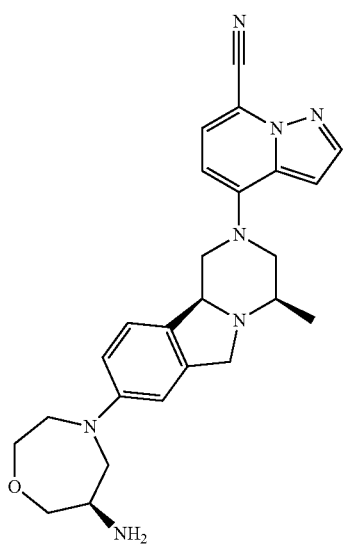 [SMILES: C[C@@H]1CN(c2ccc(C#N)n3nccc23)C[C@@H]2c3ccc(N4CCOC[C@H](N)C4)cc3CN12]

The title compound was prepared in analogy to the preparation of Example 94 by using tert-butyl N-[(6R)-1,4-oxazepan-6-yl]carbamate instead of tert-butyl ((3R,4R)-4-methoxypyrrolidin-3-yl)-carbamate. Example 101 (10.0 mg) was obtained. MS: calc'd 444 [(M+H)$^+$], measured 444 [(M+H)]. $^1$H NMR (400 MHz, METHANOL-d$_4$) δ ppm 8.09 (d, J=2.3 Hz, 1H), 7.50 (d, J=7.9 Hz, 1H), 7.27 (d, J=8.3 Hz, 1H), 6.92-7.03 (m, 2H), 6.84 (dd, J=2.3, 8.3 Hz, 1H), 6.72 (d, J=8.1 Hz, 1H), 4.48 (d, J=12.6 Hz, 1H), 4.24-4.38 (m, 2H), 4.16 (dd, J=5.7, 15.5 Hz, 1H), 4.01-4.09 (m, 1H), 3.89-4.00 (m, 4H), 3.74-3.87 (m, 2H), 3.46-3.68 (m, 4H), 2.95-3.09 (m, 2H), 1.39 (d, J=6.5 Hz, 3H).

Example 102

4-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]pyrazolo[1,5-a]pyridine-7-carbonitrile

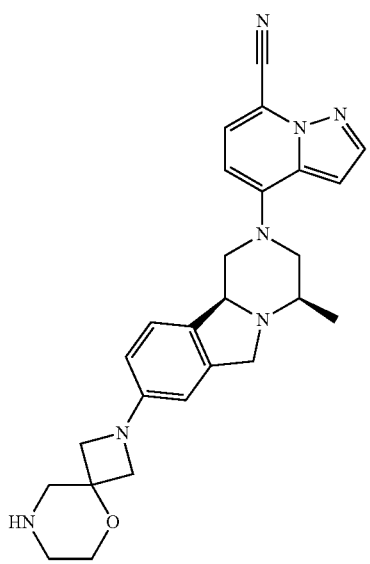 [SMILES: C[C@@H]1CN(c2ccc(C#N)n3nccc23)C[C@@H]2c3ccc(N4CC5(CNCCO5)C4)cc3CN12]

The title compound was prepared in analogy to the preparation of Example 94 by using tert-butyl 5-oxa-2,8-diazaspiro[3.5]nonane-8-carboxylate instead of tert-butyl ((3R,4R)-4-methoxypyrrolidin-3-yl)-carbamate. Example 102 (20.2 mg) was obtained. MS: calc'd 456 [(M+H)$^+$], measured 456 [(M+H)$^+$]. $^1$H NMR (400 MHz, METHANOL-d$_4$) δ ppm 8.09 (d, J=2.4 Hz, 1H), 7.51 (d, J=7.9 Hz, 1H), 7.28 (d, J=8.1 Hz, 1H), 6.98 (d, J=2.4 Hz, 1H), 6.73 (d, J=7.9 Hz, 1H), 6.64 (d, J=1.7 Hz, 1H), 6.52 (dd, J=2.1, 8.2 Hz, 1H), 4.58 (d, J=13.1 Hz, 1H), 4.50-4.54 (m, 1H), 4.24-4.34 (m, 1H), 4.12 (d, J=13.0 Hz, 1H), 4.06 (d, J=8.4 Hz, 2H), 3.90-3.98 (m, 3H), 3.79 (d, J=8.4 Hz, 2H), 3.63-3.73 (m, 1H), 3.54 (s, 2H), 3.23-3.29 (m, 2H), 3.04-3.11 (m, 2H), 1.43 (d, J=6.5 Hz, 3H).

Example 103

4-[(4R,10bS)-8-[(3R)-3-amino-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile

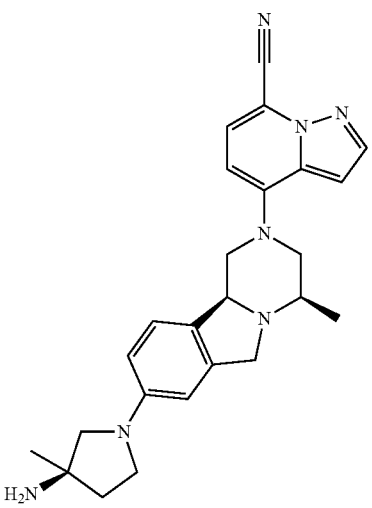 [SMILES: C[C@@H]1CN(c2ccc(C#N)n3nccc23)C[C@@H]2c3ccc(N4CC[C@@](C)(N)C4)cc3CN12]

The title compound was prepared in analogy to the preparation of Example 94 by using tert-butyl N-[(3R)-3-methylpyrrolidin-3-yl]carbamate (CAS: 167888-15-5, PharmaBlock, Catalog: PBXA3113) instead of tert-butyl ((3R,4R)-4-methoxy-pyrrolidin-3-yl)-carbamate. Example 103 (20 mg) was obtained. MS: calc'd 428 [(M+H)$^+$], measured 428 [(M+H)$^+$]. $^1$H NMR (400 MHz, METHANOL-d$_4$) δ ppm 8.08 (d, J=2.3 Hz, 1H), 7.49 (d, J=7.9 Hz, 1H), 7.20 (d, J=7.9 Hz, 1H), 6.94 (d, J=2.4 Hz, 1H), 6.71 (d, J=1.8 Hz, 1H), 6.68 (d, J=8.1 Hz, 1H), 6.57 (dd, J=2.1, 8.3 Hz, 1H), 4.22-4.35 (m, 2H), 4.01 (br d, J=10.8 Hz, 1H), 3.87 (br d, J=12.3 Hz, 1H), 3.64-3.76 (m, 2H), 3.57 (d, J=10.6 Hz, 1H), 3.39-3.47 (m, 2H), 3.22-3.31 (m, 1H), 2.95-3.05 (m, 1H), 2.84-2.91 (m, 1H), 2.18-2.33 (m, 2H), 1.60 (s, 3H), 1.31 (d, J=6.5 Hz, 3H).

Example 104

4-[(4R,10bS)-8-[(3R,4R)-4-amino-3-methoxy-1-piperidyl]-4-methyl-3,4,6,10b-tetrahydro-1H-pyrazino[2,1-a]isoindol-2-yl]pyrazolo[1,5-a]pyridine-7-carbonitrile

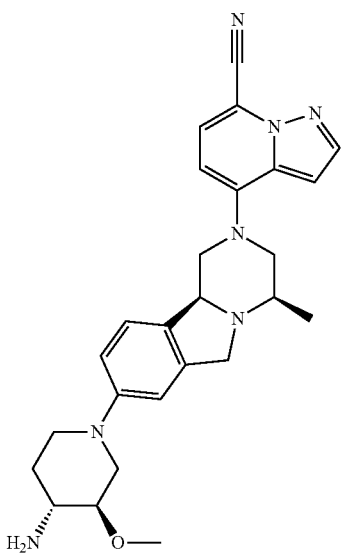 [SMILES: CO[C@@H]1CN(c2ccc3c(c2)CN2[C@H](C)CN(c4ccc(C#N)n5nccc45)C[C@H]32)CC[C@H]1N]

The title compound was prepared in analogy to the preparation of Example 94 by using tert-butyl N-[(3R,4R)-3-methoxypiperidin-4-yl]carbamate (CAS: 907544-18-7, PharmaBlock, Catalog: PB07428) instead of tert-butyl ((3R,4R)-4-methoxypyrrolidin-3-yl)-carbamate. Example 104 (10 mg) was obtained. MS: calc'd 458 [(M+H)$^+$], measured 458 [(M+H)$^+$]. $^1$H NMR (400 MHz, METHANOL-d$_4$) δ ppm 8.07 (d, J=2.4 Hz, 1H), 7.49 (d, J=8.1 Hz, 1H), 7.20 (d, J=8.1 Hz, 1H), 7.07 (d, J=1.6 Hz, 1H), 6.88-6.97 (m, 2H), 6.69 (d, J=7.9 Hz, 1H), 4.27 (br d, J=11.9 Hz, 2H), 3.95-4.04 (m, 1H), 3.81-3.93 (m, 2H), 3.59-3.70 (m, 2H), 3.52 (s, 3H), 3.13-3.23 (m, 3H), 2.94-3.05 (m, 1H), 2.68-2.88 (m, 3H), 2.41-2.53 (m, 1H), 1.97-2.04 (m, 1H), 1.29 (d, J=6.5 Hz, 3H).

Example 105

4-[(4R,10bS)-8-[(3R,4S)-4-amino-3-methoxy-1-piperidyl]-4-methyl-3,4,6,10b-tetrahydro-1H-pyrazino[2,1-a]isoindol-2-yl]pyrazolo[1,5-a]pyridine-7-carbonitrile

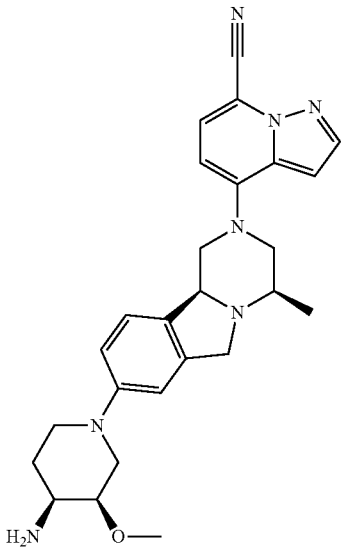 [SMILES: CO[C@@H]1CN(c2ccc3c(c2)CN2[C@H](C)CN(c4ccc(C#N)n5nccc45)C[C@H]32)CC[C@@H]1N]

The title compound was prepared in analogy to the preparation of Example 94 by using bis(tert-butyl N-[(3R,4S)-3-methoxypiperidin-4-yl]carbamate) oxalic acid (PharmaBlock, Catalog: PB97963-1) instead of tert-butyl ((3R,4R)-4-methoxypyrrolidin-3-yl)-carbamate. Example 105 (10 mg) was obtained. MS: calc'd 458 [(M+H)$^+$], measured 458 [(M+H)$^+$]. $^1$H NMR (400 MHz, METHANOL-d$_4$) δ ppm 8.10 (d, J=2.3 Hz, 1H), 7.52 (d, J=7.9 Hz, 1H), 7.34 (d, J=8.4 Hz, 1H), 7.13 (d, J=1.6 Hz, 1H), 6.92-7.05 (m, 2H), 6.75 (d, J=7.9 Hz, 1H), 4.61-4.79 (m, 2H), 4.30 (br d, J=13.2 Hz, 2H), 4.09-4.19 (m, 1H), 3.98 (br d, J=12.7 Hz, 1H), 3.84-3.91 (m, 1H), 3.73-3.80 (m, 1H), 3.68 (br s, 1H), 3.47-3.55 (m, 1H), 3.48 (s, 3H), 3.9-3.21 (m, 2H), 2.85-2.99 (m, 2H), 2.05-2.18 (m, 1H), 1.86-1.96 (m, 1H), 1.48 (d, J=6.6 Hz, 3H).

Example 106

4-[(4R,10bS)-8-[(3R,4S)-3-amino-4-methoxy-1-piperidyl]-4-methyl-3,4,6,10b-tetrahydro-1H-pyrazino[2,1-a]isoindol-2-yl]pyrazolo[1,5-a]pyridine-7-carbonitrile

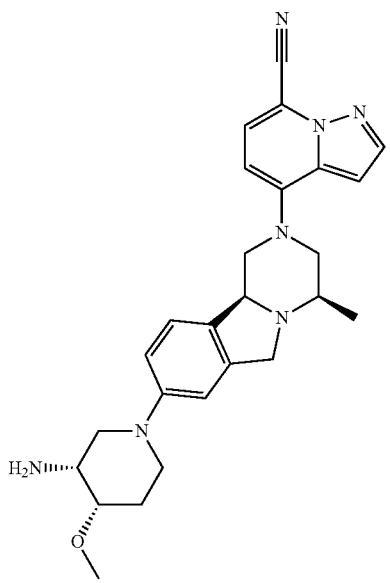 [SMILES: CO[C@H]1CCN(c2ccc3c(c2)CN2[C@H](C)CN(c4ccc(C#N)n5nccc45)C[C@H]32)C[C@H]1N]

The title compound was prepared in analogy to the preparation of Example 94 by using tert-butyl N-[(3R,4S)-4-methoxy-3-piperidyl]carbamate (CAS: 2227197-47-7, PharmaBlock, Catalog: PBZ5288-1) instead of tert-butyl ((3R,4R)-4-methoxypyrrolidin-3-yl)-carbamate. Example 106 (10 mg) was obtained. MS: calc'd 458 [(M+H)+], measured 458 [(M+H)+]. $^1$H NMR (400 MHz, METHANOL-$d_4$) δ ppm 8.08 (d, J=2.4 Hz, 1H), 7.51 (d, J=7.9 Hz, 1H), 7.28 (d, J=8.2 Hz, 1H), 7.12 (d, J=1.7 Hz, 1H), 6.99 (dd, J=2.3, 8.4 Hz, 1H), 6.96 (d, J=2.4 Hz, 1H), 6.71 (d, J=7.9 Hz, 1H), 4.43 (d, J=12.6 Hz, 1H), 4.27-4.33 (m, 1H), 4.22 (br d, J=10.9 Hz, 1H), 3.86-3.96 (m, 2H), 3.59-3.75 (m, 2H), 3.36-3.49 (m, 3H), 3.48 (s, 3H), 3.23-3.30 (m, 1H), 3.00-3.12 (m, 2H), 2.89-2.98 (m, 1H), 1.96-2.09 (m, 2H), 1.36 (d, J=6.5 Hz, 3H).

Example 107

4-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]pyrazolo[1,5-a]pyridine-7-carbonitrile

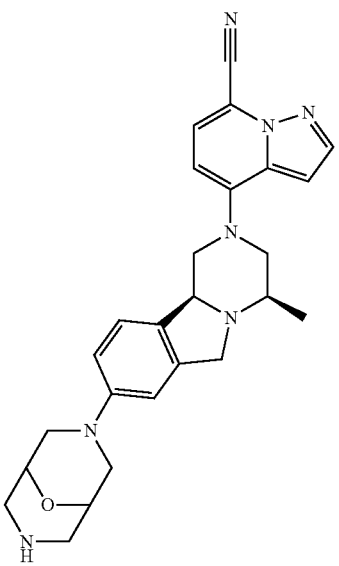 [SMILES: C[C@@H]1CN(c2ccc(C#N)n3nccc23)C[C@@H]2c3ccc(N4CC5CNCC(C4)O5)cc3CN12]

The title compound was prepared in analogy to the preparation of Example 94 by using tert-butyl 9-oxa-3,7-diazabicyclo[3.3.1]nonane-3-carboxylate instead of tert-butyl ((3R,4R)-4-methoxypyrrolidin-3-yl)-carbamate. Example 107 (10 mg) was obtained. MS: calc'd 456 [(M+H)+], measured 456 [(M+H)+]. $^1$H NMR (400 MHz, METHANOL-$d_4$) δ ppm 8.08 (d, J=2.3 Hz, 1H), 7.50 (d, J=7.9 Hz, 1H), 7.29 (d, J=8.2 Hz, 1H), 7.21 (d, J=1.8 Hz, 1H), 7.06 (dd, J=2.1, 8.3 Hz, 1H), 6.96 (d, J=2.4 Hz, 1H), 6.71 (d, J=8.1 Hz, 1H), 4.37 (d, J=12.5 Hz, 1H), 4.23-4.33 (m, 3H), 4.08 (br d, J=10.4 Hz, 1H), 3.87-3.94 (m, 1H), 3.75-3.82 (m, 3H), 3.52-3.64 (m, 5H), 3.19-3.28 (m, 2H), 2.99-3.06 (m, 1H), 2.84-2.94 (m, 1H), 1.33 (d, J=6.4 Hz, 3H).

Example 108

4-[(4R,10bS)-8-[(3R,4R)-4-amino-3-hydroxy-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile

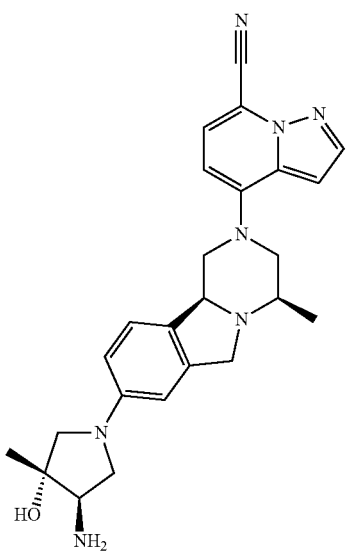 [SMILES: C[C@@H]1CN(c2ccc(C#N)n3nccc23)C[C@@H]2c3ccc(N4C[C@@H](N)[C@](C)(O)C4)cc3CN12]

The title compound was prepared in analogy to the preparation of Example 94 by using tert-butyl N-[(3R,4R)-4-hydroxy-4-methyl-pyrrolidin-3-yl]carbamate instead of tert-butyl ((3R,4R)-4-methoxypyrrolidin-3-yl)-carbamate. Example 108 (10 mg) was obtained. MS: calc'd 444 [(M+H)$^+$], measured 444 [(M+H)$^+$]. $^1$H NMR (400 MHz, METHANOL-d$_4$) δ ppm 8.08 (d, J=2.4 Hz, 1H), 7.50 (d, J=7.9 Hz, 1H), 7.24 (d, J=8.3 Hz, 1H), 6.96 (d, J=2.4 Hz, 1H), 6.66-6.76 (m, 2H), 6.56 (dd, J=2.1, 8.3 Hz, 1H), 4.45 (d, J=12.7 Hz, 1H), 4.28 (br d, J=9.4 Hz, 2H), 3.78-3.98 (m, 3H), 3.63-3.74 (m, 1H), 3.59 (d, J=10.4 Hz, 1H), 3.46-3.53 (m, 2H), 3.37 (d, J=10.5 Hz, 1H), 2.92-3.10 (m, 2H), 1.51 (s, 3H), 1.37 (d, J=6.6 Hz, 3H).

Example 109

4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile

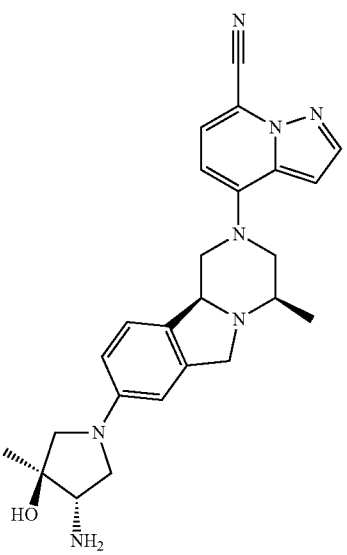 [SMILES: C[C@@H]1CN(c2ccc(C#N)n3nccc23)C[C@@H]2c3ccc(N4C[C@H](N)[C@@](C)(O)C4)cc3CN12]

The title compound was prepared in analogy to the preparation of Example 94 by using tert-butyl N-[(3S,4S)-4-hydroxy-4-methyl-pyrrolidin-3-yl]carbamate instead of tert-butyl ((3R,4R)-4-methoxypyrrolidin-3-yl)-carbamate. Example 109 (27 mg) was obtained. MS: calc'd 444 [(M+H)$^+$], measured 444 [(M+H)$^+$]. $^1$H NMR (400 MHz, METHANOL-d$_4$) δ ppm 8.08 (d, J=2.3 Hz, 1H), 7.50 (d, J=8.1 Hz, 1H), 7.24 (d, J=8.2 Hz, 1H), 6.96 (d, J=2.4 Hz, 1H), 6.64-6.74 (m, 2H), 6.56 (dd, J=2.1, 8.3 Hz, 1H), 4.47 (d, J=12.6 Hz, 1H), 4.24-4.33 (m, 2H), 3.81-3.99 (m, 3H), 3.66-3.71 (m, 1H), 3.59 (d, J=10.4 Hz, 1H), 3.46-3.54 (m, 2H), 3.37 (d, J=10.4 Hz, 1H), 2.91-3.10 (m, 2H), 1.51 (s, 3H), 1.38 (d, J=6.6 Hz, 3H).

Example 110

4-[(4R,10bS)-8-[(3R,4R)-3-amino-4-hydroxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile

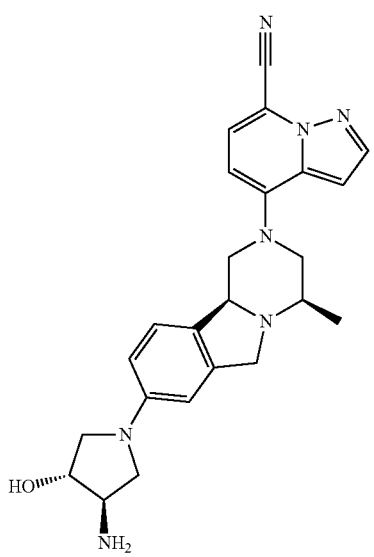 [SMILES: C[C@@H]1CN(c2ccc(C#N)n3nccc23)C[C@@H]2c3ccc(N4C[C@@H](N)[C@H](O)C4)cc3CN12]

The title compound was prepared in analogy to the preparation of Example 94 by using tert-butyl N-[(3R,4R)-4-methyl-pyrrolidin-3-yl]carbamate (CAS: 1820575-70-9, BePharm, Catalog: BD761646) instead of tert-butyl ((3R,4R)-4-methoxypyrrolidin-3-yl)-carbamate. Example 110 (40 mg) was obtained. MS: calc'd 430 [(M+H)$^+$], measured 430 [(M+H)$^+$]. $^1$H NMR (400 MHz, METHANOL-d$_4$) δ ppm 8.07-8.12 (m, 1H), 7.51 (d, J=8.1 Hz, 1H), 7.30 (d, J=8.3 Hz, 1H), 6.99 (d, J=2.4 Hz, 1H), 6.71-6.76 (m, 2H), 6.64 (dd, J=2.1, 8.3 Hz, 1H), 4.46-4.63 (m, 3H), 4.25-4.33 (m, 1H), 4.15 (d, J=13.1 Hz, 1H), 3.96 (br d, J=12.5 Hz, 1H), 3.67-3.88 (m, 4H), 3.46 (d, J=6.6 Hz, 1H), 3.25-3.29 (m, 1H), 3.03-3.12 (m, 2H), 1.43 (d, J=6.6 Hz, 3H).

Example 111

4-[(4R,10bS)-8-[(3S,4S)-3-amino-4-hydroxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile

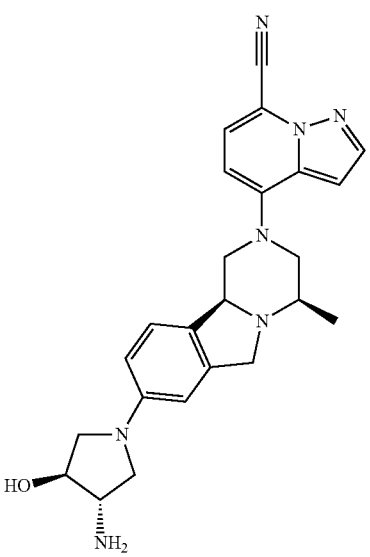 [SMILES: C[C@@H]1CN(c2ccc(C#N)n3nccc23)C[C@@H]2c3ccc(N4C[C@H](N)[C@@H](O)C4)cc3CN12]

The title compound was prepared in analogy to the preparation of Example 94 by using tert-butyl N-[(3S,4S)-4-hydroxy-pyrrolidin-3-yl]carbamate (CAS: 870632-91-0, BePharm, Catalog: BD447697) instead of tert-butyl ((3R,4R)-4-methoxypyrrolidin-3-yl)-carbamate. Example 111 (42 mg) was obtained. MS: calc'd 430 [(M+H)$^+$], measured 430 [(M+H)$^+$]. $^1$H NMR (400 MHz, METHANOL-d$_4$) δ ppm 8.09 (d, J=2.3 Hz, 1H), 7.51 (d, J=7.9 Hz, 1H), 7.28 (d, J=8.3 Hz, 1H), 6.98 (d, J=2.6 Hz, 1H), 6.70-6.76 (m, 2H), 6.62 (dd, J=2.1, 8.3 Hz, 1H), 4.36-4.58 (m, 3H), 4.30 (br d, J=12.5 Hz, 1H), 4.04 (d, J=13.0 Hz, 1H), 3.94 (br d, J=12.8 Hz, 1H), 3.72-3.86 (m, 3H), 3.56-3.64 (m, 1H), 3.45 (d, J=6.7 Hz, 1H), 3.24-3.29 (m, 1H), 3.00-3.10 (m, 2H), 1.41 (d, J=6.5 Hz, 3H).

Example 112

4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]-3-fluoro-pyrazolo[1,5-a]pyridine-7-carbonitrile The title compound was prepared according to the following scheme:

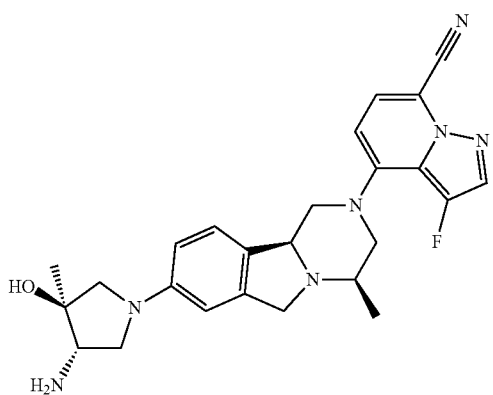 [SMILES: C[C@@H]1CN(c2ccc(C#N)n3ncc(F)c23)C[C@@H]2c3ccc(N4C[C@H](N)[C@@](C)(O)C4)cc3CN12]

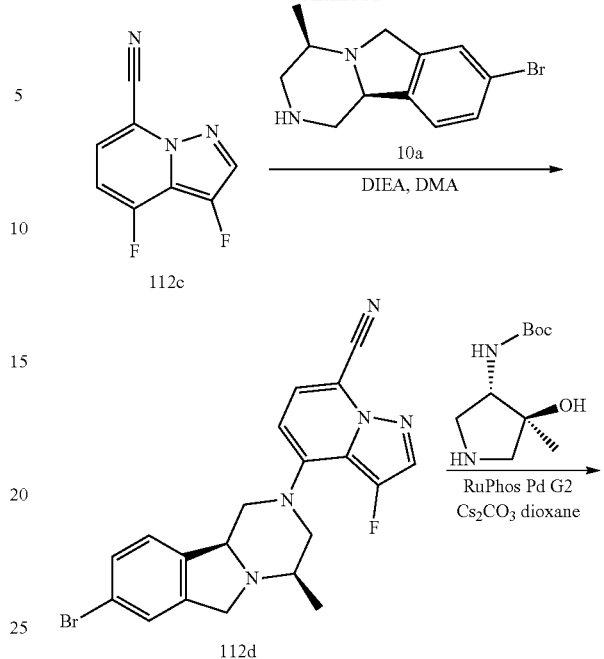

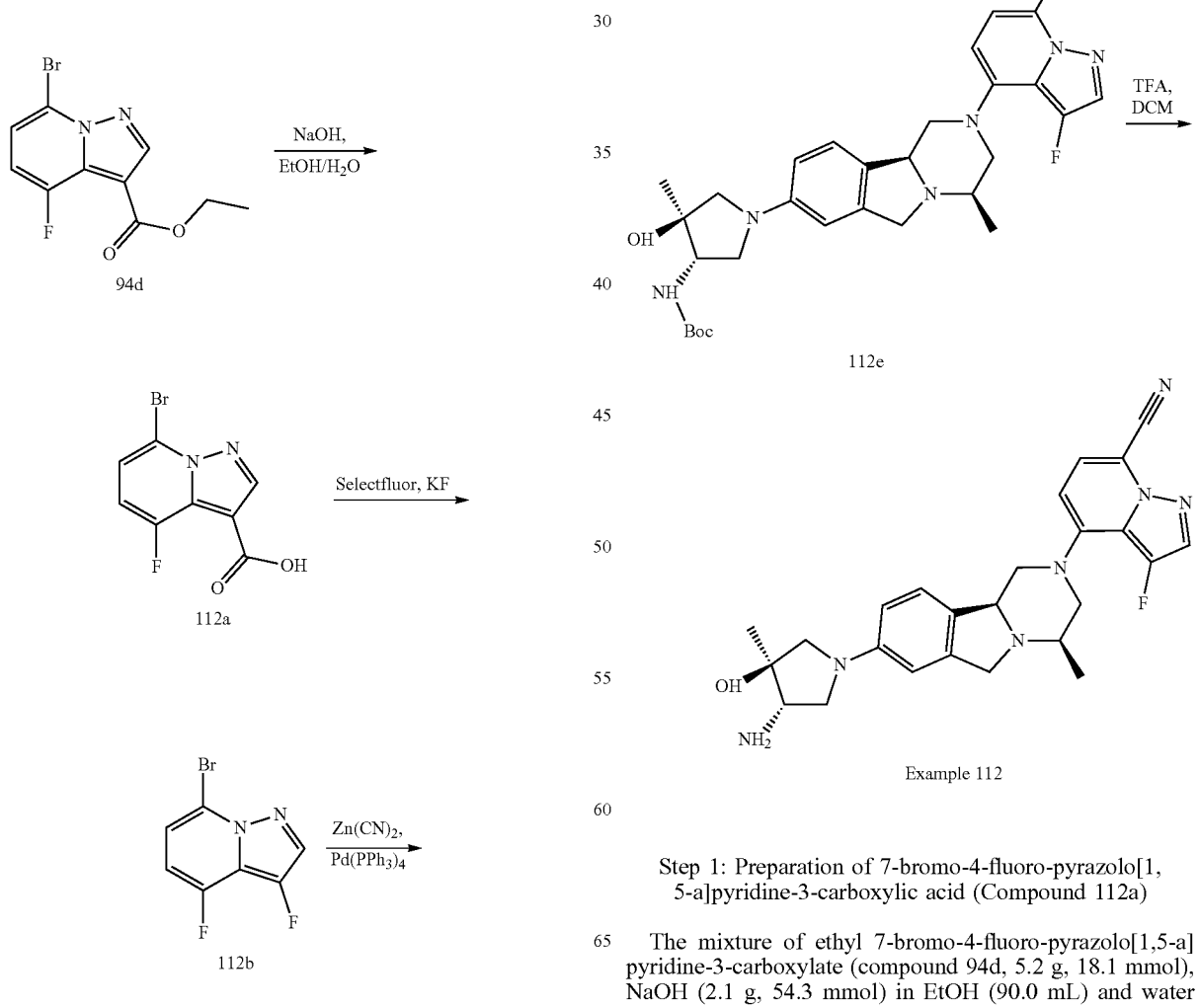

Step 1: Preparation of 7-bromo-4-fluoro-pyrazolo[1,5-a]pyridine-3-carboxylic acid (Compound 112a)

The mixture of ethyl 7-bromo-4-fluoro-pyrazolo[1,5-a]pyridine-3-carboxylate (compound 94d, 5.2 g, 18.1 mmol), NaOH (2.1 g, 54.3 mmol) in EtOH (90.0 mL) and water (70.0 mL) was stirred at 60° C. for 2 hrs. The reaction mixture was concentrated and then diluted with water. After adjusting pH to 4 with 1 N HCl, grey solid was precipitated, which was collected by filtration to afford compound 112a (4.0 g, 85.6% yield). MS: calc'd 259 [(M+H)$^+$], measured 259 [(M+H)$^+$].

Step 2: Preparation of 7-bromo-3,4difluoro-pyrazolo[1,5-a]pyridine (Compound 112b)

To a solution of 7-bromo-4-fluoro-pyrazolo[1,5-a]pyridine-3-carboxylic acid (compound 112a, 4.0 g, 15.4 mmol) and KF (3.6 g, 61.8 mmol) in DCE (60.0 mL) and water (50.0 mL) was added Selectfluor (10.9 g, 30.9 mmol). The reaction was stirred at 70° C. for 18 hrs. The reaction was quenched with water, extracted with DCM twice. The combined organic layers were dried over Na$_2$SO$_4$, filtered and the filtrate was concentrated in vacuo to afford crude compound 112b (2.8 g, 78% yield). MS: calc'd 233 [(M+H)$^+$], measured 233 [(M+H)$^+$].

Step 3: Preparation of 3,4-difluoropyrazolo[1,5-a]pyridine-7-carbonitrile (compound 112c)

A solution of 7-bromo-3,4-difluoro-pyrazolo[1,5-a]pyridine (compound 112b, 2.8 g, 12.0 mmol) and zinc cyanide (5.6 g, 48.0 mmol) in DMF (70.0 mL) was added tetrakis(triphenylphosphine)palladium (1.4 g, 1.2 mmol). The reaction mixture was stirred at 120° C. for 18 hrs under N$_2$ atmosphere. The mixture was quenched with water and extracted with EtOAc twice. The combined organic layers were dried over Na$_2$SO$_4$, filtered and the filtrate was concentrated in vacuo. The residue was purified by column chromatography to afford compound 112c (810.0 mg) as a white solid. MS: calc'd 180 [(M+H)$^+$], measured 180 [(M+H)$^+$]. $^1$H NMR (400 MHz, CHLOROFORM-d) δ ppm 8.00 (d, J=3.6 Hz, 1H), 7.31 (dd, J=4.7, 8.0 Hz, 1H), 6.83 (t, J=8.4 Hz, 1H).

Step 4: Preparation of 4-[(4R,10bS)-8-bromo-4-methyl-3,4,6,10b-tetrahydro-1H-pyrazino[2,1-a]isoindol-2-yl]-3-fluoro-pyrazolo[1,5-a]pyridine-7-carbonitrile (compound 112d)

A mixture of 3,4-difluoropyrazolo[1,5-a]pyridine-7-carbonitrile (compound 112c, 200.0 mg, 1.12 mmol), (4R,10bS)-8-bromo-4-methyl-1,2,3,4,6,10b-hexahydropyrazino[2,1-a]isoindole (compound 10a, 351.1 mg, 1.32 mmol) and DIEA (800.0 mg, 6.19 mmol) in DMA (20 mL) was stirred at 130° C. for 15 hrs. The reaction mixture was quenched with H$_2$O (50 mL), extracted with EtOAc (50 mL) for three times. The combined organic layers were washed with brine, dried over Na$_2$SO$_4$, filtered and the filtrate was concentrated in vacuo. The residue was purified by prep-TLC (PE:EA=1:1) to afford compound 112d (224.4 mg, 49.2% yield). MS: calc'd 426 and 428 [(M+H)$^+$], measured 426 and 428 [(M+H)$^+$].

Step 5: Preparation of tert-butyl N-[(3S,4S)-1-[(4R,10bS)-2-(7-cyano-3-fluoro-pyrazolo[1,5-a]pyridin-4-yl)-4-methyl-3,4,6,10b-tetrahydro-1H-pyrazino[2,1-a]isoindol-8-yl]-4-hydroxy-4-methyl-pyrrolidin-3-yl]carbamate (Compound 112e)

A mixture of tert-butyl N-[(3S,4S)-4-hydroxy-4-methyl-pyrrolidin-3-yl]carbamate (31.0 mg, 140 μmol), 4-[(4R,10bS)-8-bromo-4-methyl-3,4,6,10b-tetrahydro-1H-pyrazino[2,1-a]isoindol-2-yl]-3-fluoro-pyrazolo[1,5-a]pyridine-7-carbonitrile (compound 112d, 50.0 mg, 120 μmol), RuPhos Pd G2 (20.0 mg, 20 μmol) and cesium carbonate (115.0 mg, 350 μmol) in 1,4-dioxane (5 mL) was degassed and purged with Ar for 3 times, and then the mixture was stirred at 100° C. for 16 hrs under Ar atmosphere. The mixture was diluted with DCM (80 mL, filtered and the filtrate was concentrated in vacuo. The residue was purified by Prep-TLC (PE:EA=1:2) to afford compound 112e (40 mg, 37% yield). MS: calc'd 562 [(M+H)$^+$], measured 562 [(M+H)$^+$].

Step 6: Preparation of 4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]-3-fluoro-pyrazolo[1,5-a]pyridine-7-carbonitrile; 2,2,2-trifluoroacetic acid (Example 112)

To a solution of tert-butyl N-[(3S,4S)-1-[(4R,10bS)-2-(7-cyano-3-fluoro-pyrazolo[1,5-a]pyridin-4-yl)-4-methyl-3,4,6,10b-tetrahydro-1H-pyrazino[2,1-a]isoindol-8-yl]-4-hydroxy-4-methyl-pyrrolidin-3-yl]carbamate (compound 112e, 40.0 mg, 70 μmol) in DCM (10 mL) was added TFA (3 mL). The mixture was stirred at room temperature for 2 hrs. The reaction mixture was stirred at room temperature for 2 hrs, then concentrated to afford a crude product, which was purified by pre-HPLC to afford Example 112 (5.5 mg, 17% yield). MS calc'd 462 [(M+H)$^+$], measured 462.4 [(M+H)$^+$]. $^1$H NMR (400 MHz, DMSO-d$_6$) δ ppm 8.31 (d, J=3.6 Hz, 1H), 8.20-8.24 (m, 3H), 7.73 (d, J=8.0 Hz, 1H), 7.28 (d, J=6.8 Hz, 1H), 6.76 (d, J=8.0 Hz, 1H), 6.63 (br s, 1H), 6.49-6.58 (m, 1H), 5.54-5.63 (m, 1H), 4.85-5.07 (s, 1H), 4.40-4.51 (m, 1H), 3.85-4.06 (m, 1H), 3.71 (dd, J=5.2, 10.8 Hz, 1H), 3.58-3.60 (m, 1H), 3.45-3.49 (m, 2H), 3.28-3.29 (m, 2H), 3.23 (d, J=10.0 Hz, 2H), 2.95-3.10 (m, 2H), 1.36-1.35 (m, 6H).

Example 113

4-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]-3-fluoro-pyrazolo[1,5-a]pyridine-7-carbonitrile

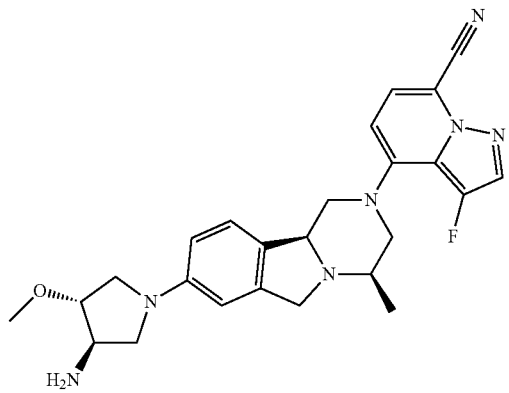 [SMILES: CO[C@@H]1CN(c2ccc3c(c2)CN2[C@H](C)CN(c4ccc(C#N)n5ncc(F)c45)C[C@H]32)C[C@H]1N]

The title compound was prepared in analogy to the preparation of Example 112 by using tert-butyl N-[(3R,4R)-4-methoxypyrrolidin-3-yl]carbamate instead of tert-butyl N-[(3S,4S)-4-hydroxy-4-methyl-pyrrolidin-3-yl]carbamate.

Example 113 (70 mg) was obtained. MS: calc'd 462 [(M+H)+], measured 462 [(M+H)+]. $^1$H NMR (400 MHz, METHANOL-$d_4$) δ ppm 8.06 (d, J=3.5 Hz, 1H), 7.46 (d, J=7.9 Hz, 1H), 7.22 (d, J=8.3 Hz, 1H), 6.76 (d, J=1.8 Hz, 1H), 6.63 (d, J=8.1 Hz, 2H), 4.48 (d, J=12.6 Hz, 1H), 4.30 (br d, J=10.0 Hz, 1H), 4.07-4.16 (m, 2H), 3.98 (br d, J=12.6 Hz, 1H), 3.84-3.94 (m, 2H), 3.63-3.74 (m, 2H), 3.41-3.55 (m, 5H), 3.30 (br d, J=3.5 Hz, 1H), 2.90-3.07 (m, 2H), 1.37 (d, J=6.6 Hz, 3H).

Example 114

The following tests were carried out in order to determine the activity of the compounds of formula (I), (Ia) or (Ib) in HEK293-Blue-hTLR-7/8/9 cells assay.

HEK293-Blue-hTLR-7 Cells Assay:

A stable HEK293-Blue-hTLR-7 cell line was purchased from InvivoGen (Cat. #: hkb-htlr7, San Diego, California, USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Ca. USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound 1n a serial dilution in the presence of final DMSO at 1% and 10 μL of 20 uM R848 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR7 activation leads to downstream NF-κB activation has been widely accepted, and therefore similar reporter assay was modified for evaluating TLR7 antagonist.

HEK293-Blue-hTLR-8 Cells Assay:

A stable HEK293-Blue-hTLR-8 cell line was purchased from InvivoGen (Cat. #: hkb-htlr8, San Diego, California, USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR8 cells were incubated at a density of 250,000-450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound 1n a serial dilution in the presence of final DMSO at 1% and 10 μL of 60 uM R848 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR8 activation leads to downstream NF-κB activation has been widely accepted, and therefore similar reporter assay was modified for evaluating TLR8 antagonist.

HEK293-Blue-hTLR-9 Cells Assay:

A stable HEK293-Blue-hTLR-9 cell line was purchased from InvivoGen (Cat. #: hkb-htlr9, San Diego. California USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, California USA), for incubation of 20 hrs. The cell culture supernatant SEAP reporter activity was determined using QUANTI-Blue™ kit (Cat. #: rep-qb1, Invivogen, San Diego, California, USA) at a wavelength of 640 nm, a detection medium that turns purple or blue in the presence of alkaline phosphatase.

HEK293-Blue-hTLR9 cells were incubated at a density of 250.000-450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound 1n a serial dilution in the presence of final DMSO at 1% and 10 μL of 20 uM ODN2006 in above DMEM, perform incubation under 37° C. in a $CO_2$ incubator for 20 hrs. Then 20 μL of the supernatant from each well was incubated with 180 μL Quanti-blue substrate solution at 37° C. for 2 h and the absorbance was read at 620~655 nm using a spectrophotometer. The signaling pathway that TLR9 activation leads to downstream NF-κB activation has been widely accepted, and therefore similar reporter assay was modified for evaluating TLR9 antagonist.

The compounds of formula (I) have TLR7 and/or TLR8 inhibitory activities ($IC_{50}$ value) <0.1 μM. Moreover, most compounds also have TLR9 inhibitory activity <0.3 JAM. Activity data of the compounds of the present invention were shown in Table 1.

TABLE 1

The activity of the compounds of present invention in HEK293-Blue-hTLR-7/8/9 cells assays

| Example No | HEK/hTLR7 $IC_{50}$ (nM) | HEK/hTLR8 $IC_{50}$ (nM) | HEK/hTLR9 $IC_{50}$ (nM) |
|---|---|---|---|
| 1 | <3.2 | <3.2 | 106.0 |
| 2 | 71.5 | <3.2 | 125.0 |
| 3 | 42.6 | <3.2 | 87.7 |
| 4 | 18.3 | <3.2 | 101.0 |

TABLE 1-continued

The activity of the compounds of present invention
in HEK293-Blue-hTLR-7/8/9 cells assays

| Example No | HEK/hTLR7 $IC_{50}$ (nM) | HEK/hTLR8 $IC_{50}$ (nM) | HEK/hTLR9 $IC_{50}$ (nM) |
|---|---|---|---|
| 5 | 4.9 | <3.2 | 132.7 |
| 6 | <3.2 | <3.2 | 156.3 |
| 7 | <3.2 | <3.2 | 99.2 |
| 8 | <3.2 | <3.2 | 150.3 |
| 9 | <3.2 | <3.2 | 130.2 |
| 10 | <3.2 | <3.2 | 92.5 |
| 11 | 3.4 | <3.2 | 92.0 |
| 12 | <3.2 | <3.2 | 71.2 |
| 14 | 4.5 | <3.2 | 81.1 |
| 15 | 5.8 | <3.2 | 83.2 |
| 16 | 6.9 | <3.2 | 95.2 |
| 16A | 5.3 | <3.2 | 113.4 |
| 16B | 4.5 | <3.2 | 97.5 |
| 17 | <3.2 | <3.2 | 81.0 |
| 18 | 4.9 | <3.2 | 114.1 |
| 19 | 3.6 | <3.2 | 65.3 |
| 20 | 3.4 | <3.2 | 86.9 |
| 21 | 5.8 | <3.2 | 56.1 |
| 22 | <3.2 | <3.2 | 103.7 |
| 23 | 7.0 | <3.2 | 92.4 |
| 24 | 3.4 | <3.2 | 90.5 |
| 25 | <3.2 | <3.2 | 115.7 |
| 26 | 5.8 | <3.2 | 55.8 |
| 28 | 15.6 | <3.2 | 83.4 |
| 29 | <3.2 | <3.2 | 43.3 |
| 30 | <3.2 | <3.2 | 96.6 |
| 31 | 4.1 | <3.2 | 93.7 |
| 32 | 3.5 | <3.2 | 89.2 |
| 33 | <3.2 | <3.2 | 100.1 |
| 34 | 7.4 | <3.2 | 66.6 |
| 35 | <3.2 | <3.2 | 111.4 |
| 36 | 3.3 | <3.2 | 100.3 |
| 37 | <3.2 | <3.2 | 102.9 |
| 38 | 1.7 | <0.3 | 66.8 |
| 39 | 3.0 | <0.3 | 122.6 |
| 40a | 3.7 | 1.4 | 59.5 |
| 40b | 4.3 | 0.9 | 70.8 |
| 41 | <3.2 | <3.2 | <31.8 |
| 42 | <3.2 | <3.2 | 65.4 |
| 43 | 4.0 | <3.2 | 55.5 |
| 44 | 19.1 | 0.4 | 102.0 |
| 45 | 4.5 | <3.2 | 78.5 |
| 45A | 3.5 | 1.5 | 78.3 |
| 45B | 3.3 | 1.2 | 74.1 |
| 46 | 15.6 | 0.4 | 143.8 |
| 47 | 4.8 | 0.6 | 146.2 |
| 48 | 5.8 | 0.7 | 193.2 |
| 49 | 4.5 | 0.6 | 185.6 |
| 51 | 1.4 | <0.3 | 138.8 |
| 52 | 8.5 | <3.2 | 194.9 |
| 53A | 3.9 | <3.2 | 56.0 |
| 53B | 8.9 | <3.2 | 68.0 |
| 54 | 4.0 | <3.2 | 63.6 |
| 54A | 4.5 | <3.2 | 92.2 |
| 54B | 5.7 | <3.2 | 87.3 |
| 55 | 6.5 | <3.2 | 118.0 |
| 55A | 7.7 | <3.2 | 111.2 |
| 55B | 16.1 | <3.2 | 156.1 |
| 56 | 6.9 | <3.2 | 103.4 |
| 56A | 11.1 | <3.2 | 83.0 |
| 56B | 4.5 | <3.2 | 92.1 |
| 57 | 11.1 | <3.2 | 105.2 |
| 58 | <3.2 | <3.2 | 84.3 |
| 59 | <3.2 | <3.2 | 73.5 |
| 60 | 3.2 | <3.2 | 113.0 |
| 61 | 5.7 | <3.2 | 93.0 |
| 62 | 5.9 | <3.2 | 84.5 |
| 63 | 7.3 | 6.2 | 72.7 |
| 64 | <3.2 | <3.2 | 125.3 |
| 65 | 4.4 | <3.2 | 95.8 |
| 66 | <3.2 | <3.2 | 141.2 |
| 68 | 3.3 | <3.2 | 73.5 |
| 69 | 18.2 | <3.2 | 171.2 |
| 70 | 9.0 | 0.5 | 74.0 |
| 71 | <3.2 | <3.2 | 114.9 |
| 72 | <3.2 | <3.2 | 108.1 |
| 74 | 3.9 | <0.3 | 136.4 |
| 75 | 47.8 | 12.4 | 202.8 |
| 76 | 22.8 | 12.7 | 150.3 |
| 77 | 12.6 | <3.2 | 140.7 |
| 78 | 1.2 | 0.4 | 83.6 |
| 79 | 7.6 | 2.8 | 113.4 |
| 80 | 17.9 | <3.2 | 63.6 |
| 81 | 7.4 | <3.2 | 126.0 |
| 83 | 2.7 | 1.0 | 168.1 |
| 84 | 2.6 | 1.3 | 186.4 |
| 85 | 6.9 | 9.2 | 151.2 |
| 88 | 3.7 | 0.7 | 165.4 |
| 90 | 2.9 | <0.3 | 163.6 |
| 91 | 1.7 | 0.6 | 70.5 |
| 92 | 3.1 | <0.3 | 148.1 |
| 93 | 3.8 | 2.1 | 69.9 |
| 94 | 13.7 | 5.6 | 148.9 |
| 95 | 20.8 | 4.6 | 214.9 |
| 96 | 32.6 | 4.0 | 192.6 |
| 97 | 5.0 | 1.0 | 161.0 |
| 98 | 23.2 | 8.8 | 196.7 |
| 101 | 26.4 | 5.2 | 165.1 |
| 103 | 25.8 | 4.8 | 142.3 |
| 104 | 6.1 | 3.2 | 90.3 |
| 105 | 4.9 | 4.1 | 162.6 |
| 106 | 22.6 | 2.9 | 134.8 |
| 107 | 14.5 | 16.5 | 67.9 |
| 108 | 17.5 | 8.9 | 125.6 |
| 109 | 28.1 | 6.7 | 160.0 |
| 110 | 19 | 5 | 53 |
| 111 | 14 | 2 | 38 |
| 112 | 11.4 | 3.6 | 226.7 |
| 113 | 6.0 | 2.0 | 135.0 |

Example 113

Human Microsomal Stability Assay

Human liver microsomes (Cat. NO.: 452117, Corning, USA) were preincubated with test compound for 10 minutes at 37° C. in 100 mM potassium phosphate buffer, pH 7.4. The reactions were initiated by adding NADPH regenerating system. The final incubation mixtures contained 1 &M test compound, 0.5 mg/mL liver microsomal protein, 1 mM MgCl2, 1 mM NADP, 1 unit/mL isocitric dehydrogenase and 6 mM isocitric acid in 100 mM potassium phosphate buffer, pH 7.4. After incubation times of 0, 3, 6, 9, 15 and 30 minutes at 37° C., 300 μL of cold ACN (including internal standard) was added to 100 μL incubation mixture to terminate the reaction. Following precipitation and centrifugation, 100 μL supernatant will be taken out and added 300 uL water. The amount of compound remaining in the samples was determined by LC-MS/MS. Controls of no NADPH regenerating system at zero and 30 minutes were also prepared and analyzed. The results were categorized as: low (<7.0 mLJmin/kg), medium (7.0-16.2 mL/min/kg) and high (16.2-23.2 mLJmin/kg). Test results were summarized in Table 2.

TABLE 2

Human microsomal stability results

| Example No | CL (h) (mL/min/kg) |
|---|---|
| 1 | 6.8 |
| 2 | 6.8 |
| 3 | 6.2 |
| 4 | 6.2 |
| 6 | 6.6 |
| 7 | 7.8 |
| 11 | 6.2 |
| 12 | 6.2 |
| 14 | 6.2 |
| 16A | 8.5 |
| 16B | 8.1 |
| 17 | 6.2 |
| 19 | 7.7 |
| 20 | 6.5 |
| 21 | 6.2 |
| 25 | 8.0 |
| 26 | 6.2 |
| 27 | 7.7 |
| 28 | 8.7 |
| 30 | 8.8 |
| 32 | 8.7 |
| 36 | 6.2 |
| 37 | 6.5 |
| 38 | 6.2 |
| 39 | 6.2 |
| 40A | 7.0 |
| 40B | 7.6 |
| 45 | 6.2 |
| 45A | 6.2 |
| 45B | 6.2 |
| 46 | 8.8 |
| 48 | 8.9 |
| 52 | 8.1 |
| 53A | 8.6 |
| 54 | 8.9 |
| 54A | 7.5 |
| 54B | 7.0 |
| 60 | 7.4 |
| 61 | 7.3 |
| 62 | 7.5 |
| 65 | 6.2 |
| 68 | 7.9 |
| 69 | 8.4 |
| 75 | 6.2 |
| 79 | 6.2 |
| 85 | 7.8 |
| 86 | 7.7 |
| 87 | 8.0 |
| 88 | 6.2 |
| 92 | 6.4 |
| 93 | 8.4 |
| 96 | 6.2 |
| 100 | 8.0 |
| 104 | 7.0 |
| 112 | 8.6 |

Example 114 hERG Channel Inhibition Assay

The hERG channel inhibition assay is a highly sensitive measurement that identifies compounds exhibiting hERG inhibition related to cardiotoxicity in vivo. The hERG K$^+$ channels were cloned in humans and stably expressed in a CHO (Chinese hamster ovary) cell line. CHO$_{hERG}$ cells were used for patch-clamp (voltage-clamp, whole-cell) experiments. Cells were stimulated by a voltage pattern to activate hERG channels and conduct $I_{KhERG}$ currents (rapid delayed outward rectifier potassium current of the hERG channel). After the cells were stabilized for a few minutes, the amplitude and kinetics of $I_{KhERG}$ were recorded at a stimulation frequency of 0.1 Hz (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of $I_{KhERG}$ are recorded in each concentration of the drug which were compared to the control values (taken as 100%). (references: Redfem W S, Carlsson L, Davis A S, Lynch W G, MacKenzie I, Palethorpe S, Siegl P K, Strang I, Sullivan A T, Wallis R, Camm A J, Hammond T G. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti M C, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26). Results of hERG are given in Table 3.

TABLE 3 hERG results

| Example No | hERG IC$_{20}$ (μM) | hERG IC$_{50}$ (μM) |
|---|---|---|
| 2 | >10 | >20 |
| 12 | >10 | >20 |
| 14 | >10 | >20 |
| 15 | >10 | >20 |
| 16 | >10 | >20 |
| 21 | >10 | >20 |
| 22 | 5.0 | >20 |
| 26 | 5.0 | >20 |
| 28 | >10 | >20 |
| 35 | >10 | >20 |
| 36 | >10 | >20 |
| 37 | 8.6 | >20 |
| 38 | >10 | >20 |
| 39 | >10 | >20 |
| 40B | >10 | >20 |
| 41 | >10 | >20 |
| 42 | 6.7 | >20 |
| 43 | 5.2 | >20 |
| 44 | 6.4 | >20 |
| 45A | 7.4 | >20 |
| 45B | >10 | >20 |
| 53A | 6.6 | >20 |
| 54 | >10 | >20 |
| 54B | >10 | >20 |
| 56 | >10 | >20 |
| 57 | >10 | >20 |
| 59 | >10 | >20 |
| 60 | >10 | >20 |
| 64 | 8.5 | >20 |
| 68 | 5.6 | >20 |
| 72 | >10 | >20 |
| 94 | >10 | >20 |

Example 115

3T3 In Vitro Phototoxicity Assay

Phototoxicity is defined as a toxic response that is elicited after the first exposure of the skin to certain chemicals and subsequent exposure to light, or that is induced similarly by skin irradiation after systemic administration of a chemical substance. The assay used in this study is designed to detect the phototoxic potential of a chemical by using a simple in vitro cytotoxicity assay with Balb/c 3T3 mouse fibroblasts. The principle of this test is a comparison of the cytotoxicity of a chemical when tested with and without exposure to a non-toxic dose of UVA-light. Cytotoxicity is expressed as a dose dependent reduction of the growth rate of cells as determined by uptake of the vital dye Neutral Red one day after treatment.

Method

Preparation of Stock Solution and Dosage of Test Item

A small amount of substance was weighed and formulated freshly in DMSO just before the start of the exposure of the cells. This stock solution or appropriate dilutions with DMSO were added to the cell suspensions to obtain the required final concentrations. All solutions were generally prepared in Eppendorf caps and discarded after use.

Reference Substance

Chlorpromazine (HCL) (Sigma, Batch/Lot No.: 120M1328V), test concentration: 300 µg/mL, Solvent: PBS/3% DMSO Measurement of UV Absorption Spectrum The absorption spectra as such or with UV-A or with UV-B pre-irradiation were recorded between 240 nm and 400 nm with a Lambda-2 spectral photometer (Perkin Elmer).

| UV radiation sources: | for UV-A: | Sol 500 with filter H1 | |
|---|---|---|---|
| | | Main spectrum: | 315-690 nm |
| | | Irradiance: | approx. 1.67 mW/cm$^2$ |
| | | Radiation dose: | approx. 5 J/cm$^2$ |
| | for UV-B: | Philips TL 20W/12 | |
| | | Main spectrum: | 290-320 nm |
| | | Irradiance: | approx. 0.083 mW/cm$^2$ |
| | | Radiation dose: | approx. 0.05 J/cm$^2$ | streptomycin) at 37° C. in a humidified atmosphere of 6% C02. Before cells approach confluence they were removed from flasks by trypsinisation. Prior to use in an assay, the cells were transferred to 96-well microtiter plates at a concentration of 1×104 cells/well in 100 µl volumes of sDMEM and allowed to attach for 24 h.

Exposure to Test Item

For incubation with murine fibroblasts, the test item was diluted in PBS/3% DMSO (detailed concentrations see in results).

Culture medium (Dulbecco's Modified Eagle Medium (DMEM), GlutaMAX (Gibco Ref 21885-025), 10% Fetal Bovine Serum (FBS) (Gibco Ref 10270-106), 100 IU/ml Penicillin and 100 µg/ml Streptomycin (Gibco Ref 15140-122)) was removed from the wells and murine fibroblasts were washed with PBS. Afterwards 100 µL of PBS/3% DMSO containing the test item was added and target cells were incubated for 1 h at 37° C. with 6% $CO_2$.

UV Exposure

For each test item the microtiter plates were prepared according to Table 4. "UVA plates" were exposed to approx. 5 J/cm2 UVA light, the "Dark plates" were kept in the dark and served as cytotoxicity control. Plates with chlorpromazine hydrochloride served as positive control. UV flux was measured with a UV-meter (Dr. Gröbel RM21).

Following UV irradiation, the test item was removed from the wells (one washing step with PBS) and replaced with sDMEM. Target cells were then incubated overnight at 37° C. in 6% CO2.

TABLE 4

96-well micro titer plate setup

| | 1 | 2 | 3 | 4 | 5 | 6 | 7 | 8 | 9 | 10 | 11 | 12 |
|---|---|---|---|---|---|---|---|---|---|---|---|---|
| A | S1 | S2 | U01 | U02 | U03 | U04 | U05 | U06 | U07 | U08 | S2 | S1 |
| B | S1 | S2 | | | | | | | | | S2 | S1 |
| C | S1 | S2 | | | | | | | | | S2 | S1 |
| D | S1 | S2 | | | | | | | | | S2 | S1 |
| E | S1 | S2 | | | | | | | | | S2 | S1 |
| F | S1 | S2 | | | | | | | | | S2 | S1 |
| G | S1 | S2 | | | | | | | | | S2 | S1 |
| H | S1 | S2 | | | | | | | | | S2 | S1 |

Determination of Phototoxicity

For this study the Neutral Red uptake (NRU) assay of Borenfreund and Puemer (Borenfreund, E, Puemer J A. Toxicity determined in vitro by morphological alterations and Neutral Red absorption. Toxicology Lett. 1985; 24:119-124) modified according to INVITTOX protocol No 78 (ERGATT/FRAME data bank of in vitro techniques in toxicology. INVITTOX PROTOCOL No 78. 3T3 NRU Phototoxicity Assay. March 1994) has been adapted to examine a possible phototoxic potential of the test item. This assay is based on the active uptake of the Neutral Red dye into the lysosomes of cultured murine fibroblasts. Because lysosomal membranes are known to be a site of action of many phototoxic compounds, this assay can provide a measure of potential for phototoxic injury.

Preparation of Cell Culture

A murine fibroblasts clone A 31 (ATCC no. CCL 163—passage No. 108) were cultured in 175 cm2 tissue culture grade flasks, containing sDMEM (Dulbecco's Minimal Essential Medium, supplemented with 10% fetal calf serum, 2 mM L-glutamine, 100 units/ml Penicillin and 100 µg/ml 96-Well Microtiter Plates were Prepared as Follows:

Each plate contained wells with cells and solvent but without test item which were either not incubated with Neutral Red solution (0% standard—S1) or were stained with Neutral Red (100% standard—S2) for calculation of the standard cell viability curve. Wells labeled with U01-U08 contained the different test item concentrations.

Neutral Red Uptake

The ready to use Neutral Red (NR) staining solution was freshly prepared as follows:
  0.4% aqueous stock solution was shielded from light and
    filtered before use to remove NR crystals.
  1:40 dilution of the stock solution was then prepared in
    sDMEM and added to the cells.

After the incubation the wells to be assayed were filled with 100 µL of the sDMEM containing Neutral Red. The target cells were incubated with the NR for 3 h at 37° C. in 6% $CO_2$.

Measurement of Neutral Red uptake

Unincorporated Neutral Red was removed from the target cells and the wells washed with at least 100 µL of PBS. 150

μL of Neutral Red desorb solution (1% glacial acetic acid, 50% ethanol in aqua bidest) was then added to quantitatively extract the incorporated dye. After at least 10 mins of vigorous shaking of the plates on a microtiter plate shaker until Neutral Red has been extracted from the cells and formed a homogeneous solution, the absorption of the resulting colored solution was measured with a SPECTRAmax PLUS microtiter plate reader (Molecular Devices) at 540 nm.

Calculation of Cell Viability

Cell viability was calculated with the SOFTmax Pro software package (Molecular Devices). First a two-point standard curve (0% and 100% viability) was calculated with the linear curve fit option of the program based on the following formula:

$$Y = A + (B \times X)$$

(A=y-intercept of the line; B=slope of the line;

0% cell viability=cells with solvent, but without test item and Neutral Red;

100% cell viability=cells with solvent and Neutral Red, but without test item)

By this means the viability of the cells incubated with increasing concentrations of the test chemical was calculated. Chlorpromazine (HCl) served as positive control in the experiment.

Calculation of IC50 Values

All calculations were performed with the SOFTmax Pro analysis software package (Molecular Devices—for details see:

http://www.mbl.edu/jbpc/files/2014/05/SoftMax_Pro_User-_Guide.pdf)

Calculation of Discrimination Factor for Phototoxicity

For evaluation of phototoxic potential, the $IC_{50}$ values determined with and without UV exposure were compared.

$$\text{Factor} = IC_{50}(-UV)/IC_{50}(+UV)$$

For discrimination between phototoxic and non-phototoxic test chemicals a cut-off factor of >5 was applied (Liebsch M, Spielmann H, Balls M, Brand M, Daring B, Dupuis J, Holzhilter H G, Klecak G, L. Eplattenier H, Lovell W, Maurer T, Moldenhauer F, Moore L, Pape W, Pfannenbecker U, Potthast J M, De Silva O, Steiling W, Willshaw A. First results of the EC/COLIPA Validation Project. In Vitro Phototoxicity Testing. In: In Vitro Skin Toxicology: Irritation, Phototoxicity, Sensitization; Vol. 10. Alternative Methods in Toxicology-Eds. Rougier A, Maibach H I, Goldberg A M; Mary Ann Liebert Publ.: New York, USA 1994, pp. 243-251).

Test items which are not cytotoxic to murine fibroblasts even at the highest concentrations tested, but show a strong dose dependent decrease in cell viability after UV exposure are considered also phototoxic (Spielmann H, Balls M, Dupuis J, Pape W J W, Pechovitch G, Silva DeO, Holzhütter, H G, Clothier R, Desolle P, Gerberick F, Liebsch M, Lowell W W, Maurer T, Pfannenbecker U, Potthast J M, Csato M, Sladowski D, Steiling W, Brantom P. The international EU/COLIPA in vitro phototoxicity validation study: Results of phase II (blind trial). Part 1: The 3T3 NRU phototoxicity test. Toxicology in Vitro 1998, 12: 305-327).

The test results were shown below, the compounds of this invention showed very good phototoxicity profile.

TABLE 5

The 3T3 test results for the compound of this invention

| Example No | Phototoxicity factor | $IC_{50}$ (UV-A) (μg/mL) |
|---|---|---|
| 14 | 1.00 | >100 |
| 30 | >1.9 | 54.6 |
| 39 | 1.00 | >100 |
| 54B | 1.00 | >100 |
| 90 | >2 | 50.6 |
| 94 | 1.99 | 39.0 |

The invention claimed is:

1. A compound of formula (I),

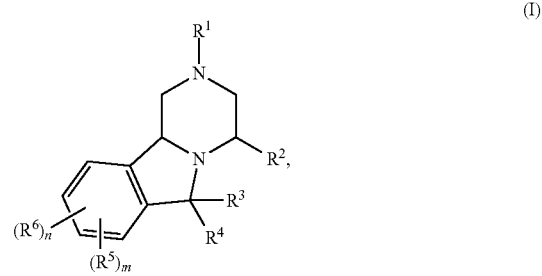

(I)

wherein:

$R^1$ is

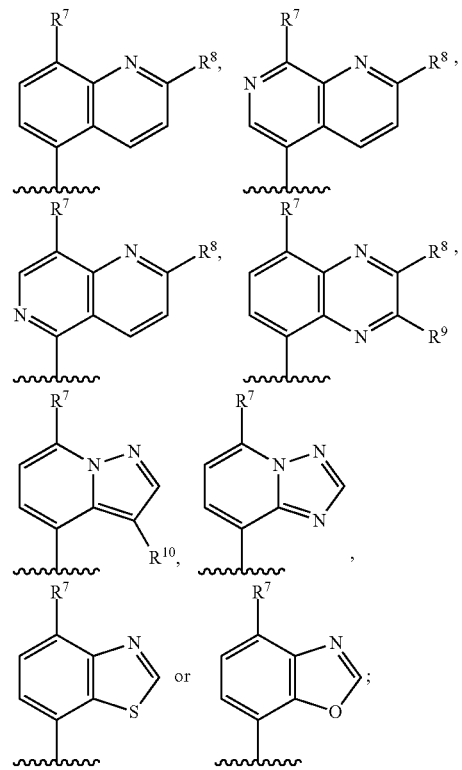

wherein $R_7$ is $C_{1-6}$alkyl, $C_{1-6}$alkoxy, halo$C_{1-6}$alkyl, halogen, nitro or cyano;

$R^8$ is H or deuterium;
$R^9$ is H, deuterium or $C_{1-6}$alkyl;
$R^{10}$ is H or halogen;
$R^2$ is H or $C_{1-6}$alkyl;
$R^3$ is H;
$R^4$ is H;
$R^5$ is H, piperazinyl, halogen, $C_{1-6}$alkyl, halopyrrolidinylamino or hydroxypyrrolidinyl$C_{1-6}$alkylamino;
$R^6$ is H, $(C_{1-6}alkyl)_2$amino$C_{1-6}$alkoxy, $(C_{1-6}alkyl)_2$amino$C_{1-6}$alkylamino, 1,2,3,4,6,6a-hexahydropyrrolo[3,4-c]pyrrolyl substituted by $C_{1-6}$alkoxy, 1,4-diazepanyl substituted by one or two substituents independently selected from hydroxy and $C_{1-6}$alkyl, 1,4-oxazepanyl substituted by amino, 1,4-oxazepanylamino, 1,6-diazaspiro[3.3]heptanyl, 2,5-diazabicyclo[2.2.1]heptanylcarbonyl, 2,6-diazaspiro[3.3]heptanyl unsubstituted or substituted by $C_{1-6}$alkyl, 2-oxa-7-azaspiro[3.4]octanyl substituted by amino, 3,4,4a,5,7,7a-hexahydro-2H-pyrrolo[3,4-b][1,4]oxazinyl, 3,4a,5,6,7,7a-hexahydro-2H-pyrrolo[3,4-b][1,4]oxazinyl, 3,8-diazabicyclo[3.2.1]octanylcarbonyl, 3-oxa-7,9-diazabicyclo[3.3.1]nonanyl, 3-oxo-1,5,6,7,8,8a-hexahydroimidazo[1,5-a]pyrazinyl, 5-oxa-2,8-diazaspiro[3.5]nonanyl, 9-oxa-3,7-diazabicyclo[3.3.1]nonanyl, amino $(C_{1-6}alkyl)$ piperidinylcarbonyl, azetidinyl unsubstituted or substituted by one or two substituents independently selected from amino and $C_{1-6}$alkyl, azetidinylamino, azetidinyloxy, $C_{1-6}$alkoxypiperidinylamino, $C_{1-6}$alkoxypyrrolidinyl $(C_{1-6}alkyl)$ amino, $C_{1-6}$alkoxypyrrolidinylamino, haloazetidinyl $(C_{1-6}alkyl)$ amino, halopyrrolidinylamino, halopyrrolidinyl$C_{1-6}$alkoxy, halopyrrolidinyl$C_{1-6}$alkylamino, halopyrrolidinyloxy, hydroxypyrrolidinyl$C_{1-6}$alkylamino, morpholinyl$C_{1-6}$alkylamino, piperazinyl unsubstituted or substituted by $C_{1-6}$alkoxy$C_{1-6}$alkyl, hydroxy$C_{1-6}$alkyl or $C_{1-6}$alkyl, piperazinylcarbonyl, piperidinyl unsubstituted or substituted by one or two substituents independently selected from amino, $C_{1-6}$alkoxy and $C_{1-6}$alkyl, piperidinylamino, or
pyrrolidinyl substituted by one, two or three substituents independently selected from amino, $C_{1-6}$alkoxy, $C_{1-6}$alkyl, $C_{1-6}$alkylamino, halogen, hydroxy and hydroxy$C_{1-6}$alkyl;
m is 0, 1, 2, or 3;
n is 1, 2, 3 or 4;
and
m+n≤4;
with the proviso that $R^5$ and $R^6$ are not H simultaneously; or a pharmaceutically acceptable salt thereof.

2. A compound of formula (Ia),

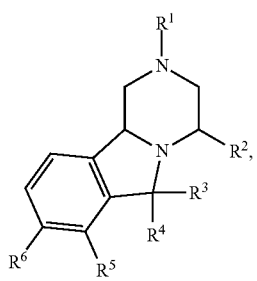
(Ia)

wherein:
$R^1$ is

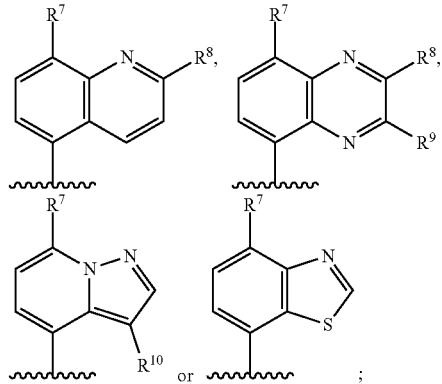

wherein $R^7$ is $C_{1-6}$alkyl, halo$C_{1-6}$alkyl, halogen or cyano;
$R^8$ is H or deuterium;
$R^9$ is H or deuterium;
$R^{10}$ is H or halogen;
$R^2$ is H or $C_{1-6}$alkyl;
$R^3$ is H;
$R^4$ is H;
$R^5$ is H, piperazinyl, halopyrrolidinylamino or hydroxypyrrolidinyl$C_{1-6}$alkylamino;
$R^6$ is H, $(C_{1-6}alkyl)_2$amino$C_{1-6}$alkoxy, $(C_{1-6}alkyl)_2$amino$C_{1-6}$alkylamino, 1,2,3,4,6,6a-hexahydropyrrolo[3,4-c]pyrrolyl substituted by $C_{1-6}$alkoxy, 1,4-diazepanyl substituted by one or two substituents independently selected from hydroxy and $C_{1-6}$alkyl, 1,4-oxazepanyl substituted by amino, 1,4-oxazepanylamino, 1,6-diazaspiro[3.3]heptanyl, 2,5-diazabicyclo[2.2.1]heptanylcarbonyl, 2,6-diazaspiro[3.3]heptanyl unsubstituted or substituted by $C_{1-6}$alkyl, 2-oxa-7-azaspiro[3.4]octanyl substituted by amino, 3,4,4a,5,7,7a-hexahydro-2H-pyrrolo[3,4-b][1,4]oxazinyl, 3,4a,5,6,7,7a-hexahydro-2H-pyrrolo[3,4-b][1,4]oxazinyl, 3,8-diazabicyclo[3.2.1]octanylcarbonyl, 3-oxa-7,9-diazabicyclo[3.3.1]nonanyl, 3-oxo-1,5,6,7,8,8a-hexahydroimidazo[1,5-a]pyrazinyl, 5-oxa-2,8-diazaspiro[3.5]nonanyl, 9-oxa-3,7-diazabicyclo[3.3.1]nonanyl, amino $(C_{1-6}alkyl)$ piperidinylcarbonyl, azetidinyl unsubstituted or substituted by one or two substituents independently selected from amino and $C_{1-6}$alkyl, azetidinylamino, azetidinyloxy, $C_{1-6}$alkoxypiperidinylamino, $C_{1-6}$alkoxypyrrolidinyl $(C_{1-6}alkyl)$ amino, $C_{1-6}$alkoxypyrrolidinylamino, haloazetidinyl $(C_{1-6}alkyl)$ amino, halopyrrolidinylamino, halopyrrolidinyl$C_{1-6}$alkoxy, halopyrrolidinyl$C_{1-6}$alkylamino, halopyrrolidinyloxy, hydroxypyrrolidinyl$C_{1-6}$alkylamino, morpholinyl$C_{1-6}$alkylamino, piperazinyl unsubstituted or substituted by $C_{1-6}$alkoxy$C_{1-6}$alkyl, hydroxy$C_{1-6}$alkyl or $C_{1-6}$alkyl, piperazinylcarbonyl, piperidinyl unsubstituted or substituted by one or two substituents independently selected from amino, $C_{1-6}$alkoxy and $C_{1-6}$alkyl, piperidinylamino; or pyrrolidinyl substituted by one, two or three substituents independently selected from amino, $C_{1-6}$alkoxy, $C_{1-6}$alkyl, $C_{1-6}$alkylamino, halogen, hydroxy and hydroxy$C_{1-6}$alkyl;
or a pharmaceutically acceptable salt thereof.

3. A compound of formula (Ib),

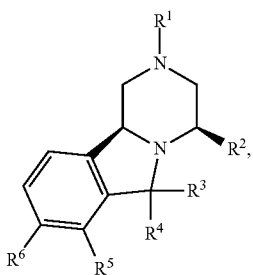

wherein:
R¹ is

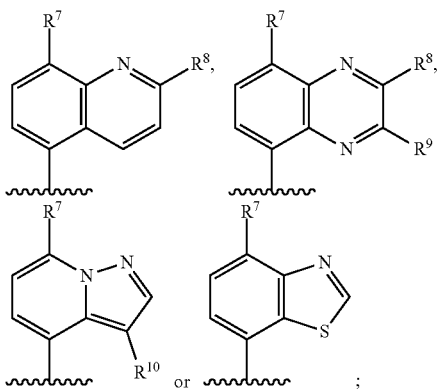

wherein R⁷ is $C_{1-6}$alkyl, halo$C_{1-6}$alkyl, halogen or cyano;
R⁸ is H or deuterium;
R⁹ is H or deuterium;
R¹⁰ is H or halogen;
R² is H or $C_{1-6}$alkyl;
R³ is H;
R⁴ is H;
R⁵ is H, piperazinyl, halopyrrolidinylamino or hydroxypyrrolidinyl$C_{1-6}$alkylamino;
R⁶ is H, $(C_{1-6}$alkyl$)_2$amino$C_{1-6}$alkoxy, $(C_{1-6}$alkyl$)_2$amino$C_{1-6}$alkylamino, 1,2,3,4,6,6a-hexahydropyrrolo[3,4-c]pyrrolyl substituted by $C_{1-6}$alkoxy, 1,4-diazepanyl substituted by one or two substituents independently selected from hydroxy and $C_{1-6}$alkyl, 1,4-oxazepanyl substituted by amino, 1,4-oxazepanylamino, 1,6-diazaspiro[3.3]heptanyl, 2,5-diazabicyclo[2.2.1]heptanylcarbonyl, 2,6-diazaspiro[3.3]heptanyl unsubstituted or substituted by $C_{1-6}$alkyl, 2-oxa-7-azaspiro[3.4]octanyl substituted by amino, 3,4,4a,5,7,7a-hexahydro-2H-pyrrolo[3,4-b][1,4]oxazinyl, 3,4a,5,6,7,7a-hexahydro-2H-pyrrolo[3,4-b][1,4]oxazinyl, 3,8-diazabicyclo[3.2.1]octanylcarbonyl, 3-oxa-7,9-diazabicyclo[3.3.1]nonanyl, 3-oxo-1,5,6,7,8,8a-hexahydroimidazo[1,5-a]pyrazinyl, 5-oxa-2,8-diazaspiro[3.5]nonanyl, 9-oxa-3,7-diazabicyclo[3.3.1]nonanyl, amino $(C_{1-6}$alkyl) piperidinylcarbonyl, azetidinyl unsubstituted or substituted by one or two substituents independently selected from amino and $C_{1-6}$alkyl, azetidinylamino, azetidinyloxy, $C_{1-6}$alkoxypiperidinylamino, $C_{1-6}$alkoxypyrrolidinyl $(C_{1-6}$alkyl) amino, $C_{1-6}$alkoxypyrrolidinylamino, haloazetidinyl $(C_{1-6}$alkyl) amino, halopyrrolidinylamino, halopyrrolidinyl$C_{1-6}$alkoxy, halopyrrolidinyl$C_{1-6}$alkylamino, halopyrrolidinyloxy, hydroxypyrrolidinyl$C_{1-6}$alkylamino, morpholinyl$C_{1-6}$alkylamino, piperazinyl unsubstituted or substituted by $C_{1-6}$alkoxy$C_{1-6}$alkyl, hydroxy$C_{1-6}$alkyl or $C_{1-6}$alkyl, piperazinylcarbonyl, piperidinyl unsubstituted or substituted by one or two substituents independently selected from amino, $C_{1-6}$alkoxy and $C_{1-6}$alkyl, piperidinylamino; or
pyrrolidinyl substituted by one, two or three substituents independently selected from amino, $C_{1-6}$alkoxy, $C_{1-6}$alkyl, $C_{1-6}$alkylamino, halogen, hydroxy and hydroxy$C_{1-6}$alkyl;
or a pharmaceutically acceptable salt thereof.

4. A compound according to claim 1, wherein:
R⁶ is H, $(C_{1-6}$alkoxy$C_{1-6}$alkyl) piperazinyl, $(C_{1-6}$alkyl$)_2$amino$C_{1-6}$alkoxy, $(C_{1-6}$alkyl$)_2$amino$C_{1-6}$alkylamino, (hydroxy$C_{1-6}$alkyl) piperazinyl,
1,4-oxazepanylamino, 1,6-diazaspiro[3.3]heptanyl, 2,5-diazabicyclo[2.2.1]heptanylcarbonyl, 2,6-diazaspiro[3.3]heptanyl, 3,4,4a,5,7,7a-hexahydro-2H-pyrrolo[3,4-b][1,4]oxazinyl, 3,4a,5,6,7,7a-hexahydro-2H-pyrrolo[3,4-b][1,4]oxazinyl, 3,8-diazabicyclo[3.2.1]octanylcarbonyl, 3-oxa-7,9-diazabicyclo[3.3.1]nonanyl, 3-oxo-1,5,6,7,8,8a-hexahydroimidazo[1,5-a]pyrazinyl, 5-oxa-2,8-diazaspiro[3.5]nonanyl, 9-oxa-3,7-diazabicyclo[3.3.1]nonanyl, amino $(C_{1-6}$alkoxy) piperidinyl, amino $(C_{1-6}$alkoxy) pyrrolidinyl, amino $(C_{1-6}$alkyl) azetidinyl, amino $(C_{1-6}$alkyl) piperidinyl, amino $(C_{1-6}$alkyl) piperidinylcarbonyl, amino $(C_{1-6}$alkyl) pyrrolidinyl, amino (hydroxy) $(C_{1-6}$alkyl) pyrrolidinyl, amino (hydroxy) pyrrolidinyl, amino (hydroxy$C_{1-6}$alkyl) pyrrolidinyl, amino-1,4-oxazepanyl, amino-2-oxa-7-azaspiro[3.4]octanyl, aminoazetidinyl, aminohalopyrrolidinyl, aminopyrrolidinyl, azetidinyl, azetidinylamino, azetidinyloxy, $C_{1-6}$alkoxy $(C_{1-6}$alkylamino) pyrrolidinyl, $C_{1-6}$alkoxy-1,2,3,4,6,6a-hexahydropyrrolo[3,4-c]pyrrolyl, $C_{1-6}$alkoxypiperidinylamino, $C_{1-6}$alkoxypyrrolidinyl $(C_{1-6}$alkyl) amino, $C_{1-6}$alkoxypyrrolidinylamino, $C_{1-6}$alkyl-2,6-diazaspiro[3.3]heptanyl, $C_{1-6}$alkylpiperazinyl, haloazetidinyl $(C_{1-6}$alkyl) amino, halopyrrolidinylamino, halopyrrolidinyl$C_{1-6}$alkoxy, halopyrrolidinyl$C_{1-6}$alkylamino, halopyrrolidinyloxy, hydroxy $(C_{1-6}$alkyl)-1,4-diazepanyl, hydroxy $(C_{1-6}$alkylamino) pyrrolidinyl, hydroxy-1,4-diazepanyl, hydroxypyrrolidinyl$C_{1-6}$alkylamino, morpholinyl$C_{1-6}$alkylamino, piperazinyl, piperazinylcarbonyl, piperidinyl or piperidinylamino.

5. A compound according to claim 4, wherein:
R⁶ is H, (hydroxymethyl) piperazin-1-yl, 1,4-oxazepan-6-ylamino, 1,6-diazaspiro[3.3]heptan-6-yl, 2-(dimethylamino) ethoxy, 2-(dimethylamino) ethylamino, 2,5-diazabicyclo[2.2.1]heptanyl-2-carbonyl, 2,6-diazaspiro[3.3]heptan-2-yl, 2-morpholinylethylamino, 3-(methoxymethyl) piperazin-1-yl, 3,4,4a,5,7,7a-hexahydro-2H-pyrrolo[3,4-b][1,4]oxazin-6-yl, 3,4a,5,6,7,7a-hexahydro-2H-pyrrolo[3,4-b][1,4]oxazin-4-yl, 3,8-diazabicyclo[3.2.1]octanyl-3-carbonyl, 3a-methoxy-1,2,3,4,6,6a-hexahydropyrrolo[3,4-c]pyrrol-5-yl, 3-amino-3-(hydroxymethyl) pyrrolidin-1-yl, 3-amino-3-methyl-azetidin-1-yl, 3-amino-3-methyl-pyrrolidin-1-yl, 3-amino-4-fluoro-pyrrolidin-1-yl, 3-amino-4-hydroxy-pyrrolidin-1-yl, 3-amino-4-methoxy-pyrrolidin-1-piperidinyl, 3-amino-4-methoxy-pyrrolidin-1-yl, 3-aminoazetidin-1-yl, 3-aminopyrrolidin-1-yl, 3-fluoroazetidin-3-ylmethylamino, 3-hydroxy-4-(methylamino) pyrrolidin-1-yl, 3-hydroxypyrrolidin-1-ylethylamino, 3-methoxy-4-(methylamino) pyrrolidin-1-yl, 3-methoxy-4-piperidinylamino, 3-methylpiperazin-1-yl, 3-oxa-7,9-diazabicyclo[3.3.1]nonan-7-yl, 3-oxo-1,5,6,7,8,8a-hexahydroimidazo[1,5-a]pyrazin-2-yl, 3-piperidinylamino, 4-amino-3-hydroxy-3-methyl-pyrrolidin-1-yl, 4-amino-3-methoxy-1-piperidinyl, 4-amino-4-methyl-1-piperidinyl, 4-amino-4-methyl-piperidinyl-1-carbonyl, 4-fluoropyrrolidin-2-ylmethoxy, 4-fluoropyrrolidin-2-ylmethylamino, 4-fluoropyrrolidin-3-ylamino, 4-fluoropyrrolidin-3-yloxy, 4-methoxy-pyrrolidin-3-yl (methyl) amino, 4-methoxypyrrolidin-3-ylamino, 5-amino-2-oxa-7-azaspiro[3.4]octan-7-yl, 5-oxa-2,8-diazaspiro[3.5]nonan-2-yl, 5-oxa-2,8-diazaspiro[3.5]nonan-8-yl, 6-amino-1,4-oxazepan-4-yl, 6-hydroxy-1,4-diazepan-1-yl, 6-hydroxy-6-methyl-1,4-diazepan-1-yl, 6-methyl-2,6-diazaspiro[3.3]heptan-2-yl, 9-oxa-3,7-diazabicyclo[3.3.1]nonan-3-yl, azetidin-3-yl, azetidin-3-ylamino, azetidin-3-yloxy, hydroxy-1,4-diazepan-1-yl, morpholin-2-ylmethylamino, morpholin-3-ylmethylamino, piperazin-1-yl, piperazinyl-1-carbonyl, or piperidin-4-yl.

6. A compound according to claim 4, wherein:
$R^1$ is

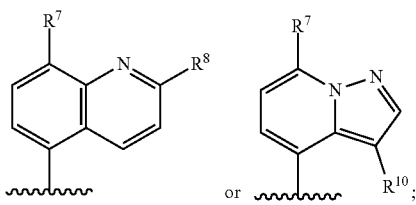

wherein:
$R^7$ is cyano;
$R^8$ is H or deuterium; and
$R^{10}$ is H or halogen.

7. A compound according to claim 6, wherein:
$R^1$ is

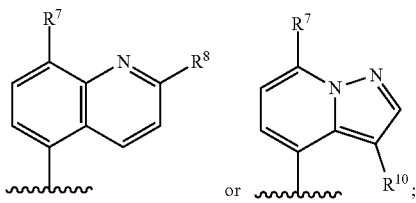

wherein: $R^7$ is cyano;
$R^8$ is H or deuterium; and
$R^{10}$ is H or fluoro.

8. A compound according to claim 6, wherein:
$R^2$ is $C_{1-6}$alkyl and $R^5$ is H.

9. A compound according to claim 8, wherein:
$R^6$ is $(C_{1-6}alkyl)_2aminoC_{1-6}alkylamino$, 1,4-diazepanyl substituted by hydroxy, 1,4-oxazepanyl substituted by amino, 3,4,4a,5,7,7a-hexahydro-2H-pyrrolo[3,4-b][1,4]oxazinyl, 5-oxa-2,8-diazaspiro[3.5]nonanyl, 9-oxa-3,7-diazabicyclo[3.3.1]nonanyl, azetidinyl substituted twice by amino and $C_{1-6}$alkyl, $C_{1-6}$alkoxypyrrolidinylamino, halopyrrolidinylamino, or pyrrolidinyl substituted by two or three substituents independently selected from amino, $C_{1-6}$alkoxy, $C_{1-6}$alkyl and hydroxy.

10. A compound according to claim 9, wherein:
$R^6$ is $(C_{1-6}alkyl)_2aminoC_{1-6}alkylamino$, 3,4,4a,5,7,7a-hexahydro-2H-pyrrolo[3,4-b][1,4]oxazinyl, 5-oxa-2,8-diazaspiro[3.5]nonanyl, 9-oxa-3,7-diazabicyclo[3,3,1]nonanyl, amino $(C_{1-6}alkoxy)$ pyrrolidinyl, amino $(C_{1-6}alkyl)$ azetidinyl, amino $(C_{1-6}alkyl)$ pyrrolidinyl, amino (hydroxy) $(C_{1-6}alkyl)$ pyrrolidinyl, amino (hydroxy) pyrrolidinyl, amino-1,4-oxazepanyl, $C_{1-6}$alkoxypyrrolidinylamino, halopyrrolidinylamino, or hydroxy-1,4-diazepanyl.

11. A compound according to claim 10, wherein:
$R^6$ is 2-(dimethylamino) ethylamino, 3,4,4a,5,7,7a-hexahydro-2H-pyrrolo[3,4-b][1,4]oxazin-6-yl, 3-amino-3-methyl-azetidin-1-yl, 3-amino-3-methyl-pyrrolidin-1-yl, 3-amino-4-hydroxy-pyrrolidin-1-yl, 3-amino-4-methoxy-pyrrolidin-1-yl, 4-amino-3-hydroxy-3-methyl-pyrrolidin-1-yl, 4-fluoropyrrolidin-3-ylamino, 4-methoxypyrrolidin-3-ylamino, 5-oxa-2,8-diazaspiro[3.5]nonan-2-yl, 5-oxa-2,8-diazaspiro[3.5]nonan-8-yl, 6-amino-1,4-oxazepan-4-yl, 9-oxa-3,7-diazabicyclo[3.3.1]nonan-3-yl, or hydroxy-1,4-diazepan-1-yl.

12. A compound according to claim 1, wherein:
$R^1$ is

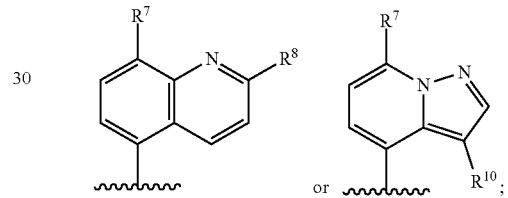

wherein $R^7$ is cyano;
$R^8$ is H or deuterium;
$R^{10}$ is H or halogen;
$R^2$ is $C_{1-6}$alkyl;
$R^3$ is H;
$R^4$ is H;
$R^5$ is H;
$R^6$ is $(C_{1-6}alkyl)_2aminoC_{1-6}alkylamino$, 1,4-diazepanyl substituted by hydroxy,
1,4-oxazepanyl substituted by amino, 3,4,4a,5,7,7a-hexahydro-2H-pyrrolo[3,4-b][1,4]oxazinyl, 5-oxa-2,8-diazaspiro[3.5]nonanyl, 9-oxa-3,7-diazabicyclo[3.3.1]nonanyl, azetidinyl substituted twice by amino and $C_{1-6}$alkyl, $C_{1-6}$alkoxypyrrolidinylamino, halopyrrolidinylamino, or
pyrrolidinyl substituted by two or three substituents independently selected from amino, $C_{1-6}$alkoxy, $C_{1-6}$alkyl and hydroxy,
or a pharmaceutically acceptable salt thereof.

13. A compound according to claim 12, wherein:
$R^1$ is

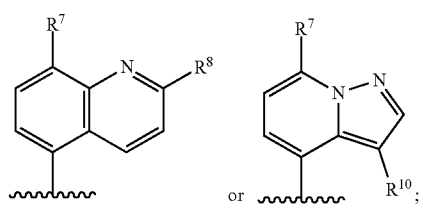

wherein $R^7$ is cyano;
$R^8$ is H or deuterium;
$R^{10}$ is H or halogen;
$R^2$ is $C_{1-6}$alkyl;
$R^3$ is H;
$R^4$ is H;
$R^5$ is H;
$R^6$ is $(C_{1-6}alkyl)_2aminoC_{1-6}alkylamino$, 3,4,4a,5,7,7a-hexahydro-2H-pyrrolo[3,4-b][1,4]oxazinyl, 5-oxa-2,8-diazaspiro[3.5]nonanyl, 9-oxa-3,7-diazabicyclo[3.3.1]nonanyl, amino ($C_{1-6}$alkoxy) pyrrolidinyl, amino ($C_{1-6}$alkyl) azetidinyl, amino ($C_{1-6}$alkyl) pyrrolidinyl, amino (hydroxy) ($C_{1-6}$alkyl) pyrrolidinyl, amino (hydroxy) pyrrolidinyl, amino-1,4-oxazepanyl, $C_{1-6}$alkoxypyrrolidinylamino, halopyrrolidinylamino or hydroxy-1,4-diazepanyl,
or a pharmaceutically acceptable salt thereof.

14. A compound according to claim 12, wherein:
$R^1$ is

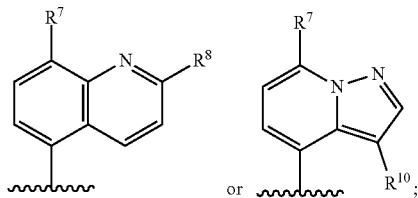

wherein $R^7$ is cyano; $R^8$ is H or deuterium; $R^{10}$ is H or fluoro;
$R^2$ is methyl;
$R^3$ is H;
$R^4$ is H;
$R^5$ is H;
$R^6$ is 2-(dimethylamino) ethylamino, 3,4,4a,5,7,7a-hexahydro-2H-pyrrolo[3,4-b][1,4]oxazin-6-yl, 3-amino-3-methyl-azetidin-1-yl, 3-amino-3-methyl-pyrrolidin-1-yl, 3-amino-4-hydroxy-pyrrolidin-1-yl, 3-amino-4-methoxy-pyrrolidin-1-yl, 4-amino-3-hydroxy-3-methyl-pyrrolidin-1-yl, 4-fluoropyrrolidin-3-ylamino, 4-methoxypyrrolidin-3-ylamino, 5-oxa-2,8-diazaspiro[3.5]nonan-2-yl, 5-oxa-2,8-diazaspiro[3.5]nonan-8-yl, 6-amino-1,4-oxazepan-4-yl, 9-oxa-3,7-diazabicyclo[3.3.1]nonan-3-yl or hydroxy-1,4-diazepan-1-yl,
or a pharmaceutically acceptable salt thereof.

15. A compound selected from:
5-[(4R,10bS)-4-methyl-8-piperazin-1-yl-3,4,6, 10b-tetrahydro-1/-pyrazino[2,1-a]isoindol-2-yl]quinoline-8-carbonitrile;
5-[(4S,10bR)-4-methyl-8-piperazin-1-yl-3,4,6, 10b-tetrahydro-1H-pyrazino[2,1-a]isoindol-2-yl]quinoline-8-carbonitrile;
5-(8-piperazin-1-yl-3,4,6,10b-tetrahydro-1H-pyrazino[2,1-a]isoindol-2-yl) quinoline-8-carbonitrile;
7-(8-piperazin-1-yl-3,4,6,10b-tetrahydro-1H-pyrazino[2,1-a]isoindol-2-yl)-1,3-benzothiazole-4-carbonitrile;
4-[(4R,10bS)-4-methyl-8-piperazin-1-yl-3,4,6, 10b-tetrahydro-1H-pyrazino[2,1-a]isoindol-2-yl]pyrazolo[1,5-a]pyridine-7-carbonitrile;
7-[(4R,10bS)-4-methyl-8-piperazin-1-yl-3,4,6,10b-tetrahydro-1H-pyrazino[2,1-a]isoindol-2-yl]-1,3-benzothiazole-4-carbonitrile;
8-[(4R,10bS)-4-methyl-8-piperazin-1-yl-3,4,6, 10b-tetrahydro-1H-pyrazino[2,1-a]isoindol-2-yl]quinoxaline-5-carbonitrile;
5-[(4R,10bS)-4-methyl-7-piperazin-1-yl-3,4,6, 10b-tetrahydro-1/-pyrazino[2,1-a]isoindol-2-yl]quinoline-8-carbonitrile;
5-[(4R, 10bS)-4-methyl-8-(4-piperidyl)-3,4,6, 10b-tetrahydro-1H-pyrazino[2,1-a]isoindol-2-yl]quinoline-8-carbonitrile;
5-[(4R, 10bS)-8-[(2R)-2-(hydroxymethyl) piperazin-1-yl]-4-methyl-3,4,6,10b-tetrahydro-1H-pyrazino[2,1-a]isoindol-2-yl]quinoline-8-carbonitrile;
5-[(4R, 10bS)-8-[(2S)-2-(hydroxymethyl) piperazin-1-yl]-4-methyl-3,4,6,10b-tetrahydro-1H-pyrazino[2,1-a]isoindol-2-yl]quinoline-8-carbonitrile;
5-[(4R, 10bS)-8-[(3S)-3-(hydroxymethyl) piperazin-1-yl]-4-methyl-3,4,6,10b-tetrahydro-1H-pyrazino[2,1-a]isoindol-2-yl]quinoline-8-carbonitrile;
5-[(4R, 10bS)-4-methyl-8-(3-oxa-7,9-diazabicyclo[3.3.1]nonan-7-yl)-3,4,6,10b-tetrahydro-1H-pyrazino[2, 1-a]isoindol-2-yl]quinoline-8-carbonitrile;
5-[(4R,10bS)-4-methyl-8-(9-oxa-3,7-diazabicyclo[3.3.1]nonan-3-yl)-3,4,6,10b-tetrahydro-1H-pyrazino[2, 1-a]isoindol-2-yl]quinoline-8-carbonitrile;
5-[(4R, 10bS)-8-(6-hydroxy-1,4-diazepan-1-yl)-4-methyl-3,4,6,10b-tetrahydro-1H-pyrazino[2,1-a]isoindol-2-yl]quinoline-8-carbonitrile;
5-[(4R, 10bS)-8-[trans-3-amino-4-methoxy-pyrrolidin-1-yl]-4-methyl-3,4,6, 10b-tetrahydro-1H-pyrazino[2,1-a]isoindol-2-yl]quinoline-8-carbonitrile;
5-[(4R,10bS)-8-[(3S,4S)-3-amino-4-methoxy-pyrrolidin-1-yl]-4-methyl-3,4,6,10b-tetrahydro-1H-pyrazino[2,1-a]isoindol-2-yl]quinoline-8-carbonitrile;
5-[(4R, 10bS)-8-[(3R,4R)-3-amino-4-methoxy-pyrrolidin-1-yl]-4-methyl-3,4,6, 10b-tetrahydro-1H-pyrazino[2,1-a]isoindol-2-yl]quinoline-8-carbonitrile;
5-[(4R, 10bS)-8-[cis-3-amino-4-methoxy-pyrrolidin-1-yl]-4-methyl-3,4,6,10b-tetrahydro-1H-pyrazino[2,1-a]isoindol-2-yl]quinoline-8-carbonitrile;
5-[(4R, 10bS)-8-(5-amino-2-oxa-7-azaspiro[3.4]octan-7-yl)-4-methyl-3,4,6,10b-tetrahydro-1H-pyrazino[2, 1-a]isoindol-2-yl]quinoline-8-carbonitrile;
5-[(4R,10bS)-8-[3-amino-3-(hydroxymethyl) pyrrolidin-1-yl]-4-methyl-3,4,6,10b-tetrahydro-1H-pyrazino[2,1-a]isoindol-2-yl]quinoline-8-carbonitrile;
5-[(4R,10bS)-8-[(3R)-3-aminopyrrolidin-1-yl]-4-methyl-3,4,6, 10b-tetrahydro-1H-pyrazino[2,1-a]isoindol-2-yl]quinoline-8-carbonitrile;
5-[(4R,10bS)-8-[trans-3-amino-4-hydroxy-pyrrolidin-1-yl]-4-methyl-3,4,6,10b-tetrahydro-1H-pyrazino[2,1-a]isoindol-2-yl]quinoline-8-carbonitrile;
5-[(4R, 10bS)-8-(3-aminoazetidin-1-yl)-4-methyl-3,4,6, 10b-tetrahydro-1H-pyrazino[2,1-a]isoindol-2-yl]quinoline-8-carbonitrile;
5-[(4R,10bS)-8-[(3S,4S)-3-methoxy-4-(methylamino) pyrrolidin-1-yl]-4-methyl-3,4,6, 10b-tetrahydro-1H-pyrazino[2,1-a]isoindol-2-yl]quinoline-8-carbonitrile;
5-[(4R, 10bS)-4-methyl-8-(5-oxa-2,8-diazaspiro[3.5]nonan-8-yl)-3,4,6, 10b-tetrahydro-1H-pyrazino[2, 1-a]isoindol-2-yl]quinoline-8-carbonitrile;
5-[(4R, 10bS)-8-[2-(dimethylamino) ethoxy]-4-methyl-3, 4,6,10b-tetrahydro-1H-pyrazino[2,1-a]isoindol-2-yl]quinoline-8-carbonitrile;
5-[(4R,10bS)-8-[2-(dimethylamino) ethylamino]-4-methyl-3,4,6,10b-tetrahydro-1H-pyrazino[2,1-a]isoindol-2-yl]quinoline-8-carbonitrile;
5-[(4R,10bS)-8-(azetidin-3-yloxy)-4-methyl-3,4,6, 10b-tetrahydro-1H-pyrazino[2,1-a]isoindol-2-yl]quinoline-8-carbonitrile;

5-[(4R, 10bS)-8-(azetidin-3-ylamino)-4-methyl-3,4,6, 10b-tetrahydro-1H-pyrazino[2,1-a]isoindol-2-yl]quinoline-8-carbonitrile;

5-[(4R,10bS)-8-(azetidin-3-yl)-4-methyl-3,4,6, 10b-tetrahydro-1H-pyrazino[2,1-a]isoindol-2-yl]quinoline-8-carbonitrile;

5-[(4R,10bS)-8-[[(3S,4R)-4-fluoropyrrolidin-3-yl] amino]-4-methyl-3,4,6,10b-tetrahydro-1H-pyrazino[2,1-a]isoindol-2-yl]quinoline-8-carbonitrile;

5-[(4R,10bS)-8-[[(3S,4S)-4-fluoropyrrolidin-3-yl] amino]-4-methyl-3,4,6, 10b-tetrahydro-1H-pyrazino[2,1-a]isoindol-2-yl]quinoline-8-carbonitrile;

5-[(4R,10bS)-8-[[(3R,4S)-4-fluoropyrrolidin-3-yl] amino]-4-methyl-3,4,6,10b-tetrahydro-1H-pyrazino[2,1-a]isoindol-2-yl]quinoline-8-carbonitrile;

5-[(4R, 10bS)-8-[(3R,4R)-4-fluoropyrrolidin-3-yl] amino]-4-methyl-3,4,6,10b-tetrahydro-1H-pyrazino[2,1-a]isoindol-2-yl]quinoline-8-carbonitrile;

5-[(4R, 10bS)-8-[[(3R,4R)-4-methoxypyrrolidin-3-yl] amino]-4-methyl-3,4,6,10b-tetrahydro-1H-pyrazino[2,1-a]isoindol-2-yl]quinoline-8-carbonitrile;

5-[(4R, 10bS)-4-methyl-8-(5-oxa-2,8-diazaspiro[3.5] nonan-2-yl)-3,4,6, 10b-tetrahydro-1H-pyrazino[2,1-a]isoindol-2-yl]quinoline-8-carbonitrile;

5-[(4R,10bS)-8-(2,6-diazaspiro[3.3]heptan-2-yl)-4-methyl-3,4,6, 10b-tetrahydro-1H-pyrazino[2,1-a]isoindol-2-yl]quinoline-8-carbonitrile;

5-[(4R, 10bS)-8-(1,6-diazaspiro[3.3]heptan-6-yl)-4-methyl-3,4,6,10b-tetrahydro-1H-pyrazino[2,1-a]isoindol-2-yl]quinoline-8-carbonitrile;

5-[(4R, 10bS)-4-methyl-8-(6-methyl-2,6-diazaspiro[3.3] heptan-2-yl)-3,4,6, 10b-tetrahydro-1H-pyrazino[2,1-a]isoindol-2-yl]quinoline-8-carbonitrile;

5-[(4R,10bS)-8-(3-amino-3-methyl-azetidin-1-yl)-4-methyl-3,4,6,10b-tetrahydro-1H-pyrazino[2,1-a]isoindol-2-yl]quinoline-8-carbonitrile;

5-[(4R,10bS)-8-[(3S,4S)-3-amino-4-hydroxy-pyrrolidin-1-yl]-4-methyl-3,4,6,10b-tetrahydro-1H-pyrazino[2,1-a]isoindol-2-yl]quinoline-8-carbonitrile;

5-[(4R, 10bS)-8-[(3R,4R)-3-amino-4-hydroxy-pyrrolidin-1-yl]-4-methyl-3,4,6, 10b-tetrahydro-1H-pyrazino[2, 1-a]isoindol-2-yl]quinoline-8-carbonitrile;

5-[(4R,10bS)-8-(3a-methoxy-1,2,3,4,6,6a-hexahydropyrrolo[3,4-c]pyrrol-5-yl)-4-methyl-3,4,6, 10b-tetrahydro-1H-pyrazino[2,1-a]isoindol-2-yl]quinoline-8-carbonitrile;

5-[(4R,10bS)-8-[(3S,4S)-3-hydroxy-4-(methylamino) pyrrolidin-1-yl]-4-methyl-3,4,6, 10b-tetrahydro-1H-pyrazino[2,1-a]isoindol-2-yl]quinoline-8-carbonitrile;

5-[(4R, 10bS)-4-methyl-8-[(3R,4R)-3-hydroxy-4-(methylamino) pyrrolidin-1-yl]-3,4,6, 10b-tetrahydro-1H-pyrazino[2,1-a]isoindol-2-yl]quinoline-8-carbonitrile;

5-[(4R, 10bS)-4-methyl-8-[(4aR,7aR)-3,4,4a,5,7,7a-hexahydro-2H-pyrrolo[3,4-b][1,4]oxazin-6-yl]-3,4,6, 10b-tetrahydro-1H-pyrazino[2,1-a]isoindol-2-yl]quinoline-8-carbonitrile;

5-[(4R,10bS)-4-methyl-8-[trans-(3R,4R)-4-amino-3-hydroxy-3-methyl-pyrrolidin-1-yl]-3,4,6, 10b-tetrahydro-1H-pyrazino[2,1-a]isoindol-2-yl]quinoline-8-carbonitrile;

5-[(4R,10bS)-8-[(3R,4R)-4-amino-3-hydroxy-3-methyl-pyrrolidin-1-yl]-4-methyl-3,4,6,10b-tetrahydro-1H-pyrazino[2,1-a]isoindol-2-yl]quinoline-8-carbonitrile;

5-[(4R, 10bS)-8-[(3S,4S)-4-amino-3-hydroxy-3-methyl-pyrrolidin-1-yl]-4-methyl-3,4,6, 10b-tetrahydro-1H-pyrazino[2,1-a]isoindol-2-yl]quinoline-8-carbonitrile;

5-[(4R,10bS)-8-[(3S,4R)-3-amino-4-fluoro-pyrrolidin-1-yl]-4-methyl-3,4,6,10b-tetrahydro-1H-pyrazino[2,1-a]isoindol-2-yl]quinoline-8-carbonitrile;

5-[(4R, 10bS)-8-[(3R,4S)-3-amino-4-fluoro-pyrrolidin-1-yl]-4-methyl-3,4,6, 10b-tetrahydro-1H-pyrazino[2,1-a]isoindol-2-yl]quinoline-8-carbonitrile;

5-[(4R,10bS)-8-[(3R,4R)-3-amino-4-fluoro-pyrrolidin-1-yl]-4-methyl-3,4,6,10b-tetrahydro-1H-pyrazino[2, 1-a]isoindol-2-yl]quinoline-8-carbonitrile;

5-[(4R,10bS)-8-[(3S,4S)-3-amino-4-fluoro-pyrrolidin-1-yl]-4-methyl-3,4,6,10b-tetrahydro-1H-pyrazino[2,1-a]isoindol-2-yl]quinoline-8-carbonitrile;

5-[(4R,10bS)-8-[(3R)-3-(methoxymethyl) piperazin-1-yl]-4-methyl-3,4,6,10b-tetrahydro-1H-pyrazino[2,1-a]isoindol-2-yl]quinoline-8-carbonitrile;

5-[(4R,10bS)-8-(4-amino-4-methyl-1-piperidyl)-4-methyl-3,4,6,10b-tetrahydro-1H-pyrazino[2, 1-a]isoindol-2-yl]quinoline-8-carbonitrile;

5-[(4R,10bS)-8-(3,4a,5,6,7,7a-hexahydro-2H-pyrrolo[3,4-b][1,4]oxazin-4-yl)-4-methyl-3,4,6,10b-tetrahydro-1H-pyrazino[2,1-a]isoindol-2-yl]quinoline-8-carbonitrile;

5-[(4R, 10bS)-8-[(6S)-6-hydroxy-1,4-diazepan-1-yl]-4-methyl-3,4,6, 10b-tetrahydro-1H-pyrazino[2,1-a]isoindol-2-yl]quinoline-8-carbonitrile;

5-[(4R, 10bS)-8-[(6R)-6-hydroxy-1,4-diazepan-1-yl]-4-methyl-3,4,6, 10b-tetrahydro-1H-pyrazino[2,1-a]isoindol-2-yl]quinoline-8-carbonitrile;

5-[(4R,10bS)-8-(6-amino-1,4-oxazepan-4-yl)-4-methyl-3,4,6,10b-tetrahydro-1H-pyrazino[2,1-a]isoindol-2-yl]quinoline-8-carbonitrile;

5-[(4R,10bS)-8-[(6R)-6-amino-1,4-oxazepan-4-yl]-4-methyl-3,4,6,10b-tetrahydro-1H-pyrazino[2,1-a]isoindol-2-yl]quinoline-8-carbonitrile;

5-[(4R,10bS)-8-[(6S)-6-amino-1,4-oxazepan-4-yl]-4-methyl-3,4,6, 10b-tetrahydro-1H-pyrazino[2,1-a]isoindol-2-yl]quinoline-8-carbonitrile;

5-[(4R, 10bS)-8-(6-hydroxy-6-methyl-1,4-diazepan-1-yl)-4-methyl-3,4,6, 10b-tetrahydro-1H-pyrazino[2,1-a]isoindol-2-yl]quinoline-8-carbonitrile;

5-[(4R, 10bS)-8-[(6S)-6-hydroxy-6-methyl-1,4-diazepan-1-yl]-4-methyl-3,4,6,10b-tetrahydro-1H-pyrazino[2,1-a]isoindol-2-yl]quinoline-8-carbonitrile;

5-[(4R, 10bS)-8-[(6R)-6-hydroxy-6-methyl-1,4-diazepan-1-yl]-4-methyl-3,4,6,10b-tetrahydro-1H-pyrazino[2,1-a]isoindol-2-yl]quinoline-8-carbonitrile;

5-[(4R,10bS)-4-methyl-8-(1,4-oxazepan-6-ylamino)-3,4,6, 10b-tetrahydro-1H-pyrazino[2,1-a]isoindol-2-yl]quinoline-8-carbonitrile;

5-[(4R,10bS)-4-methyl-8-[[(6R)-1,4-oxazepan-6-yl] amino]-3,4,6,10b-tetrahydro-1H-pyrazino[2,1-a]isoindol-2-yl]quinoline-8-carbonitrile;

5-[(4R, 10bS)-4-methyl-8-[[(6S)-1,4-oxazepan-6-yl] amino]-3,4,6, 10b-tetrahydro-1H-pyrazino[2,1-a]isoindol-2-yl]quinoline-8-carbonitrile;

5-[(4R,10bS)-4-methyl-8-(morpholin-3-ylmethylamino)-3,4,6,10b-tetrahydro-1H-pyrazino[2,1-a]isoindol-2-yl]quinoline-8-carbonitrile;

5-[(4R, 10bS)-4-methyl-8-[[(2S)-morpholin-2-yl]methylamino]-3,4,6,10b-tetrahydro-1H-pyrazino[2,1-a]isoindol-2-yl]quinoline-8-carbonitrile;

5-[(4R, 10bS)-4-methyl-8-[[(2R)-morpholin-2-yl]methylamino]-3,4,6,10b-tetrahydro-1/-pyrazino[2,1-a]isoindol-2-yl]quinoline-8-carbonitrile;

5-[(4R, 10bS)-8-[[(3S,4R)-4-methoxypyrrolidin-3-yl] amino]-4-methyl-3,4,6, 10b-tetrahydro-1H-pyrazino[2,1-a]isoindol-2-yl]quinoline-8-carbonitrile;

5-[(4R,10bS)-8-[[(3R,4S)-4-methoxypyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3S,4S)-4-methoxypyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[[(3R,4R)-4-methoxypyrrolidin-3-yl]amino]-4,9-dimethyl-3,4,6,10b-tetrahydro-1H-pyrazino[2,1-a]isoindol-2-yl]quinoline-8-carbonitrile;

5-[(4R,10bS)-8-[[(3S,4S)-4-methoxypyrrolidin-3-yl]methyl-amino]-4-methyl-3,4,6,10b-tetrahydro-1H-pyrazino[2,1-a]isoindol-2-yl]quinoline-8-carbonitrile;

5-[(4R,10bS)-4-methyl-8-[[(3R)-3-piperidyl]amino]-3,4,6,10b-tetrahydro-1H-pyrazino[2,1-a]isoindol-2-yl]quinoline-8-carbonitrile;

5-[(4R,10bS)-8-[(3S,4R)-3-methoxy-4-piperidyl]amino]-4-methyl-3,4,6,10b-tetrahydro-1H-pyrazino[2,1-a]isoindol-2-yl]quinoline-8-carbonitrile;

5-[(4R,10bS)-4-methyl-8-(2-morpholinoethylamino)-3,4,6,10b-tetrahydro-1H-pyrazino[2,1-a]isoindol-2-yl]quinoline-8-carbonitrile;

5-[(4R,10bS)-8-[2-[(3S)-3-hydroxypyrrolidin-1-yl]ethyl-amino]-4-methyl-3,4,6,10b-tetrahydro-1H-pyrazino[2,1-a]isoindol-2-yl]quinoline-8-carbonitrile;

5-[(4R,10bS)-8-[(3-fluoroazetidin-3-yl)methylamino]-4-methyl-3,4,6,10b-tetrahydro-1H-pyrazino[2,1-a]isoindol-2-yl]quinoline-8-carbonitrile;

5-[(4R,10bS)-8-[(2S,4S)-4-fluoropyrrolidin-2-yl]methylamino]-4-methyl-3,4,6,10b-tetrahydro-1H-pyrazino[2,1-a]isoindol-2-yl]quinoline-8-carbonitrile;

5-[(4R,10bS)-8-[(8aS)-3-oxo-1,5,6,7,8,8a-hexahydroimidazo[1,5-a]pyrazin-2-yl]-4-methyl-3,4,6,10b-tetrahydro-1H-pyrazino[2,1-a]isoindol-2-yl]quinoline-8-carbonitrile;

5-[(4R,10bS)-8-[(8aR)-3-oxo-1,5,6,7,8,8a-hexahydroimidazo[1,5-a]pyrazin-2-yl]-4-methyl-3,4,6,10b-tetrahydro-1H-pyrazino[2,1-a]isoindol-2-yl]quinoline-8-carbonitrile;

5-[(4R,10bS)-8-[(3S,4S)-4-fluoropyrrolidin-3-yl]oxy-4-methyl-3,4,6,10b-tetrahydro-1H-pyrazino[2,1-a]isoindol-2-yl]quinoline-8-carbonitrile;

5-[(4R,10bS)-8-[(2S,4S)-4-fluoropyrrolidin-2-yl]methoxy]-4-methyl-3,4,6,10b-tetrahydro-1H-pyrazino[2,1-a]isoindol-2-yl]quinoline-8-carbonitrile;

(4R,10bS)-N-[(3S,4R)-4-fluoropyrrolidin-3-yl]-4-methyl-2-(8-methyl-5-quinolyl)-3,4,6,10b-tetrahydro-1H-pyrazino[2,1-a]isoindol-8-amine;

(4R,10bS)-N-[(3S,4R)-4-fluoropyrrolidin-3-yl]-4-methyl-2-(8-methylquinoxalin-5-yl)-3,4,6,10b-tetrahydro-1H-pyrazino[2,1-a]isoindol-8-amine;

(4R,10bS)-N-[(3S,4R)-4-fluoropyrrolidin-3-yl]-4-methyl-2-[8-(trifluoromethyl)quinoxalin-5-yl]-3,4,6,10b-tetrahydro-1H-pyrazino[2,1-a]isoindol-8-amine;

7-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]-1,3-benzothiazole-4-carbonitrile;

(4R,10bS)-2-(8-chloro-5-quinolyl)-N-[(3S,4R)-4-fluoropyrrolidin-3-yl]-4-methyl-3,4,6,10b-tetrahydro-1H-pyrazino[2,1-a]isoindol-8-amine;

5-[(4R,10bS)-7-[2-[(3S)-3-hydroxypyrrolidin-1-yl]ethyl-amino]-4-methyl-3,4,6,10b-tetrahydro-1H-pyrazino[2,1-a]isoindol-2-yl]quinoline-8-carbonitrile;

5-[(4R,10bS)-7-[[(3S,4R)-4-fluoropyrrolidin-3-yl]amino]-4-methyl-3,4,6,10b-tetrahydro-1H-pyrazino[2,1-a]isoindol-2-yl]quinoline-8-carbonitrile;

5-[(4R,10bS)-8-[(3R,4R)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile;

5-[(4R,10bS)-8-[(3S,4S)-4-amino-3-hydroxy-3-methyl-pyrrolidin-1-yl]-9-fluoro-4-methyl-3,4,6,10b-tetrahydro-1H-pyrazino[2,1-a]isoindol-2-yl]quinoline-8-carbonitrile;

5-[(4R,10bS)-8-(2,6-diazaspiro[3.3]heptan-2-yl)-9-fluoro-4-methyl-3,4,6,10b-tetrahydro-1H-pyrazino[2,1-a]isoindol-2-yl]quinoline-8-carbonitrile;

5-[(4R,10bS)-9-fluoro-4-methyl-8-(9-oxa-3,7-diazabicyclo[3.3.1]nonan-3-yl)-3,4,6,10b-tetrahydro-1H-pyrazino[2,1-a]isoindol-2-yl]quinoline-8-carbonitrile;

5-[(4R,10bS)-4-methyl-8-(piperazine-1-carbonyl)-3,4,6,10b-tetrahydro-1H-pyrazino[2,1-a]isoindol-2-yl]quinoline-8-carbonitrile;

5-[(4R,10bS)-8-[(1S,4S)-2,5-diazabicyclo[2.2.1]heptane-2-carbonyl]-4-methyl-3,4,6,10b-tetrahydro-1H-pyrazino[2,1-a]isoindol-2-yl]quinoline-8-carbonitrile;

5-[(4R,10bS)-8-(4-amino-4-methyl-piperidine-1-carbonyl)-4-methyl-3,4,6,10b-tetrahydro-1H-pyrazino[2,1-a]isoindol-2-yl]quinoline-8-carbonitrile;

5-[(4R,10bS)-8-(3,8-diazabicyclo[3.2.1]octane-3-carbonyl)-4-methyl-3,4,6,10b-tetrahydro-1H-pyrazino[2,1-a]isoindol-2-yl]quinoline-8-carbonitrile;

5-[(4R,10bS)-4-methyl-8-(5-oxa-2,8-diazaspiro[3.5]nonan-2-yl)-3,4,6,10b-tetrahydro-1H-pyrazino[2,1-a]isoindol-2-yl]-2-deuterio-quinoline-8-carbonitrile;

5-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]-2-deuterio-quinoline-8-carbonitrile;

5-[(4R,10bS)-8-(3-amino-3-methyl-azetidin-1-yl)-4-methyl-3,4,6,10b-tetrahydro-1H-pyrazino[2,1-a]isoindol-2-yl]-2-deuterio-quinoline-8-carbonitrile;

5-[(4R,10bS)-4-methyl-8-(9-oxa-3,7-diazabicyclo[3.3.1]nonan-3-yl)-3,4,6,10b-tetrahydro-1H-pyrazino[2,1-a]isoindol-2-yl]-2-deuterio-quinoline-8-carbonitrile;

4-[(4R,10bS)-8-[(3R,4R)-3-amino-4-methoxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-3-amino-4-methoxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R)-3-aminopyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-4-methyl-8-[(3R)-3-methylpiperazin-1-yl]-3,4,6,10b-tetrahydro-1H-pyrazino[2,1-a]isoindol-2-yl]pyrazolo[1,5-a]pyridine-7-carbonitrile;

4-[(4R,10bS)-8-[[(3S,4R)-4-fluoropyrrolidin-3-yl]amino]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4S)-3-amino-4-fluoro-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-(4-amino-4-methyl-1-piperidyl)-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(6R)-6-amino-1,4-oxazepan-4-yl]-4-methyl-3,4,6,10b-tetrahydro-1H-pyrazino[2,1-a]isoindol-2-yl]pyrazolo[1,5-a]pyridine-7-carbonitrile;

4-[(4R, 10bS)-4-methyl-8-(5-oxa-2,8-diazaspiro[3.5]
nonan-2-yl)-3,4,6,10b-tetrahydro-1/-pyrazino[2,1-a]
isoindol-2-yl]pyrazolo[1,5-a]pyridine-7-carbonitrile;

4-[(4R,10bS)-8-[(3R)-3-amino-3-methyl-pyrrolidin-1-
yl]-4-methyl-3,4,6,10b-tetrahydro-1H-pyrazino[2, 1-a]
isoindol-2-yl]pyrazolo[1,5-a]pyridine-7-carbonitrile;

4-[(4R,10bS)-8-[(3R,4R)-4-amino-3-methoxy-1-piperidyl]-4-methyl-3,4,6,10b-tetrahydro-1H-pyrazino[2,
1-a]isoindol-2-yl]pyrazolo[1,5-a]pyridine-7-carbonitrile;

4-[(4R,10bS)-8-[(3R,4S)-4-amino-3-methoxy-1-piperidyl]-4-methyl-3,4,6,10b-tetrahydro-1H-pyrazino[2,
1-a]isoindol-2-yl]pyrazolo[1,5-a]pyridine-7-carbonitrile;

4-[(4R,10bS)-8-[(3S,4S)-3-amino-4-methoxy-1-piperidyl]-4-methyl-3,4,6,10b-tetrahydro-1H-pyrazino[2,
1-a]isoindol-2-yl]pyrazolo[1,5-a]pyridine-7-carbonitrile;

4-[(4R,10bS)-4-methyl-8-(9-oxa-3,7-diazabicyclo[3.3.1]
nonan-3-yl)-3,4,6,10b-tetrahydro-1H-pyrazino[2,1-a]
isoindol-2-yl]pyrazolo[1,5-a]pyridine-7-carbonitrile;

4-[(4R, 10bS)-8-[(3R,4R)-4-amino-3-hydroxy-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3R,4R)-3-amino-4-hydroxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-3-amino-4-hydroxy-pyrrolidin-1-yl]-4-methyl-3,4,6,10b-tetrahydro-1H-pyrazino[2,1-a]isoindol-2-yl]pyrazolo[1,5-a]pyridine-7-carbonitrile;

4-[(4R,10bS)-8-[(3S,4S)-4-amino-3-hydroxy-3-methyl-pyrrolidin-1-yl]-4-methyl-3,4,6,10b-tetrahydro-1H-pyrazino[2,1-a]isoindol-2-yl]-3-fluoro-pyrazolo[1,5-a]pyridine-7-carbonitrile; and 4-[(4R, 10bS)-8-[(3R,4R)-3-amino-4-methoxy-pyrrolidin-1-yl]-4-methyl-3,4,6, 10b-tetrahydro-1H-pyrazino[2,1-a]isoindol-2-yl]-3-fluoro-pyrazolo[1,5-a]pyridine-7-carbonitrile;

or a pharmaceutically acceptable salt, enantiomer or diastereomer thereof.

16. A process for preparing a compound of formula (I) according to claim 1, the method comprising one of the following steps:

a) performing a substitution reaction between a compound of formula (XII),

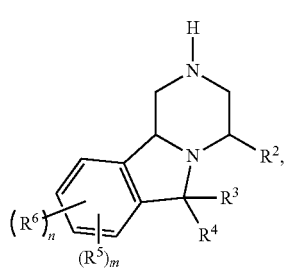

(XII)

and $R^1$-$X^1$ in the presence of a base, wherein $X^1$ is halogen;

b) performing a reaction between a compound of formula (XII),

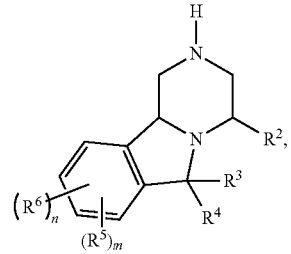

(XII)

and $R^1$-$X^1$ under Buchwald-Hartwig amination conditions in the presence of a catalyst and a base, wherein $X^1$ is halo;

c) performing a Buchwald-Hartwig amination reaction of a compound of formula (XV),

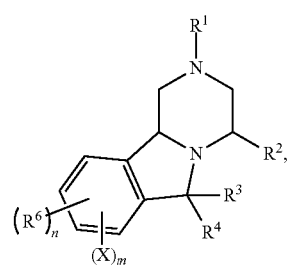

(XV)

and $R^1$-X in the presence of a catalyst and a base, wherein X is halo;

d) performing a Suzuki coupling reaction of a compound of formula (XV),

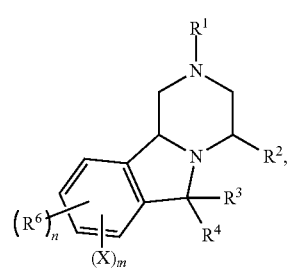

(XV)

and a boronic reagent in the presence of a catalyst and a base;

e) performing a Stille coupling reaction of a compound of formula (XV),

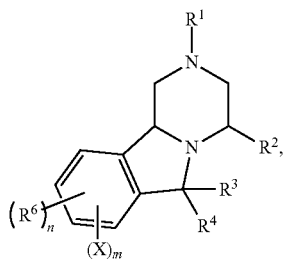

and an organotin reagent in the presence of a catalyst; or f) performing a Negishi coupling reaction of a compound of formula (XV),

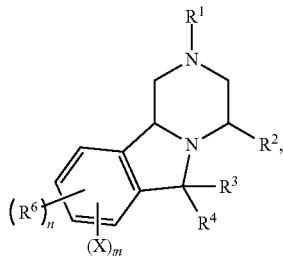

and an organozinc reagent in the presence of a catalyst;

wherein:
the base in a) is DIPEA;
the catalyst in steps b) and c) is Ruphos Pd—G2;
the base in steps b) and c) is $Cs_2CO_3$;
the catalyst in d) is tetrakis (triphenylphosphine) palladium (0) or [1,1'-bis (diphenylphosphino) ferrocene] dichloropalladium (II);
the base in d) is $K_2CO_3$;
the catalyst in e) is tetrakis (triphenylphosphine) palladium (0);
the catalyst in f) is tetrakis (triphenylphosphine) palladium (0) or [1,1'-bis (diphenylphosphino) ferrocene] dichloropalladium (II);
X is halogen;
m is 0, 1, 2, or 3;
n is 1, 2, 3 or 4;
m+n≤4;
$R^7$ is Boc;
$R^8$ is benzyl; and
$R^9$ is alkylsilyl.

17. A pharmaceutical composition comprising a compound in accordance with claim 1 and a therapeutically inert carrier.

18. A compound or pharmaceutically acceptable salt, enantiomer or diastereomer thereof when manufactured according to a process of claim 16.

19. A method for the treatment of systemic lupus erythematosus or lupus nephritis, which method comprises:
administering a therapeutically effective amount of a compound or pharmaceutically acceptable salt, enantiomer or diastereomer thereof, as defined in claim 1 to a subject in need thereof.

* * * * *